United States Patent
Wilmen et al.

(10) Patent No.: US 9,382,305 B2
(45) Date of Patent: Jul. 5, 2016

(54) RELAXIN FUSION POLYPEPTIDES AND USES THEREOF

(75) Inventors: Andreas Wilmen, Köln (DE); Ulrich Haupts, Odenthal (DE); Christoph Freiberg, Wuppertal (DE); Mark Trautwein, Wülfrath (DE); Lars Linden, Düsseldorf (DE); Kirsten Leineweber, Velbert-Neviges (DE); Hanna Tinel, Wuppertal (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 16 days.

(21) Appl. No.: 14/130,493

(22) PCT Filed: Jun. 29, 2012

(86) PCT No.: PCT/EP2012/062665
§ 371 (c)(1),
(2), (4) Date: Mar. 7, 2014

(87) PCT Pub. No.: WO2013/004607
PCT Pub. Date: Jan. 10, 2013

(65) Prior Publication Data
US 2014/0187491 A1   Jul. 3, 2014

(30) Foreign Application Priority Data

Jul. 1, 2011 (EP) ..................... 11172413
Jul. 5, 2011 (EP) ..................... 11172681

(51) Int. Cl.
C07K 14/64 (2006.01)
C07K 19/00 (2006.01)
A61K 38/22 (2006.01)
C12N 15/16 (2006.01)
C07K 16/18 (2006.01)
A61K 38/00 (2006.01)

(52) U.S. Cl.
CPC ............... *C07K 14/64* (2013.01); *C07K 16/18* (2013.01); *A61K 38/00* (2013.01); *C07K 2319/31* (2013.01); *C07K 2319/75* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis |
| 4,399,216 A | 8/1983 | Axel et al. |
| 4,510,245 A | 4/1985 | Cousens et al. |
| 4,634,665 A | 1/1987 | Axel et al. |
| 4,657,760 A | 4/1987 | Kung et al. |
| 4,683,195 A | 7/1987 | Mullis et al. |
| 4,758,516 A | 7/1988 | Hudson et al. |
| 4,816,397 A | 3/1989 | Boss et al. |
| 4,902,502 A | 2/1990 | Nitecki et al. |
| 4,968,615 A | 11/1990 | Koszinowski et al. |
| 5,122,614 A | 6/1992 | Zalipsky |
| 5,168,062 A | 12/1992 | Stinski |
| 5,179,017 A | 1/1993 | Axel et al. |
| 5,206,344 A | 4/1993 | Katre et al. |
| 5,219,564 A | 6/1993 | Zalipsky et al. |
| 5,225,212 A | 7/1993 | Martin et al. |
| 5,281,698 A | 1/1994 | Nitecki |
| 5,304,473 A * | 4/1994 | Belagaje ............... C07K 14/62 435/252.33 |
| 5,382,657 A | 1/1995 | Karasiewicz et al. |
| 5,473,034 A | 12/1995 | Yasui et al. |
| 5,476,653 A | 12/1995 | Pitt et al. |
| 5,516,673 A | 5/1996 | Margel et al. |
| 5,525,491 A | 6/1996 | Huston et al. |
| 5,629,384 A | 5/1997 | Veronese et al. |
| 5,643,575 A | 7/1997 | Martinez et al. |
| 5,736,625 A | 4/1998 | Callstrom et al. |
| 5,824,778 A | 10/1998 | Ishikawa et al. |
| 5,932,462 A | 8/1999 | Harris et al. |
| 5,985,265 A | 11/1999 | Kinstler et al. |
| 6,833,364 B1 | 12/2004 | Straub et al. |
| 6,864,287 B1 | 3/2005 | Alonso-Alija et al. |
| 7,271,149 B2 | 9/2007 | Glaesner et al. |
| 2002/0151011 A1 | 10/2002 | Fleer et al. |
| 2002/0173514 A1 | 11/2002 | Stasch et al. |
| 2004/0176446 A1 | 9/2004 | Alonso-Alija et al. |
| 2004/0224945 A1 | 11/2004 | Straub et al. |
| 2005/0063943 A1 | 3/2005 | Sommermeyer et al. |
| 2005/0065113 A1 | 3/2005 | Sommermeyer et al. |

(Continued)

FOREIGN PATENT DOCUMENTS

EP   0154316 A2   9/1985
EP   0183503 A2   6/1986

(Continued)

OTHER PUBLICATIONS

Schmidt SR. Fusion-proteins as biopharmaceuticals—applications and challenges. Curr Opin Drug Discov Devel. Mar. 2009;12(2):284-95.*

(Continued)

*Primary Examiner* — David Romeo
(74) *Attorney, Agent, or Firm* — Thomas C. Blankinship; Yonggang Ji

(57) ABSTRACT

The present invention provides Relaxin fusion polypeptides A-L-B with a non-wild type array of the Relaxin A-chain and Relaxin B-chain, wherein the A- and B-chains are connected by a linker peptide. The invention further provides Relaxin fusion polypeptides with extended half-life. Furthermore, the invention provides nucleic acid sequences encoding the foregoing fusion polypeptides, vectors containing the same, pharmaceutical compositions and medical use of such fusion polypeptides.

17 Claims, 18 Drawing Sheets

(56) References Cited

U.S. PATENT DOCUMENTS

| | | | |
|---|---|---|---|
| 2006/0052397 | A1 | 3/2006 | Alonso-Alija et al. |
| 2007/0179139 | A1 | 8/2007 | Alonso-Alija et al. |
| 2008/0058314 | A1 | 3/2008 | Alonso-Alija et al. |
| 2009/0203906 | A1 | 8/2009 | Alonso-Alija et al. |
| 2010/0104588 | A1 | 4/2010 | Dennis |
| 2011/0130332 | A1* | 6/2011 | Park .................. C07K 14/64 514/12.7 |
| 2011/0243942 | A1 | 10/2011 | Wang |
| 2012/0046229 | A1 | 2/2012 | Kraynov et al. |
| 2015/0160217 | A1 | 6/2015 | Wong et al. |

FOREIGN PATENT DOCUMENTS

| | | |
|---|---|---|
| EP | 0229108 A1 | 7/1987 |
| EP | 0322094 A1 | 6/1989 |
| EP | 0399666 A1 | 11/1990 |
| EP | 0400472 A2 | 12/1990 |
| EP | 0402378 A1 | 12/1990 |
| EP | 0439508 A1 | 8/1991 |
| EP | 0510356 B1 | 10/1992 |
| EP | 0605963 A2 | 7/1994 |
| EP | 0809996 A2 | 12/1997 |
| EP | 0413622 B2 | 2/1998 |
| EP | 0921131 A1 | 6/1999 |
| WO | 9013540 A1 | 11/1990 |
| WO | 9013659 A1 | 11/1990 |
| WO | 9216555 A1 | 10/1992 |
| WO | 9607670 A1 | 3/1993 |
| WO | 9315200 A1 | 8/1993 |
| WO | 9404193 A1 | 3/1994 |
| WO | 9848837 A9 | 4/1994 |
| WO | 9414758 A1 | 7/1994 |
| WO | 9417039 A1 | 8/1994 |
| WO | 9418247 A1 | 8/1994 |
| WO | 9428024 A1 | 12/1994 |
| WO | 9500162 A1 | 1/1995 |
| WO | 9506058 A1 | 3/1995 |
| WO | 9511924 A1 | 5/1995 |
| WO | 9513090 A1 | 5/1995 |
| WO | 9513312 A1 | 5/1995 |
| WO | 9533490 A1 | 12/1995 |
| WO | 9600080 A1 | 1/1996 |
| WO | 9621469 A1 | 7/1996 |
| WO | 9640791 A1 | 12/1996 |
| WO | 9641813 A2 | 12/1996 |
| WO | 9703106 A1 | 1/1997 |
| WO | 9716549 A2 | 5/1997 |
| WO | 9718832 A1 | 5/1997 |
| WO | 9726265 A1 | 7/1997 |
| WO | 9732607 A2 | 9/1997 |
| WO | 9805363 A3 | 5/1998 |
| WO | 9832466 A1 | 7/1998 |
| WO | 9841562 A1 | 9/1998 |
| WO | 9903861 A1 | 1/1999 |
| WO | 9932134 A1 | 7/1999 |
| WO | 9932139 A1 | 7/1999 |
| WO | 9932140 A1 | 7/1999 |
| WO | 9955377 A2 | 11/1999 |
| WO | 0006568 A1 | 2/2000 |
| WO | 0006569 A1 | 2/2000 |
| WO | 0119355 A2 | 3/2001 |
| WO | 0158468 A1 | 8/2001 |
| WO | 0145746 A3 | 10/2001 |
| WO | 0158957 A3 | 5/2002 |
| WO | 0177137 A9 | 5/2002 |
| WO | 2005092391 A3 | 7/2006 |
| WO | 2006053299 A3 | 8/2006 |
| WO | 2005092390 A9 | 12/2006 |
| WO | 2010054699 A1 | 5/2010 |
| WO | 2013004607 A1 | 1/2013 |
| WO | 2013007563 A1 | 1/2013 |

OTHER PUBLICATIONS

Abuchowski, A. et al., "Alteration of immunological properties of bovine serum albumin by covalent attachment of polyethylene glycol," J. Biol. Chem., 1977, 252:3578-81.

Bani, D. et al., "Relaxin Protects Against Myocardial Injury Caused by Ischemia and Reperfusion in Rat Heart," Am. J. Pathol, 1998, 152(5):1367-76.

Bani-Sacchi, T. et al., "Relaxin-induced increased coronary flow through stimulation of nitric oxide production," Br. J. Pharmacol, 1995, 116:1589-94.

Barlos et al., "An optimized chemical synthesis of human relaxin-2," An J Pept Sci., 2010,16:200-11.

Bartsch et al., J "Phosphodiesterase 4 Inhibition Synergizes with Relaxin Signaling to Promote Decidualization of Human Endometrial Stromal Cell," Clin Endocrinol Metab, 2004, 89(1):324-34.

Bartsch et al., "Phosphodiesterase 4 Inhibition Synergizes with Relaxin Signaling to Promote Decidualization of Human Endometrial Stromal Cells," Mol Hum Reprod., 2001, 7(9):799-809.

Behrens et al., "Plasma Proteins," Fed. Proc. Fed. Am. Soc. Exp. Biol.,1975(34):591.

Bennett RG., "Relaxin and its role in the development and treatment of fibrosis," Transl Res., 2009, 154:1-6.

Benton et al., "The use of UCOE vectors in combination with a preadapted serum free, suspension cell line allows for rapid production of large quantities of protein," Cytotechnology, 2002, 38(1-3):43-46.

Büllesbach and Schwabe, "The Relaxin Receptor-binding Site Geometry Suggests a Novel Gripping Mode of Interaction," J Biol Chem., 2000, 27, (45):35276-80.

Toth et al., "Relaxin stimulates atrial natriuretic peptide secretion in perfused rat heart," J Endocrinol, 1996, 150:487-95.

Teerlink et al., "Relaxin for the treatment of patients with acute heart failure (Pre-RELAX-AHF): a multicentre, randomised, placebo-controlled, parallel-group, dose-fi nding phase IIb study," Lancet, 2009, 373:1429-39.

Dschietzig et al., "Intravenous Recombinant Human Relaxin in Compensated Heart Failure: A Safety, Tolerability, and Pharmacodynamic Trial," J Cardiac Fail, 2009, 15(3):182-90.

Dschietzig et al., "Relaxin—a pleiotropic hormone and its emerging role for experimental and clinical therapeutics," Pharmacol & Therap., 2006, 112:38-56.

Taylor R.F., "Dictionary of Steroids. Two Volumes Chemical Data, structures and Bibliographies, Index," J Pharm Pharmacol,1992, 44:71.

Halls et al., "Signal Switching after Stimulation of LGR7 Receptors by Human Relaxin 2," Ann. N.Y. Acad. Sci., 2005, 1041:288-91.

Harris et al., "A Novel Process for Modifying Pharmacokinetics," Clin Pharmacokinet, 2001, 40(7):539-51.

Hossain et al., "The A-chain of Human Relaxin Family Peptides Has Distinct Roles in the Binding and Activation of the Different Relaxin Family Peptide Receptors," J Biol Chem, 2008, 283(25):17287-97.

Hsu, S. Y , "New insights into the evolution of the relaxin—LGR signaling system," TRENDS Endocrinol Metab., 2003, 14(7):303-309.

Urlaub et al., "Isolation of Chinese hamster cell mutants deficient in dihydrofolate reductase activity," Proc. Natl. Acad. Sci. USA,1980, 77(7):4216-20.

Kaufman and Sharp, "Amplification and Expression of Sequences Cotransfected with a Modular Dihydrofolate Reductase Complementary DNA Gene,"J Mol Biol, 1982,159:601-621.

Kaufman and Sharp, "Construction of a modular dihydrofolate reductase cDNA gene: analysis of signals utilized for efficient expression,"Mol Cell Biol.,1982, 2(11):1304-19.

Kim, B.J. et al., "Transferrin Fusion Technology: A Novel Approach to Prolonging Biological Half-Life of Insulinotropic Peptides," J. Pharm Exp. Thera., 2010, 334(3):682-692.

Kong et al., "Membrane receptors: Structure and function of the relaxin family peptide receptors," Mol Cell Endocrinol., 2010, 320:1-15.

(56) References Cited

OTHER PUBLICATIONS

Lawn et al., "The sequence of human serum albumin cDNA and its expression in *E. coli*," Nucleic Acids Res.,1981, 9 (22):6103-14.

McGuane and Parry, "Relaxin and the extracellular matrix: molecular mechanisms of action and implications for aardiovascular disease," Expert Rev Mol Med, 2005, 7(21):1-18.

Meloun, et al., "Complete Amino Acid Sequence of Human Serum Albumin," FEBS Letters, 1975, 58 (1-2):134-7.

Metra et al., "Dyspnoea and worsening heart failure in patients with acute heart failure: results from the Pre-RELAX-AHF study," Eur J Heart Fail, 2010, 12:1130-9.

Minghetti, et al., J. "Molecular Structure of the Human Albumin Gene Is Revealed by Nucleotide Sequence within q11-22 of Chromosome 4," Biol. Chem.,1986, 261(15):6747-57.

Nistri et al., "Relaxin inhibits lipopolysaccharide-induced adhesion of neutrophils to coronary endothelial cells by a nitric oxidemediated mechanism," FASEB J., 2003:2109-2111.

Park et al., "Regulation of Receptor Signaling by Relaxin A Chain Motifs: Derivation of Pan-Specific and LGR7-Specific Human Relaxin Analogs," J Biol Chem, 2008, 283:32099-32109.

Pasut and Veronese, "Effects of relaxin on rat atrial myocytes. Inhibition f /to via PKA-dependent phosphorylation," Drugs of Today, 2009, 45(9), 687-95.

Perna et al., "Novel drug development opportunity for relaxin in acute myocardial infarction: evidences from a swine model," FASEB J., 2005, 19:1525-1527.

Piedras-Renteria et al., "Effects of relaxin on rat atrial myocytes. I. Inhibition of /to via PKA-dependent phosphorylation," Am Physiol Soc., 1997, 272:H1791-7.

Radestock et al., "Relaxin reduces xenograft tumour growth of human MDA-MB-231 breast cancer cells," Breast Cancer Res., 2008, 10(4):71.

Rajpal et al., "Single-Chain Insulins as Receptor Agonists," Mol Endocrinol, 2009, 23(5):679-88.

Reijonen and Kwok, "Use of HLA class II tetramers in tracking antigen-specific T cells and mapping T-cell epitopes," Methods, 2003, 29:282-88.

Santora et al., "Antiarthritic Effects of Relaxin, in Combination with Estrogen, in Rat Adjuvant-Induced Arthritis," J. Pharmacol. Exp. Ther., 2007, 322:887-93.

Schmidt Sr., "Relaxin, the Relaxin-Like Factor and Their Receptors," Cur. Opi. in Drug Discov. a. Dev., 2009, 12 (2):284-295.

Schwabe and Büllesbach, "Relaxin, the Relaxin-Like Factor and Their Receptors," Adv Exp Med Biol (2007) 612 pp. 14-25.

Shafer et al., "Preparation of Cyanuric-Chloride Activated Poly(Ethylene Glycol)," J. Polym. Sci. Polym. Chem. Ed., 1986, 24:375-8.

Shaw et al., "Secretion of bioactive human insulin following plasmid-mediatedgene transfer to non-neuroendocrine cell lines, primary cultures and rat skeletal muscle in vivo," J Endocrinol, 2002, 172:653-72.

Cosen-Binker et al., "Relaxin prevents the development of severe acute pancreatitis," World J. Gastroenterol, 2006, 12 (10):1558-68.

Hudson et al., "Structure of a genomic clone encoding biologically active human relaxin," Nature, 1983, 301:628-31.

Durocher et al., "High-level and high-throughput recombinant protein production by transient transfection of suspension-growing human 293-EBNA 1 cells," Nucl.Acids Res., 2002, 30(2):1-9.

Dennis et al., "Albumin Binding as a General Strategy for Improving the Pharmacokinetics of Proteins," The Journal of Biological Chemistry, 2002, 277(38):35035-35043.

Wilkinson et al., "Evolution of the relaxin-like peptide family," BMC Evol. Biol., 2005, 5(14):1-17.

Witt et al., "Mutations in the gene encoding the serine protease inhibitor, Kazal type 1 are associated with chronic pancreatitis," Nat Genet, 2000, 25:213-16.

Zhang et al., Obestatin, "a Peptide Encoded by the Ghrelin Gene Opposes Ghrelin's Effects on Food Intake," Peptides, 2005, 26:1632-1639.

\* cited by examiner

Figure 2

| Clone | Construct |
|---|---|
| hRelaxin 2 | B \| C \| A |
| scR1 | Myc \| A \| 3aaG \| B \| FXa \| HA His |
| scR2 | Myc \| A \| 5aaGS \| B \| FXa \| HA His |
| scR3 | Myc \| A \| 7aaGS \| B \| FXa \| HA His |
| scR4 | Myc \| A \| 9aaGS \| B \| FXa \| HA His |
| scR5 | Myc \| A \| 11aaGS \| B \| FXa \| HA His |
| scR6 | Myc \| A \| 15aaGS \| B \| FXa \| HA His |
| scR7 | Myc \| A \| 6aaGS \| B |
| scR8 | Myc \| A \| 12aaGS \| B |
| scR9 | Myc \| A \| 13aaGS \| B |
| scR10 | Myc \| A \| 14aaGS \| B |
| scR11 | A \| 9aaGS + C \| B |
| scR12 | A \| 9aaGS + K \| B |
| scR13 | A \| short linker \| B |
| scR14 | A (RLN3) \| 9aaGS \| B (RLN3) |
| scR15 | Myc \| A (RLN3) \| 9aaGS \| B (RLN3) |
| scR16 | Myc \| B (RLN2) \| 9aaGS \| A (RLN2) |
| scR17 | Myc \| A (RLN3) \| 9aaGS \| B (RLN2) |
| scR18 | Myc \| B (RLN2) \| 9aaGS \| A (RLN3) |
| scR19 | Myc \| A (RLN2) \| 9aaGS \| B (RLN3) |
| scR20 | Myc \| B (RLN3) \| 9aaGS \| A (RLN2) |

Figure 3

| Clone | Construct |
|---|---|
| Relaxin Fc | B \| C \| A \| FXa \| hIgG1 Fc |
| scR-Fc 1 | Myc \| A \| 9aaGS \| B \| FXa \| hIgG1 Fc |
| scR-Fc 2 | A \| 9aaGS \| B \| GGSP \| hIgG1 Fc |
| scR-Fc 3 | A \| 9aaGS \| B \| (GGS)₂P \| hIgG1 Fc |
| scR-Fc 4 | A \| 9aaGS \| B \| (GGS)₃P \| hIgG1 Fc |
| scR-Fc 5 | hIgG1 Fc \| GGSP \| A \| 9aaGS \| B |
| scR-Fc 6 | hIgG1 Fc \| (GGS)₂P \| A \| 9aaGS \| B |
| scR-Fc 7 | hIgG1 Fc \| (GGS)₃P \| A \| 9aaGS \| B |
| scR-Fc 8 | A \| 9aaGS \| B \| GGSP \| rIgG2b Fc \| 6 X His |
| scR-Fc 9 | A \| 9aaGS \| B \| (GGS)₂P \| rIgG2b Fc \| 6 X His |
| scR-Fc 10 | A \| 9aaGS \| B \| (GGS)₃P \| rIgG2b Fc \| 6 X His |
| scR-Fc 11 | 6 X His \| rIgG2b Fc \| GGSP \| A \| 9aaGS \| B |
| scR-Fc 12 | 6 X His \| rIgG2b Fc \| (GGS)₂P \| A \| 9aaGS \| B |
| scR-Fc 13 | 6 X His \| rIgG2b Fc \| (GGS)₃P \| A \| 9aaGS \| B |
| scR-Fc 14 | A \| 9aaGS \| B \| hIgG1 Fc |
| scR-Fc 15 | A \| 9aaGS \| B \| (GS)3 \| hIgG1 Fc |
| scR-Fc 16 | A \| 9aaGS \| B \| (GS)3 \| C del hIgG1 Fc |
| scR-Fc 17 | A \| 9aaGS \| B \| (GS)3 \| rIgG2b Fc |
| scR-Fc 18 | A \| 9aaGS \| B \| linker \| hIgG1 Fc |
| scR-Var1 | A \| 9aaGS \| B \| PEG linker |
| scR-Var2 | PEG linker \| A \| 9aaGS \| B |
| scR-Var3 | Transferrin \| FXa \| A \| 9aaGS \| B |
| scR-Var4 | Transferrin \| FXa \| B \| C \| A |
| scR-Var5 | Albumin \| FXa \| A \| 9aaGS \| B |
| scR-Var6 | Albumin \| FXa \| B \| C \| A |
| scR-Var7 | A \| linker \| B \| FXa \| hIgG1 Fc |
| scR-Var8 | hIgG1 Fc \| FXa \| A \| linker \| B |

| | hRelaxin 2 | scR-Fc 5 | scR-Fc 6 | scR-Fc 7 |
|---|---|---|---|---|
| EC50 | 3.595e-011 | 1.346e-010 | 4.232e-010 | 7.411e-010 |

|  | wtRelaxin Kontr. | scR-Fc 11 | scR-Fc 12 | scR-Fc 13 |
|---|---|---|---|---|
| EC50 | 2.664e-011 | 1.204e-009 | 9.530e-010 | 8.953e-010 |

| | hRelaxin 2 | scR-Var 3 | scR-Var 4 | scR-Var 5 | scR-Var 6 |
|---|---|---|---|---|---|
| EC50 | 3.243e-011 | 1.119e-009 | 1.305e-010 | 5.508e-009 | 8.368e-009 |

Figure 11 a and b
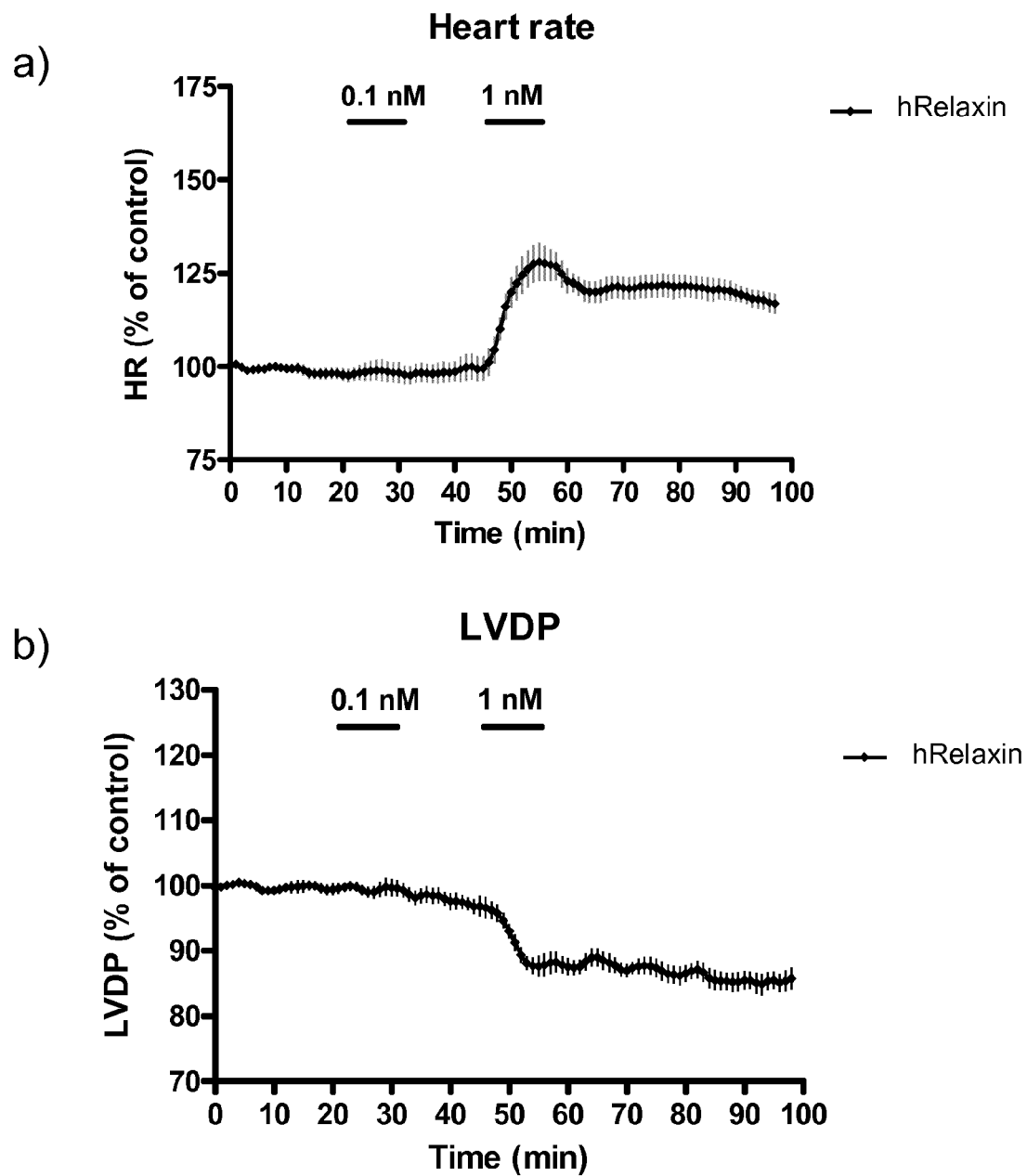

Figure 11 c and d
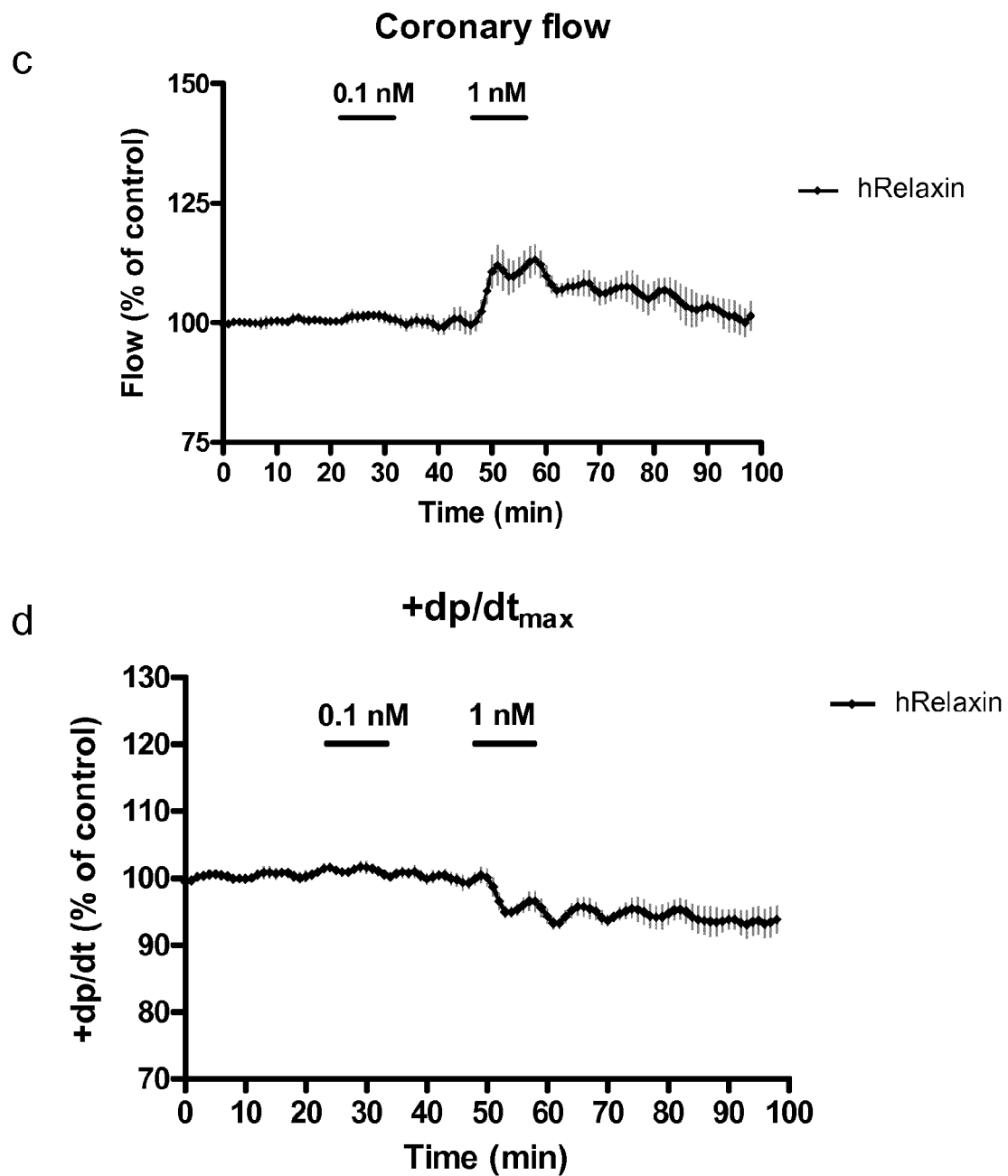

Figure 11 e and f
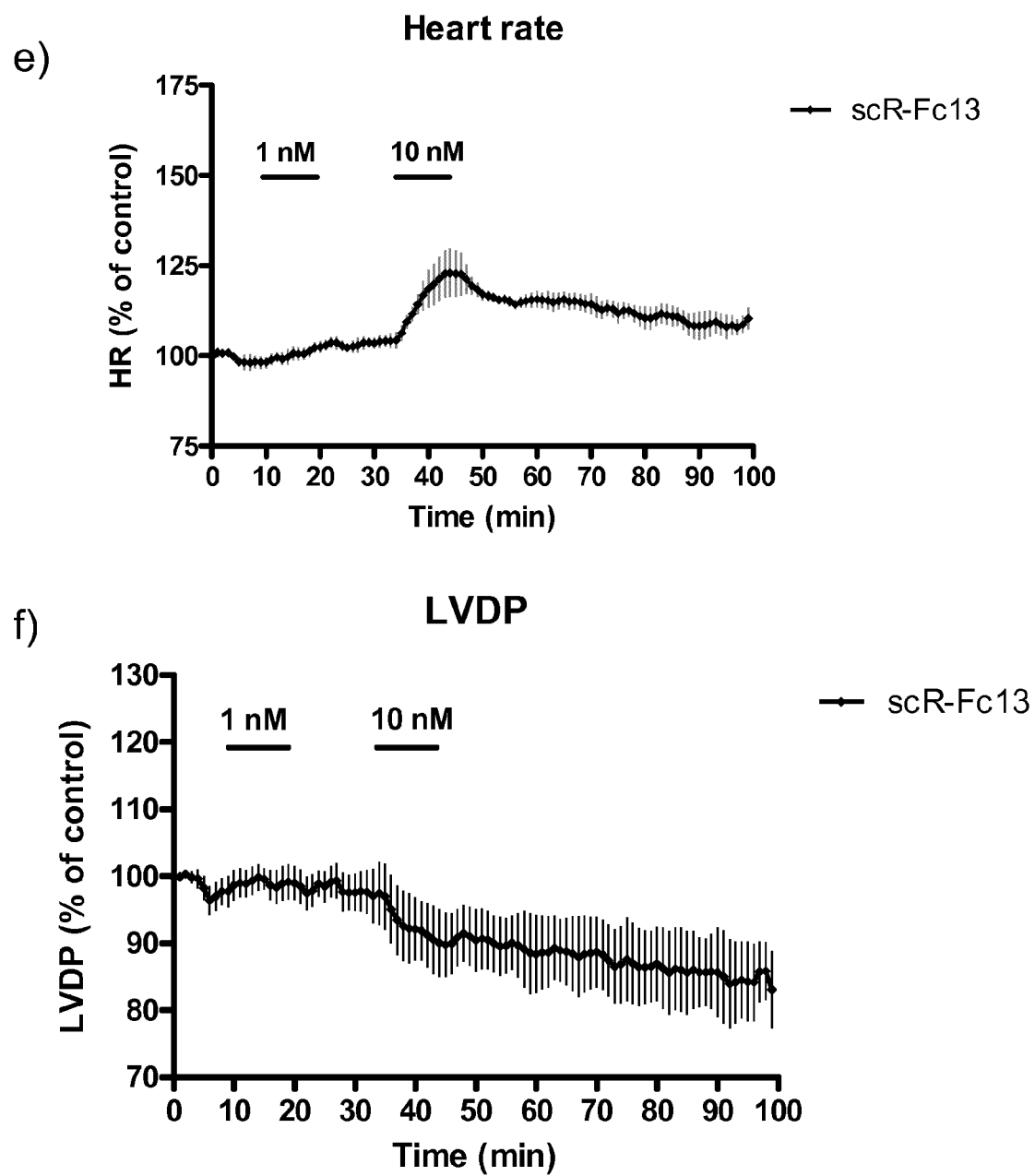

Figure 11 g and h
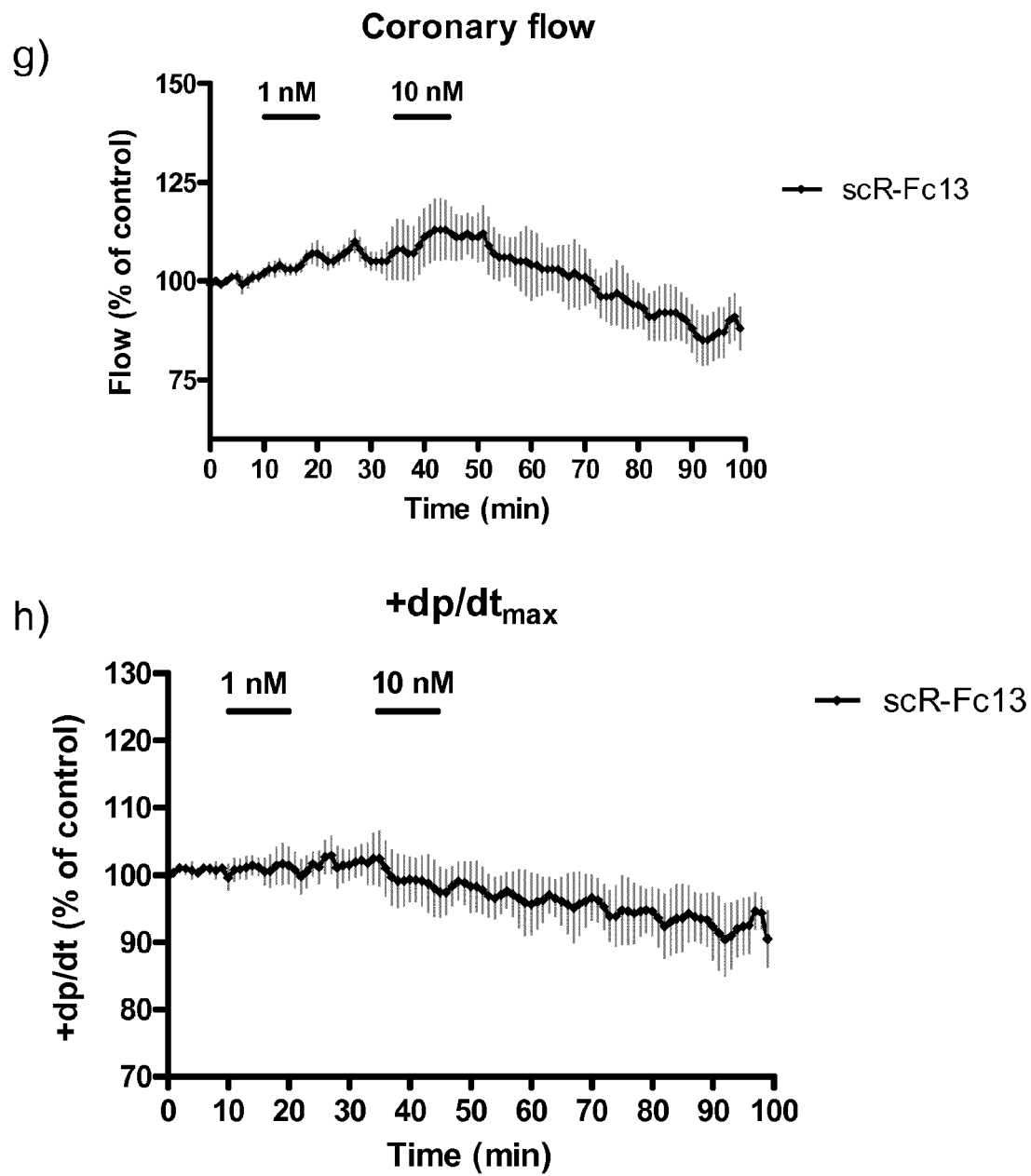

SEQUENCE LISTING

```
<160> NUMBER OF SEQ ID NOS: 176

<210> SEQ ID NO 1
<211> LENGTH: 80
<212> TYPE: PRT
<213> ORGANISM: Artificial Sequence
<220> FEATURE:
<223> OTHER INFORMATION: relaxin fusion polypeptide

<400> SEQUENCE: 1

Glu Gln Lys Leu Ile Ser Glu Glu Asp Leu Gln Leu Tyr Ser Ala Leu
1               5                   10                  15

Ala Asn Lys Cys Cys His Val Gly Cys Thr Lys Arg Ser Leu Ala Arg
            20                  25                  30

Phe Cys Gly Gly Gly Ser Trp Met Glu Glu Val Ile Lys Leu Cys Gly
        35                  40                  45

Arg Glu Leu Val Arg Ala Gln Ile Ala Ile Cys Gly Met Ser Thr Trp
    50                  55                  60

Ser Tyr Pro Tyr Asp Val Pro Asp Tyr Ala His His His His His
65                  70                  75                  80

<210> SEQ ID NO 2
<211> LENGTH: 82
<212> TYPE: PRT
<213> ORGANISM: Artificial Sequence
<220> FEATURE:
<223> OTHER INFORMATION: relaxin fusion polypeptide

<400> SEQUENCE: 2

Glu Gln Lys Leu Ile Ser Glu Glu Asp Leu Gln Leu Tyr Ser Ala Leu
1               5                   10                  15

Ala Asn Lys Cys Cys His Val Gly Cys Thr Lys Arg Ser Leu Ala Arg
            20                  25                  30

Phe Cys Gly Gly Gly Ser Gly Ser Trp Met Glu Glu Val Ile Lys Leu
        35                  40                  45

Cys Gly Arg Glu Leu Val Arg Ala Gln Ile Ala Ile Cys Gly Met Ser
    50                  55                  60
```

```
Thr Trp Ser Tyr Pro Tyr Asp Val Pro Asp Tyr Ala His His His
 65                  70                  75                  80

His His
```

```
<210> SEQ ID NO 3
<211> LENGTH: 84
<212> TYPE: PRT
<213> ORGANISM: Artificial Sequence
<220> FEATURE:
<223> OTHER INFORMATION: relaxin fusion polypeptide

<400> SEQUENCE: 3

Glu Gln Lys Leu Ile Ser Glu Glu Asp Leu Gln Leu Tyr Ser Ala Leu
  1               5                  10                  15

Ala Asn Lys Cys Cys His Val Gly Cys Thr Lys Arg Ser Leu Ala Arg
             20                  25                  30

Phe Cys Gly Gly Gly Ser Gly Gly Ser Trp Met Glu Glu Val Ile
         35                  40                  45

Lys Leu Cys Gly Arg Glu Leu Val Arg Ala Gln Ile Ala Ile Cys Gly
 50                  55                  60

Met Ser Thr Trp Ser Tyr Pro Tyr Asp Val Pro Asp Tyr Ala His His
 65                  70                  75                  80

His His His His
```

```
<210> SEQ ID NO 4
<211> LENGTH: 86
<212> TYPE: PRT
<213> ORGANISM: Artificial Sequence
<220> FEATURE:
<223> OTHER INFORMATION: relaxin fusion polypeptide

<400> SEQUENCE: 4

Glu Gln Lys Leu Ile Ser Glu Glu Asp Leu Gln Leu Tyr Ser Ala Leu
  1               5                  10                  15

Ala Asn Lys Cys Cys His Val Gly Cys Thr Lys Arg Ser Leu Ala Arg
             20                  25                  30

Phe Cys Gly Gly Gly Ser Gly Gly Gly Ser Trp Met Glu Glu
         35                  40                  45

Val Ile Lys Leu Cys Gly Arg Glu Leu Val Arg Ala Gln Ile Ala Ile
 50                  55                  60

Cys Gly Met Ser Thr Trp Ser Tyr Pro Tyr Asp Val Pro Asp Tyr Ala
 65                  70                  75                  80

His His His His His His
                 85
```

```
<210> SEQ ID NO 5
<211> LENGTH: 88
<212> TYPE: PRT
<213> ORGANISM: Artificial Sequence
<220> FEATURE:
<223> OTHER INFORMATION: relaxin fusion polypeptide

<400> SEQUENCE: 5

Glu Gln Lys Leu Ile Ser Glu Glu Asp Leu Gln Leu Tyr Ser Ala Leu
  1               5                  10                  15

Ala Asn Lys Cys Cys His Val Gly Cys Thr Lys Arg Ser Leu Ala Arg
             20                  25                  30

Phe Cys Gly Gly Gly Ser Gly Gly Gly Ser Gly Gly Ser Trp Met
         35                  40                  45
```

```
Glu Val Ile Lys Leu Cys Gly Arg Glu Leu Val Arg Ala Gln Ile
        50                  55                  60
Ala Ile Cys Gly Met Ser Thr Trp Ser Tyr Pro Tyr Asp Val Pro Asp
65                  70                  75                  80
Tyr Ala His His His His His His
                85
```

<210> SEQ ID NO 6
<211> LENGTH: 92
<212> TYPE: PRT
<213> ORGANISM: Artificial Sequence
<220> FEATURE:
<223> OTHER INFORMATION: relaxin fusion polypeptide

<400> SEQUENCE: 6

```
Glu Gln Lys Leu Ile Ser Glu Glu Asp Leu Gln Leu Tyr Ser Ala Leu
1               5                   10                  15
Ala Asn Lys Cys Cys His Val Gly Cys Thr Lys Arg Ser Leu Ala Arg
                20                  25                  30
Phe Cys Gly Gly Gly Ser Gly Gly Gly Ser Gly Gly Gly Ser Gly Gly
            35                  40                  45
Gly Ser Trp Met Glu Glu Val Ile Lys Leu Cys Gly Arg Glu Leu Val
        50                  55                  60
Arg Ala Gln Ile Ala Ile Cys Gly Met Ser Thr Trp Ser Tyr Pro Tyr
65                  70                  75                  80
Asp Val Pro Asp Tyr Ala His His His His His
                85                  90
```

<210> SEQ ID NO 7
<211> LENGTH: 68
<212> TYPE: PRT
<213> ORGANISM: Artificial Sequence
<220> FEATURE:
<223> OTHER INFORMATION: relaxin fusion polypeptide

<400> SEQUENCE: 7

```
Glu Gln Lys Leu Ile Ser Glu Glu Asp Leu Gln Leu Tyr Ser Ala Leu
1               5                   10                  15
Ala Asn Lys Cys Cys His Val Gly Cys Thr Lys Arg Ser Leu Ala Arg
                20                  25                  30
Phe Cys Gly Gly Gly Ser Gly Gly Ser Trp Met Glu Glu Val Ile Lys
            35                  40                  45
Leu Cys Gly Arg Glu Leu Val Arg Ala Gln Ile Ala Ile Cys Gly Met
        50                  55                  60
Ser Thr Trp Ser
65
```

<210> SEQ ID NO 8
<211> LENGTH: 74
<212> TYPE: PRT
<213> ORGANISM: Artificial Sequence
<220> FEATURE:
<223> OTHER INFORMATION: relaxin fusion polypeptide

<400> SEQUENCE: 8

```
Glu Gln Lys Leu Ile Ser Glu Glu Asp Leu Gln Leu Tyr Ser Ala Leu
1               5                   10                  15
Ala Asn Lys Cys Cys His Val Gly Cys Thr Lys Arg Ser Leu Ala Arg
                20                  25                  30
```

```
Phe Cys Gly Gly Gly Ser Gly Gly Ser Gly Gly Ser Ser Trp
            35                  40                  45

Met Glu Glu Val Ile Lys Leu Cys Gly Arg Glu Leu Val Arg Ala Gln
 50                  55                  60

Ile Ala Ile Cys Gly Met Ser Thr Trp Ser
 65                  70
```

<210> SEQ ID NO 9
<211> LENGTH: 75
<212> TYPE: PRT
<213> ORGANISM: Artificial Sequence
<220> FEATURE:
<223> OTHER INFORMATION: relaxin fusion polypeptide

<400> SEQUENCE: 9

```
Glu Gln Lys Leu Ile Ser Glu Glu Asp Leu Gln Leu Tyr Ser Ala Leu
 1               5                  10                  15

Ala Asn Lys Cys Cys His Val Gly Cys Thr Lys Arg Ser Leu Ala Arg
                20                  25                  30

Phe Cys Gly Gly Gly Ser Gly Gly Ser Gly Gly Ser Gly Ser
            35                  40                  45

Trp Met Glu Glu Val Ile Lys Leu Cys Gly Arg Glu Leu Val Arg Ala
 50                  55                  60

Gln Ile Ala Ile Cys Gly Met Ser Thr Trp Ser
 65                  70                  75
```

<210> SEQ ID NO 10
<211> LENGTH: 76
<212> TYPE: PRT
<213> ORGANISM: Artificial Sequence
<220> FEATURE:
<223> OTHER INFORMATION: relaxin fusion polypeptide

<400> SEQUENCE: 10

```
Glu Gln Lys Leu Ile Ser Glu Glu Asp Leu Gln Leu Tyr Ser Ala Leu
 1               5                  10                  15

Ala Asn Lys Cys Cys His Val Gly Cys Thr Lys Arg Ser Leu Ala Arg
                20                  25                  30

Phe Cys Gly Gly Gly Ser Gly Gly Ser Gly Gly Ser Gly Gly
            35                  40                  45

Ser Trp Met Glu Glu Val Ile Lys Leu Cys Gly Arg Glu Leu Val Arg
     50                  55                  60

Ala Gln Ile Ala Ile Cys Gly Met Ser Thr Trp Ser
 65                  70                  75
```

<210> SEQ ID NO 11
<211> LENGTH: 62
<212> TYPE: PRT
<213> ORGANISM: Artificial Sequence
<220> FEATURE:
<223> OTHER INFORMATION: relaxin fusion polypeptide

<400> SEQUENCE: 11

```
Gln Leu Tyr Ser Ala Leu Ala Asn Lys Cys Cys His Val Gly Cys Thr
 1               5                  10                  15

Lys Arg Ser Leu Ala Arg Phe Cys Gly Gly Gly Ser Gly Cys Gly Gly
                20                  25                  30

Ser Gly Ser Trp Met Glu Glu Val Ile Lys Leu Cys Gly Arg Glu Leu
            35                  40                  45

Val Arg Ala Gln Ile Ala Ile Cys Gly Met Ser Thr Trp Ser
```

```
                    50                  55                  60

<210> SEQ ID NO 12
<211> LENGTH: 62
<212> TYPE: PRT
<213> ORGANISM: Artificial Sequence
<220> FEATURE:
<223> OTHER INFORMATION: relaxin fusion polypeptide

<400> SEQUENCE: 12

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Lys Gly Gly
            20                  25                  30

Ser Gly Ser Trp Met Glu Glu Val Ile Lys Leu Cys Gly Arg Glu Leu
        35                  40                  45

Val Arg Ala Gln Ile Ala Ile Cys Gly Met Ser Thr Trp Ser
    50                  55                  60

<210> SEQ ID NO 13
<211> LENGTH: 61
<212> TYPE: PRT
<213> ORGANISM: Artificial Sequence
<220> FEATURE:
<223> OTHER INFORMATION: relaxin fusion polypeptide

<400> SEQUENCE: 13

Gln Leu Tyr Ser Ala Leu Ala Asn Lys Cys Cys His Val Gly Cys Thr
1               5                   10                  15

Lys Arg Ser Leu Ala Arg Phe Cys Lys Arg Ser Leu Ser Arg Lys Lys
            20                  25                  30

Arg Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser
    50                  55                  60

<210> SEQ ID NO 14
<211> LENGTH: 60
<212> TYPE: PRT
<213> ORGANISM: Artificial Sequence
<220> FEATURE:
<223> OTHER INFORMATION: relaxin fusion polypeptide

<400> SEQUENCE: 14

Asp Val Leu Ala Gly Leu Ser Ser Ser Cys Cys Lys Trp Gly Cys Ser
1               5                   10                  15

Lys Ser Glu Ile Ser Ser Leu Cys Gly Gly Gly Ser Gly Gly Gly Ser
            20                  25                  30

Gly Arg Ala Ala Pro Tyr Gly Val Arg Leu Cys Gly Arg Glu Phe Ile
        35                  40                  45

Arg Ala Val Ile Phe Thr Cys Gly Gly Ser Arg Trp
    50                  55                  60

<210> SEQ ID NO 15
<211> LENGTH: 70
<212> TYPE: PRT
<213> ORGANISM: Artificial Sequence
<220> FEATURE:
<223> OTHER INFORMATION: relaxin fusion polypeptide

<400> SEQUENCE: 15

Glu Gln Lys Leu Ile Ser Glu Glu Asp Leu Asp Val Leu Ala Gly Leu
```

```
1               5                   10                  15
Ser Ser Ser Cys Cys Lys Trp Gly Cys Ser Lys Ser Glu Ile Ser Ser
                20                  25                  30

Leu Cys Gly Gly Gly Gly Gly Gly Ser Gly Arg Ala Ala Pro Tyr
        35                  40                  45

Gly Val Arg Leu Cys Gly Arg Glu Phe Ile Arg Ala Val Ile Phe Thr
        50                  55                  60

Cys Gly Gly Ser Arg Trp
65                  70
```

<210> SEQ ID NO 16
<211> LENGTH: 308
<212> TYPE: PRT
<213> ORGANISM: Artificial Sequence
<220> FEATURE:
<223> OTHER INFORMATION: relaxin fusion polypeptide

<400> SEQUENCE: 16

```
Glu Gln Lys Leu Ile Ser Glu Glu Asp Leu Gln Leu Tyr Ser Ala Leu
1               5                   10                  15

Ala Asn Lys Cys Cys His Val Gly Cys Thr Lys Arg Ser Leu Ala Arg
                20                  25                  30

Phe Cys Gly Gly Gly Ser Gly Gly Ser Gly Ser Trp Met Glu Glu
        35                  40                  45

Val Ile Lys Leu Cys Gly Arg Glu Leu Val Arg Ala Gln Ile Ala Ile
        50                  55                  60

Cys Gly Met Ser Thr Trp Ser Ile Glu Gly Arg Met Asp Pro Lys Ala
65                  70                  75                  80

Cys Asp Lys Thr His Thr Cys Pro Pro Cys Pro Ala Pro Glu Leu Leu
                85                  90                  95

Gly Gly Pro Ser Val Phe Leu Phe Pro Pro Lys Pro Lys Asp Thr Leu
            100                 105                 110

Met Ile Ser Arg Thr Pro Glu Val Thr Cys Val Val Val Asp Val Ser
            115                 120                 125

His Glu Asp Pro Glu Val Lys Phe Asn Trp Tyr Val Asp Gly Val Glu
        130                 135                 140

Val His Asn Ala Lys Thr Lys Pro Arg Glu Glu Gln Tyr Asn Ser Thr
145                 150                 155                 160

Tyr Arg Val Val Ser Val Leu Thr Val Leu His Gln Asp Trp Leu Asn
                165                 170                 175

Gly Lys Glu Tyr Lys Cys Lys Val Ser Asn Lys Ala Leu Pro Ala Pro
            180                 185                 190

Ile Glu Lys Thr Ile Ser Lys Ala Lys Gly Gln Pro Arg Glu Pro Gln
            195                 200                 205

Val Tyr Thr Leu Pro Pro Ser Arg Asp Glu Leu Thr Lys Asn Gln Val
        210                 215                 220

Ser Leu Thr Cys Leu Val Lys Gly Phe Tyr Pro Ser Asp Ile Ala Val
225                 230                 235                 240

Glu Trp Glu Ser Asn Gly Gln Pro Glu Asn Asn Tyr Lys Thr Thr Pro
                245                 250                 255

Pro Val Leu Asp Ser Asp Gly Ser Phe Phe Leu Tyr Ser Lys Leu Thr
            260                 265                 270

Val Asp Lys Ser Arg Trp Gln Gln Gly Asn Val Phe Ser Cys Ser Val
            275                 280                 285

Met His Glu Ala Leu His Asn His Tyr Thr Gln Lys Ser Leu Ser Leu
```

Ser Pro Gly Lys
305

<210> SEQ ID NO 17
<211> LENGTH: 292
<212> TYPE: PRT
<213> ORGANISM: Artificial Sequence
<220> FEATURE:
<223> OTHER INFORMATION: relaxin fusion polypeptide

<400> SEQUENCE: 17

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Gly Ser
    50                  55                  60

Pro Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Asp Glu Leu Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290

<210> SEQ ID NO 18
<211> LENGTH: 295
<212> TYPE: PRT
<213> ORGANISM: Artificial Sequence
<220> FEATURE:
<223> OTHER INFORMATION: relaxin fusion polypeptide

<400> SEQUENCE: 18

```
Gln Leu Tyr Ser Ala Leu Ala Asn Lys Cys Cys His Val Gly Cys Thr
  1               5                  10                  15
Lys Arg Ser Leu Ala Arg Phe Cys Gly Gly Gly Ser Gly Gly Gly Ser
             20                  25                  30
Gly Ser Trp Met Glu Glu Val Ile Lys Leu Cys Gly Arg Glu Leu Val
         35                  40                  45
Arg Ala Gln Ile Ala Ile Cys Gly Met Ser Thr Trp Ser Gly Gly Ser
     50                  55                  60
Gly Gly Ser Pro Asp Lys Thr His Thr Cys Pro Pro Cys Pro Ala Pro
 65                  70                  75                  80
Glu Leu Leu Gly Gly Pro Ser Val Phe Leu Phe Pro Pro Lys Pro Lys
                 85                  90                  95
Asp Thr Leu Met Ile Ser Arg Thr Pro Glu Val Thr Cys Val Val Val
            100                 105                 110
Asp Val Ser His Glu Asp Pro Glu Val Lys Phe Asn Trp Tyr Val Asp
            115                 120                 125
Gly Val Glu Val His Asn Ala Lys Thr Lys Pro Arg Glu Glu Gln Tyr
        130                 135                 140
Asn Ser Thr Tyr Arg Val Val Ser Val Leu Thr Val Leu His Gln Asp
145                 150                 155                 160
Trp Leu Asn Gly Lys Glu Tyr Lys Cys Lys Val Ser Asn Lys Ala Leu
                165                 170                 175
Pro Ala Pro Ile Glu Lys Thr Ile Ser Lys Ala Lys Gly Gln Pro Arg
            180                 185                 190
Glu Pro Gln Val Tyr Thr Leu Pro Pro Ser Arg Asp Glu Leu Thr Lys
        195                 200                 205
Asn Gln Val Ser Leu Thr Cys Leu Val Lys Gly Phe Tyr Pro Ser Asp
210                 215                 220
Ile Ala Val Glu Trp Glu Ser Asn Gly Gln Pro Glu Asn Asn Tyr Lys
225                 230                 235                 240
Thr Thr Pro Pro Val Leu Asp Ser Asp Gly Ser Phe Phe Leu Tyr Ser
                245                 250                 255
Lys Leu Thr Val Asp Lys Ser Arg Trp Gln Gln Gly Asn Val Phe Ser
            260                 265                 270
Cys Ser Val Met His Glu Ala Leu His Asn His Tyr Thr Gln Lys Ser
        275                 280                 285
Leu Ser Leu Ser Pro Gly Lys
    290                 295
```

<210> SEQ ID NO 19
<211> LENGTH: 298
<212> TYPE: PRT
<213> ORGANISM: Artificial Sequence
<220> FEATURE:
<223> OTHER INFORMATION: relaxin fusion polypeptide

<400> SEQUENCE: 19

```
Gln Leu Tyr Ser Ala Leu Ala Asn Lys Cys Cys His Val Gly Cys Thr
  1               5                  10                  15
Lys Arg Ser Leu Ala Arg Phe Cys Gly Gly Gly Ser Gly Gly Gly Ser
             20                  25                  30
Gly Ser Trp Met Glu Glu Val Ile Lys Leu Cys Gly Arg Glu Leu Val
         35                  40                  45
```

```
Arg Ala Gln Ile Ala Ile Cys Gly Met Ser Thr Trp Ser Gly Gly Ser
 50                  55                  60

Gly Gly Ser Gly Gly Ser Pro Asp Lys Thr His Thr Cys Pro Pro Cys
 65                  70                  75                  80

Pro Ala Pro Glu Leu Leu Gly Gly Pro Ser Val Phe Leu Phe Pro Pro
                 85                  90                  95

Lys Pro Lys Asp Thr Leu Met Ile Ser Arg Thr Pro Glu Val Thr Cys
                100                 105                 110

Val Val Val Asp Val Ser His Glu Asp Pro Glu Val Lys Phe Asn Trp
                115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
                180                 185                 190

Gln Pro Arg Glu Pro Gln Val Tyr Thr Leu Pro Pro Ser Arg Asp Glu
            195                 200                 205

Leu Thr Lys Asn Gln Val Ser Leu Thr Cys Leu Val Lys Gly Phe Tyr
210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
                260                 265                 270

Val Phe Ser Cys Ser Val Met His Glu Ala Leu His Asn His Tyr Thr
            275                 280                 285

Gln Lys Ser Leu Ser Leu Ser Pro Gly Lys
    290                 295

<210> SEQ ID NO 20
<211> LENGTH: 292
<212> TYPE: PRT
<213> ORGANISM: Artificial Sequence
<220> FEATURE:
<223> OTHER INFORMATION: relaxin fusion polypeptide

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Gly Gly Ser Pro Gln Leu Tyr Ser Ala Leu Ala Asn Lys
225                 230                 235                 240

Cys Cys His Val Gly Cys Thr Lys Arg Ser Leu Ala Arg Phe Cys Gly
                245                 250                 255

Gly Gly Ser Gly Gly Gly Ser Gly Ser Trp Met Glu Glu Val Ile Lys
                260                 265                 270

Leu Cys Gly Arg Glu Leu Val Arg Ala Gln Ile Ala Ile Cys Gly Met
            275                 280                 285

Ser Thr Trp Ser
            290

<210> SEQ ID NO 21
<211> LENGTH: 295
<212> TYPE: PRT
<213> ORGANISM: Artificial Sequence
<220> FEATURE:
<223> OTHER INFORMATION: relaxin fusion polypeptide

<400> SEQUENCE: 21

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Pro Gln Leu Tyr Ser Ala Leu
225                 230                 235                 240

Ala Asn Lys Cys Cys His Val Gly Cys Thr Lys Arg Ser Leu Ala Arg
            245                 250                 255

Phe Cys Gly Gly Gly Ser Gly Gly Ser Gly Ser Trp Met Glu Glu
        260                 265                 270

Val Ile Lys Leu Cys Gly Arg Glu Leu Val Arg Ala Gln Ile Ala Ile
    275                 280                 285

Cys Gly Met Ser Thr Trp Ser
290                 295

<210> SEQ ID NO 22
<211> LENGTH: 298
<212> TYPE: PRT
<213> ORGANISM: Artificial Sequence
<220> FEATURE:
<223> OTHER INFORMATION: relaxin fusion polypeptide

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Met
    195                 200                 205

His Glu Ala Leu His Asn His Tyr Thr Gln Lys Ser Leu Ser Leu Ser
    210                 215                 220

Pro Gly Lys Gly Gly Ser Gly Gly Ser Pro Gln Leu Tyr
225                 230                 235                 240

```
Ser Ala Leu Ala Asn Lys Cys Cys His Val Gly Cys Thr Lys Arg Ser
            245                 250                 255

Leu Ala Arg Phe Cys Gly Gly Ser Gly Gly Gly Ser Gly Ser Trp
        260                 265                 270

Met Glu Glu Val Ile Lys Leu Cys Gly Arg Glu Leu Val Arg Ala Gln
        275                 280                 285

Ile Ala Ile Cys Gly Met Ser Thr Trp Ser
        290                 295
```

<210> SEQ ID NO 23
<211> LENGTH: 297
<212> TYPE: PRT
<213> ORGANISM: Artificial Sequence
<220> FEATURE:
<223> OTHER INFORMATION: relaxin fusion polypeptide

<400> SEQUENCE: 23

```
Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Gly Ser
50                  55                  60

Pro Thr Cys Pro Thr Cys His Lys Cys Pro Val Pro Glu Leu Leu Gly
65                  70                  75                  80

Gly Pro Ser Val Phe Ile Phe Pro Pro Lys Pro Lys Asp Ile Leu Leu
                85                  90                  95

Ile Ser Gln Asn Ala Lys Val Thr Cys Val Val Val Asp Val Ser Glu
            100                 105                 110

Glu Glu Pro Asp Val Gln Phe Ser Trp Phe Val Asn Asn Val Glu Val
        115                 120                 125

His Thr Ala Gln Thr Gln Pro Arg Glu Glu Gln Tyr Asn Ser Thr Phe
130                 135                 140

Arg Val Val Ser Ala Leu Pro Ile Gln His Gln Asp Trp Met Ser Gly
145                 150                 155                 160

Lys Glu Phe Lys Cys Lys Val Asn Asn Lys Ala Leu Pro Ser Pro Ile
                165                 170                 175

Glu Lys Thr Ile Ser Lys Pro Lys Gly Leu Val Arg Lys Pro Gln Val
            180                 185                 190

Tyr Val Met Gly Pro Pro Thr Glu Gln Leu Thr Glu Gln Thr Val Ser
        195                 200                 205

Leu Thr Cys Leu Thr Ser Gly Phe Leu Pro Asn Asp Ile Gly Val Glu
210                 215                 220

Trp Thr Ser Asn Gly His Ile Glu Lys Asn Tyr Lys Asn Thr Glu Pro
225                 230                 235                 240

Val Met Asp Ser Asp Gly Ser Phe Phe Met Tyr Ser Lys Leu Asn Val
                245                 250                 255

Glu Arg Ser Arg Trp Asp Ser Arg Ala Pro Phe Val Cys Ser Val Val
            260                 265                 270

His Glu Gly Leu His Asn His His Val Glu Lys Ser Ile Ser Arg Pro
        275                 280                 285

Pro Gly Lys His His His His His
        290                 295
```

<210> SEQ ID NO 24
<211> LENGTH: 300
<212> TYPE: PRT
<213> ORGANISM: Artificial Sequence
<220> FEATURE:
<223> OTHER INFORMATION: relaxin fusion polypeptide

<400> SEQUENCE: 24

```
Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Gly Gly Gly Gly Ser
                20                  25                  30

Gly Ser Trp Met Glu Glu Val Ile Lys Leu Cys Gly Arg Glu Leu Val
            35                  40                  45

Arg Ala Gln Ile Ala Ile Cys Gly Met Ser Thr Trp Ser Gly Gly Ser
    50                  55                  60

Gly Gly Ser Pro Thr Cys Pro Thr Cys His Lys Cys Pro Val Pro Glu
65                  70                  75                  80

Leu Leu Gly Gly Pro Ser Val Phe Ile Phe Pro Pro Lys Pro Lys Asp
                85                  90                  95

Ile Leu Leu Ile Ser Gln Asn Ala Lys Val Thr Cys Val Val Val Asp
            100                 105                 110

Val Ser Glu Glu Glu Pro Asp Val Gln Phe Ser Trp Phe Val Asn Asn
        115                 120                 125

Val Glu Val His Thr Ala Gln Thr Gln Pro Arg Glu Glu Gln Tyr Asn
130                 135                 140

Ser Thr Phe Arg Val Val Ser Ala Leu Pro Ile Gln His Gln Asp Trp
145                 150                 155                 160

Met Ser Gly Lys Glu Phe Lys Cys Lys Val Asn Asn Lys Ala Leu Pro
                165                 170                 175

Ser Pro Ile Glu Lys Thr Ile Ser Lys Pro Lys Gly Leu Val Arg Lys
            180                 185                 190

Pro Gln Val Tyr Val Met Gly Pro Pro Thr Glu Gln Leu Thr Glu Gln
        195                 200                 205

Thr Val Ser Leu Thr Cys Leu Thr Ser Gly Phe Leu Pro Asn Asp Ile
210                 215                 220

Gly Val Glu Trp Thr Ser Asn Gly His Ile Glu Lys Asn Tyr Lys Asn
225                 230                 235                 240

Thr Glu Pro Val Met Asp Ser Asp Gly Ser Phe Phe Met Tyr Ser Lys
                245                 250                 255

Leu Asn Val Glu Arg Ser Arg Trp Asp Ser Arg Ala Pro Phe Val Cys
            260                 265                 270

Ser Val Val His Glu Gly Leu His Asn His His Val Glu Lys Ser Ile
        275                 280                 285

Ser Arg Pro Pro Gly Lys His His His His His
    290                 295                 300
```

<210> SEQ ID NO 25
<211> LENGTH: 303
<212> TYPE: PRT
<213> ORGANISM: Artificial Sequence
<220> FEATURE:
<223> OTHER INFORMATION: relaxin fusion polypeptide

<400> SEQUENCE: 25

```
Gln Leu Tyr Ser Ala Leu Ala Asn Lys Cys Cys His Val Gly Cys Thr
1               5                   10                  15
```

Lys Arg Ser Leu Ala Arg Phe Cys Gly Gly Ser Gly Gly Gly Ser
    20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Gly Ser
50                  55                  60

Gly Gly Ser Gly Gly Ser Pro Thr Cys Pro Thr Cys His Lys Cys Pro
65                  70                  75                  80

Val Pro Glu Leu Leu Gly Gly Pro Ser Val Phe Ile Phe Pro Pro Lys
                85                  90                  95

Pro Lys Asp Ile Leu Leu Ile Ser Gln Asn Ala Lys Val Thr Cys Val
            100                 105                 110

Val Val Asp Val Ser Glu Glu Glu Pro Asp Val Gln Phe Ser Trp Phe
        115                 120                 125

Val Asn Asn Val Glu Val His Thr Ala Gln Thr Gln Pro Arg Glu Glu
130                 135                 140

Gln Tyr Asn Ser Thr Phe Arg Val Val Ser Ala Leu Pro Ile Gln His
145                 150                 155                 160

Gln Asp Trp Met Ser Gly Lys Glu Phe Lys Cys Lys Val Asn Asn Lys
                165                 170                 175

Ala Leu Pro Ser Pro Ile Glu Lys Thr Ile Ser Lys Pro Lys Gly Leu
            180                 185                 190

Val Arg Lys Pro Gln Val Tyr Val Met Gly Pro Pro Thr Glu Gln Leu
        195                 200                 205

Thr Glu Gln Thr Val Ser Leu Thr Cys Leu Thr Ser Gly Phe Leu Pro
210                 215                 220

Asn Asp Ile Gly Val Glu Trp Thr Ser Asn Gly His Ile Glu Lys Asn
225                 230                 235                 240

Tyr Lys Asn Thr Glu Pro Val Met Asp Ser Asp Gly Ser Phe Phe Met
                245                 250                 255

Tyr Ser Lys Leu Asn Val Glu Arg Ser Arg Trp Asp Ser Arg Ala Pro
            260                 265                 270

Phe Val Cys Ser Val Val His Glu Gly Leu His Asn His His Val Glu
        275                 280                 285

Lys Ser Ile Ser Arg Pro Pro Gly Lys His His His His His
    290                 295                 300

<210> SEQ ID NO 26
<211> LENGTH: 298
<212> TYPE: PRT
<213> ORGANISM: Artificial Sequence
<220> FEATURE:
<223> OTHER INFORMATION: relaxin fusion polypeptide

<400> SEQUENCE: 26

His His His His His His Pro Thr Cys Pro Thr Cys His Lys Cys Pro
1               5                   10                  15

Val Pro Glu Leu Leu Gly Gly Pro Ser Val Phe Ile Phe Pro Pro Lys
                20                  25                  30

Pro Lys Asp Ile Leu Leu Ile Ser Gln Asn Ala Lys Val Thr Cys Val
            35                  40                  45

Val Val Asp Val Ser Glu Glu Glu Pro Asp Val Gln Phe Ser Trp Phe
        50                  55                  60

Val Asn Asn Val Glu Val His Thr Ala Gln Thr Gln Pro Arg Glu Glu
65                  70                  75                  80

```
Gln Tyr Asn Ser Thr Phe Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Ala Leu Pro Ser Pro Ile Glu Lys Thr Ile Ser Lys Pro Lys Gly Leu
        115                 120                 125

Val Arg Lys Pro Gln Val Tyr Val Met Gly Pro Pro Thr Glu Gln Leu
    130                 135                 140

Thr Glu Gln Thr Val Ser Leu Thr Cys Leu Thr Ser Gly Phe Leu Pro
145                 150                 155                 160

Asn Asp Ile Gly Val Glu Trp Thr Ser Asn Gly His Ile Glu Lys Asn
                165                 170                 175

Tyr Lys Asn Thr Glu Pro Val Met Asp Ser Asp Gly Ser Phe Phe Met
            180                 185                 190

Tyr Ser Lys Leu Asn Val Glu Arg Ser Arg Trp Asp Ser Arg Ala Pro
        195                 200                 205

Phe Val Cys Ser Val Val His Glu Gly Leu His Asn His His Val Glu
    210                 215                 220

Lys Ser Ile Ser Arg Pro Pro Gly Lys Gly Gly Ser Pro Gln Leu Tyr
225                 230                 235                 240

Ser Ala Leu Ala Asn Lys Cys Cys His Val Gly Cys Thr Lys Arg Ser
                245                 250                 255

Leu Ala Arg Phe Cys Gly Gly Ser Gly Gly Gly Ser Gly Ser Trp
            260                 265                 270

Met Glu Glu Val Ile Lys Leu Cys Gly Arg Glu Leu Val Arg Ala Gln
        275                 280                 285

Ile Ala Ile Cys Gly Met Ser Thr Trp Ser
    290                 295

<210> SEQ ID NO 27
<211> LENGTH: 301
<212> TYPE: PRT
<213> ORGANISM: Artificial Sequence
<220> FEATURE:
<223> OTHER INFORMATION: relaxin fusion polypeptide

<400> SEQUENCE: 27

His His His His His His Pro Thr Cys Pro Thr Cys His Lys Cys Pro
1               5                   10                  15

Val Pro Glu Leu Leu Gly Gly Pro Ser Val Phe Ile Phe Pro Pro Lys
            20                  25                  30

Pro Lys Asp Ile Leu Leu Ile Ser Gln Asn Ala Lys Val Thr Cys Val
        35                  40                  45

Val Val Asp Val Ser Glu Glu Pro Asp Val Gln Phe Ser Trp Phe
    50                  55                  60

Val Asn Asn Val Glu Val His Thr Ala Gln Thr Gln Pro Arg Glu Glu
65                  70                  75                  80

Gln Tyr Asn Ser Thr Phe Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Ala Leu Pro Ser Pro Ile Glu Lys Thr Ile Ser Lys Pro Lys Gly Leu
        115                 120                 125

Val Arg Lys Pro Gln Val Tyr Val Met Gly Pro Pro Thr Glu Gln Leu
    130                 135                 140
```

```
Thr Glu Gln Thr Val Ser Leu Thr Cys Leu Thr Ser Gly Phe Leu Pro
145                 150                 155                 160

Asn Asp Ile Gly Val Glu Trp Thr Ser Asn Gly His Ile Glu Lys Asn
                165                 170                 175

Tyr Lys Asn Thr Glu Pro Val Met Asp Ser Asp Gly Ser Phe Phe Met
            180                 185                 190

Tyr Ser Lys Leu Asn Val Glu Arg Ser Arg Trp Asp Ser Arg Ala Pro
        195                 200                 205

Phe Val Cys Ser Val Val His Glu Gly Leu His Asn His His Val Glu
    210                 215                 220

Lys Ser Ile Ser Arg Pro Pro Gly Lys Gly Ser Gly Gly Ser Pro
225                 230                 235                 240

Gln Leu Tyr Ser Ala Leu Ala Asn Lys Cys Cys His Val Gly Cys Thr
                245                 250                 255

Lys Arg Ser Leu Ala Arg Phe Cys Gly Gly Ser Gly Gly Gly Ser
            260                 265                 270

Gly Ser Trp Met Glu Glu Val Ile Lys Leu Cys Gly Arg Glu Leu Val
        275                 280                 285

Arg Ala Gln Ile Ala Ile Cys Gly Met Ser Thr Trp Ser
    290                 295                 300

<210> SEQ ID NO 28
<211> LENGTH: 304
<212> TYPE: PRT
<213> ORGANISM: Artificial Sequence
<220> FEATURE:
<223> OTHER INFORMATION: relaxin fusion polypeptide

<400> SEQUENCE: 28

His His His His His His Pro Thr Cys Pro Thr Cys His Lys Cys Pro
1               5                   10                  15

Val Pro Glu Leu Leu Gly Gly Pro Ser Val Phe Ile Phe Pro Pro Lys
            20                  25                  30

Pro Lys Asp Ile Leu Leu Ile Ser Gln Asn Ala Lys Val Thr Cys Val
        35                  40                  45

Val Val Asp Val Ser Glu Glu Glu Pro Asp Val Gln Phe Ser Trp Phe
    50                  55                  60

Val Asn Asn Val Glu Val His Thr Ala Gln Thr Gln Pro Arg Glu Glu
65                  70                  75                  80

Gln Tyr Asn Ser Thr Phe Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Ala Leu Pro Ser Pro Ile Glu Lys Thr Ile Ser Lys Pro Lys Gly Leu
        115                 120                 125

Val Arg Lys Pro Gln Val Tyr Val Met Gly Pro Pro Thr Glu Gln Leu
    130                 135                 140

Thr Glu Gln Thr Val Ser Leu Thr Cys Leu Thr Ser Gly Phe Leu Pro
145                 150                 155                 160

Asn Asp Ile Gly Val Glu Trp Thr Ser Asn Gly His Ile Glu Lys Asn
                165                 170                 175

Tyr Lys Asn Thr Glu Pro Val Met Asp Ser Asp Gly Ser Phe Phe Met
            180                 185                 190

Tyr Ser Lys Leu Asn Val Glu Arg Ser Arg Trp Asp Ser Arg Ala Pro
        195                 200                 205
```

```
Phe Val Cys Ser Val Val His Glu Gly Leu His Asn His Val Glu
    210                 215                 220
Lys Ser Ile Ser Arg Pro Gly Lys Gly Ser Gly Gly Ser Gly
225                 230                 235                 240
Gly Ser Pro Gln Leu Tyr Ser Ala Leu Ala Asn Lys Cys Cys His Val
                245                 250                 255
Gly Cys Thr Lys Arg Ser Leu Ala Arg Phe Cys Gly Gly Ser Gly
            260                 265                 270
Gly Gly Ser Gly Ser Trp Met Glu Glu Val Ile Lys Leu Cys Gly Arg
        275                 280                 285
Glu Leu Val Arg Ala Gln Ile Ala Ile Cys Gly Met Ser Thr Trp Ser
    290                 295                 300
```

<210> SEQ ID NO 29
<211> LENGTH: 288
<212> TYPE: PRT
<213> ORGANISM: Artificial Sequence
<220> FEATURE:
<223> OTHER INFORMATION: relaxin fusion polypeptide

<400> SEQUENCE: 29

```
Gln Leu Tyr Ser Ala Leu Ala Asn Lys Cys Cys His Val Gly Cys Thr
1               5                   10                  15
Lys Arg Ser Leu Ala Arg Phe Cys Gly Gly Gly Ser Gly Gly Gly Ser
            20                  25                  30
Gly Ser Trp Met Glu Glu Val Ile Lys Leu Cys Gly Arg Glu Leu Val
        35                  40                  45
Arg Ala Gln Ile Ala Ile Cys Gly Met Ser Thr Trp Ser Asp Lys Thr
    50                  55                  60
His Thr Cys Pro Pro Cys Pro Ala Pro Glu Leu Leu Gly Gly Pro Ser
65                  70                  75                  80
Val Phe Leu Phe Pro Pro Lys Pro Lys Asp Thr Leu Met Ile Ser Arg
                85                  90                  95
Thr Pro Glu Val Thr Cys Val Val Val Asp Val Ser His Glu Asp Pro
            100                 105                 110
Glu Val Lys Phe Asn Trp Tyr Val Asp Gly Val Glu Val His Asn Ala
        115                 120                 125
Lys Thr Lys Pro Arg Glu Glu Gln Tyr Asn Ser Thr Tyr Arg Val Val
    130                 135                 140
Ser Val Leu Thr Val Leu His Gln Asp Trp Leu Asn Gly Lys Glu Tyr
145                 150                 155                 160
Lys Cys Lys Val Ser Asn Lys Ala Leu Pro Ala Pro Ile Glu Lys Thr
                165                 170                 175
Ile Ser Lys Ala Lys Gly Gln Pro Arg Glu Pro Gln Val Tyr Thr Leu
            180                 185                 190
Pro Pro Ser Arg Asp Glu Leu Thr Lys Asn Gln Val Ser Leu Thr Cys
        195                 200                 205
Leu Val Lys Gly Phe Tyr Pro Ser Asp Ile Ala Val Glu Trp Glu Ser
    210                 215                 220
Asn Gly Gln Pro Glu Asn Asn Tyr Lys Thr Thr Pro Pro Val Leu Asp
225                 230                 235                 240
Ser Asp Gly Ser Phe Phe Leu Tyr Ser Lys Leu Thr Val Asp Lys Ser
                245                 250                 255
Arg Trp Gln Gln Gly Asn Val Phe Ser Cys Ser Val Met His Glu Ala
            260                 265                 270
```

Leu His Asn His Tyr Thr Gln Lys Ser Leu Ser Leu Ser Pro Gly Lys
        275                 280                 285

<210> SEQ ID NO 30
<211> LENGTH: 294
<212> TYPE: PRT
<213> ORGANISM: Artificial Sequence
<220> FEATURE:
<223> OTHER INFORMATION: relaxin fusion polypeptide

<400> SEQUENCE: 30

Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Gly Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Ser Gly
50                  55                  60

Ser Gly Ser Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Asp Glu Leu Thr Lys Asn
        195                 200                 205

Gln Val Ser Leu Thr Cys Leu Val Lys Gly Phe Tyr Pro Ser Asp Ile
210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 31
<211> LENGTH: 294
<212> TYPE: PRT
<213> ORGANISM: Artificial Sequence
<220> FEATURE:
<223> OTHER INFORMATION: relaxin fusion polypeptide

<400> SEQUENCE: 31

```
Gln Leu Tyr Ser Ala Leu Ala Asn Lys Cys Cys His Val Gly Cys Thr
1               5                   10                  15
Lys Arg Ser Leu Ala Arg Phe Cys Gly Gly Gly Ser Gly Gly Gly Ser
            20                  25                  30
Gly Ser Trp Met Glu Glu Val Ile Lys Leu Cys Gly Arg Glu Leu Val
        35                  40                  45
Arg Ala Gln Ile Ala Ile Cys Gly Met Ser Thr Trp Ser Gly Ser Gly
    50                  55                  60
Ser Gly Ser Asp Lys Thr His Thr Ala Pro Ala Pro Ala Pro Glu
65                  70                  75                  80
Leu Leu Gly Gly Pro Ser Val Phe Leu Phe Pro Pro Lys Pro Lys Asp
                85                  90                  95
Thr Leu Met Ile Ser Arg Thr Pro Glu Val Thr Cys Val Val Val Asp
            100                 105                 110
Val Ser His Glu Asp Pro Glu Val Lys Phe Asn Trp Tyr Val Asp Gly
        115                 120                 125
Val Glu Val His Asn Ala Lys Thr Lys Pro Arg Glu Glu Gln Tyr Asn
    130                 135                 140
Ser Thr Tyr Arg Val Val Ser Val Leu Thr Val Leu His Gln Asp Trp
145                 150                 155                 160
Leu Asn Gly Lys Glu Tyr Lys Cys Lys Val Ser Asn Lys Ala Leu Pro
                165                 170                 175
Ala Pro Ile Glu Lys Thr Ile Ser Lys Ala Lys Gly Gln Pro Arg Glu
            180                 185                 190
Pro Gln Val Tyr Thr Leu Pro Pro Ser Arg Asp Glu Leu Thr Lys Asn
        195                 200                 205
Gln Val Ser Leu Thr Cys Leu Val Lys Gly Phe Tyr Pro Ser Asp Ile
    210                 215                 220
Ala Val Glu Trp Glu Ser Asn Gly Gln Pro Glu Asn Asn Tyr Lys Thr
225                 230                 235                 240
Thr Pro Pro Val Leu Asp Ser Asp Gly Ser Phe Phe Leu Tyr Ser Lys
                245                 250                 255
Leu Thr Val Asp Lys Ser Arg Trp Gln Gln Gly Asn Val Phe Ser Cys
            260                 265                 270
Ser Val Met His Glu Ala Leu His Asn His Tyr Thr Gln Lys Ser Leu
        275                 280                 285
Ser Leu Ser Pro Gly Lys
    290
```

<210> SEQ ID NO 32
<211> LENGTH: 294
<212> TYPE: PRT
<213> ORGANISM: Artificial Sequence
<220> FEATURE:
<223> OTHER INFORMATION: relaxin fusion polypeptide

<400> SEQUENCE: 32

```
Gln Leu Tyr Ser Ala Leu Ala Asn Lys Cys Cys His Val Gly Cys Thr
1               5                   10                  15
Lys Arg Ser Leu Ala Arg Phe Cys Gly Gly Gly Ser Gly Gly Gly Ser
            20                  25                  30
Gly Ser Trp Met Glu Glu Val Ile Lys Leu Cys Gly Arg Glu Leu Val
        35                  40                  45
Arg Ala Gln Ile Ala Ile Cys Gly Met Ser Thr Trp Ser Gly Ser Gly
```

Ser Gly Ser Pro Thr Cys Pro Thr Cys His Lys Cys Pro Val Pro Glu
65                  70                  75                  80

Leu Leu Gly Gly Pro Ser Val Phe Ile Phe Pro Pro Lys Pro Lys Asp
                85                  90                  95

Ile Leu Leu Ile Ser Gln Asn Ala Lys Val Thr Cys Val Val Val Asp
            100                 105                 110

Val Ser Glu Glu Pro Asp Val Gln Phe Ser Trp Phe Val Asn Asn
        115                 120                 125

Val Glu Val His Thr Ala Gln Thr Gln Pro Arg Glu Glu Gln Tyr Asn
        130                 135                 140

Ser Thr Phe Arg Val Val Ser Ala Leu Pro Ile Gln His Gln Asp Trp
145                 150                 155                 160

Met Ser Gly Lys Glu Phe Lys Cys Lys Val Asn Asn Lys Ala Leu Pro
                165                 170                 175

Ser Pro Ile Glu Lys Thr Ile Ser Lys Pro Lys Gly Leu Val Arg Lys
            180                 185                 190

Pro Gln Val Tyr Val Met Gly Pro Pro Thr Glu Gln Leu Thr Glu Gln
        195                 200                 205

Thr Val Ser Leu Thr Cys Leu Thr Ser Gly Phe Leu Pro Asn Asp Ile
210                 215                 220

Gly Val Glu Trp Thr Ser Asn Gly His Ile Glu Lys Asn Tyr Lys Asn
225                 230                 235                 240

Thr Glu Pro Val Met Asp Ser Asp Gly Ser Phe Phe Met Tyr Ser Lys
                245                 250                 255

Leu Asn Val Glu Arg Ser Arg Trp Asp Ser Arg Ala Pro Phe Val Cys
            260                 265                 270

Ser Val Val His Glu Gly Leu His Asn His His Val Glu Lys Ser Ile
                275                 280                 285

Ser Arg Pro Pro Gly Lys
        290

<210> SEQ ID NO 33
<211> LENGTH: 311
<212> TYPE: PRT
<213> ORGANISM: Artificial Sequence
<220> FEATURE:
<223> OTHER INFORMATION: relaxin fusion polypeptide

<400> SEQUENCE: 33

Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Gly Gly Ser
            20                  25                  30

Gly Ser Trp Met Glu Glu Val Ile Lys Leu Cys Gly Arg Glu Leu Val
            35                  40                  45

Arg Ala Gln Ile Ala Ile Cys Gly Met Ser Thr Trp Ser Gly Gly Gly
        50                  55                  60

Ser Gly Gly Gly Ser Gly Thr Leu Val Thr Val Ser Ser Glu Ser Lys
65                  70                  75                  80

Tyr Gly Pro Pro Cys Pro Pro Cys Pro Ala Pro Glu Ala Ala Ala Pro
                85                  90                  95

Glu Leu Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val

```
                115                 120                 125
Asp Val Ser His Glu Asp Pro Glu Val Lys Phe Asn Trp Tyr Val Asp
    130                 135                 140

Gly Val Glu Val His Asn Ala Lys Thr Lys Pro Arg Glu Glu Gln Tyr
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Ala Leu
            180                 185                 190

Pro Ala Pro Ile Glu Lys Thr Ile Ser Lys Ala Lys Gly Gln Pro Arg
        195                 200                 205

Glu Pro Gln Val Tyr Thr Leu Pro Pro Ser Arg Asp Glu Leu Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Lys Leu Thr Val Asp Lys Ser Arg Trp Gln Gln Gly Asn Val Phe Ser
        275                 280                 285

Cys Ser Val Met His Glu Ala Leu His Asn His Tyr Thr Gln Lys Ser
    290                 295                 300

Leu Ser Leu Ser Pro Gly Lys
305                 310

<210> SEQ ID NO 34
<211> LENGTH: 67
<212> TYPE: PRT
<213> ORGANISM: Artificial Sequence
<220> FEATURE:
<223> OTHER INFORMATION: relaxin fusion polypeptide

<400> SEQUENCE: 34

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Gly Ser
    50                  55                  60

Gly Cys Gly
65

<210> SEQ ID NO 35
<211> LENGTH: 67
<212> TYPE: PRT
<213> ORGANISM: Artificial Sequence
<220> FEATURE:
<223> OTHER INFORMATION: relaxin fusion polypeptide

<400> SEQUENCE: 35

Gly Cys Gly Ser Gly Gly Gln Leu Tyr Ser Ala Leu Ala Asn Lys Cys
1               5                   10                  15

Cys His Val Gly Cys Thr Lys Arg Ser Leu Ala Arg Phe Cys Gly Gly
            20                  25                  30
```

```
Gly Ser Gly Gly Ser Ser Trp Met Glu Val Ile Lys Leu
        35              40              45

Cys Gly Arg Glu Leu Val Arg Ala Gln Ile Ala Ile Cys Gly Met Ser
 50                  55                  60

Thr Trp Ser
 65

<210> SEQ ID NO 36
<211> LENGTH: 746
<212> TYPE: PRT
<213> ORGANISM: Artificial Sequence
<220> FEATURE:
<223> OTHER INFORMATION: relaxin fusion polypeptide

<400> SEQUENCE: 36

Val Pro Asp Lys Thr Val Arg Trp Cys Ala Val Ser Glu His Glu Ala
 1               5                  10                  15

Thr Lys Cys Gln Ser Phe Arg Asp His Met Lys Ser Val Ile Pro Ser
             20                  25                  30

Asp Gly Pro Ser Val Ala Cys Val Lys Lys Ala Ser Tyr Leu Asp Cys
         35                  40                  45

Ile Arg Ala Ile Ala Ala Asn Glu Ala Asp Ala Val Thr Leu Asp Ala
 50                  55                  60

Gly Leu Val Tyr Asp Ala Tyr Leu Ala Pro Asn Asn Leu Lys Pro Val
 65                  70                  75                  80

Val Ala Glu Phe Tyr Gly Ser Lys Glu Asp Pro Gln Thr Phe Tyr Tyr
                 85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
        195                 200                 205

Thr Ile Phe Glu Asn Leu Ala Asn Lys Ala Asp Arg Asp Gln Tyr Glu
210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285

His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320
```

```
Thr Ala Ile Arg Asn Leu Arg Glu Gly Thr Cys Pro Glu Ala Pro Thr
            325                 330                 335

Asp Glu Cys Lys Pro Val Lys Trp Cys Ala Leu Ser His His Glu Arg
        340                 345                 350

Leu Lys Cys Asp Glu Trp Ser Val Asn Ser Val Gly Lys Ile Glu Cys
        355                 360                 365

Val Ser Ala Glu Thr Thr Glu Asp Cys Ile Ala Lys Ile Met Asn Gly
    370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                405                 410                 415

Asn Cys Glu Asp Thr Pro Glu Ala Gly Tyr Phe Ala Val Ala Val Val
        420                 425                 430

Lys Lys Ser Ala Ser Asp Leu Thr Trp Asp Asn Leu Lys Gly Lys Lys
            435                 440                 445

Ser Cys His Thr Ala Val Gly Arg Thr Ala Gly Trp Asn Ile Pro Met
    450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
        500                 505                 510

Gly Tyr Tyr Gly Tyr Thr Gly Ala Phe Arg Cys Leu Val Glu Lys Gly
            515                 520                 525

Asp Val Ala Phe Val Lys His Gln Thr Val Pro Gln Asn Thr Gly Gly
    530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
        580                 585                 590

Lys Glu Ala Cys Val His Lys Ile Leu Arg Gln Gln Gln His Leu Phe
            595                 600                 605

Gly Ser Asn Val Thr Asp Cys Ser Gly Asn Phe Cys Leu Phe Arg Ser
    610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
                645                 650                 655

Lys Ala Val Gly Asn Leu Arg Lys Cys Ser Thr Ser Ser Leu Leu Glu
        660                 665                 670

Ala Cys Thr Phe Arg Arg Pro Ile Glu Gly Arg Met Asp Gln Leu Tyr
            675                 680                 685

Ser Ala Leu Ala Asn Lys Cys Cys His Val Gly Cys Thr Lys Arg Ser
    690                 695                 700

Leu Ala Arg Phe Cys Gly Gly Ser Gly Gly Ser Gly Ser Gly Ser Trp
705                 710                 715                 720

Met Glu Glu Val Ile Lys Leu Cys Gly Arg Glu Leu Val Arg Ala Gln
                725                 730                 735

Ile Ala Ile Cys Gly Met Ser Thr Trp Ser
```

-continued

```
                      740                 745

<210> SEQ ID NO 37
<211> LENGTH: 846
<212> TYPE: PRT
<213> ORGANISM: Artificial Sequence
<220> FEATURE:
<223> OTHER INFORMATION: relaxin fusion polypeptide

<400> SEQUENCE: 37

Val Pro Asp Lys Thr Val Arg Trp Cys Ala Val Ser Glu His Glu Ala
1               5                  10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
    50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Tyr
                85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
    130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
        195                 200                 205

Thr Ile Phe Glu Asn Leu Ala Asn Lys Ala Asp Arg Asp Gln Tyr Glu
    210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285

His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
```

```
                355                 360                 365
Val Ser Ala Glu Thr Thr Glu Asp Cys Ile Ala Lys Ile Met Asn Gly
370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                405                 410                 415

Asn Cys Glu Asp Thr Pro Glu Ala Gly Tyr Phe Ala Val Ala Val Val
                420                 425                 430

Lys Lys Ser Ala Ser Asp Leu Thr Trp Asp Asn Leu Lys Gly Lys Lys
                435                 440                 445

Ser Cys His Thr Ala Val Gly Arg Thr Ala Gly Trp Asn Ile Pro Met
                450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
                500                 505                 510

Gly Tyr Tyr Gly Tyr Thr Gly Ala Phe Arg Cys Leu Val Glu Lys Gly
                515                 520                 525

Asp Val Ala Phe Val Lys His Gln Thr Val Pro Gln Asn Thr Gly Gly
530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
                580                 585                 590

Lys Glu Ala Cys Val His Lys Ile Leu Arg Gln Gln Gln His Leu Phe
                595                 600                 605

Gly Ser Asn Val Thr Asp Cys Ser Gly Asn Phe Cys Leu Phe Arg Ser
610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
                645                 650                 655

Lys Ala Val Gly Asn Leu Arg Lys Cys Ser Thr Ser Ser Leu Leu Glu
                660                 665                 670

Ala Cys Thr Phe Arg Arg Pro Ile Glu Gly Arg Met Asp Asp Ser Trp
                675                 680                 685

Met Glu Glu Val Ile Lys Leu Cys Gly Arg Glu Leu Val Arg Ala Gln
690                 695                 700

Ile Ala Ile Cys Gly Met Ser Thr Trp Ser Lys Arg Ser Leu Ser Gln
705                 710                 715                 720

Glu Asp Ala Pro Gln Thr Pro Arg Pro Val Ala Glu Ile Val Pro Ser
                725                 730                 735

Phe Ile Asn Lys Asp Thr Glu Thr Ile Asn Met Met Ser Glu Phe Val
                740                 745                 750

Ala Asn Leu Pro Gln Glu Leu Lys Leu Thr Leu Ser Glu Met Gln Pro
                755                 760                 765

Ala Leu Pro Gln Leu Gln Gln His Val Pro Val Leu Lys Asp Ser Ser
                770                 775                 780
```

```
Leu Leu Phe Glu Glu Phe Lys Leu Ile Arg Asn Arg Gln Ser Glu
785                 790                 795                 800

Ala Ala Asp Ser Ser Pro Ser Glu Leu Lys Tyr Leu Gly Leu Asp Thr
                805                 810                 815

His Ser Arg Lys Lys Arg Gln Leu Tyr Ser Ala Leu Ala Asn Lys Cys
        820                 825                 830

Cys His Val Gly Cys Thr Lys Arg Ser Leu Ala Arg Phe Cys
    835                 840                 845

<210> SEQ ID NO 38
<211> LENGTH: 652
<212> TYPE: PRT
<213> ORGANISM: Artificial Sequence
<220> FEATURE:
<223> OTHER INFORMATION: relaxin fusion polypeptide

<400> SEQUENCE: 38

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300
```

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Ile Glu Gly Arg Met Asp Gln
            580                 585                 590

Leu Tyr Ser Ala Leu Ala Asn Lys Cys Cys His Val Gly Cys Thr Lys
        595                 600                 605

Arg Ser Leu Ala Arg Phe Cys Gly Gly Ser Gly Gly Ser Gly
610                 615                 620

Ser Trp Met Glu Glu Val Ile Lys Leu Cys Gly Arg Glu Leu Val Arg
625                 630                 635                 640

Ala Gln Ile Ala Ile Cys Gly Met Ser Thr Trp Ser
            645                 650

<210> SEQ ID NO 39
<211> LENGTH: 752
<212> TYPE: PRT
<213> ORGANISM: Artificial Sequence
<220> FEATURE:
<223> OTHER INFORMATION: relaxin fusion polypeptide

<400> SEQUENCE: 39

Asp Ala His Lys Ser Glu Val Ala His Arg Phe Lys Asp Leu Gly Glu
1               5                   10                  15

```
Glu Asn Phe Lys Ala Leu Val Leu Ile Ala Phe Ala Gln Tyr Leu Gln
                 20                  25                  30

Gln Cys Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430
```

```
Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu Ile Glu Gly Arg Met Asp Asp
            580                 585                 590

Ser Trp Met Glu Glu Val Ile Lys Leu Cys Gly Arg Glu Leu Val Arg
        595                 600                 605

Ala Gln Ile Ala Ile Cys Gly Met Ser Thr Trp Ser Lys Arg Ser Leu
            610                 615                 620

Ser Gln Glu Asp Ala Pro Gln Thr Pro Arg Pro Val Ala Glu Ile Val
625                 630                 635                 640

Pro Ser Phe Ile Asn Lys Asp Thr Glu Thr Ile Asn Met Met Ser Glu
                645                 650                 655

Phe Val Ala Asn Leu Pro Gln Glu Leu Lys Leu Thr Leu Ser Glu Met
            660                 665                 670

Gln Pro Ala Leu Pro Gln Leu Gln Gln His Val Pro Val Leu Lys Asp
        675                 680                 685

Ser Ser Leu Leu Phe Glu Glu Phe Lys Lys Leu Ile Arg Asn Arg Gln
690                 695                 700

Ser Glu Ala Ala Asp Ser Ser Pro Ser Glu Leu Lys Tyr Leu Gly Leu
705                 710                 715                 720

Asp Thr His Ser Arg Lys Lys Arg Gln Leu Tyr Ser Ala Leu Ala Asn
                725                 730                 735

Lys Cys Cys His Val Gly Cys Thr Lys Arg Ser Leu Ala Arg Phe Cys
            740                 745                 750

<210> SEQ ID NO 40
<211> LENGTH: 298
<212> TYPE: PRT
<213> ORGANISM: Artificial Sequence
<220> FEATURE:
<223> OTHER INFORMATION: relaxin fusion polypeptide

<400> SEQUENCE: 40

Gln Leu Tyr Ser Ala Leu Ala Asn Lys Cys Cys His Val Gly Cys Thr
1               5                   10                  15

Lys Arg Ser Leu Ala Arg Phe Cys Lys Arg Ser Leu Ser Arg Lys Lys
            20                  25                  30

Arg Ser Trp Met Glu Glu Val Ile Lys Leu Cys Gly Arg Glu Leu Val
        35                  40                  45
```

Arg Ala Gln Ile Ala Ile Cys Gly Met Ser Thr Trp Ser Ile Glu Gly
50              55                  60

Arg Met Asp Pro Lys Ala Cys Asp Lys Thr His Thr Cys Pro Pro Cys
65              70                  75                  80

Pro Ala Pro Glu Leu Leu Gly Gly Pro Ser Val Phe Leu Phe Pro Pro
            85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
            115                 120                 125

Tyr Val Asp Gly Val Glu Val His Asn Ala Lys Thr Lys Pro Arg Glu
130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Asp Glu
            195                 200                 205

Leu Thr Lys Asn Gln Val Ser Leu Thr Cys Leu Val Lys Gly Phe Tyr
210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
            275                 280                 285

Gln Lys Ser Leu Ser Leu Ser Pro Gly Lys
            290                 295

<210> SEQ ID NO 41
<211> LENGTH: 298
<212> TYPE: PRT
<213> ORGANISM: Artificial Sequence
<220> FEATURE:
<223> OTHER INFORMATION: relaxin fusion polypeptide

<400> SEQUENCE: 41

Pro Lys Ala Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
            50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

```
Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys Ile Glu Gly Arg Met Asp Gln Leu Tyr
                225                 230                 235                 240

Ser Ala Leu Ala Asn Lys Cys Cys His Val Gly Cys Thr Lys Arg Ser
            245                 250                 255

Leu Ala Arg Phe Cys Lys Arg Ser Leu Ser Arg Lys Lys Arg Ser Trp
        260                 265                 270

Met Glu Glu Val Ile Lys Leu Cys Gly Arg Glu Leu Val Arg Ala Gln
    275                 280                 285

Ile Ala Ile Cys Gly Met Ser Thr Trp Ser
        290                 295

<210> SEQ ID NO 42
<211> LENGTH: 55
<212> TYPE: PRT
<213> ORGANISM: Artificial Sequence
<220> FEATURE:
<223> OTHER INFORMATION: relaxin fusion polypeptide

<400> SEQUENCE: 42

Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Trp Met Glu Glu
            20                  25                  30

Val Ile Lys Leu Cys Gly Arg Glu Leu Val Arg Ala Gln Ile Ala Ile
        35                  40                  45

Cys Gly Met Ser Thr Trp Ser
    50                  55

<210> SEQ ID NO 43
<211> LENGTH: 57
<212> TYPE: PRT
<213> ORGANISM: Artificial Sequence
<220> FEATURE:
<223> OTHER INFORMATION: relaxin fusion polypeptide

<400> SEQUENCE: 43

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Trp Met
            20                  25                  30

Glu Glu Val Ile Lys Leu Cys Gly Arg Glu Leu Val Arg Ala Gln Ile
        35                  40                  45

Ala Ile Cys Gly Met Ser Thr Trp Ser
    50                  55
```

<210> SEQ ID NO 44
<211> LENGTH: 59
<212> TYPE: PRT
<213> ORGANISM: Artificial Sequence
<220> FEATURE:
<223> OTHER INFORMATION: relaxin fusion polypeptide

<400> SEQUENCE: 44

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
            20                  25                  30

Trp Met Glu Glu Val Ile Lys Leu Cys Gly Arg Glu Leu Val Arg Ala
        35                  40                  45

Gln Ile Ala Ile Cys Gly Met Ser Thr Trp Ser
    50                  55

<210> SEQ ID NO 45
<211> LENGTH: 61
<212> TYPE: PRT
<213> ORGANISM: Artificial Sequence
<220> FEATURE:
<223> OTHER INFORMATION: relaxin fusion polypeptide

<400> SEQUENCE: 45

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser
    50                  55                  60

<210> SEQ ID NO 46
<211> LENGTH: 63
<212> TYPE: PRT
<213> ORGANISM: Artificial Sequence
<220> FEATURE:
<223> OTHER INFORMATION: relaxin fusion polypeptide

<400> SEQUENCE: 46

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
            20                  25                  30

Gly Gly Gly Ser Trp Met Glu Glu Val Ile Lys Leu Cys Gly Arg Glu
        35                  40                  45

Leu Val Arg Ala Gln Ile Ala Ile Cys Gly Met Ser Thr Trp Ser
    50                  55                  60

<210> SEQ ID NO 47
<211> LENGTH: 67
<212> TYPE: PRT
<213> ORGANISM: Artificial Sequence
<220> FEATURE:
<223> OTHER INFORMATION: relaxin fusion polypeptide

<400> SEQUENCE: 47

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
                20                  25                  30

Gly Gly Gly Ser Gly Gly Gly Ser Trp Met Glu Glu Val Ile Lys Leu
            35                  40                  45

Cys Gly Arg Glu Leu Val Arg Ala Gln Ile Ala Ile Cys Gly Met Ser
 50                  55                  60

Thr Trp Ser
 65

<210> SEQ ID NO 48
<211> LENGTH: 58
<212> TYPE: PRT
<213> ORGANISM: Artificial Sequence
<220> FEATURE:
<223> OTHER INFORMATION: relaxin fusion polypeptide

<400> SEQUENCE: 48

Gln Leu Tyr Ser Ala Leu Ala Asn Lys Cys Cys His Val Gly Cys Thr
 1               5                  10                  15

Lys Arg Ser Leu Ala Arg Phe Cys Gly Gly Gly Ser Gly Gly Ser Trp
                20                  25                  30

Met Glu Glu Val Ile Lys Leu Cys Gly Arg Glu Leu Val Arg Ala Gln
            35                  40                  45

Ile Ala Ile Cys Gly Met Ser Thr Trp Ser
 50                  55

<210> SEQ ID NO 49
<211> LENGTH: 64
<212> TYPE: PRT
<213> ORGANISM: Artificial Sequence
<220> FEATURE:
<223> OTHER INFORMATION: relaxin fusion polypeptide

<400> SEQUENCE: 49

Gln Leu Tyr Ser Ala Leu Ala Asn Lys Cys Cys His Val Gly Cys Thr
 1               5                  10                  15

Lys Arg Ser Leu Ala Arg Phe Cys Gly Gly Gly Ser Gly Gly Gly Ser
                20                  25                  30

Gly Gly Gly Ser Ser Trp Met Glu Glu Val Ile Lys Leu Cys Gly Arg
            35                  40                  45

Glu Leu Val Arg Ala Gln Ile Ala Ile Cys Gly Met Ser Thr Trp Ser
 50                  55                  60

<210> SEQ ID NO 50
<211> LENGTH: 65
<212> TYPE: PRT
<213> ORGANISM: Artificial Sequence
<220> FEATURE:
<223> OTHER INFORMATION: relaxin fusion polypeptide

<400> SEQUENCE: 50

Gln Leu Tyr Ser Ala Leu Ala Asn Lys Cys Cys His Val Gly Cys Thr
 1               5                  10                  15

Lys Arg Ser Leu Ala Arg Phe Cys Gly Gly Gly Ser Gly Gly Gly Ser
                20                  25                  30

Gly Gly Gly Ser Gly Ser Trp Met Glu Glu Val Ile Lys Leu Cys Gly
            35                  40                  45

Arg Glu Leu Val Arg Ala Gln Ile Ala Ile Cys Gly Met Ser Thr Trp
 50                  55                  60

```
Ser
65

<210> SEQ ID NO 51
<211> LENGTH: 66
<212> TYPE: PRT
<213> ORGANISM: Artificial Sequence
<220> FEATURE:
<223> OTHER INFORMATION: relaxin fusion polypeptide

<400> SEQUENCE: 51

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
            20                  25                  30

Gly Gly Gly Ser Gly Gly Ser Trp Met Glu Glu Val Ile Lys Leu Cys
        35                  40                  45

Gly Arg Glu Leu Val Arg Ala Gln Ile Ala Ile Cys Gly Met Ser Thr
    50                  55                  60

Trp Ser
65

<210> SEQ ID NO 52
<211> LENGTH: 298
<212> TYPE: PRT
<213> ORGANISM: Artificial Sequence
<220> FEATURE:
<223> OTHER INFORMATION: relaxin fusion polypeptide

<400> SEQUENCE: 52

Gln Leu Tyr Ser Ala Leu Ala Asn Lys Cys Cys His Val Gly Cys Thr
1               5                   10                  15

Lys Arg Ser Leu Ala Arg Phe Cys Gly Gly Gly Ser Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Ile Glu Gly
    50                  55                  60

Arg Met Asp Pro Lys Ala Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Asp Glu
        195                 200                 205

Leu Thr Lys Asn Gln Val Ser Leu Thr Cys Leu Val Lys Gly Phe Tyr
    210                 215                 220
```

-continued

```
Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
            245                 250                 255

Leu Tyr Ser Lys Leu Thr Val Asp Lys Ser Arg Trp Gln Gln Gly Asn
        260                 265                 270

Val Phe Ser Cys Ser Val Met His Glu Ala Leu His Asn His Tyr Thr
    275                 280                 285

Gln Lys Ser Leu Ser Leu Ser Pro Gly Lys
    290                 295
```

<210> SEQ ID NO 53
<211> LENGTH: 291
<212> TYPE: PRT
<213> ORGANISM: Artificial Sequence
<220> FEATURE:
<223> OTHER INFORMATION: relaxin fusion polypeptide

<400> SEQUENCE: 53

```
Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Gly Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Gly Ser
50                  55                  60

Pro Thr Cys Pro Thr Cys His Lys Cys Pro Val Pro Glu Leu Leu Gly
65                  70                  75                  80

Gly Pro Ser Val Phe Ile Phe Pro Pro Lys Pro Lys Asp Ile Leu Leu
            85                  90                  95

Ile Ser Gln Asn Ala Lys Val Thr Cys Val Val Val Asp Val Ser Glu
        100                 105                 110

Glu Glu Pro Asp Val Gln Phe Ser Trp Phe Val Asn Asn Val Glu Val
    115                 120                 125

His Thr Ala Gln Thr Gln Pro Arg Glu Glu Gln Tyr Asn Ser Thr Phe
130                 135                 140

Arg Val Val Ser Ala Leu Pro Ile Gln His Gln Asp Trp Met Ser Gly
145                 150                 155                 160

Lys Glu Phe Lys Cys Lys Val Asn Asn Lys Ala Leu Pro Ser Pro Ile
            165                 170                 175

Glu Lys Thr Ile Ser Lys Pro Lys Gly Leu Val Arg Lys Pro Gln Val
        180                 185                 190

Tyr Val Met Gly Pro Pro Thr Glu Gln Leu Thr Glu Gln Thr Val Ser
    195                 200                 205

Leu Thr Cys Leu Thr Ser Gly Phe Leu Pro Asn Asp Ile Gly Val Glu
210                 215                 220

Trp Thr Ser Asn Gly His Ile Glu Lys Asn Tyr Lys Asn Thr Glu Pro
225                 230                 235                 240

Val Met Asp Ser Asp Gly Ser Phe Phe Met Tyr Ser Lys Leu Asn Val
            245                 250                 255

Glu Arg Ser Arg Trp Asp Ser Arg Ala Pro Phe Val Cys Ser Val Val
        260                 265                 270

His Glu Gly Leu His Asn His His Val Glu Lys Ser Ile Ser Arg Pro
    275                 280                 285
```

```
Pro Gly Lys
    290

<210> SEQ ID NO 54
<211> LENGTH: 294
<212> TYPE: PRT
<213> ORGANISM: Artificial Sequence
<220> FEATURE:
<223> OTHER INFORMATION: relaxin fusion polypeptide

<400> SEQUENCE: 54

Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Gly Gly Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Gly Ser
    50                  55                  60

Gly Gly Ser Pro Thr Cys Pro Thr Cys His Lys Cys Pro Val Pro Glu
65                  70                  75                  80

Leu Leu Gly Gly Pro Ser Val Phe Ile Phe Pro Pro Lys Pro Lys Asp
                85                  90                  95

Ile Leu Leu Ile Ser Gln Asn Ala Lys Val Thr Cys Val Val Val Asp
            100                 105                 110

Val Ser Glu Glu Glu Pro Asp Val Gln Phe Ser Trp Phe Val Asn Asn
        115                 120                 125

Val Glu Val His Thr Ala Gln Thr Gln Pro Arg Glu Glu Gln Tyr Asn
    130                 135                 140

Ser Thr Phe Arg Val Val Ser Ala Leu Pro Ile Gln His Gln Asp Trp
145                 150                 155                 160

Met Ser Gly Lys Glu Phe Lys Cys Lys Val Asn Asn Lys Ala Leu Pro
                165                 170                 175

Ser Pro Ile Glu Lys Thr Ile Ser Lys Pro Lys Gly Leu Val Arg Lys
            180                 185                 190

Pro Gln Val Tyr Val Met Gly Pro Pro Thr Glu Gln Leu Thr Glu Gln
        195                 200                 205

Thr Val Ser Leu Thr Cys Leu Thr Ser Gly Phe Leu Pro Asn Asp Ile
    210                 215                 220

Gly Val Glu Trp Thr Ser Asn Gly His Ile Glu Lys Asn Tyr Lys Asn
225                 230                 235                 240

Thr Glu Pro Val Met Asp Ser Asp Gly Ser Phe Phe Met Tyr Ser Lys
                245                 250                 255

Leu Asn Val Glu Arg Ser Arg Trp Asp Ser Arg Ala Pro Phe Val Cys
            260                 265                 270

Ser Val Val His Glu Gly Leu His Asn His His Val Glu Lys Ser Ile
        275                 280                 285

Ser Arg Pro Pro Gly Lys
    290

<210> SEQ ID NO 55
<211> LENGTH: 297
<212> TYPE: PRT
<213> ORGANISM: Artificial Sequence
<220> FEATURE:
<223> OTHER INFORMATION: relaxin fusion polypeptide
```

<400> SEQUENCE: 55

Gln Leu Tyr Ser Ala Leu Ala Asn Lys Cys Cys His Val Gly Cys Thr
1               5                   10                  15

Lys Arg Ser Leu Ala Arg Phe Cys Gly Gly Ser Gly Gly Ser
            20                  25                  30

Gly Ser Trp Met Glu Glu Val Ile Lys Leu Cys Gly Arg Glu Leu Val
        35                  40                  45

Arg Ala Gln Ile Ala Ile Cys Gly Met Ser Thr Trp Ser Gly Gly Ser
    50                  55                  60

Gly Gly Ser Gly Gly Ser Pro Thr Cys Pro Thr Cys His Lys Cys Pro
65                  70                  75                  80

Val Pro Glu Leu Leu Gly Gly Pro Ser Val Phe Ile Phe Pro Pro Lys
                85                  90                  95

Pro Lys Asp Ile Leu Leu Ile Ser Gln Asn Ala Lys Val Thr Cys Val
            100                 105                 110

Val Val Asp Val Ser Glu Glu Pro Asp Val Gln Phe Ser Trp Phe
            115                 120                 125

Val Asn Asn Val Glu Val His Thr Ala Gln Thr Gln Pro Arg Glu Glu
130                 135                 140

Gln Tyr Asn Ser Thr Phe Arg Val Val Ser Ala Leu Pro Ile Gln His
145                 150                 155                 160

Gln Asp Trp Met Ser Gly Lys Glu Phe Lys Cys Lys Val Asn Asn Lys
                165                 170                 175

Ala Leu Pro Ser Pro Ile Glu Lys Thr Ile Ser Lys Pro Lys Gly Leu
            180                 185                 190

Val Arg Lys Pro Gln Val Tyr Val Met Gly Pro Pro Thr Glu Gln Leu
        195                 200                 205

Thr Glu Gln Thr Val Ser Leu Thr Cys Leu Thr Ser Gly Phe Leu Pro
210                 215                 220

Asn Asp Ile Gly Val Glu Trp Thr Ser Asn Gly His Ile Glu Lys Asn
225                 230                 235                 240

Tyr Lys Asn Thr Glu Pro Val Met Asp Ser Asp Gly Ser Phe Phe Met
                245                 250                 255

Tyr Ser Lys Leu Asn Val Glu Arg Ser Arg Trp Asp Ser Arg Ala Pro
            260                 265                 270

Phe Val Cys Ser Val Val His Glu Gly Leu His Asn His His Val Glu
        275                 280                 285

Lys Ser Ile Ser Arg Pro Pro Gly Lys
    290                 295

<210> SEQ ID NO 56
<211> LENGTH: 292
<212> TYPE: PRT
<213> ORGANISM: Artificial Sequence
<220> FEATURE:
<223> OTHER INFORMATION: relaxin fusion polypeptide

<400> SEQUENCE: 56

Pro Thr Cys Pro Thr Cys His Lys Cys Pro Val Pro Glu Leu Leu Gly
1               5                   10                  15

Gly Pro Ser Val Phe Ile Phe Pro Pro Lys Pro Lys Asp Ile Leu Leu
            20                  25                  30

Ile Ser Gln Asn Ala Lys Val Thr Cys Val Val Val Asp Val Ser Glu
        35                  40                  45

Glu Glu Pro Asp Val Gln Phe Ser Trp Phe Val Asn Asn Val Glu Val

```
                50                  55                  60
His Thr Ala Gln Thr Gln Pro Arg Glu Glu Gln Tyr Asn Ser Thr Phe
 65                  70                  75                  80

Arg Val Val Ser Ala Leu Pro Ile Gln His Gln Asp Trp Met Ser Gly
                 85                  90                  95

Lys Glu Phe Lys Cys Lys Val Asn Asn Lys Ala Leu Pro Ser Pro Ile
                100                 105                 110

Glu Lys Thr Ile Ser Lys Pro Lys Gly Leu Val Arg Lys Pro Gln Val
                115                 120                 125

Tyr Val Met Gly Pro Pro Thr Glu Gln Leu Thr Glu Gln Thr Val Ser
                130                 135                 140

Leu Thr Cys Leu Thr Ser Gly Phe Leu Pro Asn Asp Ile Gly Val Glu
145                 150                 155                 160

Trp Thr Ser Asn Gly His Ile Glu Lys Asn Tyr Lys Asn Thr Glu Pro
                165                 170                 175

Val Met Asp Ser Asp Gly Ser Phe Phe Met Tyr Ser Lys Leu Asn Val
                180                 185                 190

Glu Arg Ser Arg Trp Asp Ser Arg Ala Pro Phe Val Cys Ser Val Val
                195                 200                 205

His Glu Gly Leu His Asn His His Val Glu Lys Ser Ile Ser Arg Pro
                210                 215                 220

Pro Gly Lys Gly Gly Ser Pro Gln Leu Tyr Ser Ala Leu Ala Asn Lys
225                 230                 235                 240

Cys Cys His Val Gly Cys Thr Lys Arg Ser Leu Ala Arg Phe Cys Gly
                245                 250                 255

Gly Gly Ser Gly Gly Gly Ser Gly Ser Trp Met Glu Glu Val Ile Lys
                260                 265                 270

Leu Cys Gly Arg Glu Leu Val Arg Ala Gln Ile Ala Ile Cys Gly Met
                275                 280                 285

Ser Thr Trp Ser
    290

<210> SEQ ID NO 57
<211> LENGTH: 295
<212> TYPE: PRT
<213> ORGANISM: Artificial Sequence
<220> FEATURE:
<223> OTHER INFORMATION: relaxin fusion polypeptide

<400> SEQUENCE: 57

Pro Thr Cys Pro Thr Cys His Lys Cys Pro Val Pro Glu Leu Leu Gly
 1               5                  10                  15

Gly Pro Ser Val Phe Ile Phe Pro Pro Lys Pro Lys Asp Ile Leu Leu
                20                  25                  30

Ile Ser Gln Asn Ala Lys Val Thr Cys Val Val Val Asp Val Ser Glu
                35                  40                  45

Glu Glu Pro Asp Val Gln Phe Ser Trp Phe Val Asn Asn Val Glu Val
                50                  55                  60

His Thr Ala Gln Thr Gln Pro Arg Glu Glu Gln Tyr Asn Ser Thr Phe
 65                  70                  75                  80

Arg Val Val Ser Ala Leu Pro Ile Gln His Gln Asp Trp Met Ser Gly
                 85                  90                  95

Lys Glu Phe Lys Cys Lys Val Asn Asn Lys Ala Leu Pro Ser Pro Ile
                100                 105                 110

Glu Lys Thr Ile Ser Lys Pro Lys Gly Leu Val Arg Lys Pro Gln Val
```

```
            115                 120                 125
Tyr Val Met Gly Pro Pro Thr Glu Gln Leu Thr Glu Gln Thr Val Ser
        130                 135                 140
Leu Thr Cys Leu Thr Ser Gly Phe Leu Pro Asn Asp Ile Gly Val Glu
145                 150                 155                 160
Trp Thr Ser Asn Gly His Ile Glu Lys Asn Tyr Lys Asn Thr Glu Pro
                165                 170                 175
Val Met Asp Ser Asp Gly Ser Phe Phe Met Tyr Ser Lys Leu Asn Val
            180                 185                 190
Glu Arg Ser Arg Trp Asp Ser Arg Ala Pro Phe Val Cys Ser Val Val
        195                 200                 205
His Glu Gly Leu His Asn His Val Glu Lys Ser Ile Ser Arg Pro
210                 215                 220
Pro Gly Lys Gly Gly Ser Gly Gly Ser Pro Gln Leu Tyr Ser Ala Leu
225                 230                 235                 240
Ala Asn Lys Cys Cys His Val Gly Cys Thr Lys Arg Ser Leu Ala Arg
                245                 250                 255
Phe Cys Gly Gly Gly Ser Gly Gly Gly Ser Gly Ser Trp Met Glu Glu
            260                 265                 270
Val Ile Lys Leu Cys Gly Arg Glu Leu Val Arg Ala Gln Ile Ala Ile
        275                 280                 285
Cys Gly Met Ser Thr Trp Ser
290                 295

<210> SEQ ID NO 58
<211> LENGTH: 298
<212> TYPE: PRT
<213> ORGANISM: Artificial Sequence
<220> FEATURE:
<223> OTHER INFORMATION: relaxin fusion polypeptide

<400> SEQUENCE: 58

Pro Thr Cys Pro Thr Cys His Lys Cys Pro Val Pro Glu Leu Leu Gly
1               5                   10                  15
Gly Pro Ser Val Phe Ile Phe Pro Pro Lys Pro Lys Asp Ile Leu Leu
            20                  25                  30
Ile Ser Gln Asn Ala Lys Val Thr Cys Val Val Val Asp Val Ser Glu
        35                  40                  45
Glu Glu Pro Asp Val Gln Phe Ser Trp Phe Val Asn Asn Val Glu Val
    50                  55                  60
His Thr Ala Gln Thr Gln Pro Arg Glu Glu Gln Tyr Asn Ser Thr Phe
65                  70                  75                  80
Arg Val Val Ser Ala Leu Pro Ile Gln His Gln Asp Trp Met Ser Gly
                85                  90                  95
Lys Glu Phe Lys Cys Lys Val Asn Asn Lys Ala Leu Pro Ser Pro Ile
            100                 105                 110
Glu Lys Thr Ile Ser Lys Pro Lys Gly Leu Val Arg Lys Pro Gln Val
        115                 120                 125
Tyr Val Met Gly Pro Pro Thr Glu Gln Leu Thr Glu Gln Thr Val Ser
    130                 135                 140
Leu Thr Cys Leu Thr Ser Gly Phe Leu Pro Asn Asp Ile Gly Val Glu
145                 150                 155                 160
Trp Thr Ser Asn Gly His Ile Glu Lys Asn Tyr Lys Asn Thr Glu Pro
                165                 170                 175
Val Met Asp Ser Asp Gly Ser Phe Phe Met Tyr Ser Lys Leu Asn Val
```

```
                180                 185                 190
Glu Arg Ser Arg Trp Asp Ser Arg Ala Pro Phe Val Cys Ser Val Val
            195                 200                 205

His Glu Gly Leu His Asn His His Val Glu Lys Ser Ile Ser Arg Pro
        210                 215                 220

Pro Gly Lys Gly Gly Ser Gly Gly Ser Gly Gly Ser Pro Gln Leu Tyr
225                 230                 235                 240

Ser Ala Leu Ala Asn Lys Cys Cys His Val Gly Cys Thr Lys Arg Ser
                245                 250                 255

Leu Ala Arg Phe Cys Gly Gly Ser Gly Gly Gly Ser Gly Ser Trp
            260                 265                 270

Met Glu Glu Val Ile Lys Leu Cys Gly Arg Glu Leu Val Arg Ala Gln
        275                 280                 285

Ile Ala Ile Cys Gly Met Ser Thr Trp Ser
        290                 295
```

<210> SEQ ID NO 59
<211> LENGTH: 240
<212> TYPE: DNA
<213> ORGANISM: Artificial Sequence
<220> FEATURE:
<223> OTHER INFORMATION: relaxin fusion polypeptide

<400> SEQUENCE: 59

```
gaacagaaac tgattagcga agaagatctg cagctgtata gcgcgctggc gaacaaatgc     60
tgccatgtgg gctgcaccaa acgcagcctg gcgcgctttt gcggcggcgg cagctggatg    120
gaagaagtga ttaaactgtg cggccgcgaa ctggtgcgcg cgcagattgc gatttgcggc    180
atgagcacct ggagctatcc gtatgatgtg ccggattatg cgcatcatca tcatcatcat    240
```

<210> SEQ ID NO 60
<211> LENGTH: 246
<212> TYPE: DNA
<213> ORGANISM: Artificial Sequence
<220> FEATURE:
<223> OTHER INFORMATION: relaxin fusion polypeptide

<400> SEQUENCE: 60

```
gaacagaaac tgattagcga agaagatctg cagctgtata gcgcgctggc gaacaaatgc     60
tgccatgtgg gctgcaccaa acgcagcctg gcgcgctttt gcggcggcgg cagcggcagc    120
tggatggaag aagtgattaa actgtgcggc cgcgaactgg tgcgcgcgca gattgcgatt    180
tgcggcatga gcacctggag ctatccgtat gatgtgccgg attatgcgca tcatcatcat    240
catcat                                                               246
```

<210> SEQ ID NO 61
<211> LENGTH: 252
<212> TYPE: DNA
<213> ORGANISM: Artificial Sequence
<220> FEATURE:
<223> OTHER INFORMATION: relaxin fusion polypeptide

<400> SEQUENCE: 61

```
gaacagaaac tgattagcga agaagatctg cagctgtata gcgcgctggc gaacaaatgc     60
tgccatgtgg gctgcaccaa acgcagcctg gcgcgctttt gcggcggcgg cagcggcggc    120
ggcagctgga tggaagaagt gattaaactg tgcggccgcg aactggtgcg cgcgcagatt    180
gcgatttgcg gcatgagcac ctggagctat ccgtatgatg tgccggatta tgcgcatcat    240
```
catcatcatc at 252

<210> SEQ ID NO 62
<211> LENGTH: 258
<212> TYPE: DNA
<213> ORGANISM: Artificial Sequence
<220> FEATURE:
<223> OTHER INFORMATION: relaxin fusion polypeptide

<400> SEQUENCE: 62

```
gaacagaaac tgattagcga agaagatctg cagctgtata gcgcgctggc gaacaaatgc      60
tgccatgtgg gctgcaccaa acgcagcctg gcgcgctttt cggcggcgg cagcggcggc     120
ggcagcggca gctggatgga agaagtgatt aaactgtgcg gccgcgaact ggtgcgcgcg     180
cagattgcga tttgcggcat gagcacctgg agctatccgt atgatgtgcc ggattatgcg     240
catcatcatc atcatcat                                                    258
```

<210> SEQ ID NO 63
<211> LENGTH: 264
<212> TYPE: DNA
<213> ORGANISM: Artificial Sequence
<220> FEATURE:
<223> OTHER INFORMATION: relaxin fusion polypeptide

<400> SEQUENCE: 63

```
gaacagaaac tgattagcga agaagatctg cagctgtata gcgcgctggc gaacaaatgc      60
tgccatgtgg gctgcaccaa acgcagcctg gcgcgctttt cggcggcgg cagcggcggc     120
ggcagcggcg gcggcagctg gatggaagaa gtgattaaac tgtgcggccg cgaactggtg     180
cgcgcgcaga ttgcgatttg cggcatgagc acctggagct atccgtatga tgtgccggat     240
tatgcgcatc atcatcatca tcat                                             264
```

<210> SEQ ID NO 64
<211> LENGTH: 276
<212> TYPE: DNA
<213> ORGANISM: Artificial Sequence
<220> FEATURE:
<223> OTHER INFORMATION: relaxin fusion polypeptide

<400> SEQUENCE: 64

```
gaacagaaac tgattagcga agaagatctg cagctgtata gcgcgctggc gaacaaatgc      60
tgccatgtgg gctgcaccaa acgcagcctg gcgcgctttt cggcggcgg cagcggcggc     120
ggcagcggcg gcggcagcgg cggcggcagc tggatggaag aagtgattaa actgtgcggc     180
cgcgaactgg tgcgcgcgca gattgcgatt tgcggcatga gcacctggag ctatccgtat     240
gatgtgccgg attatgcgca tcatcatcat catcat                                276
```

<210> SEQ ID NO 65
<211> LENGTH: 204
<212> TYPE: DNA
<213> ORGANISM: Artificial Sequence
<220> FEATURE:
<223> OTHER INFORMATION: relaxin fusion polypeptide

<400> SEQUENCE: 65

```
gaacagaaac tgattagcga agaagatctg cagctgtata gcgcgctggc gaacaaatgc      60
tgccatgtgg gctgcaccaa acgcagcctg gcgcgctttt cggcggcgg cagcggcggc     120
agctggatgg aagaagtgat taaactgtgc ggccgcgaac tggtgcgcgc gcagattgcg     180
atttgcggca tgagcacctg gagc                                             204
```

<210> SEQ ID NO 66
<211> LENGTH: 222
<212> TYPE: DNA
<213> ORGANISM: Artificial Sequence
<220> FEATURE:
<223> OTHER INFORMATION: relaxin fusion polypeptide

<400> SEQUENCE: 66

```
gaacagaaac tgattagcga agaagatctg cagctgtata gcgcgctggc gaacaaatgc      60
tgccatgtgg gctgcaccaa acgcagcctg gcgcgctttt gcggcggcgg cagcggcggc     120
ggcagcggcg gcggcagcag ctggatggaa gaagtgatta aactgtgcgg ccgcgaactg     180
gtgcgcgcgc agattgcgat ttgcggcatg agcacctgga gc                       222
```

<210> SEQ ID NO 67
<211> LENGTH: 225
<212> TYPE: DNA
<213> ORGANISM: Artificial Sequence
<220> FEATURE:
<223> OTHER INFORMATION: relaxin fusion polypeptide

<400> SEQUENCE: 67

```
gaacagaaac tgattagcga agaagatctg cagctgtata gcgcgctggc gaacaaatgc      60
tgccatgtgg gctgcaccaa acgcagcctg gcgcgctttt gcggcggcgg cagcggcggc     120
ggcagcggcg gcggcagcgg cagctggatg gaagaagtga ttaaactgtg cggccgcgaa     180
ctggtgcgcg cgcagattgc gatttgcggc atgagcacct ggagc                    225
```

<210> SEQ ID NO 68
<211> LENGTH: 228
<212> TYPE: DNA
<213> ORGANISM: Artificial Sequence
<220> FEATURE:
<223> OTHER INFORMATION: relaxin fusion polypeptide

<400> SEQUENCE: 68

```
gaacagaaac tgattagcga agaagatctg cagctgtata gcgcgctggc gaacaaatgc      60
tgccatgtgg gctgcaccaa acgcagcctg gcgcgctttt gcggcggcgg cagcggcggc     120
ggcagcggcg gcggcagcgg cggcagctgg atggaagaag tgattaaact gtgcggccgc     180
gaactggtgc gcgcgcagat tgcgatttgc ggcatgagca cctggagc                 228
```

<210> SEQ ID NO 69
<211> LENGTH: 186
<212> TYPE: DNA
<213> ORGANISM: Artificial Sequence
<220> FEATURE:
<223> OTHER INFORMATION: relaxin fusion polypeptide

<400> SEQUENCE: 69

```
cagctgtata gcgcgctggc gaacaaatgc tgccatgtgg gctgcaccaa acgcagcctg      60
gcgcgctttt gcggcggcgg cagcggctgc ggcggcagcg gcagctggat ggaagaagtg     120
attaaactgt gcggccgcga actggtgcgc gcgcagattg cgatttgcgg catgagcacc     180
tggagc                                                               186
```

<210> SEQ ID NO 70
<211> LENGTH: 186
<212> TYPE: DNA
<213> ORGANISM: Artificial Sequence
<220> FEATURE:

<223> OTHER INFORMATION: relaxin fusion polypeptide

<400> SEQUENCE: 70

```
cagctgtata gcgcgctggc gaacaaatgc tgccatgtgg gctgcaccaa acgcagcctg    60
gcgcgctttt gcggcggcgg cagcggcaaa ggcggcagcg gcagctggat ggaagaagtg   120
attaaactgt gcggccgcga actggtgcgc gcgcagattg cgatttgcgg catgagcacc   180
tggagc                                                              186
```

<210> SEQ ID NO 71
<211> LENGTH: 183
<212> TYPE: DNA
<213> ORGANISM: Artificial Sequence
<220> FEATURE:
<223> OTHER INFORMATION: relaxin fusion polypeptide

<400> SEQUENCE: 71

```
cagctgtata gcgcgctggc gaacaaatgc tgccatgtgg gctgcaccaa acgcagcctg    60
gcgcgctttt gcaaacgcag cctgagccgc aaaaaacgca gctggatgga agaagtgatt   120
aaactgtgcg gccgcgaact ggtgcgcgcg cagattgcga tttgcggcat gagcacctgg   180
agc                                                                 183
```

<210> SEQ ID NO 72
<211> LENGTH: 180
<212> TYPE: DNA
<213> ORGANISM: Artificial Sequence
<220> FEATURE:
<223> OTHER INFORMATION: relaxin fusion polypeptide

<400> SEQUENCE: 72

```
gatgtgctgg cgggcctgag cagcagctgc tgcaaatggg gctgcagcaa aagcgaaatt    60
agcagcctgt gcggcggcgg cagcggcggc ggcagcggcc gcggcggcgcc gtatggcgtg   120
cgcctgtgcg gccgcgaatt tattcgcgcg gtgattttta cctgcggcgg cagccgctgg   180
```

<210> SEQ ID NO 73
<211> LENGTH: 210
<212> TYPE: DNA
<213> ORGANISM: Artificial Sequence
<220> FEATURE:
<223> OTHER INFORMATION: relaxin fusion polypeptide

<400> SEQUENCE: 73

```
gaacagaaac tgattagcga agaagatctg gatgtgctgg cgggcctgag cagcagctgc    60
tgcaaatggg gctgcagcaa aagcgaaatt agcagcctgt gcggcggcgg cagcggcggc   120
ggcagcggcc gcggcggcgcc gtatggcgtg cgcctgtgcg gccgcgaatt tattcgcgcg   180
gtgattttta cctgcggcgg cagccgctgg                                    210
```

<210> SEQ ID NO 74
<211> LENGTH: 924
<212> TYPE: DNA
<213> ORGANISM: Artificial Sequence
<220> FEATURE:
<223> OTHER INFORMATION: relaxin fusion polypeptide

<400> SEQUENCE: 74

```
gaacagaaac tgattagcga agaagatctg cagctgtata gcgcgctggc gaacaaatgc    60
tgccatgtgg gctgcaccaa acgcagcctg gcgcgctttt gcggcggcgg cagcggcggc   120
ggcagcggca gctggatgga agaagtgatt aaactgtgcg gccgcgaact ggtgcgcgcg   180
```

```
cagattgcga tttgcggcat gagcacctgg agcattgaag gccgcatgga tccgaaagcg      240
tgcgataaaa cccatacctg cccgccgtgc ccggcgccgg aactgctggg cggcccgagc      300
gtgtttctgt ttccgccgaa accgaaagat accctgatga ttagccgcac cccggaagtg      360
acctgcgtgg tggtggatgt gagccatgaa gatccggaag tgaaatttaa ctggtatgtg      420
gatggcgtgg aagtgcataa cgcgaaaacc aaaccgcgcg aagaacagta taacagcacc      480
tatcgcgtgg tgagcgtgct gaccgtgctg catcaggatt ggctgaacgg caaagaatat      540
aaatgcaaag tgagcaacaa agcgctgccg gcgccgattg aaaaaaccat tagcaaagcg      600
aaaggccagc cgcgcgaacc gcaggtgtat accctgccgc cgagccgcga tgaactgacc      660
aaaaaccagg tgagcctgac ctgcctggtg aaaggctttt atccgagcga tattgcggtg      720
gaatgggaaa gcaacggcca gccggaaaac aactataaaa ccaccccgcc ggtgctggat      780
agcgatggca gcttttttct gtatagcaaa ctgaccgtgg ataaaagccg ctggcagcag      840
ggcaacgtgt ttagctgcag cgtgatgcat gaagcgctgc ataaccatta tacccagaaa      900
agcctgagcc tgagcccggg caaa                                             924
```

```
<210> SEQ ID NO 75
<211> LENGTH: 876
<212> TYPE: DNA
<213> ORGANISM: Artificial Sequence
<220> FEATURE:
<223> OTHER INFORMATION: relaxin fusion polypeptide

<400> SEQUENCE: 75
cagctgtata gcgcgctggc gaacaaatgc tgccatgtgg gctgcaccaa acgcagcctg       60
gcgcgctttt gcggcggcgg cagcggcggc ggcagcggca gctggatgga agaagtgatt      120
aaactgtgcg gccgcgaact ggtgcgcgcg cagattgcga tttgcggcat gagcacctgg      180
agcggcggca gccccggataa acccatacct gcccgccgt gcccggcgcc ggaactgctg      240
ggcggcccga gcgtgtttct gtttccgccg aaaccgaaag ataccctgat gattagccgc      300
accccggaag tgacctgcgt ggtggtggat gtgagccatg aagatccgga agtgaaattt      360
aactggtatg tggatggcgt ggaagtgcat aacgcgaaaa ccaaaccgcg cgaagaacag      420
tataacagca cctatcgcgt ggtgagcgtg ctgaccgtgc tgcatcagga ttggctgaac      480
ggcaaagaat ataaatgcaa agtgagcaac aaagcgctgc cggcgccgat tgaaaaaacc      540
attagcaaag cgaaaggcca gccgcgcgaa ccgcaggtgt ataccctgcc gccgagccgc      600
gatgaactga ccaaaaaacca ggtgagcctg acctgcctgg tgaaaggctt ttatccgagc      660
gatattgcgg tggaatggga aagcaacggc cagccggaaa acaactataa aaccaccccg      720
ccggtgctgg atagcgatgg cagctttttt ctgtatagca aactgaccgt ggataaaagc      780
cgctggcagc agggcaacgt gtttagctgc agcgtgatgc atgaagcgct gcataaccat      840
tatacccaga aaagcctgag cctgagcccg ggcaaa                                876
```

```
<210> SEQ ID NO 76
<211> LENGTH: 885
<212> TYPE: DNA
<213> ORGANISM: Artificial Sequence
<220> FEATURE:
<223> OTHER INFORMATION: relaxin fusion polypeptide

<400> SEQUENCE: 76
cagctgtata gcgcgctggc gaacaaatgc tgccatgtgg gctgcaccaa acgcagcctg       60
```

```
gcgcgcttttt cggcggcggc cagcggcggc ggcagcggca gctggatgga agaagtgatt    120
aaactgtgcg gccgcgaact ggtgcgcgcg cagattgcga tttgcggcat gagcacctgg    180
agcggcggca gcggcggcag cccggataaa acccatacct gcccgccgtg cccggcgccg    240
gaactgctgg gcgccccgag cgtgtttctg tttccgccga aaccgaaaga taccctgatg    300
attagccgca ccccggaagt gacctgcgtg gtggtggatg tgagccatga agatccggaa    360
gtgaaattta actggtatgt ggatggcgtg gaagtgcata cgcgaaaac caaaccgcgc    420 gaagaacagt ataacagcac ctatcgcgtg gtgagcgtgc tgaccgtgct gcatcaggat    480
tggctgaacg gcaaagaata taaatgcaaa gtgagcaaca agcgctgcc ggcgccgatt    540 gaaaaaacca ttagcaaagc gaaaggccag ccgcgcgaac cgcaggtgta ccctgccg    600 ccgagccgcg atgaactgac caaaaaccag gtgagcctga cctgcctggt gaaaggcttt    660
tatccgagcg atattgcggt ggaatgggaa agcaacggcc agccggaaaa caactataaa    720
accaccccgc cggtgctgga tagcgatggc agcttttttc tgtatagcaa actgaccgtg    780
gataaaagcc gctggcagca gggcaacgtg tttagctgca gcgtgatgca tgaagcgctg    840
cataaccatt atacccagaa aagcctgagc ctgagcccgg gcaaa                    885

<210> SEQ ID NO 77
<211> LENGTH: 894
<212> TYPE: DNA
<213> ORGANISM: Artificial Sequence
<220> FEATURE:
<223> OTHER INFORMATION: relaxin fusion polypeptide

<400> SEQUENCE: 77
cagctgtata gcgcgctggc gaacaaatgc tgccatgtgg gctgcaccaa acgcagcctg     60
gcgcgctttt cggcggcgg cagcggcggc ggcagcggca gctggatgga agaagtgatt    120
aaactgtgcg gccgcgaact ggtgcgcgcg cagattgcga tttgcggcat gagcacctgg    180
agcggcggca gcggcggcag cggcggcagc ccggataaa cccatacctg cccgccgtgc    240
ccggcgccgg aactgctggg cggccccgagc gtgtttctgt ttccgccgaa accgaaagat    300
accctgatga ttagccgcac cccggaagtg acctgcgtgg tggtggatgt gagccatgaa    360
gatccggaag tgaaatttaa ctggtatgtg gatggcgtgg aagtgcataa cgcgaaaacc    420
aaaccgcgcg aagaacagta taacagcacc tatcgcgtgg tgagcgtgct gaccgtgctg    480
catcaggatt ggctgaacgg caaagaatat aaatgcaaag tgagcaacaa agcgctgccg    540
gcgccgattg aaaaaaccat tagcaaagcg aaaggccagc cgcgcgaacc gcaggtgtat    600
accctgccgc cgagccgcga tgaactgacc aaaaaccagg tgagcctgac ctgcctggtg    660
aaaggctttt atccgagcga tattgcggtg gaatgggaaa gcaacggcca gccggaaaac    720
aactataaaa ccaccccgcc ggtgctggat agcgatggca gcttttttct gtatagcaaa    780
ctgaccgtgg ataaaagccg ctggcagcag ggcaacgtgt ttagctgcag cgtgatgcat    840
gaagcgctgc ataaccatta tacccagaaa agcctgagcc tgagcccggg caaa          894

<210> SEQ ID NO 78
<211> LENGTH: 876
<212> TYPE: DNA
<213> ORGANISM: Artificial Sequence
<220> FEATURE:
<223> OTHER INFORMATION: relaxin fusion polypeptide

<400> SEQUENCE: 78
gataaaaccc ataccctgcc cgccgtgccc ggcgccggaa ctgctgggcg gccccgagcgtg    60
```

```
tttctgtttc cgccgaaacc gaaagatacc ctgatgatta gccgcacccc ggaagtgacc    120
tgcgtggtgg tggatgtgag ccatgaagat ccggaagtga aatttaactg gtatgtggat    180
ggcgtggaag tgcataacgc gaaaaccaaa ccgcgcgaag aacagtataa cagcacctat    240
cgcgtggtga gcgtgctgac cgtgctgcat caggattggc tgaacggcaa agaatataaa    300
tgcaaagtga gcaacaaagc gctgccggcg ccgattgaaa aaaccattag caaagcgaaa    360
ggccagccgc gcgaaccgca ggtgtatacc ctgccgccga ccgcgatgaa actgaccaaa    420
aaccaggtga gcctgacctg cctggtgaaa ggctttatc cgagcgatat tgcggtggaa     480
tgggaaagca acggccagcc ggaaaacaac tataaaacca ccccgccggt gctggatagc    540
gatggcagct ttttctgtat agcaaactg accgtggata aaagccgctg gcagcagggc     600
aacgtgttta gctgcagcgt gatgcatgaa gcgctgcata accattatac ccagaaaagc    660
ctgagcctga gcccgggcaa aggcggcagc cgcagctgt atagcgcgct ggcgaacaaa     720
tgctgccatg tgggctgcac caaacgcagc ctggcgcgct tttgcggcgg cggcagcggc    780
ggcggcagcg gcagctggat ggaagaagtg attaaactgt gcggccgcga actggtgcgc    840
gcgcagattg cgatttgcgg catgagcacc tggagc                              876
```

<210> SEQ ID NO 79
<211> LENGTH: 885
<212> TYPE: DNA
<213> ORGANISM: Artificial Sequence
<220> FEATURE:
<223> OTHER INFORMATION: relaxin fusion polypeptide

<400> SEQUENCE: 79

```
gataaaaccc atacctgccc gccgtgcccg gcgccggaac tgctgggcgg cccgagcgtg     60
tttctgtttc cgccgaaacc gaaagatacc ctgatgatta gccgcacccc ggaagtgacc    120
tgcgtggtgg tggatgtgag ccatgaagat ccggaagtga aatttaactg gtatgtggat    180
ggcgtggaag tgcataacgc gaaaaccaaa ccgcgcgaag aacagtataa cagcacctat    240
cgcgtggtga gcgtgctgac cgtgctgcat caggattggc tgaacggcaa agaatataaa    300
tgcaaagtga gcaacaaagc gctgccggcg ccgattgaaa aaaccattag caaagcgaaa    360
ggccagccgc gcgaaccgca ggtgtatacc ctgccgccga ccgcgatgaa actgaccaaa    420
aaccaggtga gcctgacctg cctggtgaaa ggctttatc cgagcgatat tgcggtggaa     480
tgggaaagca acggccagcc ggaaaacaac tataaaacca ccccgccggt gctggatagc    540
gatggcagct ttttctgtat agcaaactg accgtggata aaagccgctg gcagcagggc     600
aacgtgttta gctgcagcgt gatgcatgaa gcgctgcata accattatac ccagaaaagc    660
ctgagcctga gcccgggcaa aggcggcagc ggcggcagcc gcagctgta tagcgcgctg     720 gcgaacaaat gctgccatgt gggctgcacc aaacgcagcc tggcgcgctt ttgcggcggc    780
ggcagcggcg gcggcagcgg cagctggatg gaagaagtg ttaaactgtg cggccgcgaa     840
ctggtgcgcg cgcagattgc gatttgcggc atgagcacct ggagc                    885
```

<210> SEQ ID NO 80
<211> LENGTH: 894
<212> TYPE: DNA
<213> ORGANISM: Artificial Sequence
<220> FEATURE:
<223> OTHER INFORMATION: relaxin fusion polypeptide

<400> SEQUENCE: 80

```
gataaaaccc atacctgccc gccgtgcccg gcgccggaac tgctgggcgg cccgagcgtg      60
tttctgtttc cgccgaaacc gaaagatacc ctgatgatta gccgcacccc ggaagtgacc     120
tgcgtggtgg tggatgtgag ccatgaagat ccggaagtga atttaactg gtatgtggat      180 ggcgtggaag tgcataacgc gaaaaccaaa ccgcgcgaag aacagtataa cagcacctat     240
cgcgtggtga gcgtgctgac cgtgctgcat caggattggc tgaacggcaa agaatataaa     300
tgcaaagtga gcaacaaagc gctgccggcg ccgattgaaa aaccattag caaagcgaaa     360 ggccagccgc gcgaaccgca ggtgtatacc ctgccgccga gccgcgatga actgaccaaa     420
aaccaggtga gcctgacctg cctggtgaaa ggcttttatc cgagcgatat tgcggtggaa     480
tgggaaagca acggccagcc ggaaaacaac tataaaacca ccccgccggt gctggatagc     540
gatggcagct tttttctgta tagcaaactg accgtggata aagccgctg gcagcagggc      600 aacgtgttta gctgcagcgt gatgcatgaa gcgctgcata ccattatac ccagaaaagc      660 ctgagcctga gcccgggcaa aggcggcagc ggcggcagcg gcggcagccc gcagctgtat     720
agcgcgctgg cgaacaaatg ctgccatgtg gctgcacca acgcagcct ggcgcgcttt      780 tgcggcggcg cagcggcgg cggcagcggc agctggatgg aagaagtgat taaactgtgc      840
ggccgcgaac tggtgcgcgc gcagattgcg atttgcggca tgagcacctg gagc          894
```

<210> SEQ ID NO 81
<211> LENGTH: 891
<212> TYPE: DNA
<213> ORGANISM: Artificial Sequence
<220> FEATURE:
<223> OTHER INFORMATION: relaxin fusion polypeptide

<400> SEQUENCE: 81

```
cagctgtata gcgcgctggc gaacaaatgc tgccatgtgg gctgcaccaa acgcagcctg      60
gcgcgctttt gcggcggcgg cagcggcggc ggcagcggca gctggatgga agaagtgatt     120
aaactgtgcg gccgcgaact ggtgcgcgcg cagattgcga tttgcggcat gagcacctgg     180
agcggcggca gcccgacctg cccgacctgc cataaatgcc cggtgccgga actgctgggc     240
ggcccgagcg tgtttatttt tccgccgaaa ccgaaagata ttctgctgat tagccagaac     300
gcgaaagtga ccctgcgtgt ggtggatgtg agcgaagaag aaccggatgt gcagtttagc     360
tggtttgtga acaacgtgga agtgcatacc gcgcagaccc agccgcgcga agaacagtat     420
aacagcacct ttcgcgtggt gagcgcgctg ccgattcagc atcaggattg gatgagcggc     480
aaagaattta atgcaaagt gaacaacaaa gcgctgccga gcccgattga aaaaaccatt     540
agcaaaccga aaggcctggt gcgcaaaccg caggtgtatg tgatgggccc gccgaccgaa     600
cagctgaccg aacagaccgt gagcctgacc tgcctgacca gcggctttct gccgaacgat     660
attggcgtgg aatggaccag caacggccat attgaaaaaa actataaaaa caccgaaccg     720
gtgatggata gcgatggcag cttttttatg tatagcaaac tgaacgtgga acgcagccgc     780
tgggatagcc gcgcgccgtt tgtgtgcagc gtggtgcatg aaggcctgca taaccatcat     840
gtggaaaaaa gcattagccg cccgccgggc aaacatcatc atcatcatca t             891
```

<210> SEQ ID NO 82
<211> LENGTH: 900
<212> TYPE: DNA
<213> ORGANISM: Artificial Sequence
<220> FEATURE:
<223> OTHER INFORMATION: relaxin fusion polypeptide

<400> SEQUENCE: 82

```
cagctgtata gcgcgctggc gaacaaatgc tgccatgtgg gctgcaccaa acgcagcctg      60
gcgcgctttt gcggcggcgg cagcggcggc ggcagcggca gctggatgga agaagtgatt     120
aaactgtgcg gccgcgaact ggtgcgcgcg cagattgcga tttgcggcat gagcacctgg     180
agcggcggca gcggcggcag cccgacctgc ccgacctgcc ataaatgccc ggtgccggaa     240
ctgctgggcg gcccgagcgt gtttattttt ccgccgaaac cgaaagatat tctgctgatt     300
agccagaacg cgaaagtgac ctgcgtggtg gtggatgtga cgaagaaga accggatgtg     360 cagtttagct ggtttgtgaa caacgtggaa gtgcataccg cgcagaccca gccgcgcgaa     420
gaacagtata cagcaccctt tcgcgtggtg agcgcgctgc cgattcagca tcaggattgg     480
atgagcggca aagaatttaa atgcaaagtg aacaacaaag cgctgccgag cccgattgaa     540
aaaaccatta gcaaaccgaa aggcctggtg cgcaaaccgc aggtgtatgt gatgggcccg     600
ccgaccgaac agctgaccga acagaccgtg agcctgacct gcctgaccag cggctttctg     660
ccgaacgata ttggcgtgga atggaccagc aacggccata ttgaaaaaaa ctataaaaac     720
accgaaccgg tgatggatag cgatggcagc ttttttatgt atagcaaact gaacgtggaa     780
cgcagccgct gggatagccg cgcgccgttt gtgtgcagcg tggtgcatga aggcctgcat     840
aaccatcatg tggaaaaaag cattagccgc ccgccgggca acatcatca tcatcatcat     900
```

<210> SEQ ID NO 83
<211> LENGTH: 909
<212> TYPE: DNA
<213> ORGANISM: Artificial Sequence
<220> FEATURE:
<223> OTHER INFORMATION: relaxin fusion polypeptide

<400> SEQUENCE: 83

```
cagctgtata gcgcgctggc gaacaaatgc tgccatgtgg gctgcaccaa acgcagcctg      60
gcgcgctttt gcggcggcgg cagcggcggc ggcagcggca gctggatgga agaagtgatt     120
aaactgtgcg gccgcgaact ggtgcgcgcg cagattgcga tttgcggcat gagcacctgg     180
agcggcggca gcggcggcag cggcggcagc ccgacctgcc cgacctgcca taatgcccg     240 gtgccggaac tgctgggcgg cccgagcgtg tttattttc cgccgaaacc gaaagatatt     300
ctgctgatta gccagaacgc gaaagtgacc tgcgtggtgg tggatgtgag cgaagaagaa     360
ccggatgtgc agtttagctg gtttgtgaac aacgtggaag tgcataccgc gcagacccag     420
ccgcgcgaag aacagtataa cagcaccttt cgcgtggtga gcgcgctgcc gattcagcat     480
caggattgga tgagcggcaa agaatttaaa tgcaaagtga acaacaaagc gctgccgagc     540
ccgattgaaa aaaccattag caaaccgaaa ggcctggtgc gcaaaccgca ggtgtatgtg     600
atgggcccgc cgaccgaaca gctgaccgaa cagaccgtga gcctgacctg cctgaccagc     660
ggctttctgc cgaacgatat tggcgtggaa tggaccagca acggccatat tgaaaaaaac     720
tataaaaaca ccgaaccggt gatggatagc gatggcagct tttttatgta tagcaaactg     780
aacgtggaac gcagccgctg ggatagccgc gcgccgtttg tgtgcagcgt ggtgcatgaa     840
ggcctgcata accatcatgt ggaaaaaagc attagccgcc cgccgggcaa acatcatcat     900
catcatcat                                                             909
```

<210> SEQ ID NO 84
<211> LENGTH: 894
<212> TYPE: DNA
<213> ORGANISM: Artificial Sequence
<220> FEATURE:

<223> OTHER INFORMATION: relaxin fusion polypeptide

<400> SEQUENCE: 84

```
catcatcatc atcatcatcc gacctgcccg acctgccata aatgcccggt gccggaactg      60
ctgggcggcc cgagcgtgtt tattttccg ccgaaaccga agatattct gctgattagc       120
cagaacgcga agtgacctg cgtggtggtg gatgtgagcg aagaagaacc ggatgtgcag     180
tttagctggt ttgtgaacaa cgtggaagtg cataccgcgc agacccagcc gcgcgaagaa     240
cagtataaca gcacctttcg cgtggtgagc gcgctgccga ttcagcatca ggattggatg     300
agcggcaaag aatttaaatg caaagtgaac aacaaagcgc tgccgagccc gattgaaaaa     360
accattagca aaccgaaagg cctggtgcgc aaaccgcagg tgtatgtgat gggcccgccg     420
accgaacagc tgaccgaaca gaccgtgagc ctgacctgcc tgaccagcgg ctttctgccg     480
aacgatattg cgtggaatg gaccagcaac ggccatattg aaaaaaacta taaaacacc      540
gaaccggtga tggatagcga tggcagctt tttatgtata gcaaactgaa cgtggaacgc     600
agccgctggg atagccgcgc gccgtttgtg tgcagcgtgg tgcatgaagg cctgcataac     660
catcatgtgg aaaaaagcat tagccgcccg ccgggcaaag cggcagccc gcagctgtat       720
agcgcgctgc gaacaaatg ctgccatgtg gctgcacca acgcagcct ggcgcgcttt        780
tgcggcggcg gcagcggcgg cggcagcggc agctggatgg aagaagtgat taaactgtgc     840
ggccgcgaac tggtgcgcgc gcagattgcg atttgcggca tgagcacctg gagc           894
```

<210> SEQ ID NO 85
<211> LENGTH: 903
<212> TYPE: DNA
<213> ORGANISM: Artificial Sequence
<220> FEATURE:
<223> OTHER INFORMATION: relaxin fusion polypeptide

<400> SEQUENCE: 85

```
catcatcatc atcatcatcc gacctgcccg acctgccata aatgcccggt gccggaactg      60
ctgggcggcc cgagcgtgtt tattttccg ccgaaaccga agatattct gctgattagc       120
cagaacgcga agtgacctg cgtggtggtg gatgtgagcg aagaagaacc ggatgtgcag     180
tttagctggt ttgtgaacaa cgtggaagtg cataccgcgc agacccagcc gcgcgaagaa     240
cagtataaca gcacctttcg cgtggtgagc gcgctgccga ttcagcatca ggattggatg     300
agcggcaaag aatttaaatg caaagtgaac aacaaagcgc tgccgagccc gattgaaaaa     360
accattagca aaccgaaagg cctggtgcgc aaaccgcagg tgtatgtgat gggcccgccg     420
accgaacagc tgaccgaaca gaccgtgagc ctgacctgcc tgaccagcgg ctttctgccg     480
aacgatattg cgtggaatg gaccagcaac ggccatattg aaaaaaacta taaaacacc      540
gaaccggtga tggatagcga tggcagctt tttatgtata gcaaactgaa cgtggaacgc     600
agccgctggg atagccgcgc gccgtttgtg tgcagcgtgg tgcatgaagg cctgcataac     660
catcatgtgg aaaaaagcat tagccgcccg ccgggcaaag cggcagcgg cggcagcccg      720
cagctgtata gcgcgctggc gaacaaatgc tgccatgtgg ctgcaccaa cgcagcctg       780
gcgcgctttt gcggcggcgg cagcggcggc ggcagcggca gctggatgga agaagtgatt     840
aaactgtgcg gccgcgaact ggtgcgcgcg cagattgcga tttgcggcat gagcacctgg     900
agc                                                                   903
```

<210> SEQ ID NO 86
<211> LENGTH: 912

```
<212> TYPE: DNA
<213> ORGANISM: Artificial Sequence
<220> FEATURE:
<223> OTHER INFORMATION: relaxin fusion polypeptide

<400> SEQUENCE: 86
catcatcatc atcatcatcc gacctgcccg acctgccata atgcccggt gccggaactg      60
ctgggcggcc cgagcgtgtt tattttccg ccgaaaccga agatattct gctgattagc      120
cagaacgcga aagtgacctg cgtggtggtg gatgtgagcg aagaagaacc ggatgtgcag    180
tttagctggt ttgtgaacaa cgtggaagtg cataccgcgc agacccagcc gcgcgaagaa    240
cagtataaca gcaccttttc gcgtggtgagc gcgctgccga ttcagcatca ggattggatg    300
agcggcaaag aatttaaatg caaagtgaac aacaaagcgc tgccgagccc gattgaaaaa    360
accattagca aaccgaaagg cctggtgcgc aaaccgcagg tgtatgtgat gggcccgccg    420
accgaacagc tgaccgaaca gaccgtgagc ctgacctgcc tgaccagcgg ctttctgccg    480
aacgatattg cgtggaatg gaccagcaac ggccatattg aaaaaaacta taaaaacacc    540
gaaccggtga tggatagcga tggcagcttt tttatgtata gcaaactgaa cgtggaacgc    600
agccgctggg atagccgcgc gccgtttgtg tgcagcgtgg tgcatgaagg cctgcataac    660
catcatgtgg aaaaaagcat tagccgcccg ccgggcaaag gcggcagcgg cggcagcggc    720
ggcagcccgc agctgtatag cgcgctggcg aacaaatgct gccatgtggg ctgcaccaaa    780
cgcagcctgg cgcgcttttg cggcggcggc agcggcggcg gcagcggcag ctggatggaa    840
gaagtgatta aactgtgcgg ccgcgaactg gtgcgcgcgc agattgcgat ttgcggcatg    900
agcacctgga gc                                                        912

<210> SEQ ID NO 87
<211> LENGTH: 864
<212> TYPE: DNA
<213> ORGANISM: Artificial Sequence
<220> FEATURE:
<223> OTHER INFORMATION: relaxin fusion polypeptide

<400> SEQUENCE: 87
cagctgtata gcgcgctggc gaacaaatgc tgccatgtgg gctgcaccaa acgcagcctg     60
gcgcgctttt gcggcggcgg cagcggcggc ggcagcggca gctggatgga agaagtgatt    120
aaactgtgcg gccgcgaact ggtgcgcgcg cagattgcga tttgcggcat gagcacctgg    180
agcgataaaa cccataccctg cccgccgtgc ccggcgccgg aactgctggg cggcccgagc    240
gtgtttctgt ttccgccgaa accgaaagat accctgatga ttagccgcac ccgaagtg      300
acctgcgtgg tggtggatgt gagccatgaa gatccggaag tgaaatttaa ctggtatgtg    360
gatggcgtga agtgcataa cgcgaaaacc aaaccgcgcg aagaacagta taacagcacc    420
tatcgcgtgg tgagcgtgct gaccgtgctg catcaggatt ggctgaacgg caaagaatat    480
aaatgcaaag tgagcaacaa agcgctgccg gcgccgatta aaaaaaccat tagcaaagcg    540
aaaggccagc cgcgcgaacc gcaggtgtat accctgccgc cgagccgcga tgaactgacc    600
aaaaaccagg tgagcctgac ctgcctggtg aaaggctttt atccgagcga tattgcggtg    660
gaatgggaaa gcaacggcca gccggaaaac aactataaaa ccaccccgcc ggtgctggat    720
agcgatggca gcttttttct gtatagcaaa ctgaccgtgg ataaaagccg ctggcagcag    780
ggcaacgtgt ttagctgcag cgtgatgcat gaagcgctgc ataaccatta tacccagaaa    840
agcctgagcc tgagcccggg caaa                                           864
```

<210> SEQ ID NO 88
<211> LENGTH: 882
<212> TYPE: DNA
<213> ORGANISM: Artificial Sequence
<220> FEATURE:
<223> OTHER INFORMATION: relaxin fusion polypeptide

<400> SEQUENCE: 88

| | | | | | |
|---|---|---|---|---|---|
| cagctgtata | gcgcgctggc | gaacaaatgc | tgccatgtgg | gctgcaccaa acgcagcctg | 60 |
| gcgcgctttt | gcggcggcgg | cagcggcggc | ggcagcggca | gctggatgga agaagtgatt | 120 |
| aaactgtgcg | gccgcgaact | ggtgcgcgcg | cagattgcga | tttgcggcat gagcacctgg | 180 |
| agcggcagcg | gcagcggcag | cgataaaacc | catacctgcc | cgccgtgccc ggcgccggaa | 240 |
| ctgctgggcg | gcccgagcgt | gtttctgttt | ccgccgaaac | cgaaagatac cctgatgatt | 300 |
| agccgcaccc | cggaagtgac | ctgcgtggtg | gtggatgtga | gccatgaaga tccggaagtg | 360 |
| aaatttaact | ggtatgtgga | tggcgtggaa | gtgcataacg | cgaaaaccaa accgcgcgaa | 420 |
| gaacagtata | acagcaccta | tcgcgtggtg | agcgtgctga | ccgtgctgca tcaggattgg | 480 |
| ctgaacggca | aagaatataa | atgcaaagtg | agcaacaaag | cgctgccggc gccgattgaa | 540 |
| aaaaccatta | gcaaagcgaa | aggccagccg | cgcgaaccgc | aggtgtatac cctgccgccg | 600 |
| agccgcgatg | aactgaccaa | aaaccaggtg | agcctgacct | gcctggtgaa aggcttttat | 660 |
| ccgagcgata | ttgcggtgga | atgggaaagc | aacggccagc | cggaaaacaa ctataaaacc | 720 |
| accccgccgg | tgctggatag | cgatggcagc | ttttttctgt | atagcaaact gaccgtggat | 780 |
| aaaagccgct | ggcagcaggg | caacgtgttt | agctgcagcg | tgatgcatga agcgctgcat | 840 |
| aaccattata | cccagaaaag | cctgagcctg | agcccgggca | aa | 882 |

<210> SEQ ID NO 89
<211> LENGTH: 882
<212> TYPE: DNA
<213> ORGANISM: Artificial Sequence
<220> FEATURE:
<223> OTHER INFORMATION: relaxin fusion polypeptide

<400> SEQUENCE: 89

| | | | | | |
|---|---|---|---|---|---|
| cagctgtata | gcgcgctggc | gaacaaatgc | tgccatgtgg | gctgcaccaa acgcagcctg | 60 |
| gcgcgctttt | gcggcggcgg | cagcggcggc | ggcagcggca | gctggatgga agaagtgatt | 120 |
| aaactgtgcg | gccgcgaact | ggtgcgcgcg | cagattgcga | tttgcggcat gagcacctgg | 180 |
| agcggcagcg | gcagcggcag | cgataaaacc | catacccgcg | cgccggcgcc ggcgccggaa | 240 |
| ctgctgggcg | gcccgagcgt | gtttctgttt | ccgccgaaac | cgaaagatac cctgatgatt | 300 |
| agccgcaccc | cggaagtgac | ctgcgtggtg | gtggatgtga | gccatgaaga tccggaagtg | 360 |
| aaatttaact | ggtatgtgga | tggcgtggaa | gtgcataacg | cgaaaaccaa accgcgcgaa | 420 |
| gaacagtata | acagcaccta | tcgcgtggtg | agcgtgctga | ccgtgctgca tcaggattgg | 480 |
| ctgaacggca | aagaatataa | atgcaaagtg | agcaacaaag | cgctgccggc gccgattgaa | 540 |
| aaaaccatta | gcaaagcgaa | aggccagccg | cgcgaaccgc | aggtgtatac cctgccgccg | 600 |
| agccgcgatg | aactgaccaa | aaaccaggtg | agcctgacct | gcctggtgaa aggcttttat | 660 |
| ccgagcgata | ttgcggtgga | atgggaaagc | aacggccagc | cggaaaacaa ctataaaacc | 720 |
| accccgccgg | tgctggatag | cgatggcagc | ttttttctgt | atagcaaact gaccgtggat | 780 |
| aaaagccgct | ggcagcaggg | caacgtgttt | agctgcagcg | tgatgcatga agcgctgcat | 840 |
| aaccattata | cccagaaaag | cctgagcctg | agcccgggca | aa | 882 |

<210> SEQ ID NO 90
<211> LENGTH: 882
<212> TYPE: DNA
<213> ORGANISM: Artificial Sequence
<220> FEATURE:
<223> OTHER INFORMATION: relaxin fusion polypeptide

<400> SEQUENCE: 90

| | |
|---|---:|
| cagctgtata gcgcgctggc gaacaaatgc tgccatgtgg gctgcaccaa acgcagcctg | 60 |
| gcgcgctttt gcggcggcgg cagcggcggc ggcagcggca gctggatgga agaagtgatt | 120 |
| aaactgtgcg gccgcgaact ggtgcgcgcg cagattgcga tttgcggcat gagcacctgg | 180 |
| agcggcagcg gcagcggcag cccgacctgc ccgacctgcc ataaatgccc ggtgccggaa | 240 |
| ctgctgggcg gcccgagcgt gtttattttt ccgccgaaac cgaaagatat tctgctgatt | 300 |
| agccagaacg cgaaagtgac ctgcgtggtg gtggatgtga gcgaagaaga accggatgtg | 360 |
| cagtttagct ggtttgtgaa caacgtggaa gtgcataccg cgcagaccca gccgcgcgaa | 420 |
| gaacagtata acagcacctt cgcgtggtg agcgcgctgc cgattcagca tcaggattgg | 480 |
| atgagcggca agaatttaa atgcaaagtg aacaacaaag cgctgccgag cccgattgaa | 540 |
| aaaaccatta gcaaaccgaa aggcctggtg cgcaaaccgc aggtgtatgt gatgggcccg | 600 |
| ccgaccgaac agctgaccga acagaccgtg agcctgacct gcctgaccag cggctttctg | 660 |
| ccgaacgata ttggcgtgga atggaccagc aacggccata ttgaaaaaaa ctataaaaac | 720 |
| accgaaccgg tgatggatag cgatggcagc ttttttatgt atagcaaact gaacgtggaa | 780 |
| cgcagccgct gggatagccg cgcgccgttt gtgtgcagcg tggtgcatga aggcctgcat | 840 |
| aaccatcatg tggaaaaaag cattagccgc ccgccgggca aa | 882 |

<210> SEQ ID NO 91
<211> LENGTH: 933
<212> TYPE: DNA
<213> ORGANISM: Artificial Sequence
<220> FEATURE:
<223> OTHER INFORMATION: relaxin fusion polypeptide

<400> SEQUENCE: 91

| | |
|---|---:|
| cagctgtata gcgcgctggc gaacaaatgc tgccatgtgg gctgcaccaa acgcagcctg | 60 |
| gcgcgctttt gcggcggcgg cagcggcggc ggcagcggca gctggatgga agaagtgatt | 120 |
| aaactgtgcg gccgcgaact ggtgcgcgcg cagattgcga tttgcggcat gagcacctgg | 180 |
| agcggcggcg gcagcggcgg cggcagcggc accctggtga ccgtgagcag cgaaagcaaa | 240 |
| tatggcccgc cgtgcccgcc gtgcccggcg ccggaagcgg cggcgccgga actgctgggc | 300 |
| ggcccgagcg tgtttctgtt ccgccgaaa ccgaaagata ccctgatgat tagccgcacc | 360 |
| ccggaagtga cctgcgtggt ggtggatgtg agccatgaag atccggaagt gaaatttaac | 420 |
| tggtatgtgg atggcgtgga agtgcataac gcgaaaacca accgcgcga gaacagtat | 480 |
| aacagcacct atcgcgtggt gagcgtgctg accgtgctgc atcaggattg gctgaacggc | 540 |
| aaagaatata atgcaaagt gagcaacaaa gcgctgccgg cgccgattga aaaaaccatt | 600 |
| agcaaagcga aggccagcc gcgcgaaccg caggtgtata ccctgccgcc gagccgcgat | 660 |
| gaactgacca aaaaccaggt gagcctgacc tgcctggtga aaggctttta tccgagcgat | 720 |
| attgcgtgg aatgggaaag caacggccag ccggaaaaca actataaaac cacccccgccg | 780 |
| gtgctggata gcgatggcag cttttttctg tatagcaaac tgaccgtgga taaaagccgc | 840 |

| | |
|---|---|
| tggcagcagg gcaacgtgtt tagctgcagc gtgatgcatg aagcgctgca taaccattat | 900 |
| acccagaaaa gcctgagcct gagcccgggc aaa | 933 |

<210> SEQ ID NO 92
<211> LENGTH: 201
<212> TYPE: DNA
<213> ORGANISM: Artificial Sequence
<220> FEATURE:
<223> OTHER INFORMATION: relaxin fusion polypeptide

<400> SEQUENCE: 92

| | |
|---|---|
| cagctgtata gcgcgctggc gaacaaatgc tgccatgtgg gctgcaccaa acgcagcctg | 60 |
| gcgcgctttt gcggcggcgg cagcggcggc ggcagcggca gctggatgga agaagtgatt | 120 |
| aaactgtgcg gccgcgaact ggtgcgcgcg cagattgcga tttgcggcat gagcacctgg | 180 |
| agcggcggca gcggctgcgg c | 201 |

<210> SEQ ID NO 93
<211> LENGTH: 201
<212> TYPE: DNA
<213> ORGANISM: Artificial Sequence
<220> FEATURE:
<223> OTHER INFORMATION: relaxin fusion polypeptide

<400> SEQUENCE: 93

| | |
|---|---|
| ggctgcggca gcggcggcca gctgtatagc gcgctggcga acaaatgctg ccatgtgggc | 60 |
| tgcaccaaac gcagcctggc gcgcttttgc ggcggcggca gcggcggcgg cagcggcagc | 120 |
| tggatggaag aagtgattaa actgtgcggc cgcgaactgg tgcgcgcgca gattgcgatt | 180 |
| tgcggcatga gcacctggag c | 201 |

<210> SEQ ID NO 94
<211> LENGTH: 2238
<212> TYPE: DNA
<213> ORGANISM: Artificial Sequence
<220> FEATURE:
<223> OTHER INFORMATION: relaxin fusion polypeptide

<400> SEQUENCE: 94

| | |
|---|---|
| gtgccggata aaccgtgcgc ctggtgcgcg gtgagcgaac atgaagcgac caaatgccag | 60 |
| agctttcgcg atcatatgaa aagcgtgatt ccgagcgatg cccgagcgt ggcgtgcgtg | 120 |
| aaaaaagcga gctatctgga ttgcattcgc gcgattgcgg cgaacgaagc ggatgcggtg | 180 |
| accctggatc cgggcctggt gtatgatgcg tatctggcgc cgaacaacct gaaaccggtg | 240 |
| gtggcggaat ttatggcag caaagaagat ccgcagacct tttattatgc ggtggcggtg | 300 |
| gtgaaaaaag atagcggctt tcagatgaac cagctgcgcg gcaaaaaaag ctgccatacc | 360 |
| ggcctgggcc gcagcgcggg ctggaacatt ccgattggcc tgctgtattg cgatctgccg | 420 |
| gaaccgcgca aaccgctgga aaaagcggtg gcgaactttt ttagcggcag ctgcgcgccg | 480 |
| tgcgcggatg gcaccgattt tccgcagctg tgccagctgt gcccgggctg cggctgcagc | 540 |
| accctgaacc agtattttgg ctatagcggc gcgtttaaat gcctgaaaga tggcgcgggc | 600 |
| gatgtggcgt ttgtgaaaca tagcaccatt tttgaaaacc tggcgaacaa agcggatcgc | 660 |
| gatcagtatg aactgctgtg cctggataac acccgcaaac cggtggatga atataaagat | 720 |
| tgccatctgg cgcaggtgcc gagccatacc gtggtggcgc gcagcatggg cggcaaagaa | 780 |
| gatctgattt gggaactgct gaaccaggcg caggaacatt ttggcaaaga taaaagcaaa | 840 |
| gaatttcagc tgtttagcag cccgcatggc aaagatctgc tgtttaaaga tagcgcgcat | 900 |

-continued

```
ggctttctga aagtgccgcc gcgcatggat gcgaaaatgt atctgggcta tgaatatgtg    960
accgcgattc gcaacctgcg cgaaggcacc tgcccggaag cgccgaccga tgaatgcaaa   1020
ccggtgaaat ggtgcgcgct gagccatcat gaacgcctga atgcgatga atggagcgtg    1080 aacagcgtgg gcaaaattga atgcgtgagc gcggaaacca ccgaagattg cattgcgaaa   1140
attatgaacg gcgaagcgga tgcgatgagc ctggatggcg gctttgtgta tattgcgggc   1200
aaatgcggcc tggtgccggt gctggcgaaa actataaca aaagcgataa ctgcgaagat    1260
accccggaag cgggctattt gcggtggcg gtggtgaaaa aaagcgcgag cgatctgacc    1320
tgggataacc tgaaaggcaa aaaaagctgc cataccgcgg tgggccgcac cgcgggctgg   1380
aacattccga tgggcctgct gtataacaaa attaaccatt gccgctttga tgaattttt    1440 agcgaaggct gcgcgccggg cagcaaaaaa gatagcagcc tgtgcaaact gtgcatgggc   1500
agcggcctga acctgtgcga accgaacaac aaagaaggct attatggcta taccggcgcg   1560
tttcgctgcc tggtggaaaa aggcgatgtg gcgtttgtga acatcagac cgtgccgcag    1620 aacaccggcg gcaaaaaccc ggatccgtgg gcgaaaaacc tgaacgaaaa agattatgaa   1680
ctgctgtgcc tggatggcac ccgcaaaccg gtggaagaat atgcgaactg ccatctggcg   1740
cgcgcgccga accatgcggt ggtgacccgc aaagataaag aagcgtgcgt gcataaaatt   1800
ctgcgccagc agcagcatct gtttggcagc aacgtgaccg attgcagcgg caacttttgc   1860
ctgtttcgca gcgaaaccaa agatctgctg tttcgcgatg ataccgtgtg cctggcgaaa   1920
ctgcatgatc gcaacaccta tgaaaaatat ctgggcgaag aatatgtgaa agcggtgggc   1980
aacctgcgca aatgcagcac cagcagcctg ctggaagcgt gcacctttcg ccgcccgatt   2040
gaaggccgca tggatcagct gtatagcgcg ctggcgaaca atgcgctgcca tgtgggctgc   2100 accaaacgca gcctggcgcg ctttgcggc ggcggcagcg gcggcggcag cggcagctgg   2160
atggaagaag tgattaaaac tgtgcggccgc gaactggtgc gcgcgcagat tgcgattgc    2220 ggcatgagca cctggagc                                                  2238
```

<210> SEQ ID NO 95
<211> LENGTH: 2538
<212> TYPE: DNA
<213> ORGANISM: Artificial Sequence
<220> FEATURE:
<223> OTHER INFORMATION: relaxin fusion polypeptide

<400> SEQUENCE: 95

```
gtgccggata aaaccgtgcg ctggtgcgcg gtgagcgaac atgaagcgac caaatgccag     60
agctttcgcg atcatatgaa aagcgtgatt ccgagcgatg gcccgagcgt ggcgtgcgtg   120 aaaaagcga gctatctgga ttgcattcgc gcgattgcgg cgaacgaagc ggatgcggtg    180
accctggatg cgggcctggt gtatgatgcg tatctggcgc gaacaacct gaaaccggtg    240 gtggcggaat ttatggcag caaagaagat ccgcagacct ttattatgc ggtggcggtg    300 gtgaaaaaag atagcggctt tcagatgaac cagctgcgcg gcaaaaaaag ctgccatacc    360
ggcctgggcc gcagcgcggg ctggaacatt ccgattggcc tgctgtattg cgatctgccg   420
gaaccgcgca accgctgga aaaagcggtg gcgaactttt ttagcggcag ctgcgcgccg    480
tgcgcggatg gcaccgattt tccgcagctg tgccagctgt gcccgggctg cggctgcagc    540
accctgaacc agtattttgg ctatagcggc gcgtttaaat gcctgaaaga tggcgcgggc    600
gatgtggcgt ttgtgaaaca tagcaccatt tttgaaaacc tggcgaacaa agcggatcgc    660
```

```
gatcagtatg aactgctgtg cctggataac acccgcaaac cggtggatga atataaagat    720
tgccatctgg cgcaggtgcc gagccatacc gtggtggcgc gcagcatggg cggcaaagaa    780
gatctgattt gggaactgct gaaccaggcg caggaacatt ttggcaaaga taaaagcaaa    840
gaatttcagc tgtttagcag cccgcatggc aaagatctgc tgtttaaaga tagcgcgcat    900
ggctttctga aagtgccgcc gcgcatggat gcgaaaatgt atctgggcta tgaatatgtg    960
accgcgattc gcaacctgcg cgaaggcacc tgcccggaag cgccgaccga tgaatgcaaa   1020
ccggtgaaat ggtgcgcgct gagccatcat gaacgcctga atgcgatga atggagcgtg    1080 aacagcgtgg gcaaaattga atgcgtgagc gcggaaacca ccgaagattg cattgcgaaa   1140
attatgaacg gcgaagcgga tgcgatgagc ctggatggcg gctttgtgta tattgcgggc   1200
aaatgcggcc tggtgccggt gctggcgaaa aactataaca aaagcgataa ctgcgaagat   1260
accccggaag cgggctattt tgcggtggcg gtggtgaaaa aaagcgcgag cgatctgacc   1320
tgggataacc tgaaaggcaa aaaaagctgc cataccgcgg tgggccgcac cgcgggctgg   1380
aacattccga tgggcctgct gtataacaaa attaaccatt gccgctttga tgaattttt    1440 agcgaaggct gcgcgccggg cagcaaaaaa gatagcagcc tgtgcaaact gtgcatgggc   1500
agcggcctga acctgtgcga accgaacaac aaagaaggct attatggcta taccggcgcg   1560
tttcgctgcc tggtggaaaa aggcgatgtg gcgtttgtga acatcagac cgtgccgcag    1620 aacaccggcg gcaaaaaccc ggatccgtgg gcgaaaaacc tgaacgaaaa agattatgaa   1680
ctgctgtgcc tggatggcac ccgcaaaccg gtggaagaat atgcgaactg ccatctggcg   1740
cgcgcgccga accatgcggt ggtgacccgc aaagataaag aagcgtgcgt gcataaaatt   1800
ctgcgccagc agcagcatct gtttggcagc aacgtgaccg attgcagcgg caacttttgc   1860
ctgtttcgca gcgaaaccaa agatctgctg tttcgcgatg ataccgtgtg cctggcgaaa   1920
ctgcatgatc gcaacaccta tgaaaaatat ctgggcgaag aatatgtgaa agcggtgggc   1980
aacctgcgca aatgcagcac cagcagcctg ctggaagcgt gcacctttcg ccgcccgatt   2040
gaaggccgca tggatgatag ctggatggaa gaagtgatta aactgtgcgg ccgcgaactg   2100
gtgcgcgcgc agattgcgat tgcggcatg agcacctgga gcaaacgcag cctgagccag   2160
gaagatgcgc cgcagacccc gcgcccggtg gcggaaattg tgccgagctt tattaacaaa   2220
gataccgaaa ccattaacat gatgagcgaa tttgtggcga acctgccgca ggaactgaaa   2280
ctgaccctga gcgaaatgca gccggcgctg ccgcagctgc agcagcatgt gccggtgctg   2340
aaagatagca gcctgctgtt tgaagaattt aaaaaactga ttcgcaaccg ccagagcgaa   2400
gcggcggata gcagcccgag cgaactgaaa tatctgggcc tggatacccca tagccgcaaa   2460 aaacgccagc tgtatagcgc gctggcgaac aaatgctgcc atgtgggctg caccaaacgc   2520
agcctggcgc gcttttgc                                                 2538
```

<210> SEQ ID NO 96
<211> LENGTH: 1956
<212> TYPE: DNA
<213> ORGANISM: Artificial Sequence
<220> FEATURE:
<223> OTHER INFORMATION: relaxin fusion polypeptide

<400> SEQUENCE: 96

```
gatgcgcata aaagcgaagt ggcgcatcgc tttaaagatc tgggcgaaga aaactttaaa     60
gcgctggtgc tgattgcgtt tgcgcagtat ctgcagcagt gcccgtttga agatcatgtg    120
aaactggtga acgaagtgac cgaatttgcg aaaacctgcg tggcggatga aagcgcggaa    180
```

```
aactgcgata aaagcctgca tacccctgttt ggcgataaac tgtgcaccgt ggcgaccctg    240
cgcgaaacct atggcgaaat ggcggattgc tgcgcgaaac aggaaccgga acgcaacgaa    300
tgctttctgc agcataaaga tgataacccg aacctgccgc gcctggtgcg cccggaagtg    360
gatgtgatgt gcaccgcgtt tcatgataac gaagaaacct ttctgaaaaa atatctgtat    420
gaaattgcgc gccgccatcc gtattttat gcgccggaac tgctgttttt tgcgaaacgc    480
tataaagcgg cgtttaccga atgctgccag gcggcggata agcggcgtg cctgctgccg    540 aaactggatg aactgcgcga tgaaggcaaa gcgagcagcg cgaaacagcg cctgaaatgc    600
gcgagcctgc agaaatttgg cgaacgcgcg tttaaagcgt gggcggtggc gcgcctgagc    660
cagcgctttc gaaagcgga atttgcggaa gtgagcaaac tggtgaccga tctgaccaaa    720
gtgcataccg aatgctgcca tggcgatctg ctggaatgcg cggatgatcg cgcggatctg    780
gcgaaatata tttgcgaaaa ccaggatagc attagcagca aactgaaaga atgctgcgaa    840
aaaccgctgt ggaaaaaag ccattgcatt gcggaagtgg aaaacgatga atgccggcg    900 gatctgccga gcctggcggc ggattttgtg aaagcaaag atgtgtgcaa aaactatgcg    960
gaagcgaaag atgtgtttct ggcatgtttt ctgtatgaat atgcgcgccg ccatccggat    1020
tatagcgtgg tgctgctgct gcgcctggcg aaaacctatg aaaccaccct ggaaaaatgc    1080
tgcgcggcgg cggatccgca tgaatgctat gcgaaagtgt ttgatgaatt taaaccgctg    1140
gtggaagaac cgcagaacct gattaaacag aactgcgaac tgtttgaaca gctgggcgaa    1200
tataaatttc agaacgcgct gctggtgcgc tataccaaaa aagtgccgca ggtgagcacc    1260
ccgaccctgg tggaagtgag ccgcaacctg gcaaagtgg gcagcaaatg ctgcaaacat    1320
ccggaagcga aacgcatgcc gtgcgcggaa gattatctga gcgtggtgct gaaccagctg    1380
tgcgtgctgc atgaaaaaac cccggtgagc gatcgcgtga ccaaatgctg caccgaaagc    1440
ctggtgaacc gccgcccgtg ctttagcgcg ctggaagtgg atgaaaccta tgtgccgaaa    1500
gaatttaacg cggaaacctt tacctttcat gcggatattt gcaccctgag cgaaaaagaa    1560
cgccagatta aaaaacagac cgcgctggtg gaactggtga acataaaacc gaaagcgacc    1620
aaagaacagc tgaaagcggt gatggatgat tttgcggcgt tgtggaaaa atgctgcaaa    1680 gcggatgata agaaacctg ctttgcggaa gaaggcaaaa aactggtggc ggcgagccag    1740
gcggcgctgg gcctgattga aggccgcatg gatcagctgt atagcgcgct ggcgaacaaa    1800
tgctgccatg tgggctgcac caaacgcagc ctggcgcgct tttgcggcgg cggcagcggc    1860
ggcggcagcg gcagctggat ggaagaagtg attaaactgt gcggccgcga actggtgcgc    1920
gcgcagattg cgatttgcgg catgagcacc tggagc                              1956
```

<210> SEQ ID NO 97
<211> LENGTH: 2256
<212> TYPE: DNA
<213> ORGANISM: Artificial Sequence
<220> FEATURE:
<223> OTHER INFORMATION: relaxin fusion polypeptide

<400> SEQUENCE: 97

```
gatgcgcata aaagcgaagt ggcgcatcgc tttaaagatc tgggcgaaga aaactttaaa     60
gcgctggtgc tgattgcgtt tgcgcagtat ctgcagcagt gcccgtttga agatcatgtg    120
aaactggtga cgaagtgac cgaatttgcg aaaacctgcg tggcggatga aagcgcggaa    180
aactgcgata aaagcctgca tacccctgttt ggcgataaac tgtgcaccgt ggcgaccctg    240
```

| | |
|---|---|
| cgcgaaacct atggcgaaat ggcggattgc tgcgcgaaac aggaaccgga acgcaacgaa | 300 |
| tgctttctgc agcataaaga tgataacccg aacctgccgc gcctggtgcg cccggaagtg | 360 |
| gatgtgatgt gcaccgcgtt tcatgataac gaagaaacct ttctgaaaaa atatctgtat | 420 |
| gaaattgcgc cgccatcc gtattttat cgccggaac tgctgttttt tgcgaaacgc | 480 |
| tataaagcgg cgtttaccga atgctgccag gcggcggata agcggcgtg cctgctgccg | 540 |
| aaactggatg aactgcgcga tgaaggcaaa gcgagcagcg cgaaacagcg cctgaaatgc | 600 |
| gcgagcctgc agaaatttgg cgaacgcgcg tttaaagcgt gggcggtggc gcgcctgagc | 660 |
| cagcgctttc cgaaagcgga atttgcgaa gtgagcaaac tggtgaccga tctgaccaaa | 720 |
| gtgcataccg aatgctgcca tggcgatctg ctggaatgcg cggatgatcg cgcggatctg | 780 |
| gcgaaatata tttgcgaaaa ccaggatagc attagcagca aactgaaaga tgctgcgaa | 840 |
| aaaccgctgc tggaaaaaag ccattgcatt gcggaagtgg aaaacgatga aatgccggcg | 900 |
| gatctgccga gcctggcggc ggattttgtg gaaagcaaag atgtgtgcaa aaactatgcg | 960 |
| gaagcgaaag atgtgtttct gggcatgttt ctgtatgaat atgcgcgccg ccatccggat | 1020 |
| tatagcgtgg tgctgctgct gcgcctggcg aaaacctatg aaaccaccct ggaaaaatgc | 1080 |
| tgcgcggcg cggatccgca tgaatgctat gcgaaagtgt ttgatgaatt taaaccgctg | 1140 |
| gtggaagaac cgcagaacct gattaaacag aactgcgaac tgtttgaaca gctgggcgaa | 1200 |
| tataaatttc agaacgcgct gctggtgcgc tataccaaaa agtgccgca ggtgagcacc | 1260 |
| ccgaccctgg tggaagtgag ccgcaacctg ggcaaagtgg gcagcaaatg ctgcaaacat | 1320 |
| ccggaagcga aacgcatgcc gtgcgcggaa gattatctga gcgtggtgct gaaccagctg | 1380 |
| tgcgtgctgc atgaaaaaac cccggtgagc gatcgcgtga ccaaatgctg caccgaaagc | 1440 |
| ctggtgaacc gccgccgtg ctttagcgcg ctggaagtgg atgaaaccta tgtgccgaaa | 1500 |
| gaatttaacg cggaaaccct tacctttcat gcggatattt gcaccctgag cgaaaaagaa | 1560 |
| cgccagatta aaaaacagac cgcgctggtg gaactggtga acataaaacc gaaagcgacc | 1620 |
| aaagaacagc tgaaagcggt gatggatgat tttgcggcgt ttgtggaaaa atgctgcaaa | 1680 |
| gcggatgata agaaacctg ctttgcggaa gaaggcaaaa aactggtggc ggcgagccag | 1740 |
| gcggcgctgg gcctgattga aggccgcatg gatgatagct ggatggaaga agtgattaaa | 1800 |
| ctgtgcggcc gcgaactggt gcgcgcgcag attgcgattt cggcatgag cacctggagc | 1860 |
| aaacgcagcc tgagccagga agatgcgccg cagacccgc gcccggtggc ggaaattgtg | 1920 |
| ccgagctta ttaacaaaga taccgaaacc attaacatga tgagcgaatt tgtggcgaac | 1980 |
| ctgccgcagg aactgaaact gacccctgagc gaaatgcagc cggcgctgcc gcagctgcag | 2040 |
| cagcatgtgc cggtgctgaa agatagcagc ctgctgtttg aagaatttaa aaaactgatt | 2100 |
| cgcaaccgcc agagcgaagc ggcggatagc agcccgagcg aactgaaata tctgggcctg | 2160 |
| gatacccata ccgcaaaaa acgccagctg tatagcgcgc tggcgaacaa atgctgccat | 2220 |
| gtgggctgca ccaaacgcag cctggcgcgc ttttgc | 2256 |

<210> SEQ ID NO 98
<211> LENGTH: 894
<212> TYPE: DNA
<213> ORGANISM: Artificial Sequence
<220> FEATURE:
<223> OTHER INFORMATION: relaxin fusion polypeptide

<400> SEQUENCE: 98

| | |
|---|---|
| cagctgtata gcgcgctggc gaacaaatgc tgccatgtgg gctgcaccaa acgcagcctg | 60 |

```
gcgcgctttt gcaaacgcag cctgagccgc aaaaaacgca gctggatgga agaagtgatt      120
aaactgtgcg gccgcgaact ggtgcgcgcg cagattgcga tttgcggcat gagcacctgg      180
agcattgaag ccgcatgga tccgaaagcg tgcgataaaa cccatacctg cccgccgtgc       240
ccggcgccgg aactgctggg cggcccgagc gtgtttctgt ttccgccgaa accgaaagat      300
accctgatga ttagccgcac cccggaagtg acctgcgtgg tggtggatgt gagccatgaa      360
gatccggaag tgaaatttaa ctggtatgtg atggcgtgg aagtgcataa cgcgaaaacc       420
aaaccgcgcg aagaacagta taacagcacc tatcgcgtgg tgagcgtgct gaccgtgctg      480
catcaggatt ggctgaacgg caaagaatat aaatgcaaag tgagcaacaa agcgctgccg      540
gcgccgattg aaaaaaccat tagcaaagcg aaaggccagc cgcgcgaacc gcaggtgtat      600
accctgccgc cgagccgcga tgaactgacc aaaaaccagg tgagcctgac ctgcctggtg      660
aaaggctttt atccgagcga tattgcggtg aatgggaaa gcaacggcca gccggaaaac      720
aactataaaa ccaccccgcc ggtgctggat agcgatggca gcttttttct gtatagcaaa      780
ctgaccgtgg ataaaagccg ctggcagcag ggcaacgtgt ttagctgcag cgtgatgcat      840
gaagcgctgc ataaccatta tacccagaaa agcctgagcc tgagcccggg caaa            894

<210> SEQ ID NO 99
<211> LENGTH: 894
<212> TYPE: DNA
<213> ORGANISM: Artificial Sequence
<220> FEATURE:
<223> OTHER INFORMATION: relaxin fusion polypeptide

<400> SEQUENCE: 99
ccgaaagcgt gcgataaaac ccatacctgc ccgccgtgcc cggcgccgga actgctgggc       60
ggcccgagcg tgtttctgtt tccgccgaaa ccgaaagata ccctgatgat tagccgcacc      120
ccggaagtga cctgcgtggt ggtggatgtg agccatgaag atccggaagt gaaatttaac      180
tggtatgtgg atggcgtgga agtgcataac gcgaaaacca aaccgcgcga agaacagtat      240
aacagcacct atcgcgtggt gagcgtgctg accgtgctgc atcaggattg gctgaacggc      300
aaagaatata aatgcaaagt gagcaacaaa gcgctgccgg cgccgattga aaaaaccatt      360
agcaaagcga aaggccagcc gcgcgaaccg caggtgtata ccctgccgcc gagccgcgat      420
gaactgacca aaaaccaggt gagcctgacc tgcctggtga aaggctttta tccgagcgat      480
attgcggtgg aatgggaaag caacggccag ccggaaaaca actataaaac caccccgccg      540
gtgctggata gcgatggcag cttttttctg tatagcaaac tgaccgtgga taaaagccgc      600
tggcagcagg gcaacgtgtt tagctgcagc gtgatgcatg aagcgctgca taaccattat      660
acccagaaaa gcctgagcct gagcccgggc aaaattgaag ccgcatgga tcagctgtat      720 agcgcgctgg cgaacaaatg ctgccatgtg ggctgcacca acgcagcct ggcgcgcttt       780 tgcaaacgca gcctgagccg caaaaaacgc agctggatga agaagtgat taaactgtgc       840 ggccgcgaac tggtgcgcgc gcagattgcg atttgcggca tgagcacctg gagc            894

<210> SEQ ID NO 100
<211> LENGTH: 165
<212> TYPE: DNA
<213> ORGANISM: Artificial Sequence
<220> FEATURE:
<223> OTHER INFORMATION: relaxin fusion polypeptide

<400> SEQUENCE: 100
```

```
cagctgtata gcgcgctggc gaacaaatgc tgccatgtgg gctgcaccaa acgcagcctg    60
gcgcgctttt gcggcggcgg cagctggatg gaagaagtga ttaaactgtg cggccgcgaa   120
ctggtgcgcg cgcagattgc gatttgcggc atgagcacct ggagc                   165

<210> SEQ ID NO 101
<211> LENGTH: 171
<212> TYPE: DNA
<213> ORGANISM: Artificial Sequence
<220> FEATURE:
<223> OTHER INFORMATION: relaxin fusion polypeptide

<400> SEQUENCE: 101
cagctgtata gcgcgctggc gaacaaatgc tgccatgtgg gctgcaccaa acgcagcctg    60
gcgcgctttt gcggcggcgg cagcggcagc tggatggaag aagtgattaa actgtgcggc   120
cgcgaactgg tgcgcgcgca gattgcgatt tgcggcatga gcacctggag c             171

<210> SEQ ID NO 102
<211> LENGTH: 177
<212> TYPE: DNA
<213> ORGANISM: Artificial Sequence
<220> FEATURE:
<223> OTHER INFORMATION: relaxin fusion polypeptide

<400> SEQUENCE: 102
cagctgtata gcgcgctggc gaacaaatgc tgccatgtgg gctgcaccaa acgcagcctg    60
gcgcgctttt gcggcggcgg cagcggcggc ggcagctgga tggaagaagt gattaaactg   120
tgcggccgcg aactggtgcg cgcgcagatt gcgatttgcg gcatgagcac ctggagc      177

<210> SEQ ID NO 103
<211> LENGTH: 183
<212> TYPE: DNA
<213> ORGANISM: Artificial Sequence
<220> FEATURE:
<223> OTHER INFORMATION: relaxin fusion polypeptide

<400> SEQUENCE: 103
cagctgtata gcgcgctggc gaacaaatgc tgccatgtgg gctgcaccaa acgcagcctg    60
gcgcgctttt gcggcggcgg cagcggcggc ggcagcggca gctggatgga agaagtgatt   120
aaactgtgcg gccgcgaact ggtgcgcgcg cagattgcga tttgcggcat gagcacctgg   180
agc                                                                 183

<210> SEQ ID NO 104
<211> LENGTH: 189
<212> TYPE: DNA
<213> ORGANISM: Artificial Sequence
<220> FEATURE:
<223> OTHER INFORMATION: relaxin fusion polypeptide

<400> SEQUENCE: 104
cagctgtata gcgcgctggc gaacaaatgc tgccatgtgg gctgcaccaa acgcagcctg    60
gcgcgctttt gcggcggcgg cagcggcggc ggcagcggcg gcagctgat ggaagaa      120 gtgattaaac tgtgcggccg cgaactggtg cgcgcgcaga ttgcgatttg cggcatgagc   180
acctggagc                                                           189

<210> SEQ ID NO 105
<211> LENGTH: 201
<212> TYPE: DNA
<213> ORGANISM: Artificial Sequence
```

```
<220> FEATURE:
<223> OTHER INFORMATION: relaxin fusion polypeptide

<400> SEQUENCE: 105
cagctgtata gcgcgctggc gaacaaatgc tgccatgtgg gctgcaccaa acgcagcctg    60
gcgcgctttt gcggcggcgg cagcggcggc ggcagcggcg gcggcagcgg cggcggcagc   120
tggatggaag aagtgattaa actgtgcggc cgcgaactgg tgcgcgcgca gattgcgatt   180
tgcggcatga gcacctggag c                                            201

<210> SEQ ID NO 106
<211> LENGTH: 174
<212> TYPE: DNA
<213> ORGANISM: Artificial Sequence
<220> FEATURE:
<223> OTHER INFORMATION: relaxin fusion polypeptide

<400> SEQUENCE: 106
cagctgtata gcgcgctggc gaacaaatgc tgccatgtgg gctgcaccaa acgcagcctg    60
gcgcgctttt gcggcggcgg cagcggcggc agctggatgg aagaagtgat taaactgtgc   120
ggccgcgaac tggtgcgcgc gcagattgcg atttgcggca tgagcacctg gagc         174

<210> SEQ ID NO 107
<211> LENGTH: 192
<212> TYPE: DNA
<213> ORGANISM: Artificial Sequence
<220> FEATURE:
<223> OTHER INFORMATION: relaxin fusion polypeptide

<400> SEQUENCE: 107
cagctgtata gcgcgctggc gaacaaatgc tgccatgtgg gctgcaccaa acgcagcctg    60
gcgcgctttt gcggcggcgg cagcggcggc ggcagcggcg gcagcag ctggatggaa      120 gaagtgatta aactgtgcgg ccgcgaactg gtgcgcgcgc agattgcgat ttgcggcatg   180
agcacctgga gc                                                      192

<210> SEQ ID NO 108
<211> LENGTH: 195
<212> TYPE: DNA
<213> ORGANISM: Artificial Sequence
<220> FEATURE:
<223> OTHER INFORMATION: relaxin fusion polypeptide

<400> SEQUENCE: 108
cagctgtata gcgcgctggc gaacaaatgc tgccatgtgg gctgcaccaa acgcagcctg    60
gcgcgctttt gcggcggcgg cagcggcggc ggcagcggcg gcggcagcgg cagctggatg   120
gaagaagtga ttaaactgtg cggccgcgaa ctggtgcgcg cgcagattgc gatttgcggc   180
atgagcacct ggagc                                                   195

<210> SEQ ID NO 109
<211> LENGTH: 198
<212> TYPE: DNA
<213> ORGANISM: Artificial Sequence
<220> FEATURE:
<223> OTHER INFORMATION: relaxin fusion polypeptide

<400> SEQUENCE: 109
cagctgtata gcgcgctggc gaacaaatgc tgccatgtgg gctgcaccaa acgcagcctg    60
gcgcgctttt gcggcggcgg cagcggcggc ggcagcggcg gcggcagcgg cggcagctgg   120
```

```
atggaagaag tgattaaact gtgcggccgc gaactggtgc gcgcgcagat tgcgatttgc      180
ggcatgagca cctggagc                                                    198

<210> SEQ ID NO 110
<211> LENGTH: 894
<212> TYPE: DNA
<213> ORGANISM: Artificial Sequence
<220> FEATURE:
<223> OTHER INFORMATION: relaxin fusion polypeptide

<400> SEQUENCE: 110
cagctgtata gcgcgctggc gaacaaatgc tgccatgtgg gctgcaccaa acgcagcctg       60
gcgcgctttt gcggcggcgg cagcggcggc ggcagcggca gctggatgga agaagtgatt      120
aaactgtgcg gccgcgaact ggtgcgcgcg cagattgcga tttgcggcat gagcacctgg      180
agcattgaag gccgcatgga tccgaaagcg tgcgataaaa cccatacctg cccgccgtgc      240
ccggcgccgg aactgctggg cggcccgagc gtgtttctgt tccgccgaaa ccgaaagat       300 accctgatga ttagccgcac cccggaagtg acctgcgtgg tggtggatgt gagccatgaa      360
gatccggaag tgaaatttaa ctggtatgtg gatggcgtgg aagtgcataa cgcgaaaacc      420
aaaccgcgcg aagaacagta taacagcacc tatcgcgtgg tgagcgtgct gaccgtgctg      480
catcaggatt ggctgaacgg caaagaatat aaatgcaaag tgagcaacaa agcgctgccg      540
gcgccgattg aaaaaaccat tagcaaagcg aaaggccagc cgcgcgaacc gcaggtgtat      600
accctgccgc cgagccgcga tgaactgacc aaaaaccagg tgagcctgac ctgcctggtg      660
aaaggctttt atccgagcga tattgcggtg gaatgggaaa gcaacggcca gccggaaaac      720
aactataaaa ccaccccgcc ggtgctggat agcgatggca gctttttcct gtatagcaaa      780
ctgaccgtgg ataaaagccg ctggcagcag ggcaacgtgt ttagctgcag cgtgatgcat      840
gaagcgctgc ataaccatta cccagaaaa agcctgagcc tgagcccggg caaa            894

<210> SEQ ID NO 111
<211> LENGTH: 873
<212> TYPE: DNA
<213> ORGANISM: Artificial Sequence
<220> FEATURE:
<223> OTHER INFORMATION: relaxin fusion polypeptide

<400> SEQUENCE: 111
cagctgtata gcgcgctggc gaacaaatgc tgccatgtgg gctgcaccaa acgcagcctg       60
gcgcgctttt gcggcggcgg cagcggcggc ggcagcggca gctggatgga agaagtgatt      120
aaactgtgcg gccgcgaact ggtgcgcgcg cagattgcga tttgcggcat gagcacctgg      180
agcggcggca gcccgacctg cccgacctgc cataaatgcc cggtgccgga actgctgggc      240
ggcccgagcg tgtttatttt tccgccgaaa ccgaaagata ttctgctgat tagccagaac      300
gcgaaagtga cctgcgtggt ggtggatgtg agcgaagaag aaccggatgt gcagtttagc      360
tggtttgtga caacgtggga agtgcatacc gcgcagaccc agccgcgcga agaacagtat      420
aacagcacct ttcgcgtggt gagcgcgctg ccgattcagc atcaggattg gatgagcggc      480
aaagaattta atgcaaagt gaacaacaaa gcgctgccga cccgattga aaaaaccatt      540 agcaaaccga aaggcctggt gcgcaaaccg caggtgtatg tgatgggccc gccgaccgaa      600
cagctgaccg aacagaccgt gagcctgacc tgcctgacca cggctttct gccgaacgat      660 attggcgtgg aatggaccag caacggccat attgaaaaaa ctataaaaa caccgaaccg      720 gtgatggata gcgatggcag ctttttatg tatagcaaac tgaacgtgga acgcagccgc      780
```

| | |
|---|---|
| tgggatagcc gcgcgccgtt tgtgtgcagc gtggtgcatg aaggcctgca taaccatcat | 840 |
| gtggaaaaaa gcattagccg cccgccgggc aaa | 873 |

<210> SEQ ID NO 112
<211> LENGTH: 882
<212> TYPE: DNA
<213> ORGANISM: Artificial Sequence
<220> FEATURE:
<223> OTHER INFORMATION: relaxin fusion polypeptide

<400> SEQUENCE: 112

| | |
|---|---|
| cagctgtata gcgcgctggc gaacaaatgc tgccatgtgg gctgcaccaa acgcagcctg | 60 |
| gcgcgctttt gcggcggcgg cagcggcggc ggcagcggca gctggatgga agaagtgatt | 120 |
| aaactgtgcg gccgcgaact ggtgcgcgcg cagattgcga tttgcggcat gagcacctgg | 180 |
| agcggcggca gcggcggcag cccgacctgc ccgacctgcc ataaatgccc ggtgccggaa | 240 |
| ctgctgggcg gcccgagcgt gtttattttt ccgccgaaac cgaaagatat tctgctgatt | 300 |
| agccagaacg cgaaagtgac ctgcgtggtg gtggatgtga gcgaagaaga accggatgtg | 360 |
| cagtttagct ggtttgtgaa caacgtggaa gtgcataccg cgcagaccca gccgcgcgaa | 420 |
| gaacagtata acagcacctt tcgcgtggtg agcgcgctgc cgattcagca tcaggattgg | 480 |
| atgagcggca aagaatttaa atgcaaagtg aacaacaaag cgctgccgag cccgattgaa | 540 |
| aaaaccatta gcaaaccgaa aggcctggtg cgcaaaccgc aggtgtatgt gatgggcccg | 600 |
| ccgaccgaac agctgaccga acagaccgtg agcctgacct gcctgaccag cggctttctg | 660 |
| ccgaacgata ttggcgtgga atggaccagc aacggccata ttgaaaaaaa ctataaaaac | 720 |
| accgaaccgg tgatggatag cgatggcagc tttttttatgt atagcaaact gaacgtggaa | 780 |
| cgcagccgct gggatagccg cgcgccgttt gtgtgcagcg tggtgcatga aggcctgcat | 840 |
| aaccatcatg tggaaaaaag cattagccgc ccgccgggca aa | 882 |

<210> SEQ ID NO 113
<211> LENGTH: 891
<212> TYPE: DNA
<213> ORGANISM: Artificial Sequence
<220> FEATURE:
<223> OTHER INFORMATION: relaxin fusion polypeptide

<400> SEQUENCE: 113

| | |
|---|---|
| cagctgtata gcgcgctggc gaacaaatgc tgccatgtgg gctgcaccaa acgcagcctg | 60 |
| gcgcgctttt gcggcggcgg cagcggcggc ggcagcggca gctggatgga agaagtgatt | 120 |
| aaactgtgcg gccgcgaact ggtgcgcgcg cagattgcga tttgcggcat gagcacctgg | 180 |
| agcggcggca gcggcggcag cggcggcagc ccgacctgcc cgacctgcca taatgcccg | 240 |
| gtgccggaac tgctgggcgg cccgagcgtg tttatttttc gccgaaacc gaaagatatt | 300 |
| ctgctgatta gccagaacgc gaaagtgacc tgcgtggtgg tggatgtgag cgaagaagaa | 360 |
| ccggatgtgc agtttagctg gtttgtgaac aacgtggaag tgcataccgc gcagacccag | 420 |
| ccgcgcgaag aacagtataa cagcaccttt cgcgtggtga gcgcgctgcc gattcagcat | 480 |
| caggattgga tgagcggcaa agaatttaaa tgcaaagtga acaacaaagc gctgccgagc | 540 |
| ccgattgaaa aaaccattag caaaccgaaa ggcctggtgc gcaaaccgca ggtgtatgtg | 600 |
| atgggcccgc cgaccgaaca gctgaccgaa cagaccgtga gcctgacctg cctgaccagc | 660 |
| ggctttctgc cgaacgatat tggcgtggaa tggaccagca acggccatat tgaaaaaaac | 720 |

| | |
|---|---|
| tataaaaaca ccgaaccggt gatggatagc gatggcagct tttttatgta tagcaaactg | 780 |
| aacgtggaac gcagccgctg ggatagccgc gcgccgtttg tgtgcagcgt ggtgcatgaa | 840 |
| ggcctgcata accatcatgt ggaaaaaagc attagccgcc cgccgggcaa a | 891 |

<210> SEQ ID NO 114
<211> LENGTH: 876
<212> TYPE: DNA
<213> ORGANISM: Artificial Sequence
<220> FEATURE:
<223> OTHER INFORMATION: relaxin fusion polypeptide

<400> SEQUENCE: 114

| | |
|---|---|
| ccgacctgcc cgacctgcca taaatgcccg gtgccggaac tgctgggcgg cccgagcgtg | 60 |
| tttatttttc cgccgaaacc gaaagatatt ctgctgatta gccagaacgc gaaagtgacc | 120 |
| tgcgtggtgg tggatgtgag cgaagaagaa ccggatgtgc agtttagctg gtttgtgaac | 180 |
| aacgtggaag tgcataccgc gcagacccag ccgcgcgaag aacagtataa cagcaccttt | 240 |
| cgcgtggtga gcgcgctgcc gattcagcat caggattgga tgagcggcaa agaatttaaa | 300 |
| tgcaaagtga acaacaaagc gctgccgagc ccgattgaaa aaaccattag caaaccgaaa | 360 |
| ggcctggtgc gcaaaccgca ggtgtatgtg atgggcccgc cgaccgaaca gctgaccgaa | 420 |
| cagaccgtga gcctgacctg cctgaccagc ggctttctgc cgaacgatat tgcgtggaa | 480 |
| tggaccagca acggccatat tgaaaaaaac tataaaaaca ccgaaccggt gatggatagc | 540 |
| gatggcagct tttttatgta tagcaaactg aacgtggaac gcagccgctg ggatagccgc | 600 |
| gcgccgtttg tgtgcagcgt ggtgcatgaa ggcctgcata accatcatgt ggaaaaaagc | 660 |
| attagccgcc cgccgggcaa aggcggcagc ccgcagctgt atagcgcgct ggcgaacaaa | 720 |
| tgctgccatg tgggctgcac caaacgcagc ctggcgcgct tttgcggcgg cggcagcggc | 780 |
| ggcggcagcg gcagctggat ggaagaagtg attaaactgt gcggccgcga actggtgcgc | 840 |
| gcgcagattg cgatttgcgg catgagcacc tggagc | 876 |

<210> SEQ ID NO 115
<211> LENGTH: 885
<212> TYPE: DNA
<213> ORGANISM: Artificial Sequence
<220> FEATURE:
<223> OTHER INFORMATION: relaxin fusion polypeptide

<400> SEQUENCE: 115

| | |
|---|---|
| ccgacctgcc cgacctgcca taaatgcccg gtgccggaac tgctgggcgg cccgagcgtg | 60 |
| tttatttttc cgccgaaacc gaaagatatt ctgctgatta gccagaacgc gaaagtgacc | 120 |
| tgcgtggtgg tggatgtgag cgaagaagaa ccggatgtgc agtttagctg gtttgtgaac | 180 |
| aacgtggaag tgcataccgc gcagacccag ccgcgcgaag aacagtataa cagcaccttt | 240 |
| cgcgtggtga gcgcgctgcc gattcagcat caggattgga tgagcggcaa agaatttaaa | 300 |
| tgcaaagtga acaacaaagc gctgccgagc ccgattgaaa aaaccattag caaaccgaaa | 360 |
| ggcctggtgc gcaaaccgca ggtgtatgtg atgggcccgc cgaccgaaca gctgaccgaa | 420 |
| cagaccgtga gcctgacctg cctgaccagc ggctttctgc cgaacgatat tgcgtggaa | 480 |
| tggaccagca acggccatat tgaaaaaaac tataaaaaca ccgaaccggt gatggatagc | 540 |
| gatggcagct tttttatgta tagcaaactg aacgtggaac gcagccgctg ggatagccgc | 600 |
| gcgccgtttg tgtgcagcgt ggtgcatgaa ggcctgcata accatcatgt ggaaaaaagc | 660 |
| attagccgcc cgccgggcaa aggcggcagc ggcggcagcc gcagctgta tagcgcgctg | 720 |

```
gcgaacaaat gctgccatgt gggctgcacc aaacgcagcc tggcgcgctt ttgcggcggc    780
ggcagcggcg gcggcagcgg cagctggatg aagaagtga ttaaactgtg cggccgcgaa    840
ctggtgcgcg cgcagattgc gatttgcggc atgagcacct ggagc                  885
```

<210> SEQ ID NO 116
<211> LENGTH: 894
<212> TYPE: DNA
<213> ORGANISM: Artificial Sequence
<220> FEATURE:
<223> OTHER INFORMATION: relaxin fusion polypeptide

<400> SEQUENCE: 116

```
ccgacctgcc cgacctgcca taaatgcccg gtgccggaac tgctgggcgg cccgagcgtg     60 tttattttc cgccgaaacc gaaagatatt ctgctgatta gccagaacgc gaaagtgacc    120
tgcgtggtgg tggatgtgag cgaagaagaa ccggatgtgc agtttagctg gtttgtgaac    180
aacgtggaag tgcataccgc gcagacccag ccgcgcgaag aacagtataa cagcaccttt    240
cgcgtggtga gcgcgctgcc gattcagcat caggattgga tgagcggcaa agaatttaaa    300
tgcaaagtga acaacaaagc gctgccgagc ccgattgaaa aaaccattag caaaccgaaa    360
ggcctggtgc gcaaaccgca ggtgtatgtg atgggcccgc cgaccgaaca gctgaccgaa    420
cagaccgtga gcctgacctg cctgaccagc ggctttctgc gaacgatat ggcgtggaa    480 tggaccagca acggccatat tgaaaaaaac tataaaaaca ccgaaccggt gatggatagc    540
gatggcagct tttttatgta tagcaaactg aacgtggaac gcagccgctg gatagccgc    600 gcgccgtttg tgtgcagcgt ggtgcatgaa ggcctgcata ccatcatgt ggaaaaaagc    660 attagccgcc cgccgggcaa aggcggcagc ggcggcagcg gcggcagccc gcagctgtat    720
agcgcgctgg cgaacaaatg ctgccatgtg ggctgcacca aacgcagcct ggcgcgcttt    780
tgcggcggcg gcagcggcgg cggcagcggc agctggatgg aagaagtgat taaactgtgc    840
ggccgcgaac tggtgcgcgc gcagattgcg atttgcggca tgagcacctg gagc         894
```

<210> SEQ ID NO 117
<211> LENGTH: 24
<212> TYPE: PRT
<213> ORGANISM: Homo Sapiens

<400> SEQUENCE: 117

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 118
<211> LENGTH: 16
<212> TYPE: PRT
<213> ORGANISM: Homo Sapiens

<400> SEQUENCE: 118

Lys Cys Cys His Val Gly Cys Thr Lys Arg Ser Leu Ala Arg Phe Cys
1               5                   10                  15

<210> SEQ ID NO 119
<211> LENGTH: 28
<212> TYPE: PRT
<213> ORGANISM: Homo Sapiens

<400> SEQUENCE: 119

```
Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser
            20                  25
```

<210> SEQ ID NO 120
<211> LENGTH: 231
<212> TYPE: PRT
<213> ORGANISM: Homo Sapiens

<400> SEQUENCE: 120

```
Pro Lys Ala Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 121
<211> LENGTH: 226
<212> TYPE: PRT
<213> ORGANISM: Rattus Norvegicus

<400> SEQUENCE: 121

```
Thr Cys Pro Thr Cys His Lys Cys Pro Val Pro Glu Leu Leu Gly Gly
1               5                   10                  15

Pro Ser Val Phe Ile Phe Pro Lys Pro Lys Asp Ile Leu Leu Ile
                20                  25                  30

Ser Gln Asn Ala Lys Val Thr Cys Val Val Val Asp Val Ser Glu Glu
            35                  40                  45

Glu Pro Asp Val Gln Phe Ser Trp Phe Val Asn Asn Val Glu Val His
    50                  55                  60
```

```
Thr Ala Gln Thr Gln Pro Arg Glu Glu Gln Tyr Asn Ser Thr Phe Arg
 65                  70                  75                  80

Val Val Ser Ala Leu Pro Ile Gln His Gln Asp Trp Met Ser Gly Lys
                 85                  90                  95

Glu Phe Lys Cys Lys Val Asn Asn Lys Ala Leu Pro Ser Pro Ile Glu
            100                 105                 110

Lys Thr Ile Ser Lys Pro Lys Gly Leu Val Arg Lys Pro Gln Val Tyr
        115                 120                 125

Val Met Gly Pro Pro Thr Glu Gln Leu Thr Glu Gln Thr Val Ser Leu
    130                 135                 140

Thr Cys Leu Thr Ser Gly Phe Leu Pro Asn Asp Ile Gly Val Glu Trp
145                 150                 155                 160

Thr Ser Asn Gly His Ile Glu Lys Asn Tyr Lys Asn Thr Glu Pro Val
                165                 170                 175

Met Asp Ser Asp Gly Ser Phe Phe Met Tyr Ser Lys Leu Asn Val Glu
            180                 185                 190

Arg Ser Arg Trp Asp Ser Arg Ala Pro Phe Val Cys Ser Val Val His
        195                 200                 205

Glu Gly Leu His Asn His His Val Glu Lys Ser Ile Ser Arg Pro Pro
    210                 215                 220

Gly Lys
225

<210> SEQ ID NO 122
<211> LENGTH: 679
<212> TYPE: PRT
<213> ORGANISM: Homo Sapiens

<400> SEQUENCE: 122

Val Pro Asp Lys Thr Val Arg Trp Cys Ala Val Ser Glu His Glu Ala
  1               5                  10                  15

Thr Lys Cys Gln Ser Phe Arg Asp His Met Lys Ser Val Ile Pro Ser
             20                  25                  30

Asp Gly Pro Ser Val Ala Cys Val Lys Lys Ala Ser Tyr Leu Asp Cys
         35                  40                  45

Ile Arg Ala Ile Ala Ala Asn Glu Ala Asp Ala Val Thr Leu Asp Ala
     50                  55                  60

Gly Leu Val Tyr Asp Ala Tyr Leu Ala Pro Asn Asn Leu Lys Pro Val
 65                  70                  75                  80

Val Ala Glu Phe Tyr Gly Ser Lys Glu Asp Pro Gln Thr Phe Tyr Tyr
                 85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
    130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
```

```
                195                 200                 205
Thr Ile Phe Glu Asn Leu Ala Asn Lys Ala Asp Arg Asp Gln Tyr Glu
    210                 215                 220
Leu Leu Cys Leu Asp Asn Thr Arg Lys Pro Val Asp Glu Tyr Lys Asp
225                 230                 235                 240
Cys His Leu Ala Gln Val Pro Ser His Thr Val Val Ala Arg Ser Met
                    245                 250                 255
Gly Gly Lys Glu Asp Leu Ile Trp Glu Leu Leu Asn Gln Ala Gln Glu
            260                 265                 270
His Phe Gly Lys Asp Lys Ser Lys Glu Phe Gln Leu Phe Ser Ser Pro
        275                 280                 285
His Gly Lys Asp Leu Leu Phe Lys Asp Ser Ala His Gly Phe Leu Lys
    290                 295                 300
Val Pro Pro Arg Met Asp Ala Lys Met Tyr Leu Gly Tyr Glu Tyr Val
305                 310                 315                 320
Thr Ala Ile Arg Asn Leu Arg Glu Gly Thr Cys Pro Glu Ala Pro Thr
                    325                 330                 335
Asp Glu Cys Lys Pro Val Lys Trp Cys Ala Leu Ser His His Glu Arg
            340                 345                 350
Leu Lys Cys Asp Glu Trp Ser Val Asn Ser Val Gly Lys Ile Glu Cys
        355                 360                 365
Val Ser Ala Glu Thr Thr Glu Asp Cys Ile Ala Lys Ile Met Asn Gly
    370                 375                 380
Glu Ala Asp Ala Met Ser Leu Asp Gly Gly Phe Val Tyr Ile Ala Gly
385                 390                 395                 400
Lys Cys Gly Leu Val Pro Val Leu Ala Glu Asn Tyr Asn Lys Ser Asp
                    405                 410                 415
Asn Cys Glu Asp Thr Pro Glu Ala Gly Tyr Phe Ala Val Ala Val Val
            420                 425                 430
Lys Lys Ser Ala Ser Asp Leu Thr Trp Asp Asn Leu Lys Gly Lys Lys
        435                 440                 445
Ser Cys His Thr Ala Val Gly Arg Thr Ala Gly Trp Asn Ile Pro Met
    450                 455                 460
Gly Leu Leu Tyr Asn Lys Ile Asn His Cys Arg Phe Asp Glu Phe Phe
465                 470                 475                 480
Ser Glu Gly Cys Ala Pro Gly Ser Lys Lys Asp Ser Ser Leu Cys Lys
                    485                 490                 495
Leu Cys Met Gly Ser Gly Leu Asn Leu Cys Glu Pro Asn Asn Lys Glu
            500                 505                 510
Gly Tyr Tyr Gly Tyr Thr Gly Ala Phe Arg Cys Leu Val Glu Lys Gly
        515                 520                 525
Asp Val Ala Phe Val Lys His Gln Thr Val Pro Gln Asn Thr Gly Gly
    530                 535                 540
Lys Asn Pro Asp Pro Trp Ala Lys Asn Leu Asn Glu Lys Asp Tyr Glu
545                 550                 555                 560
Leu Leu Cys Leu Asp Gly Thr Arg Lys Pro Val Glu Glu Tyr Ala Asn
                    565                 570                 575
Cys His Leu Ala Arg Ala Pro Asn His Ala Val Val Thr Arg Lys Asp
            580                 585                 590
Lys Glu Ala Cys Val His Lys Ile Leu Arg Gln Gln Gln His Leu Phe
        595                 600                 605
Gly Ser Asn Val Thr Asp Cys Ser Gly Asn Phe Cys Leu Phe Arg Ser
    610                 615                 620
```

```
Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
            645                 650                 655

Lys Ala Val Gly Asn Leu Arg Lys Cys Ser Thr Ser Ser Leu Leu Glu
            660                 665                 670

Ala Cys Thr Phe Arg Arg Pro
            675

<210> SEQ ID NO 123
<211> LENGTH: 585
<212> TYPE: PRT
<213> ORGANISM: Homo Sapiens

<400> SEQUENCE: 123

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
```

```
            305                 310                 315                 320
    Glu Ala Lys Asp Val Phe Leu Gly Met Phe Leu Tyr Glu Tyr Ala Arg
                    325                 330                 335
    Arg His Pro Asp Tyr Ser Val Val Leu Leu Leu Arg Leu Ala Lys Thr
                340                 345                 350
    Tyr Glu Thr Thr Leu Glu Lys Cys Cys Ala Ala Ala Asp Pro His Glu
                355                 360                 365
    Cys Tyr Ala Lys Val Phe Asp Glu Phe Lys Pro Leu Val Glu Glu Pro
            370                 375                 380
    Gln Asn Leu Ile Lys Gln Asn Cys Glu Leu Phe Glu Gln Leu Gly Glu
    385                 390                 395                 400
    Tyr Lys Phe Gln Asn Ala Leu Leu Val Arg Tyr Thr Lys Lys Val Pro
                    405                 410                 415
    Gln Val Ser Thr Pro Thr Leu Val Glu Val Ser Arg Asn Leu Gly Lys
                420                 425                 430
    Val Gly Ser Lys Cys Cys Lys His Pro Glu Ala Lys Arg Met Pro Cys
                435                 440                 445
    Ala Glu Asp Tyr Leu Ser Val Val Leu Asn Gln Leu Cys Val Leu His
            450                 455                 460
    Glu Lys Thr Pro Val Ser Asp Arg Val Thr Lys Cys Cys Thr Glu Ser
    465                 470                 475                 480
    Leu Val Asn Arg Arg Pro Cys Phe Ser Ala Leu Glu Val Asp Glu Thr
                    485                 490                 495
    Tyr Val Pro Lys Glu Phe Asn Ala Glu Thr Phe Thr Phe His Ala Asp
                500                 505                 510
    Ile Cys Thr Leu Ser Glu Lys Glu Arg Gln Ile Lys Lys Gln Thr Ala
                515                 520                 525
    Leu Val Glu Leu Val Lys His Lys Pro Lys Ala Thr Lys Glu Gln Leu
            530                 535                 540
    Lys Ala Val Met Asp Asp Phe Ala Ala Phe Val Glu Lys Cys Cys Lys
    545                 550                 555                 560
    Ala Asp Asp Lys Glu Thr Cys Phe Ala Glu Glu Gly Lys Lys Leu Val
                    565                 570                 575
    Ala Ala Ser Gln Ala Ala Leu Gly Leu
                580                 585

<210> SEQ ID NO 124
<211> LENGTH: 24
<212> TYPE: PRT
<213> ORGANISM: Homo Sapiens

<400> SEQUENCE: 124

Asp Val Leu Ala Gly Leu Ser Ser Ser Cys Cys Lys Trp Gly Cys Ser
1               5                   10                  15

Lys Ser Glu Ile Ser Ser Leu Cys
            20

<210> SEQ ID NO 125
<211> LENGTH: 27
<212> TYPE: PRT
<213> ORGANISM: Homo Sapiens

<400> SEQUENCE: 125

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
```

<210> SEQ ID NO 126
<211> LENGTH: 15
<212> TYPE: PRT
<213> ORGANISM: Homo Sapiens

<400> SEQUENCE: 126

Cys Cys Lys Trp Gly Cys Ser Lys Ser Glu Ile Ser Ser Leu Cys
1               5                   10                  15

<210> SEQ ID NO 127
<211> LENGTH: 72
<212> TYPE: DNA
<213> ORGANISM: Homo Sapiens

<400> SEQUENCE: 127
cagctgtata gcgcgctggc gaacaaatgc tgccatgtgg gctgcaccaa acgcagcctg    60
gcgcgctttt gc                                                       72

<210> SEQ ID NO 128
<211> LENGTH: 48
<212> TYPE: DNA
<213> ORGANISM: Homo Sapiens

<400> SEQUENCE: 128
aaatgctgcc atgtgggctg caccaaacgc agcctggcgc gcttttgc                 48

<210> SEQ ID NO 129
<211> LENGTH: 84
<212> TYPE: DNA
<213> ORGANISM: Homo Sapiens

<400> SEQUENCE: 129
agctggatgg aagaagtgat taaactgtgc ggccgcgaac tggtgcgcgc gcagattgcg    60
atttgcggca tgagcacctg gagc                                          84

<210> SEQ ID NO 130
<211> LENGTH: 693
<212> TYPE: DNA
<213> ORGANISM: Homo Sapiens

<400> SEQUENCE: 130
ccgaaagcgt gcgataaaac ccatacctgc ccgccgtgcc cggcgccgga actgctgggc    60
ggcccgagcg tgtttctgtt tccgccgaaa ccgaaagata ccctgatgat tagccgcacc   120
ccggaagtga cctgcgtggt ggtggatgtg agccatgaag atccggaagt gaaatttaac   180
tggtatgtgg atggcgtgga agtgcataac gcgaaaacca accgcgcga agaacagtat   240 aacagcacct atcgcgtggt gagcgtgctg accgtgctgc atcaggattg gctgaacggc   300
aaagaatata atgcaaagt gagcaacaaa gcgctgccgg cgccgattga aaaaaccatt   360
agcaaagcga aaggccagcc gcgcgaaccg caggtgtata ccctgccgcc gagccgcgat   420
gaactgacca aaaaccaggt gagcctgacc tgcctggtga aaggctttta tccgagcgat   480
attgcggtgg aatgggaaag caacggccag ccggaaaaca actataaaac cacccccgccg   540 gtgctggata gcgatggcag cttttttctg tatagcaaac tgaccgtgga taaaagccgc   600
tggcagcagg gcaacgtgtt tagctgcagc gtgatgcatg aagcgctgca taaccattat   660
acccagaaaa gcctgagcct gagcccgggc aaa                                693

<210> SEQ ID NO 131
<211> LENGTH: 678
<212> TYPE: DNA
<213> ORGANISM: Rattus Norvegicus

<400> SEQUENCE: 131

```
acctgcccga cctgccataa atgcccggtg ccggaactgc tgggcggccc gagcgtgttt      60
atttttccgc cgaaaccgaa agatattctg ctgattagcc agaacgcgaa agtgacctgc     120
gtggtggtgg atgtgagcga agaagaaccg gatgtgcagt ttagctggtt tgtgaacaac     180
gtggaagtgc ataccgcgca gacccagccg cgcaagaac agtataacag cacctttcgc     240
gtggtgagcg cgctgccgat tcagcatcag gattggatga gcggcaaaga atttaaatgc     300
aaagtgaaca acaaagcgct gccgagcccg attgaaaaaa ccattagcaa accgaaaggc     360
ctggtgcgca accgcaggt gtatgtgatg ggcccgccga ccgaacagct gaccgaacag     420
accgtgagcc tgacctgcct gaccagcggc tttctgccga acgatattgg cgtggaatgg     480
accagcaacg gccatattga aaaaaactat aaaaacaccg aaccggtgat ggatagcgat     540
ggcagctttt ttatgtatag caaactgaac gtggaacgca ccgctggga tagccgcgcg     600
ccgtttgtgt gcagcgtggt gcatgaaggc ctgcataacc atcatgtgga aaaaagcatt     660
agccgcccgc cgggcaaa                                                   678
```

<210> SEQ ID NO 132
<211> LENGTH: 2037
<212> TYPE: DNA
<213> ORGANISM: Homo Sapiens

<400> SEQUENCE: 132

```
gtgccggata aaaccgtgcg ctggtgcgcg gtgagcgaac atgaagcgac caaatgccag      60
agctttcgcg atcatatgaa aagcgtgatt ccgagcgatg gcccgagcgt ggcgtgcgtg     120
aaaaaagcga gctatctgga ttgcattcgc gcgattgcgg cgaacgaagc ggatgcggtg     180
accctggatg cgggcctggt gtatgatgcg tatctggcgc cgaacaacct gaaaccggtg     240
gtggcggaat ttatggcag caaagaagat ccgcagacct tttattatgc ggtggcggtg     300
gtgaaaaaag atagcggctt tcagatgaac cagctgcgcg gcaaaaaaag ctgccatacc     360
ggcctgggcc gcagcgcggg ctggaacatt ccgattggcc tgctgtattg cgatctgccg     420
gaaccgcgca accgctgga aaaagcggtg gcgaactttt ttagcggcag ctgcgcgccg     480
tgcgcggatg gcaccgattt tccgcagctg tgccagctgt gcccgggctg cggctgcagc     540
accctgaacc agtattttgg ctatagcggc gcgtttaaat gcctgaaaga tggcgcgggc     600
gatgtggcgt ttgtgaaaca tagcaccatt tttgaaaaacc tggcgaacaa agcggatcgc     660
gatcagtatg aactgctgtg cctggataac acccgcaaac cggtggatga atataaagat     720
tgccatctgg cgcaggtgcc gagccatacc gtggtggcgc gcagcatggg cggcaaagaa     780
gatctgattt gggaactgct gaaccaggcg caggaacatt ttggcaaaga taaaagcaaa     840
gaatttcagc tgtttagcag cccgcatggc aaagatctgc tgtttaaaga tagcgcgcat     900
ggctttctga agtgccgcc gcgcatggat gcgaaaatgt atctgggcta tgaatatgtg     960
accgcgattc gcaacctgcg cgaaggcacc tgcccggaag cgccgaccga tgaatgcaaa    1020
ccggtgaaat ggtgcgcgct gagccatcat gaacgcctga atgcgatga atggagcgtg    1080
aacagcgtgg gcaaaattga atgcgtgagc gcggaaccag ccgaagattg cattgcgaaa    1140
attatgaacg gcgaagcgga tgcgatgagc ctggatggcg gctttgtgta tattgcgggc    1200
```

```
aaatgcggcc tggtgccggt gctggcggaa aactataaca aaagcgataa ctgcgaagat    1260
accccggaag cgggctattt tgcggtggcg gtggtgaaaa aaagcgcgag cgatctgacc    1320
tgggataacc tgaaaggcaa aaaaagctgc cataccgcgg tgggccgcac cgcgggctgg    1380
aacattccga tgggcctgct gtataacaaa attaaccatt gccgctttga tgaattttt     1440 agcgaaggct gcgcgccggg cagcaaaaaa gatagcagcc tgtgcaaact gtgcatgggc    1500
agcggcctga acctgtgcga accgaacaac aaagaaggct attatggcta taccggcgcg    1560
tttcgctgcc tggtggaaaa aggcgatgtg gcgtttgtga acatcagac cgtgccgcag     1620 aacaccggcg gcaaaaaccc ggatccgtgg gcgaaaaacc tgaacgaaaa agattatgaa    1680
ctgctgtgcc tggatggcac ccgcaaaccg gtggaagaat atgcgaactg ccatctggcg    1740
cgcgcgccga accatgcggt ggtgacccgc aaagataaag aagcgtgcgt gcataaaatt    1800
ctgcgccagc agcagcatct gtttggcagc aacgtgaccg attgcagcgg caacttttgc    1860
ctgtttcgca gcgaaaccaa agatctgctg tttcgcgatg ataccgtgtg cctggcgaaa    1920
ctgcatgatc gcaacaccta tgaaaaatat ctgggcgaag aatatgtgaa agcggtgggc    1980
aacctgcgca aatgcagcac cagcagcctg ctggaagcgt gcacctttcg ccgcccg       2037

<210> SEQ ID NO 133
<211> LENGTH: 1755
<212> TYPE: DNA
<213> ORGANISM: Homo Sapiens

<400> SEQUENCE: 133
gatgcgcata aaagcgaagt ggcgcatcgc tttaaagatc tgggcgaaga aaactttaaa      60
gcgctggtgc tgattgcgtt tgcgcagtat ctgcagcagt gcccgtttga agatcatgtg     120
aaactggtga acgaagtgac cgaatttgcg aaaacctgcg tggcggatga aagcgcggaa     180
aactgcgata aaagcctgca taccctgttt ggcgataaac tgtgcaccgt ggcgaccctg     240
cgcgaaacct atggcgaaat ggcggattgc tgcgcgaaac aggaaccgga acgcaacgaa     300
tgctttctgc agcataaaga tgataacccg aacctgccgc gcctggtgcg cccggaagtg     360
gatgtgatgt gcaccgcgtt tcatgataac gaagaaacct ttctgaaaaa atatctgtat     420
gaaattgcgc gccgccatcc gtattttat gcgccggaac tgctgttttt tgcgaaacgc     480
tataaagcgg cgtttaccga tgctgccag gcggcggata agcggcgtg cctgctgccg      540 aaactggatg aactgcgcga tgaaggcaaa gcgagcagcg cgaaacagcg cctgaaatgc    600
gcgagcctgc agaaatttgg cgaacgcgcg tttaaagcgt gggcggtggc cgcgcctgagc   660 cagcgctttc cgaaagcgga atttgcggaa gtgagcaaac tggtgaccga tctgaccaaa    720
gtgcataccg aatgctgcca tggcgatctg ctggaatgcg cggatgatcg cgcggatctg    780
gcgaaatata tttgcgaaaa ccaggatagc attagcagca aactgaaaga tgctgcgaa     840 aaaccgctgc tggaaaaaag ccattgcatt gcggaagtgg aaaacgatga atgccggcg     900 gatctgccga gcctggcggc ggattttgtg gaaagcaaag atgtgtgcaa aaactatgcg    960
gaagcgaaag atgtgtttct gggcatgttt ctgtatgaat atgcgcgccg ccatccggat   1020
tatagcgtgg tgctgctgct gcgcctggcg aaaacctatg aaaccaccct ggaaaaatgc   1080
tgcgcggcgg cggatccgca tgaatgctat gcgaaagtgt ttgatgaatt taaaccgctg   1140
gtggaagaac cgcagaacct gattaaacag aactgcgaac tgtttgaaca gctgggcgaa   1200
tataaatttc agaacgcgct gctggtgcgc tataccaaaa aagtgccgca ggtgagcacc   1260
```

-continued

```
ccgaccctgg tggaagtgag ccgcaacctg gcaaagtggg gcagcaaatg ctgcaaacat    1320
ccggaagcga aacgcatgcc gtgcgcggaa gattatctga gcgtggtgct gaaccagctg    1380
tgcgtgctgc atgaaaaaac cccggtgagc gatcgcgtga ccaaatgctg caccgaaagc    1440
ctggtgaacc gccgcccgtg ctttagcgcg ctggaagtgg atgaaaccta tgtgccgaaa    1500
gaatttaacg cggaaacctt tacctttcat gcggatattt gcaccctgag cgaaaaagaa    1560
cgccagatta aaaaacagac cgcgctggtg gaactggtga acataaaacc gaaagcgacc    1620
aaagaacagc tgaaagcggt gatggatgat tttgcggcgt tgtggaaaaa atgctgcaaa    1680
gcggatgata agaaacctg ctttgcggaa gaaggcaaaa aactggtggc ggcgagccag    1740
gcggcgctgg gcctg                                                    1755
```

<210> SEQ ID NO 134
<211> LENGTH: 72
<212> TYPE: DNA
<213> ORGANISM: Homo Sapiens

<400> SEQUENCE: 134

```
gatgtgctgg cgggcctgag cagcagctgc tgcaaatggg gctgcagcaa aagcgaaatt    60
agcagcctgt gc                                                        72
```

<210> SEQ ID NO 135
<211> LENGTH: 81
<212> TYPE: DNA
<213> ORGANISM: Homo Sapiens

<400> SEQUENCE: 135

```
cgcgcggcgc cgtatggcgt gcgcctgtgc ggccgcgaat ttattcgcgc ggtgattttt    60
acctgcggcg gcagccgctg g                                              81
```

<210> SEQ ID NO 136
<211> LENGTH: 45
<212> TYPE: DNA
<213> ORGANISM: Homo Sapiens

<400> SEQUENCE: 136

```
tgctgcaaat ggggctgcag caaaagcgaa attagcagcc tgtgc                    45
```

<210> SEQ ID NO 137
<211> LENGTH: 6
<212> TYPE: PRT
<213> ORGANISM: Artificial Sequence
<220> FEATURE:
<223> OTHER INFORMATION: relaxin fusion polypeptide

<400> SEQUENCE: 137

Gly Gly Gly Ser Gly Gly
1               5

<210> SEQ ID NO 138
<211> LENGTH: 7
<212> TYPE: PRT
<213> ORGANISM: Artificial Sequence
<220> FEATURE:
<223> OTHER INFORMATION: relaxin fusion polypeptide

<400> SEQUENCE: 138

Gly Gly Gly Ser Gly Gly Gly
1               5

```
<210> SEQ ID NO 139
<211> LENGTH: 9
<212> TYPE: PRT
<213> ORGANISM: Artificial Sequence
<220> FEATURE:
<223> OTHER INFORMATION: relaxin fusion polypeptide

<400> SEQUENCE: 139

Gly Gly Gly Ser Gly Gly Gly Ser Gly
1               5

<210> SEQ ID NO 140
<211> LENGTH: 12
<212> TYPE: PRT
<213> ORGANISM: Artificial Sequence
<220> FEATURE:
<223> OTHER INFORMATION: relaxin fusion polypeptide

<400> SEQUENCE: 140

Gly Gly Gly Ser Gly Gly Gly Ser Gly Gly Gly Ser
1               5                   10

<210> SEQ ID NO 141
<211> LENGTH: 10
<212> TYPE: PRT
<213> ORGANISM: Artificial Sequence
<220> FEATURE:
<223> OTHER INFORMATION: relaxin fusion polypeptide

<400> SEQUENCE: 141

Gly Gly Gly Ser Gly Cys Gly Gly Ser Gly
1               5                   10

<210> SEQ ID NO 142
<211> LENGTH: 10
<212> TYPE: PRT
<213> ORGANISM: Artificial Sequence
<220> FEATURE:
<223> OTHER INFORMATION: relaxin fusion polypeptide

<400> SEQUENCE: 142

Gly Gly Gly Ser Gly Lys Gly Gly Ser Gly
1               5                   10

<210> SEQ ID NO 143
<211> LENGTH: 14
<212> TYPE: PRT
<213> ORGANISM: Artificial Sequence
<220> FEATURE:
<223> OTHER INFORMATION: relaxin fusion polypeptide

<400> SEQUENCE: 143

Gly Gly Gly Ser Gly Gly Gly Ser Gly Gly Gly Ser Gly Gly
1               5                   10

<210> SEQ ID NO 144
<211> LENGTH: 9
<212> TYPE: PRT
<213> ORGANISM: Artificial Sequence
<220> FEATURE:
<223> OTHER INFORMATION: relaxin fusion polypeptide

<400> SEQUENCE: 144

Lys Arg Ser Leu Ser Arg Lys Lys Arg
1               5

<210> SEQ ID NO 145
```

```
<211> LENGTH: 13
<212> TYPE: PRT
<213> ORGANISM: Artificial Sequence
<220> FEATURE:
<223> OTHER INFORMATION: relaxin fusion polypeptide

<400> SEQUENCE: 145

Gly Gly Gly Ser Gly Gly Gly Ser Gly Gly Gly Ser Gly
1               5                   10

<210> SEQ ID NO 146
<211> LENGTH: 11
<212> TYPE: PRT
<213> ORGANISM: Artificial Sequence
<220> FEATURE:
<223> OTHER INFORMATION: relaxin fusion polypeptide

<400> SEQUENCE: 146

Gly Gly Gly Ser Gly Gly Gly Ser Gly Gly Gly
1               5                   10

<210> SEQ ID NO 147
<211> LENGTH: 6
<212> TYPE: PRT
<213> ORGANISM: Artificial Sequence
<220> FEATURE:
<223> OTHER INFORMATION: relaxin fusion polypeptide

<400> SEQUENCE: 147

Ile Glu Gly Arg Met Asp
1               5

<210> SEQ ID NO 148
<211> LENGTH: 4
<212> TYPE: PRT
<213> ORGANISM: Artificial Sequence
<220> FEATURE:
<223> OTHER INFORMATION: relaxin fusion polypeptide

<400> SEQUENCE: 148

Gly Gly Ser Pro
1

<210> SEQ ID NO 149
<211> LENGTH: 7
<212> TYPE: PRT
<213> ORGANISM: Artificial Sequence
<220> FEATURE:
<223> OTHER INFORMATION: relaxin fusion polypeptide

<400> SEQUENCE: 149

Gly Gly Ser Gly Gly Ser Pro
1               5

<210> SEQ ID NO 150
<211> LENGTH: 10
<212> TYPE: PRT
<213> ORGANISM: Artificial Sequence
<220> FEATURE:
<223> OTHER INFORMATION: relaxin fusion polypeptide

<400> SEQUENCE: 150

Gly Gly Ser Gly Gly Ser Gly Gly Ser Pro
1               5                   10

<210> SEQ ID NO 151
<211> LENGTH: 6
```

```
<212> TYPE: PRT
<213> ORGANISM: Artificial Sequence
<220> FEATURE:
<223> OTHER INFORMATION: relaxin fusion polypeptide

<400> SEQUENCE: 151

Gly Ser Gly Ser Gly Ser
1               5

<210> SEQ ID NO 152
<211> LENGTH: 71
<212> TYPE: PRT
<213> ORGANISM: Artificial Sequence
<220> FEATURE:
<223> OTHER INFORMATION: relaxin fusion polypeptide

<400> SEQUENCE: 152

Glu Gln Lys Leu Ile Ser Glu Glu Asp Leu Ser Trp Met Glu Glu Val
1               5                   10                  15

Ile Lys Leu Cys Gly Arg Glu Leu Val Arg Ala Gln Ile Ala Ile Cys
            20                  25                  30

Gly Met Ser Thr Trp Ser Gly Gly Gly Ser Gly Gly Gly Ser Gly Gln
        35                  40                  45

Leu Tyr Ser Ala Leu Ala Asn Lys Cys Cys His Val Gly Cys Thr Lys
    50                  55                  60

Arg Ser Leu Ala Arg Phe Cys
65                  70

<210> SEQ ID NO 153
<211> LENGTH: 71
<212> TYPE: PRT
<213> ORGANISM: Artificial Sequence
<220> FEATURE:
<223> OTHER INFORMATION: relaxin fusion polypeptide

<400> SEQUENCE: 153

Glu Gln Lys Leu Ile Ser Glu Glu Asp Leu Asp Val Leu Ala Gly Leu
1               5                   10                  15

Ser Ser Ser Cys Cys Lys Trp Gly Cys Ser Lys Ser Glu Ile Ser Ser
            20                  25                  30

Leu Cys Gly Gly Gly Ser Gly Gly Gly Ser Gly Ser Trp Met Glu Glu
        35                  40                  45

Val Ile Lys Leu Cys Gly Arg Glu Leu Val Arg Ala Gln Ile Ala Ile
    50                  55                  60

Cys Gly Met Ser Thr Trp Ser
65                  70

<210> SEQ ID NO 154
<211> LENGTH: 71
<212> TYPE: PRT
<213> ORGANISM: Artificial Sequence
<220> FEATURE:
<223> OTHER INFORMATION: relaxin fusion polypeptide

<400> SEQUENCE: 154

Glu Gln Lys Leu Ile Ser Glu Glu Asp Leu Ser Trp Met Glu Glu Val
1               5                   10                  15

Ile Lys Leu Cys Gly Arg Glu Leu Val Arg Ala Gln Ile Ala Ile Cys
            20                  25                  30

Gly Met Ser Thr Trp Ser Gly Gly Gly Ser Gly Gly Gly Ser Gly Asp
        35                  40                  45
```

```
Val Leu Ala Gly Leu Ser Ser Ser Cys Cys Lys Trp Gly Cys Ser Lys
 50                  55                  60

Ser Glu Ile Ser Ser Leu Cys
 65                  70

<210> SEQ ID NO 155
<211> LENGTH: 70
<212> TYPE: PRT
<213> ORGANISM: Artificial Sequence
<220> FEATURE:
<223> OTHER INFORMATION: relaxin fusion polypeptide

<400> SEQUENCE: 155

Glu Gln Lys Leu Ile Ser Glu Glu Asp Leu Gln Leu Tyr Ser Ala Leu
 1               5                  10                  15

Ala Asn Lys Cys Cys His Val Gly Cys Thr Lys Arg Ser Leu Ala Arg
                 20                  25                  30

Phe Cys Gly Gly Gly Ser Gly Gly Gly Ser Gly Arg Ala Ala Pro Tyr
             35                  40                  45

Gly Val Arg Leu Cys Gly Arg Glu Phe Ile Arg Ala Val Ile Phe Thr
 50                  55                  60

Cys Gly Gly Ser Arg Trp
 65                  70

<210> SEQ ID NO 156
<211> LENGTH: 70
<212> TYPE: PRT
<213> ORGANISM: Artificial Sequence
<220> FEATURE:
<223> OTHER INFORMATION: relaxin fusion polypeptide

<400> SEQUENCE: 156

Glu Gln Lys Leu Ile Ser Glu Glu Asp Leu Arg Ala Ala Pro Tyr Gly
 1               5                  10                  15

Val Arg Leu Cys Gly Arg Glu Phe Ile Arg Ala Val Ile Phe Thr Cys
                 20                  25                  30

Gly Gly Ser Arg Trp Gly Gly Ser Gly Gly Gly Ser Gly Gln Leu
             35                  40                  45

Tyr Ser Ala Leu Ala Asn Lys Cys Cys His Val Gly Cys Thr Lys Arg
 50                  55                  60

Ser Leu Ala Arg Phe Cys
 65                  70

<210> SEQ ID NO 157
<211> LENGTH: 213
<212> TYPE: DNA
<213> ORGANISM: Artificial Sequence
<220> FEATURE:
<223> OTHER INFORMATION: relaxin fusion

<400> SEQUENCE: 157
gaacagaaac tgattagcga agaagatctg agctggatgg aagaagtgat taaactgtgc      60
ggccgcgaac tggtgcgcgc gcagattgcg atttgcggca tgagcacctg agcggcggc     120 ggcagcggcg gcggcagcgg ccagctgtat agcgcgctgg cgaacaaatg ctgccatgtg     180
ggctgcacca aacgcagcct ggcgcgcttt tgc                                  213

<210> SEQ ID NO 158
<211> LENGTH: 213
<212> TYPE: DNA
<213> ORGANISM: Artificial Sequence
```

```
<220> FEATURE:
<223> OTHER INFORMATION: relaxin fusion

<400> SEQUENCE: 158
gaacagaaac tgattagcga agaagatctg gatgtgctgg cgggcctgag cagcagctgc      60
tgcaaatggg gctgcagcaa aagcgaaatt agcagcctgt gcggcggcgg cagcggcggc     120
ggcagcggca gctggatgga agaagtgatt aaactgtgcg gccgcgaact ggtgcgcgcg     180
cagattgcga tttgcggcat gagcacctgg agc                                 213

<210> SEQ ID NO 159
<211> LENGTH: 213
<212> TYPE: DNA
<213> ORGANISM: Artificial Sequence
<220> FEATURE:
<223> OTHER INFORMATION: relaxin fusion

<400> SEQUENCE: 159
gaacagaaac tgattagcga agaagatctg agctggatgg aagaagtgat taaactgtgc      60
ggccgcgaac tggtgcgcgc gcagattgcg atttgcggca tgagcacctg gagcggcggc     120
ggcagcggcg gcggcagcgg cgatgtgctg gcgggcctga gcagcagctg ctgcaaatgg     180
ggctgcagca aaagcgaaat tagcagcctg tgc                                 213

<210> SEQ ID NO 160
<211> LENGTH: 210
<212> TYPE: DNA
<213> ORGANISM: Artificial Sequence
<220> FEATURE:
<223> OTHER INFORMATION: relaxin fusion

<400> SEQUENCE: 160
gaacagaaac tgattagcga agaagatctg cagctgtata gcgcgctggc gaacaaatgc      60
tgccatgtgg gctgcaccaa acgcagcctg gcgcgctttt gcggcggcgg cagcggcggc     120
ggcagcggcc gcgcggcgcc gtatggcgtg cgcctgtgcg gccgcgaatt tattcgcgcg     180
gtgattttta cctgcggcgg cagccgctgg                                     210

<210> SEQ ID NO 161
<211> LENGTH: 210
<212> TYPE: DNA
<213> ORGANISM: Artificial Sequence
<220> FEATURE:
<223> OTHER INFORMATION: relaxin fusion

<400> SEQUENCE: 161
gaacagaaac tgattagcga agaagatctg cgcgcggcgc cgtatggcgt gcgcctgtgc      60
ggccgcgaat ttattcgcgc ggtgattttt acctgcggcg gcagccgctg gggcggcggc     120
agcggcggcg gcagcggcca gctgtatagc gcgctggcga acaaatgctg ccatgtgggc     180
tgcaccaaac gcagcctggc gcgcttttgc                                     210

<210> SEQ ID NO 162
<211> LENGTH: 9
<212> TYPE: PRT
<213> ORGANISM: Artificial Sequence
<220> FEATURE:
<223> OTHER INFORMATION: Relaxin B-chain motiv
<220> FEATURE:
<221> NAME/KEY: Xaa
<222> LOCATION: (2)..(4)
<223> OTHER INFORMATION: Xaa is an AA able to form helical structure
<220> FEATURE:
```

```
<221> NAME/KEY: Xaa
<222> LOCATION: (6)..(7)
<223> OTHER INFORMATION: Xaa is an AA  able to form helical structure
<220> FEATURE:
<221> NAME/KEY: Xaa
<222> LOCATION: (8)..(8)
<223> OTHER INFORMATION: Xaa is Ile or Val
<220> FEATURE:
<221> NAME/KEY: Xaa
<222> LOCATION: (9)..(9)
<223> OTHER INFORMATION: Xaa is an AA  able to form helical structure

<400> SEQUENCE: 162

Arg Xaa Xaa Arg Xaa Xaa Xaa Xaa
1               5

<210> SEQ ID NO 163
<211> LENGTH: 4
<212> TYPE: PRT
<213> ORGANISM: Artificial Sequence
<220> FEATURE:
<223> OTHER INFORMATION: linker

<400> SEQUENCE: 163

Gly Gly Gly Ser
1

<210> SEQ ID NO 164
<211> LENGTH: 4
<212> TYPE: PRT
<213> ORGANISM: Artificial Sequence
<220> FEATURE:
<223> OTHER INFORMATION: linker

<400> SEQUENCE: 164

Gly Gly Ser Gly
1

<210> SEQ ID NO 165
<211> LENGTH: 5
<212> TYPE: PRT
<213> ORGANISM: Artificial Sequence
<220> FEATURE:
<223> OTHER INFORMATION: linker

<400> SEQUENCE: 165

Gly Gly Gly Gly Ser
1               5

<210> SEQ ID NO 166
<211> LENGTH: 19
<212> TYPE: PRT
<213> ORGANISM: Artificial Sequence
<220> FEATURE:
<223> OTHER INFORMATION: leader sequence of the LDL receptor-related
      protein

<400> SEQUENCE: 166

Met Leu Thr Pro Pro Leu Leu Leu Leu Leu Pro Leu Leu Ser Ala Leu
1               5                   10                  15

Val Ala Ala

<210> SEQ ID NO 167
<211> LENGTH: 16
<212> TYPE: PRT
<213> ORGANISM: Artificial Sequence
<220> FEATURE:
<223> OTHER INFORMATION: leader sequence of the CD33
```

<400> SEQUENCE: 167

Met Pro Leu Leu Leu Leu Leu Pro Leu Leu Trp Ala Gly Ala Leu Ala
1               5                   10                  15

<210> SEQ ID NO 168
<211> LENGTH: 10
<212> TYPE: PRT
<213> ORGANISM: Artificial Sequence
<220> FEATURE:
<223> OTHER INFORMATION: Myc tag

<400> SEQUENCE: 168

Glu Gln Lys Leu Ile Ser Glu Glu Asp Leu
1               5                   10

<210> SEQ ID NO 169
<211> LENGTH: 9
<212> TYPE: PRT
<213> ORGANISM: Artificial Sequence
<220> FEATURE:
<223> OTHER INFORMATION: hemagglutinin tag

<400> SEQUENCE: 169

Tyr Pro Tyr Asp Val Pro Asp Tyr Ala
1               5

<210> SEQ ID NO 170
<211> LENGTH: 6
<212> TYPE: PRT
<213> ORGANISM: Artificial Sequence
<220> FEATURE:
<223> OTHER INFORMATION: 6 Histidine tag

<400> SEQUENCE: 170

His His His His His His
1               5

<210> SEQ ID NO 171
<211> LENGTH: 3
<212> TYPE: PRT
<213> ORGANISM: Artificial Sequence
<220> FEATURE:
<223> OTHER INFORMATION: linker

<400> SEQUENCE: 171

Gly Gly Gly
1

<210> SEQ ID NO 172
<211> LENGTH: 5
<212> TYPE: PRT
<213> ORGANISM: Artificial Sequence
<220> FEATURE:
<223> OTHER INFORMATION: linker

<400> SEQUENCE: 172

Gly Gly Gly Ser Gly
1               5

<210> SEQ ID NO 173
<211> LENGTH: 15
<212> TYPE: PRT
<213> ORGANISM: Artificial Sequence
<220> FEATURE:
<223> OTHER INFORMATION: linker

```
<400> SEQUENCE: 173

Gly Gly Gly Ser Gly Gly Gly Ser Gly Gly Ser Gly Gly Gly
1               5                   10                  15

<210> SEQ ID NO 174
<211> LENGTH: 21
<212> TYPE: PRT
<213> ORGANISM: Artificial Sequence
<220> FEATURE:
<223> OTHER INFORMATION: linker

<400> SEQUENCE: 174

Gly Gly Gly Ser Gly Gly Gly Ser Gly Thr Lys Val Thr Val Ser Ser
1               5                   10                  15

Glu Ser Lys Tyr Gly
            20

<210> SEQ ID NO 175
<211> LENGTH: 6
<212> TYPE: PRT
<213> ORGANISM: Artificial Sequence
<220> FEATURE:
<223> OTHER INFORMATION: linker

<400> SEQUENCE: 175

Gly Gly Ser Gly Cys Gly
1               5

<210> SEQ ID NO 176
<211> LENGTH: 6
<212> TYPE: PRT
<213> ORGANISM: Artificial Sequence
<220> FEATURE:
<223> OTHER INFORMATION: linker

<400> SEQUENCE: 176

Gly Cys Gly Ser Gly Gly
1               5
```

RELAXIN FUSION POLYPEPTIDES AND USES THEREOF

SEQUENCE LISTING

The instant application contains a Sequence Listing which has been submitted in ASCII format via EFS-Web and is hereby incorporated by reference in its entirety. Said ASCII copy, created on Dec. 10, 2015, is named eolf-seql.txt and is 213,280 bytes in size.

The present invention provides Relaxin fusion polypeptides A-L-B with a non-wild type array of the Relaxin A-chain and Relaxin B-chain, wherein the A- and B-chains are connected by a linker peptide. The invention further provides Relaxin fusion polypeptides with extended half-life. Furthermore, the invention provides nucleic acid sequences encoding the foregoing fusion polypeptides, vectors containing the same, pharmaceutical compositions and medical use of such fusion polypeptides.

BACKGROUND OF THE INVENTION

Relaxin 2 (H2 relaxin, RLN2) as a member of the insulin superfamily is a 2-chain peptide exhibiting, on the genetic level, the typical B-C-A chain prohormone structure, arranged from N- to C-terminus. Other members of this superfamily, encoded by 7 genes in human, are the relaxin genes RLN 1, RLN3, and the insulin-like peptide genes INSL3, INSL4, INSL5, and INSL6. The overall sequence homology between members of this family is low; nevertheless, phylogenetic analysis indicates that these genes have evolved from the RLN3 ancestral gene (Hsu, S. Y. (2003); Wilkinson, T. N. et al. (2005)). The mature protein has a molecular weight of approximately 6000 Da and is the product of an enzymatic cleavage of the prohormone catalyzed by the Prohormone-Convertase 1 (PC1) and 2 (PC2) (Hudson P. et al. (1983)). The resulting A- and B-chains are joined by two intermolecular cysteine bridges; the A-chain exhibits an additional intramolecular disulfide bond.

Relaxin initiates pleiotropic effects through multiple pathways on a variety of cell types. It confers its activity by binding to the class I (rhodopsin like) G-protein-coupled receptor termed LGR7 (leucine-rich G protein-coupled receptor 7) also named RXFP1 (relaxin family peptide 1 receptor), and with significantly lower affinity to LRG8/RXFP2 (relaxin family peptide 2 receptor) (Kong R C et al. (2010) Mol Cell Endocrinol. 320:1-15). Within the Relaxin molecule, an amino acid motif in the B-chain (Arg-X-X-X-Arg-X-X-Ile/Val-X) (SEQ ID NO: 162) (Schwabe and Büllesbach (2007) Adv Exp Med Biol. 612:14-25 and Büllesbach and Schwabe J Biol Chem. 2000 Nov. 10; 275(45): 35276-80) is conserved in all of the Relaxin peptides and is crucial for the interaction of these peptides with the corresponding receptor. Binding of Relaxin to LGR7/RXFP1 leads to activation of adenylate cyclase and to an increase of the second messenger molecule cAMP. Via this mechanism, Relaxin 2 for example mediates the release of atrial natriuretic peptide in rat hearts (Toth, M. et al. (1996)). A positive inotropic effect of Relaxin 2 on rat atrial myocytes has also been shown (Piedras-Renteria, E. S. et al. (1997)). Other signal transduction molecules which are activated by the Relaxin/LGR7 complex are the phosphoinositide-3 kinase, tyrosine kinases, and phosphodiesterases (Bartsch, O. et al. (2001), Bartsch, O. et al. (2004)). Additional signal transduction pathways activated by this system include the nitric oxide (NO) pathway leading to increased levels of cyclic GMP in rat and guinea-pig hearts (Bani-Sacchi, T. et al. (1995)).

Relaxin acts as a pleiotropic hormone (Dschietzig T. et al. (2006)) possessing biological activity on organs such as lung, kidney, brain, and heart. A strong antifibrotic and vasodilator activity of Relaxin is most notably responsible for the positive effects obtained with this peptide in various animal disease models as well as in clinical studies (McGuane J. T. et al. (2005)). RLN2 has multiple beneficial actions in the cardiovascular system under pathological conditions. It maintains tissue homeostasis and protects the injured myocardium during various pathophysiological processes. It exhibits prominent vasodilatory effects, e.g. affecting flow and vasodilation in rodent coronary arteries (Nistri, S. et al. (2003)) and in the vascular beds of other organs. In spontaneously hypertensive rats RLN2 lowered blood pressure, an effect mediated by increased NO production.

A cardioprotective activity of Relaxin 2 has been evaluated in different animal models such as guinea pig, rat and pig (Perna A. M. et al. (2005), Bani, D. et al. (1998)). RLN2 ameliorates myocardial injury, inflammatory cell infiltration and subsequent fibrosis, thereby alleviating severe ventricular dysfunction (Zhang J. et al. (2005)).

Relaxin 2 exhibits strong antifibrotic activity. In injured tissues, fibroblast activation and proliferation causes increased collagen production and interstitial fibrosis. Fibrosis in the heart is increased by biomechanical overload, and influences ventricular dysfunction, remodeling, and arrhythmogenesis. In animal models, continuous infusion of Relaxin 2 inhibits or even reverses cardiac dysfunction caused by cardiomyopathy, hypertension, isoprenaline-induced cardiac toxicity, diabetic cardiomyopathy and myocardial infarction. This inhibition of fibrogenesis or reversal of established fibrosis can reduce ventricular stiffening and improve diastolic function. Notably, although Relaxin 2 reduces aberrant collagen accumulation, it does not affect basal collagen content in healthy tissues, highlighting its safety for therapeutic use.

Relaxin 2 has been tested in several clinical studies as a pleiotropic vasodilator for the treatment of patients with acute heart failure with very promising outcome. In these studies, Relaxin 2 was associated with favourable relief of dyspnoea and other clinical outcomes (Teerlink J. R. et al. (2009), Metra M. et al. (2010))

Due to the limited in-vivo half life of Relaxin, treatment of patients has to be repeated every 14 to 21 days, whereby compound administration has to be performed as a continuous infusion for at least 48 hours.

Furthermore, Relaxin 2 may also be useful in the treatment of diseases such as pancreatitis, inflammation-related diseases like rheumatoid arthritis, and cancer (Cosen-Binker L. I. et al. (2006) Santora K. Et al. (2007)) or scleroderma, pulmonary, renal, and hepatic fibrosis (Bennett R G. (2009)). Relaxin 2 reduces xenograft tumour growth of human MDA-MB-231 breast cancer cells (Radestock Y, Hoang-Vu C, Hombach-Klonisch S. (2008) Breast Cancer Res. 10:R71).

The synthesis of Relaxin 2 by chemical methods is difficult. Due to the low solubility of the B-chain and the requirement for the laborious, specific introduction of cysteine bridges between A and B-chains, yields of active peptide obtained by these methods are extremely low (Barlos K. K. et al. (2010)). Alternatively, recombinant expression of Relaxin 2 can be performed. To allow efficient cleavage of the prepropeptide during post-translational modifications and the secretion of mature and biological active peptides, expression host cells are routinely co-transfected with expression constructs encoding the Prohormone-Convertase 1 and/or 2 (Park J. I. et al. (2008)). Nevertheless, the endoproteolytic processing efficiency of prepro-peptides in heterologous cells often limits the production of bioactive molecules significantly (Shaw J. A. et al. (2002)).

Therefore, it would be of great advantage to generate a Relaxin molecule which independent of endoproteolytic processing mediated by specific proteases exhibits full biological activity and can be produced in significant yields using heterologous expression systems.

For human Insulin, single-chain variants have been generated in which an uncleavable polypeptide connects the insulin B-chain with the insulin A-chain (Rajpal G. et al. (2009)). For these variants, endoproteolytic processing is dispensable.

Surprisingly, we identified a Relaxin variant in which the orientation of the two active chains, designated as A chain and B chain, are exchanged and the cleavable C chain is substituted by linker peptide. As shown in FIG. 1, instead of the genetically determined orientation of the single chains encoding Relaxin, namely B chain-C chain-A chain, the orientation of the chains of the modified molecule is: A chain-linker peptide-B chain. The resulting molecule exhibits full biological activity, independent of any endoproteolytic processing. This new single-chain Relaxin variant provided by the invention thus solves the problem of low expression yields or the requirement of co-transfection with a processing protease.

The half-life of intravenously administrated Relaxin 2 in humans is less than 10 minutes (Dschietzig T. et al. (2009)). As a consequence, in clinical trials Relaxin 2 has to be administered continuously over 48 h. Therefore, the improvement of the biological half life of Relaxin could be of great advantage.

Improving biological half life can either be performed by chemical modification such as PEGylation or HESylation of the polypeptide of interest, introduction of additional, non-natural N-glycosylation sites or by genetically fusing this polypeptide with other molecules such as the immunoglobulin Fc fragment of antibodies, transferrin, albumin, binding modules that bind in-vivo to other molecules mediating longer half-life, or other proteins, respectively. This invention provides single-chain Relaxin variants fused to the Fc part of antibodies with improved half-life. Surprisingly, these variants show biological activity in the range of the wild-type Relaxin.

SUMMARY OF THE INVENTION

The invention concerns fusion polypeptides, hereafter also referred to as single chain Relaxin (scRelaxin).

Current standard of Relaxin 2 production is the chemical synthesis of this molecule, which is a complex and expensive procedure. Due to the fact that Relaxin undergoes posttranslational modifications, especially the cleavage of the prepro-protein by the Prohormon Convertase 1 and Prohormone Convertase 2, choice of an adequate expression system is mandatory for recombinant expression. Endoproteolytic processing of proteins belonging to the insulin superfamily often limits the production of bioactive molecules from heterologous cells. To avoid the endoproteolytic processing of Relaxin, the fusion polypeptides of the invention are molecules in which the genetically encoded orientation of the two active chains of Relaxin, designated as A chain and B chain, is reversed wherein the A chain and B chain are connected by a linker peptide. In detail, instead of the genetically determined orientation of the individual DNA segments encoding Relaxin domains, namely B chain-C chain-A chain, the orientation the DNA segments in the Relaxin variants provided by this invention is: A chain-peptide linker-B chain. This results in a single chain Relaxin wherein the carboxy-terminus of Relaxin A chain is fused to the amino-terminus of the linker polypeptide L, which carboxy-terminus is fused to the amino-terminus of the Relaxin B chain, designated A-L-B (see FIG. 1 for an illustration). The resulting molecule exhibits its biological activity similar to the wild-type Relaxin, but its expression is independent of endo-proteolytic processing.

One embodiment of the invention is a fusion polypeptide comprising A-L-B, wherein A comprises a Relaxin A chain polypeptide or a functional variant thereof, B comprises a Relaxin B chain polypeptide or a functional variant thereof and L is a linker polypeptide.

In a further embodiment the Relaxin A chain polypeptide of A-L-B comprises a Relaxin 2 A chain polypeptide or a functional variant thereof and the Relaxin B chain polypeptide comprises a Relaxin 2 B chain polypeptide or a functional variant thereof.

In a preferred embodiment the Relaxin A chain polypeptide of A-L-B comprises a human minimal Relaxin 2 A chain polypeptide (SEQ ID NO: 118) or a functional variant thereof, or comprises a human Relaxin 2 A chain polypeptide (SEQ ID NO: 117) or a functional variant thereof.

In a preferred embodiment the Relaxin B chain polypeptide of A-L-B comprises a human Relaxin 2 B chain polypeptide (SEQ ID NO: 119) or a functional variant thereof.

In a more preferred embodiment the Relaxin A chain polypeptide of A-L-B comprises a human minimal Relaxin 2 A chain polypeptide (SEQ ID NO: 118) or a functional variant thereof, or comprises a human Relaxin 2 A chain polypeptide (SEQ ID NO: 117) or a functional variant thereof and the Relaxin B chain polypeptide comprises a human Relaxin 2 B chain polypeptide (SEQ ID NO: 119) or a functional variant thereof.

In an even more preferred embodiment the Relaxin A chain polypeptide of A-L-B is a human Relaxin 2 A chain polypeptide (SEQ ID NO: 117) or a functional variant thereof and the Relaxin B chain polypeptide is a human Relaxin 2 B chain polypeptide (SEQ ID NO: 119) or a functional variant thereof.

In one embodiment the linker polypeptide L of the aforementioned fusion polypeptides A-L-B consists of a polypeptide which is 6-14 amino acid residues in length. Further preferred are polypeptide linkers L which are 7-13 amino acid residues in length. Further preferred are polypeptide linkers L which are 8-12 amino acid residues in length. Even more preferred are polypeptide linkers L which are 7-11 or 9-11 amino acid residues in length. Even more preferred are polypeptide linkers L which are 9 amino acid residues in length. In a further preferred embodiment, the integer of the length of the polypeptide linker L is selected from the group consisting of the integers 6, 7, 8, 9, 10, 11, 12, 13 and 14.

The linker peptide L can be composed of any amino acid. In a preferred embodiment the linker polypeptide L comprises at least one Gly, Ser, Arg, Leu, Cys, Ala, Leu and/or Lys residue. In a more preferred embodiment the linker polypeptide L comprises Gly and Ser residues. A further preferred embodiment is a linker L which comprises Gly and Ser residues and has a ratio of Gly to Ser of at least 3 to 1.

In a further embodiment the aforementioned linker L comprises at least one attachment site for covalent coupling of a half-life extending moiety. In an embodiment of the invention the aforementioned attachment site is a Lys or a Cys residue.

A preferred embodiment of the invention is a fusion polypeptide comprising A-L-B, wherein
A is a human Relaxin 2 A chain polypeptide (SEQ ID NO: 117) or a functional variant thereof,
B is a human Relaxin 2 B chain polypeptide (SEQ ID NO: 119) or a functional variant thereof, and L is a linker polypeptide which is 6-14, 7-13, 8-12, 7-11, 9-11, or 9 amino acid residues in length. The linker peptide L can be composed of any amino acid. In a preferred embodiment the linker polypeptide L comprises at least one Gly, Ser, Arg, Leu, Cys, Ala, Leu and/or Lys residue. In a more preferred embodiment the linker polypeptide L comprises Gly and Ser residues. A further preferred embodiment is a linker L which comprises Gly and Ser residues and has a ratio of Gly to Ser of at least 3 to 1. In a further embodiment the aforementioned linker L comprises at least one attachment site for covalent coupling of a non-proteinaceous polymer half-life extending moiety. In an embodiment of the invention the aforementioned attachment site is a Lys or a Cys residue.

A preferred embodiment of the invention is a fusion polypeptide A-L-B further comprising a half-life extending moiety.

In a further embodiment the aforementioned fusion polypeptides have Relaxin activity. In a further preferred embodiment the Relaxin activity is activation of the relaxin receptor LGR7. In an even further preferred embodiment, the activation of the relaxin receptor LGR7 is determined by a method disclosed in experimental methods.

In another aspect, the invention provides a polynucleotide encoding an aforementioned fusion polypeptide. Such a polynucleotide may further comprise a coding sequence for a signal peptide allowing secretion of the fusion polypeptide. Vectors containing polynucleotides for such fusion polypeptides are included as well. Suitable vectors are for example expression vectors. A further embodiment of the invention is a host cell comprising a polynucleotide, a vector, or expression vector encoding the aforementioned fusion polypeptides. The host cell of the invention can be an eukaryotic cell or a prokaryotic cell. An eukaryotic cell can be a mammalian cell or a yeast or insect cell, preferably a mammalian cell. A prokaryotic cell can be for example an *E. coli* cell.

In another embodiment the invention provides pharmaceutical compositions comprising the aforementioned fusion polypeptides. The composition may be formulated for intravenous, intraperitoneal or subcutaneous administration.

Another embodiment of the invention provides a pharmaceutical composition or a fusion polypeptide as medicament. A further embodiment is the use of a pharmaceutical composition or a fusion polypeptide in the treatment of cardiovascular diseases, pancreatitis, inflammation, cancer, scleroderma, pulmonary, renal, and hepatic fibrosis.

BRIEF DESCRIPTION OF THE DRAWINGS

FIG. 2 Schematic representation of single chain Relaxin variants.

FIG. 3 Schematic representation of domain organisation of single chain Relaxin fusion protein variants as well as single chain Relaxin variants designed for PEGylation.

Figure 1:
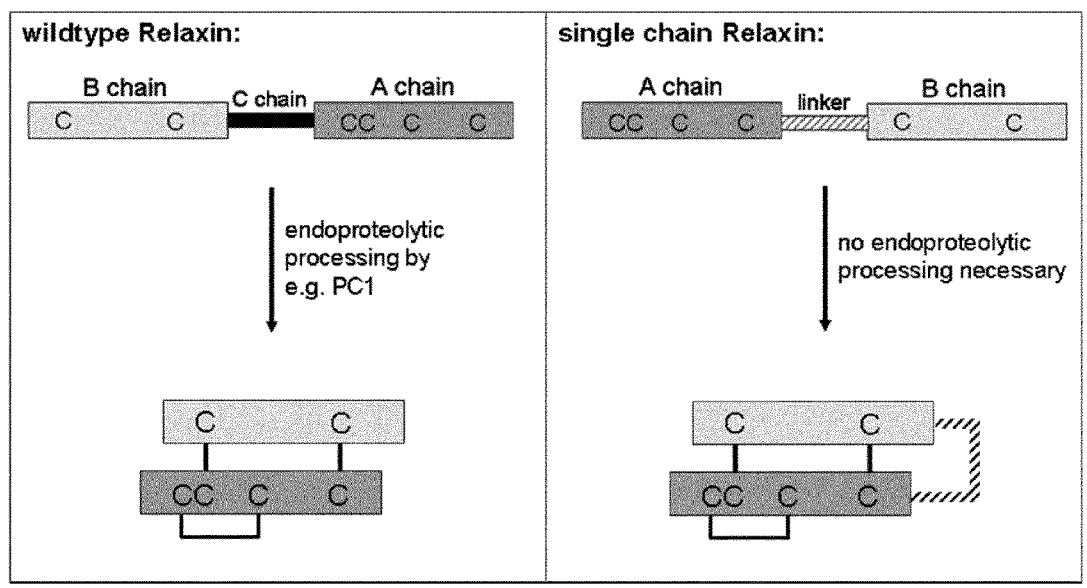
FIG. 1 Schematic representation of the genetic organization of domains of the wildtype Relaxin and single chain Relaxin as well as their corresponding polypeptides.

Relaxin activity in blood samples obtained from scR-Fc 13 treated rats by using the CHO-CRE-LGR7 cell line was determined. Blood samples collected 3, 5, and 7 days after intravenous administration of scR-Fc 13 were incubated on the CHO-CRE-LGR7 cell line and Relative Lights Units were determined. Calibration curves were determined using hRelaxin 2 (R&D Systems, catalogue number 6586-RN-025) and purified scR-Fc 13. The EC50 within the dose response curve is marked by an X. Data are expressed as Relative Light Units, representing the activity of scR-Fc variants and hRelaxin 2 induced luciferase expression. Symbols represent means, error bars represent S.E.M.

FIG. 11: Influence of hRelaxin 2 and scR-Fc 13 on heart rate, coronary flow and contractility in the isolated perfused rat heart model.

At a concentration of 1 nM, application of hRelaxin 2 leads to an increase of heart rate and coronary flow and exhibits a negative inotrophic activity (FIG. 11 *a-d*). Comparable effects were obtained with scR-Fc 13, although at a ten fold higher concentration (FIG. 11 *e-h*).

DETAILED DESCRIPTION OF THE INVENTION

Definitions

The term "amino acid residue" is intended to indicate an amino acid residue contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The term "activity of Relaxin" or "Relaxin Acitvity" is defined by the ability of Relaxin or variants thereof to the activation of the stimulatory G-protein Gs, thus the subsequent generation of the second messenger cyclic AMP, and/or the stimulation of PI3-kinase. Relaxin or variants thereof bind to LGR7 leading to the intracellular activation of the stimulatory G-protein Gs, resulting in the subsequent generation of the second messenger cyclic AMP (cAMP). However, cAMP generation is a time-dependent biphasic response. After an initial short Gs-adenylate cyclase-mediated cAMP response the receptor signal is switching to an inhibitory G protein activation and by this to PI3-kinase-mediated response. (Halls M. L., Bathgate R. A., Summers, R. J. (2005) Signal Switching after Stimulation of LGR7 Receptors by Human Relaxin 2. Ann. N.Y. Acad. Sci. 1041:288-291).

The term "half-life extending moiety" refers to a pharmaceutically acceptable moiety, domain, or "vehicle" covalently linked ("conjugated") to the Relaxin fusion polypeptide directly or via a linker, that prevents or mitigates in vivo proteolytic degradation or other activity-diminishing chemical modification of the Relaxin fusion polypeptide, increases half-life or other pharmacokinetic properties such as but not limited to increasing the rate of absorption, reduces toxicity, improves solubility, increases biological activity and/or target selectivity of the Relaxin fusion polypeptide, increases manufacturability, and/or reduces immunogenicity of the Relaxin fusion polypeptide, compared to an unconjugated form of the Relaxin fusion polypeptide. The term "half-life extending moiety" includes non-proteinaceous, half-life extending moieties, such as PEG or HES, and proteinaceous half-life extending moieties, such as serum albumin, transferrin or Fc domain.

"Polypeptide", peptide" and "protein" are used interchangeably herein and include a molecular chain of two or more amino acids linked through peptide bonds. The terms do not refer to a specific length of the product. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be synthesized, or expressed recombinantly using known protein engineering techniques. In addition, inventive fusion proteins can be derivatized as described herein by well-known organic chemistry techniques.

The term "functional variant" refers to a variant polypeptide which at least retains some of its natural biological activity. In case of the Relaxin 2 variants according to the invention, a functional variant is a variant which shows at least some of its natural activity, such as the activation of the relaxin receptor LGR7. The activation of the relaxin receptor LGR7 can be determined by a method disclosed in experimental methods.

The terms "fragment," "variant," "derivative," and "analog" when referring to polypeptides of the present invention include any polypeptides that retain at least some of the receptor binding properties of the corresponding wild-type Relaxin polypeptide. Fragments of polypeptides of the present invention include proteolytic fragments, as well as deletion fragments, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "fusion protein" indicates that the protein includes polypeptide components derived from more than one parental protein or polypeptide and/or that the fusion protein includes protein domains derived from one or more parental protein or polypeptide which are not arrayed in their wild type orientation. Typically, a fusion protein is expressed from a fusion gene in which a nucleotide sequence encoding a polypeptide sequence from one protein is appended in frame with, and optionally separated by a linker or stretcher from, a nucleotide sequence encoding a polypeptide sequence from a different protein. The fusion gene can then be expressed by a recombinant host cell as a single protein.

The term "nucleotide sequence" or "polynucleotide" is intended to indicate a consecutive stretch of two or more nucleotide molecules. The nucleotide sequence may be of genomic, cDNA, RNA, semisynthetic, synthetic origin, or any combinations thereof.

The term "$EC_{50}$" (half maximal effective concentration) refers to the effective concentration of a therapeutic compound which induces a response halfway between the baseline and maximum after some specified exposure time.

The term "immunogenicity" as used in connection with a given substance is intended to indicate the ability of the substance to induce a response from the immune system. The immune response may be a cell or antibody mediated response (see, e.g., Roitt: Essential Immunology (8th Edition, Black-well) for further definition of immunogenicity). Normally, reduced antibody reactivity will be an indication of reduced immunogenicity. The reduced immunogenicity may be determined by use of any suitable method known in the art, e.g. in vivo or in vitro.

The term "polymerase chain reaction" or "PCR" generally refers to a method for amplification of a desired nucleotide sequence in vitro, as described, for example, in U.S. Pat. No. 4,683,195 and U.S. Pat. No. 4,683,195. In general, the PCR method involves repeated cycles of primer extension synthesis, using oligonucleotide primers capable of hybridising preferentially to a template nucleic acid.

The term "vector" refers to a plasmid or other nucleotide sequences that are capable of replicating within a host cell or being integrated into the host cell genome, and as such, are useful for performing different functions in conjunction with compatible host cells (a vector-host system): to facilitate the cloning of the nucleotide sequence, i.e. to produce usable quantities of the sequence, to direct the expression of the gene product encoded by the sequence and to integrate the nucleotide sequence into the genome of the host cell. The vector will contain different components depending upon the function it is to perform.

"Cell", "host cell", "cell line" and "cell culture" are used interchangeably herein and all such terms should be understood to include progeny resulting from growth or culturing of a cell.

The term "functional in vivo half-life" is used in its normal meaning, i.e. the time at which 50% of the biological activity of the polypeptide is still present in the body/target organ, or the time at which the activity of the polypeptide is 50% of the initial value.

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The polypeptide is cleared by the action of one or more of the reticuloendothelial systems (RES), kidney, spleen or liver, by tissue factor, SEC receptor or other receptor mediated elimination, or by specific or unspecific proteolysis. Normally, clearance depends on size (relative to the cutoff for glomerular filtration), charge, attached carbohydrate chains, and the presence of cellular receptors for the protein. The functionality to be retained is normally selected from receptor binding or receptor activation. The functional in vivo half-life and the serum half-life may be determined by any suitable method known in the art and may for example generally involve the steps of suitably administering to a mammalian a suitable dose of the amino acid sequence or compound to be treated; collecting blood samples or other samples from said mammalian at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Reference is for example made to the standard handbooks, such as Kenneth, A et al: Chemical Stability of Pharmaceuticals: A Handbook for Pharmacists and in Peters et al, Pharmacokinete analysis: A Practical Approach (1996). Reference is also made to "Pharmacokinetics", M Gibaldi & D Perron, published by Marcel Dekker, 2nd Rev. edition (1982).

"Glycosylation" is a chemical modification wherein sugar moieties are added to the polypeptide at specific sites. Glycosylation of polypeptides is typically either N-linked or O-linked. N-linked refers to the attachment of a carbohydrate moiety to the side chain of an asparagine residue. The tripeptide sequences Asn-X-Ser and Asn-X-Thr ("N-X-S/T"), where X is any amino acid except proline, are the recognition sequences for enzymatic attachment of the carbohydrate moiety to the asparagine side chain. Thus, the presence of either of these tripeptide sequences (or motifs) in a polypeptide creates a potential N-linked glycosylation site. O-linked refers to the attachment of a carbohydrate moiety to the hydroxyl-group oxygen of serine and threonine.

An "isolated" fusion polypeptide is one that has been identified and separated from a component of the cell that expressed it. Contaminant components of the cell are materials that would interfere with diagnostic or therapeutic uses of the fusion polypeptide, and may include enzymes, hormones, and other proteinaceous or nonproteinaceous solutes. In preferred embodiments, the fusion polypeptide is purified (1) to greater than 95% by weight of fusion polypeptide as determined e.g. by the Lowry method, UV-Vis spectroscopy or by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or non-reducing conditions using Coomassie blue or, preferably, silver stain. Ordinarily, however, isolated fusion polypeptides will be prepared by at least one purification step.

Overview

The application provides an A-L-B fusion polypeptide, also used terms herein are single chain Relaxin abbreviated as scRelaxin or scR, wherein "A" is a Relaxin A chain, "B" is a Relaxin B chain and "L" is a linker polypeptide. The present application describes an improved Relaxin molecule, wherein the C-terminus of an A chain is linked via a polypeptide linker to the N-terminus of a B chain allowing the fusion polypeptide being expressed as a functional scRelaxin. The application relates, in part, on the surprising discovery that the A-L-B fusion polypeptides can be functionally expressed without the need for endoproteolytic prohormone processing as known for wildtype Relaxin.

Single Chain Versions of Relaxin

Relaxin A and B Domains:

One embodiment of the invention is a fusion polypeptide comprising A-L-B, wherein A comprises a Relaxin A chain polypeptide or a functional variant thereof, B comprises a Relaxin B chain polypeptide or a functional variant thereof and L is a linker polypeptide.

A further embodiment of the invention is a fusion polypeptide comprising A-L-B, wherein A comprises a Relaxin A chain polypeptide or a functional variant thereof, B comprises a Relaxin B chain polypeptide or a functional variant thereof and L is a linker polypeptide, wherein Relaxin is selected from the group of Relaxins consisting of Relaxin 1, Relaxin 2, Relaxin 3, INSL3, INSL4, INSL5, and INSL6. In a further preferred embodiment the Relaxin is Relaxin 2 or Relaxin 3. In a further embodiment the aforementioned Relaxins are human Relaxins.

In a further embodiment the Relaxin A chain polypeptide of A-L-B comprises a Relaxin 2 A chain polypeptide or a functional variant thereof. In a further embodiment the Relaxin B chain polypeptide of A-L-B comprises a Relaxin 2 B chain polypeptide or a functional variant thereof.

In a further embodiment the Relaxin A chain polypeptide of A-L-B comprises a Relaxin 2 A chain polypeptide or a functional variant thereof and the Relaxin B chain polypeptide comprises a Relaxin 2 B chain polypeptide or a functional variant thereof.

In a preferred embodiment the Relaxin A chain polypeptide of A-L-B comprises a human minimal Relaxin 2 A chain polypeptide (SEQ ID NO: 118) or a functional variant thereof, or comprises a human Relaxin 2 A chain polypeptide (SEQ ID NO: 117) or a functional variant thereof. In a preferred embodiment the Relaxin B chain polypeptide of A-L-B comprises a human Relaxin 2 B chain polypeptide (SEQ ID NO: 119) or a functional variant thereof.

In a more preferred embodiment the Relaxin A chain polypeptide of A-L-B comprises a human minimal Relaxin 2 A chain polypeptide (SEQ ID NO: 118) or a functional variant thereof, or comprises a human Relaxin 2 A chain polypeptide (SEQ ID NO: 117) or a functional variant thereof and the Relaxin B chain polypeptide comprises a human Relaxin 2 B chain polypeptide (SEQ ID NO: 119) or a functional variant thereof.

In a further embodiment the Relaxin A chain polypeptide of A-L-B comprises a Relaxin 3 A chain polypeptide or a functional variant thereof. In a further embodiment the Relaxin B chain polypeptide of A-L-B comprises a Relaxin 3 B chain polypeptide or a functional variant thereof.

In a further embodiment the Relaxin A chain polypeptide of A-L-B comprises a human Relaxin 3 A chain polypeptide (SEQ ID NO:124) or a functional variant thereof. In a further embodiment the Relaxin B chain polypeptide of A-L-B comprises a human Relaxin 3 B chain polypeptide (SEQ ID NO: 125) or a functional variant thereof. In a preferred embodiment the Relaxin A chain polypeptide of A-L-B comprises a human Relaxin 3 A chain polypeptide (SEQ ID NO: 124) or a functional variant thereof and the Relaxin B chain polypeptide comprises a human Relaxin 3 B chain polypeptide (SEQ ID NO: 125) or a functional variant thereof.

In a preferred embodiment of the aforementioned fusion polypeptides A-L-B a functional variant of the Relaxin A or B chain has 1, 2, 3, 4, 5, 6, 7, 8, 9, or 10 amino acid substitutions, insertions and/or deletions compared to the wild type Relaxin A and B chain, respectively. Further preferred is an aforementioned Relaxin 2 B variant that further comprises the conserved motif Arg-X-X-X-Arg-X-X-Ile/Val-X (SEQ ID NO: 162).

Relaxin A and B chain variants are known in the art. The well characterized binding site geometry of Relaxin provides the skilled person with guidance to design Relaxin A and B chain variants, see for example Büllesbach and Schwabe J Biol Chem. 2000 Nov. 10; 275(45):35276-80 for variations of the Relaxin B chain and Hossain et al. J Biol Chem. 2008 Jun. 20; 283(25):17287-97 for variations of the Relaxin A chain and the "minimal" Relaxin A chain. For example, for the conserved Relaxin 2 B motif (Arg-X-X-X-Arg-X-X-Ile/Val-X), SEQ ID NO: 162, X represents amino acids which are able to form a helical structure example to select appropriate amino acids X in the conserved motif as the three defined amino acids form a triangular contact region on the surface of the Relaxin B chain (Büllesbach and Schwabe J Biol Chem. 2000 Nov. 10; 275(45)).

In an even more preferred embodiment the Relaxin A chain polypeptide of A-L-B is a human Relaxin 2 A chain polypeptide (SEQ ID NO: 117) or a functional variant thereof and the Relaxin B chain polypeptide is a human Relaxin 2 B chain polypeptide (SEQ ID NO: 119) or a functional variant thereof. In an even more preferred embodiment, the functional variant of human Relaxin 2 A chain polypeptide (SEQ ID NO: 117) is a functional variant having 1, 2, 3, 4, 5, 6, 7, 8, 9, or 10 amino acid substitutions, deletions and/or insertions compared to SEQ ID NO: 117. Further preferred is a functional variant of human Relaxin 2 B chain polypeptide (SEQ ID NO: 119) wherein the functional variant has 1, 2, 3, 4, 5, 6, 7, 8, 9, or 10 amino acid substitutions, deletions and/or insertions compared to SEQ ID NO: 119. Even further preferred is an aforementioned human Relaxin 2 B variant that further comprises the conserved motif Arg-X-X-X-Arg-X-X-Ile/Val-X SEQ ID NO: 162.

In an even more preferred embodiment the Relaxin A chain polypeptide of A-L-B is a human Relaxin 2 A chain polypeptide (SEQ ID NO: 117) or a functional variant thereof having 1, 2, 3, 4, 5, 6, 7, 8, 9, or 10 amino acid exchanges compared to SEQ ID NO: 117 and the Relaxin B chain polypeptide is a human Relaxin 2 B chain polypeptide (SEQ ID NO: 119) or a functional variant thereof having 1, 2, 3, 4, 5, 6, 7, 8, 9, or 10 amino acid exchanges compared to SEQ ID NO:119 and comprising the conserved motif Arg-X-X-X-Arg-X-X-Ile/Val-X SEQ ID NO: 162.

The person skilled in the art knows how to obtain functional variants. Examples of functional variants are disclosed for the Relaxin A chain in Hossain et al J Biol Chem. 2008 Jun. 20; 283(25):17287-97 or in US Pat. publication No. US2011/0130332 and for the Relaxin B chain in Schwabe and Büllesbach (2007) Adv Exp Med Biol. 612:14-25 and Büllesbach and Schwabe J Biol Chem. 2000 Nov. 10; 275(45): 35276-80).

Linker L:

In one embodiment the linker polypeptide L of the aforementioned fusion polypeptides A-L-B consists of a polypeptide which is 6-14 amino acid residues in length. Further preferred are polypeptide linkers L which are 7-13 amino acid residues in length. Further preferred are polypeptide linkers L which are 8-12 amino acid residues in length. Even more preferred are polypeptide linkers L which are 7-11, or 9-11 amino acid residues in length. Even more preferred are polypeptide linkers L which are 9 amino acid residues in length. In a further preferred embodiment, the integer of the length of the polypeptide linker L is selected from the group consisting of the integers 6, 7, 8, 9, 10, 11, 12, 13 and 14.

The amino acid composition of the linker can vary, although a linker exhibiting a low immunogenicity score is preferred. Examples of linkers are well known to those skilled in the art and comprise sequences such as (GGGS)n (SEQ ID NO:163), (GGSG)n (SEQ ID NO:164), where n are integers. The linker peptide L can be composed of any amino acid. In a preferred embodiment the linker polypeptide L comprises at least one Gly, Ser, Arg, Cys, Leu and/or Lys residue. In a more preferred embodiment the linker polypeptide L comprises Gly and Ser residues. In a further preferred embodiment the linker peptide L is a glycine-rich linker such as for example peptides comprising the sequence [GGGGS]$_n$ (SEQ ID NO:165) as disclosed in U.S. Pat. No. 7,271,149. In other embodiments, a serine-rich linker peptide L is used, as described for example in U.S. Pat. No. 5,525,491.

A further preferred embodiment is a linker L which comprises Gly and Ser residues and has a ratio of Gly to Ser of at least 3 to 1.

In a further embodiment the aforementioned linker L comprises at least one attachment site for covalent coupling of a non-proteinaceous polymer half-life extending moiety. In an embodiment of the invention the aforementioned attachment site is a Lys or a Cys residue.

Examples of such linkers are [GlyGlyGlySerGlyGly] (SEQ ID NO: 137), [GlyGlyGlySerGlyGlyGly] (SEQ ID NO: 138), [GlyGlyGlySerGlyGlyGlySerGly] (SEQ ID NO: 139), [GlyGlyGlySerGlyGlyGlySerGlyGlySer] (SEQ ID NO: 140), [GlyGlyGlySerGlyCysGlyGlySerGly] (SEQ ID NO: 141), [GlyGlyGlySerGlyGlyGlySerGlyGlySerGlyGly] (SEQ ID NO: 143), [LysArgSerLeuSerArgLysLysArg] (SEQ ID NO: 144), [GlyGlyGlySerGlyLysGlyGlySerGly] (SEQ ID NO: 142), [GlyGlyGlySerGlyGlyGlySerGlyGlyGlySerGly] (SEQ ID NO: 145), and [GlyGlyGlySerGlyGlyGlySerGlyGlyGly] (SEQ ID NO: 146).

It is contemplated that the optimal linker length and amino acid composition can be determined by routine methods known in the art.

A preferred embodiment of the invention is a fusion polypeptide comprising A-L-B, wherein
A is a human Relaxin 2 A chain polypeptide (SEQ ID NO: 117) or a functional variant thereof having 1, 2, 3, 4, 5, 6, 7, 8, 9, or 10 amino acid substitutions compared to SEQ ID NO: 117,
B is a human Relaxin 2 B chain polypeptide (SEQ ID NO: 119) or a functional variant thereof having 1, 2, 3, 4, 5, 6, 7, 8, 9, or 10 amino acid substitutions compared to SEQ ID NO:119 and comprising the conserved motif Arg-X-X-X-Arg-X-X-Ile/Val-X (SEQ ID NO: 162), and L is a linker polypeptide which is 6-14, 7-13, 8-12, 7-11, 9-11, or 9 amino acid residues in length.

In a preferred embodiment the linker polypeptide L of the aforementioned fusion polypeptide A-L-B is 7-11, or 9-11 amino acid residues in length. Even more preferred are polypeptide linkers L which are 9 amino acid residues in length. In a further preferred embodiment, the integer of the length of the polypeptide linker L is selected from the group consisting of the integers 6, 7, 8, 9, 10, 11, 12, 13 and 14. The linker polypeptide L can be composed of any amino acid. In a preferred embodiment the linker polypeptide L is a flexible linker.

In a preferred embodiment the linker polypeptide L comprises at least one Gly, Ser, Arg, Leu, Cys, and/or Lys residue. In a further preferred embodiment the linker polypeptide L is consists of amino acid residues selected from the group of amino acids consisting of Gly, Ser, Arg, Leu, Cys, and Lys residues.

In a more preferred embodiment the linker polypeptide L comprises Gly and Ser residues. In a further preferred embodiment the linker peptide L is a glycine-rich linker such as peptides comprising the sequence [GGGGS]$_n$ (SEQ ID NO: 165) as disclosed in U.S. Pat. No. 7,271,149. In other embodiments, a serine-rich linker peptide L is used, as described in U.S. Pat. No. 5,525,491.

A further preferred embodiment is a linker polypeptide L which comprises Gly and Ser residues and has a ratio of Gly to Ser of at least 2 to 1.

A further preferred embodiment is a linker polypeptide L which comprises Gly and Ser residues and has a ratio of Gly to Ser of at least 3 to 1.

A further preferred embodiment is a linker polypeptide L which comprises Gly and Ser residues and has a ratio of Gly to Ser of at least 1 to 2.

A further preferred embodiment is a linker polypeptide L which comprises Gly and Ser residues and has a ratio of Gly to Ser of at least 1 to 3.

A further preferred embodiment is a linker polypeptide L with the aforementioned preferred length, wherein all but 4 amino acid residues of the linker L consist of Gly and/or Ser residues and the remaining 4 amino acid residues are selected from the group of natural amino acids.

A further preferred embodiment is a linker polypeptide L with the aforementioned preferred length, wherein all but 3 amino acid residues of the linker L consist of Gly and/or Ser residues and the remaining 3 amino acid residues are selected from the group of natural amino acids.

A further preferred embodiment is a linker polypeptide L with the aforementioned preferred length, wherein all but 2 amino acids residues of the linker L consist of Gly and/or Ser residues and the remaining 2 amino acid residues are selected from the group of natural amino acids.

A further preferred embodiment is a linker polypeptide L with the aforementioned preferred length, wherein all but 1 amino acid residues of the linker L consist of Gly and/or Ser residues and the remaining amino acid residue is selected from the group of natural amino acids.

In a further preferred embodiment the aforementioned group of natural amino acids excludes the amino acid prolin.

A further preferred embodiment is a linker polypeptide L with the aforementioned preferred length, wherein all but 1 amino acid residues of the linker L consist of Gly and/or Ser and the remaining amino acid is selected from the group of Cys and Lys.

In a further preferred embodiment the linker polypeptide L consists of amino acid residues selected from the group of amino acid residues consisting of Gly and Ser residues.

In a further preferred embodiment the linker L consists of amino acid residues selected from the group of amino acids consisting of Gly and Ser residues wherein the ratio of Gly to Ser is at least 2 to 1.

In a further preferred embodiment the linker L consists of amino acid residues selected from the group of amino acids consisting of Gly and Ser residues wherein the ratio of Gly to Ser is at least 3 to 1.

In a further preferred embodiment the linker L consists of amino acid residues selected from the group of amino acids consisting of Gly and Ser residues wherein the ratio of Gly to Ser is at least 1 to 2.

In a further preferred embodiment the linker L consists of amino acid residues selected from the group of amino acids consisting of Gly and Ser residues wherein the ratio of Gly to Ser is at least 1 to 3.

In a further embodiment the aforementioned linker L comprises at least one attachment site for covalent coupling of a nonproteinaceous polymer half-life extending moiety. In an embodiment of the invention the aforementioned attachment site is a Lys or a Cys residue.

Preferred linker polypeptides L are selected from the group of linker polypeptides consisting of

```
                                          (SEQ ID NO: 137)
[GlyGlyGlySerGlyGly], (SEQ ID NO: 138)
[GlyGlyGlySerGlyGlyGly], (SEQ ID NO: 139)
[GlyGlyGlySerGlyGlyGlySerGly], (SEQ ID NO: 140)
[GlyGlyGlySerGlyGlyGlySerGlyGlyGlySer], (SEQ ID NO: 141)
[GlyGlyGlySerGlyCysGlyGlySerGly], (SEQ ID NO: 143)
[GlyGlyGlySerGlyGlyGlySerGlyGlyGlySerGlyGly], (SEQ ID NO: 144)
[LysArgSerLeuSerArgLysLysArg], (SEQ ID NO: 142)
[GlyGlyGlySerGlyLysGlyGlySerGly], (SEQ ID NO: 145)
[GlyGlyGlySerGlyGlyGlySerGlyGlyGlySerGly],
and
                                          (SEQ ID NO: 146)
[GlyGlyGlySerGlyGlyGlySerGlyGly].
```

A preferred embodiment of the invention is a fusion polypeptide comprising A-L-B, wherein
A is a human Relaxin 2 A chain polypeptide (SEQ ID NO: 117) or a functional variant thereof,
B is a human Relaxin 2 B chain polypeptide (SEQ ID NO: 119) or a functional variant thereof, and
L is a linker polypeptide, which is 7, 8, 9 or 10 amino acids in length.

A preferred embodiment of the invention is a fusion polypeptide comprising A-L-B, wherein
A is a human Relaxin 2 A chain polypeptide (SEQ ID NO: 117) or a functional variant thereof having 1, 2, 3 4, 5, 6, 7, 8, 9, or 10 amino acid substitutions compared to SEQ ID NO: 117,
B is a human Relaxin 2 B chain polypeptide (SEQ ID NO: 119) or a functional variant thereof having 1, 2, 3, 4, 5, 6, 7, 8, 9, or 10 amino acid substitutions compared to SEQ ID NO:119 and comprising the conserved motif Arg-X-X-X-Arg-X-X-Ile/Val-X (SEQ ID NO: 162), and
L is a linker polypeptide, which is 7, 8, 9 or 10 amino acids in length.

A preferred embodiment of the invention is a fusion polypeptide comprising A-L-B, wherein
A is a human Relaxin 2 A chain polypeptide (SEQ ID NO: 117),
B is a human Relaxin 2 B chain polypeptide (SEQ ID NO: 119), and
L is a linker polypeptide, which is 7, 8, 9 or 10 amino acids in length.

A preferred embodiment of the invention is a fusion polypeptide comprising A-L-B, wherein
A is a human Relaxin 2 A chain polypeptide (SEQ ID NO: 117) or a functional variant thereof,
B is a human Relaxin 2 B chain polypeptide (SEQ ID NO: 119) or a functional variant thereof, and
L is a linker polypeptide, which is 9 amino acids in length.

A preferred embodiment of the invention is a fusion polypeptide comprising A-L-B, wherein
A is a human Relaxin 2 A chain polypeptide (SEQ ID NO: 117) or a functional variant thereof having 1, 2, 3 4, 5, 6, 7, 8, 9, or 10 amino acid substitutions compared to SEQ ID NO: 117,
B is a human Relaxin 2 B chain polypeptide (SEQ ID NO: 119) or a functional variant thereof having 1, 2, 3, 4, 5, 6, 7, 8, 9, or 10 amino acid substitutions compared to SEQ ID NO:119 and comprising the conserved motif Arg-X-X-X-Arg-X-X-Ile/Val-X (SEQ ID NO: 162), and
L is a linker polypeptide, which is 9 amino acids in length.

A preferred embodiment of the invention is a fusion polypeptide comprising A-L-B, wherein
A is a human Relaxin 2 A chain polypeptide (SEQ ID NO: 117),
B is a human Relaxin 2 B chain polypeptide (SEQ ID NO: 119), and
L is a linker polypeptide, which is 9 amino acids in length.

A preferred embodiment of the invention is a fusion polypeptide comprising A-L-B, wherein
A is a human Relaxin 2 A chain polypeptide (SEQ ID NO: 117) or a functional variant thereof,
B is a human Relaxin 2 B chain polypeptide (SEQ ID NO: 119) or a functional variant thereof, and
L is a linker polypeptide, which is 7, 8, 9 or 10 amino acids in length and which comprises Glycin and Serin residues in a ratio of at least 3:1.

A preferred embodiment of the invention is a fusion polypeptide comprising A-L-B, wherein
A is a human Relaxin 2 A chain polypeptide (SEQ ID NO: 117) or a functional variant thereof having 1, 2, 3 4, 5, 6, 7, 8, 9, or 10 amino acid substitutions compared to SEQ ID NO: 117,
B is a human Relaxin 2 B chain polypeptide (SEQ ID NO: 119) or a functional variant thereof having 1, 2, 3, 4, 5, 6, 7, 8, 9, or 10 amino acid substitutions compared to SEQ ID NO:119 and comprising the conserved motif Arg-X-X-X-Arg-X-X-Ile/Val-X (SEQ ID NO: 162), and
L is a linker polypeptide, which is 7, 8, 9 or 10 amino acids in length and which comprises Glycin and Serin residues in a ratio of at least 3:1.

A preferred embodiment of the invention is a fusion polypeptide comprising A-L-B, wherein
A is a human Relaxin 2 A chain polypeptide (SEQ ID NO: 117),
B is a human Relaxin 2 B chain polypeptide (SEQ ID NO: 119), and
L is a linker polypeptide, which is 7, 8, 9 or 10 amino acids in length and which comprises Glycin and Serin residues in a ratio of at least 3:1.

A preferred embodiment of the invention is a fusion polypeptide comprising A-L-B, wherein
A is a human Relaxin 2 A chain polypeptide (SEQ ID NO: 117) or a functional variant thereof,
B is a human Relaxin 2 B chain polypeptide (SEQ ID NO: 119) or a functional variant thereof, and
L is a linker polypeptide, which is 9 amino acids in length and which comprises Glycin and Serin residues in a ratio of at least 3:1.

A preferred embodiment of the invention is a fusion polypeptide comprising A-L-B, wherein
A is a human Relaxin 2 A chain polypeptide (SEQ ID NO: 117) or a functional variant thereof having 1, 2, 3 4, 5, 6, 7, 8, 9, or 10 amino acid substitutions compared to SEQ ID NO: 117,
B is a human Relaxin 2 B chain polypeptide (SEQ ID NO: 119) or a functional variant thereof having 1, 2, 3, 4, 5, 6, 7, 8, 9, or 10 amino acid substitutions compared to SEQ ID NO:119 and comprising the conserved motif Arg-X-X-X-Arg-X-X-Ile/Val-X (SEQ ID NO: 162), and
L is a linker polypeptide, which is 9 amino acids in length and which comprises Glycin and Serin residues in a ratio of at least 3:1.

A preferred embodiment of the invention is a fusion polypeptide comprising A-L-B, wherein
A is a human Relaxin 2 A chain polypeptide (SEQ ID NO: 117),
B is a human Relaxin 2 B chain polypeptide (SEQ ID NO: 119), and
L is a linker polypeptide, which is 9 amino acids in length and which comprises Glycin and Serin residues in a ratio of at least 3:1.

A preferred embodiment of the invention is a fusion polypeptide comprising A-L-B, wherein
A is a human Relaxin 2 A chain polypeptide (SEQ ID NO: 117) or a functional variant thereof,
B is a human Relaxin 2 B chain polypeptide (SEQ ID NO: 119) or a functional variant thereof, and
L is a linker polypeptide, which has the sequence GlyGlyGly-SerGlyGlyGlySerGly (SEQ ID NO: 139).

A preferred embodiment of the invention is a fusion polypeptide comprising A-L-B, wherein
A is a human Relaxin 2 A chain polypeptide (SEQ ID NO: 117) or a functional variant thereof having 1, 2, 3 4, 5, 6, 7, 8, 9, or 10 amino acid substitutions compared to SEQ ID NO: 117,
B is a human Relaxin 2 B chain polypeptide (SEQ ID NO: 119) or a functional variant thereof having 1, 2, 3, 4, 5, 6, 7, 8, 9, or 10 amino acid substitutions compared to SEQ ID NO:119 and comprising the conserved motif Arg-X-X-X-Arg-X-X-Ile/Val-X (SEQ ID NO: 162), and
L is a linker polypeptide, which has the sequence GlyGlyGly-SerGlyGlyGlySerGly (SEQ ID NO: 139).

A preferred embodiment of the invention is a fusion polypeptide comprising A-L-B, wherein
A is a human Relaxin 2 A chain polypeptide (SEQ ID NO: 117),
B is a human Relaxin 2 B chain polypeptide (SEQ ID NO: 119), and
L is a linker polypeptide, which has the sequence GlyGlyGly-SerGlyGlyGlySerGly (SEQ ID NO: 139).

A more preferred embodiment of the invention is a fusion polypeptide comprising the sequence of scR4 (SEQ ID NO: 4).

A more preferred embodiment of the invention is a fusion polypeptide comprising the sequence of scR4 w/o Tag (SEQ ID NO: 45).

A preferred embodiment of the invention is a fusion polypeptide comprising A-L-B, wherein
A is a human Relaxin 2 A chain polypeptide (SEQ ID NO: 117) or a functional variant thereof having 1, 2, 3 4, 5, 6, 7, 8, 9, or 10 amino acid substitutions compared to SEQ ID NO: 117,
B is a human Relaxin 2 B chain polypeptide (SEQ ID NO: 119) or a functional variant thereof having 1, 2, 3, 4, 5, 6, 7, 8, 9, or 10 amino acid substitutions compared to SEQ ID NO:119 and comprising the conserved motif Arg-X-X-X-Arg-X-X-Ile/Val-X (SEQ ID NO: 162), and
L is a linker polypeptide, selected from the group of linker peptides consisting of linkers having the amino acid sequence of SEQ ID NO: 137-146.

The linker length can be between 6 and 14 of amino acids while longer linker peptides that themselves mediate additional functions are conceivable.

In a further embodiment the aforementioned fusion polypeptides A-L-B have Relaxin activity. In a further preferred embodiment the Relaxin activity is activation of the relaxin receptor LGR7. Methods for determining Relaxin activity are known in the art or are provided herein. In an even further preferred embodiment, the activation of the relaxin receptor LGR7 is determined by a method disclosed in experimental methods herein. In an even further preferred embodiment, the determination of the activation of the Relaxin receptor LGR7 is determining an $EC_{50}$ value. In an even more preferred embodiment the aforementioned Relaxin activity is less than $10^5$ fold, $10^4$ fold, $10^3$ fold, 100 fold, 75 fold, 50 fold, 25 fold or 10 fold lower compared to the corresponding wild type Relaxin effective concentration inducing a half maximal activity. For example, the corresponding wild type Relaxin for a fusion polypeptide A-L-B based on human Relaxin 2 is the human Relaxin 2 protein.

Improvement of the Biological Half Life of Single Chain Relaxin Variants

The improvement of the half-life of a fusion polypeptide of the invention can be achieved by adding a half-life extending moiety.

In an embodiment of the invention the aforementioned fusion polypeptide A-L-B further comprise at least one half-life extending moiety. In one embodiment the half-life extending moieties are proteinaceous or non-proteinaceous polymers.

Half-Life Extension Via Non-Proteinaceous Polymer Half-Life Extending Moieties:

Improving the biological half-life of a fusion polypeptide A-L-B can be achieved by a non-proteinaceous polymer half-life extending moiety which is covalently coupled to a stretcher polypeptide comprising an attachment site for a non-proteinaceous polymer half-life extending moiety fused to the N- and/or C-terminus of A-L-B. Methods attaching such moieties are known in the art.

Non-proteinaceous polymer half-life extending moieties can be covalently coupled to an attachment site of the fusion polypeptide A-L-B. An attachment site can be either within A, L or B or added by a polypeptide comprising such attachment site recombinantly fused to the N-terminus and/or C-terminus of to the aforementioned fusion polypeptides A-L-B. Preferred is a coupling via the linker polypeptide L, or N- and/or C-terminally to the fusion polypeptide A-L-B fused stretcher comprising an attachment site. An attachment site can be an attachment amino acid, for example Cys or Lys, or a sugar moiety of a carbohydrate.

The non-proteinaceous polymer molecule to be coupled to the variant polypeptide may be any suitable polymer molecule, such as a natural or synthetic homo-polymer or hetero-polymer, typically with a molecular weight in the range of about 300-100,000 Da, such as about 500-20,000 Da, more preferably in the range of about 500-15,000 Da, even more preferably in the range of about 2-12 kDa, such as in the range of about 3-10 kDa. When the term "about" is used herein in connection with a certain molecular weight, the word "about" indicates an approximate average molecular weight and reflects the fact that there will normally be a certain molecular weight distribution in a given polymer preparation. Examples of homo-polymers include a polyol (i.e. poly-OH), a polyamine (i.e. poly-NH2) and a polycarboxylic acid (i.e. poly-COOH). A hetero-polymer is a polymer comprising different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, hydroxyalkyl starch (HAS), such as hydroxyethyl starch (HES), polysialic acid (PSA), poly-vinyl alcohol (PVA), poly-carboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule, since it has only few reactive groups capable of cross-linking compared to, e.g., polysaccharides such as dextran. In particular, mono-functional PEG, e.g. methoxypolyethylene glycol (mPEG), is of interest since its coupling chemistry is relatively simple (only one reactive group is available for conjugating with attachment groups on the polypeptide). Consequently, as the risk of cross-linking is eliminated, the resulting conjugated fusion polypeptides of the invention are more homogeneous and the reaction of the polymer molecules with the variant polypeptide is easier to control.

To effect covalent attachment of the polymer molecule(s) to the fusion polypeptides of the invention, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butyrate (SBA), succinimidy carboxymethylate (SCM), benzotriazole carbonate (BTC), N-hydroxysuccinmide (NHS), aldehyde, nitrophenylcarbonate (NPC), and tresylate (TRES)). Suitable activated polymer molecules are commercially available, e.g. from Shearwater Polymers, Inc., Huntsville, Ala., USA, or from PolyMASC Pharmaceuticals plc, UK.

Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPOXPEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575, both of which are incorporated herein by reference. Furthermore, the following publications disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleimide-mPEG (MAL-mPEG) and orthopyridyl-disulfide-PEG (OPSS-PEG), preferably orthopyridyl-disulfide-mPEG (OPSS-mPEG). Typically, such PEG or mPEG polymers will have a size of about 5 kDa, about 10 kD, about 12 kDa or about 20 kDa.

The conjugation of the fusion polypeptides of the invention and the activated polymer molecules is conducted by use of any conventional method, e.g. as described in the following references (which also describe suitable methods for activation of polymer molecules): Harris and Zalipsky, eds., Poly (ethylene glycol) Chemistry and Biological Applications, AZC Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.).

The skilled person will be aware that the activation method and/or conjugation chemistry to be used depends on the attachment group(s) of the fusion polypeptide (examples of which are given further above), as well as the functional groups of the polymer (e.g. being amine, hydroxyl, carboxyl, aldehyde, sulfydryl, succinimidyl, maleimide, vinysulfone or haloacetate). The PEGylation may be directed towards conjugation to all available attachment groups on the fusion polypeptide (i.e. such attachment groups that are exposed at the surface of the polypeptide) or may be directed towards one or more specific attachment groups, e.g. the N-terminal amino group as described in U.S. Pat. No. 5,985,265 or to cysteine residues. Furthermore, the conjugation may be achieved in one step or in a stepwise manner (e.g. as described in WO 99/55377).

For PEGylation to cysteine residues (see above) the fusion polypeptide is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

It will be understood that the PEGylation is designed so as to produce the optimal molecule with respect to the number of PEG molecules attached, the size and form of such molecules (e.g. whether they are linear or branched), and the attachment site(s) in the fusion polypeptide. The molecular weight of the polymer to be used may e.g. be chosen on the basis of the desired effect to be achieved.

In connection with conjugation to only a single attachment group on the protein (e.g. the N-terminal amino group), it may be advantageous that the polymer molecule, which may be linear or branched, has a high molecular weight, preferably about 10-25 kDa, such as about 15-25 kDa, e.g. about 20 kDa.

Normally, the polymer conjugation is performed under conditions aimed at reacting as many of the available polymer attachment groups with polymer molecules. This is achieved by means of a suitable molar excess of the polymer relative to the polypeptide. Typically, the molar ratios of activated polymer molecules to polypeptide are up to about 1000-1, such as up to about 200-1, or up to about 100-1. In some cases the ratio may be somewhat lower, however, such as up to about 50-1, 10-1, 5-1, 2-1 or 1-1 in order to obtain optimal reaction.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378).

Subsequent to the conjugation, residual activated polymer molecules are blocked according to methods known in the art, e.g. by addition of primary amine to the reaction mixture, and the resulting inactivated polymer molecules are removed by a suitable method.

It will be understood that depending on the circumstances, e.g. the amino acid sequence of the fusion polypeptide, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to fusion polypeptide. The PEGylated fusion polypeptides resulting from any given PEGylation process will, however, normally comprise a stochastic distribution of conjugated fusion polypeptide having slightly different degrees of PEGylation.

For improvement of the biological half life of Relaxin or of fusion polypeptides of the invention, chemical modification such as PEGylation, or HESylation are applicable.

HAS and HES non-proteinaceous polymers, as well as methods of producing HAS or HES conjugates are disclosed for example in WO02/080979, WO03/070772, WO057092391 and WO057092390.

Polysialytion is another technology, which uses the natural polymer polysialic acid (PSA) to prolong the half-life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally potysialylated bacteria were then able, by virtue of molecular mimicry, to foil the body's defence system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Half-Life Extension Via Proteinaceous Half-Life Extending Moieties:

A further possibility improving the half-life of a fusion polypeptide A-L-B is a fusion with a proteinaceous half-life extending moiety, such as the immunoglobulin Fc fragment of antibodies, transferrin, transferrin receptor or at least the transferrin-binding portion thereof, serum albumin, or variants thereof or binding modules that bind in-vivo to other molecules mediating longer half-life, e.g. serum albumin binding protein is a commonly used method.

The scRelaxin polypeptides described above can be fused directly or via a peptide linker to the Fc portion of an immunoglobulin "Immunoglobulins" are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class.

As used herein, the "Fc" portion of an immunoglobulin has the meaning commonly given to the term in the field of immunology. Specifically, this term refers to an antibody fragment that is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through non-covalent interactions and disulfide bonds. The Fc portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C. A. K., ed., W.H. Freeman and Co., 1992.

There are five types of human immunoglobulin Fc regions with different effector and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fc receptor. There are four IgG subclasses G1, G2, G3, and G4, each of which have different effect or functions. These effector functions are generally mediated through interaction with the Fc receptor (FcγR) or by binding Clq and fixing complement. Binding to FcγR can lead to antibody dependent cell mediated cytolysis, whereas binding to complement factors can lead to complement mediated cell lysis. In designing heterologous Fc fusion proteins wherein the Fc portion is being utilized solely for its ability to extend half-life, it is important to minimize any effector function. All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

Depending on the desired in vivo effect, the heterologous fusion proteins of the present invention may contain any of the isotypes described above or may contain mutated Fc regions wherein the complement and/or Fc receptor binding functions have been altered. Thus, the heterologous fusion proteins of the present invention may contain the entire Fc portion of an immunoglobulin, fragments of the Fc portion of an immunoglobulin, or analogs thereof fused to a scRelaxin compound.

Regardless of the final structure of the fusion protein, the Fc or Fc-like region must serve to prolong the in vivo plasma half-life of the scRelaxin compound fused at the C-terminus or N-terminus. Preferably, the fused scRelaxin compound retains some biological activity. Biological activity can be determined by in vitro and in vivo methods known in the art.

It is preferable that the Fc region used for the heterologous fusion proteins of the present invention be derived from an IgG1 or an IgG2 Fc region.

Generally, the Fc region used for the heterologous fusion proteins of the present invention can be derived from any species including but not limited to human, rat, mouse and pig. Preferably, the Fc region used for the present invention is derived from human or rat. However, most preferred are human Fc regions and fragments and variants thereof to reduce the risk of the fusion protein being immunogenic in humans. A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

The scRelaxin compounds described above can be fused directly or via a peptide stretcher to albumin or an analog, fragment, or derivative thereof. Generally the albumin proteins making up part of the fusion proteins of the present invention can be derived from albumin cloned from any species. However, human albumin and fragments and analogs thereof are preferred to reduce the risk of the fusion protein being immunogenic in humans. Human serum albumin (HSA) consists of a single non-glycosylated polypeptide chain of 585 amino acids with a formula molecular weight of 66,500. The amino acid sequence of HSA (SEQ ID NO:123) has been described e.g. in Meloun, et al. (1975); Behrens, et al. (1975); Lawn, et al. (1981) and Minghetti, et al. (1986). A variety of polymorphic variants as well as analogs and fragments of albumin have been described (see Weitkamp, et al. (1973)). For example, in EP0322094 and EP0399666 various fragments of human serum albumin are disclosed. It is understood that the heterologous fusion proteins of the present invention include scRelaxin compounds that are coupled to any albumin protein including fragments, analogs, and derivatives wherein such fusion protein is biologically active and has a longer plasma half-life than the scRelaxin compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the scRelaxin compound of interest. The techniques are well-known in the art, see, e.g., WO 93/15199, WO 93/15200, WO 01/77137 and EP0413622.

In an embodiment of the invention the proteinaceous half-life extending moiety has low immunogenicity, is human or humanized. In a preferred embodiment the proteinaceous half-life extending moiety is human, such as human transferrin (SEQ ID NO: 122), human serum albumin (SEQ ID NO: 123), or human IgG1 Fc (SEQ ID NO: 120).

Additionally, other proteins, protein domains or peptides improving the biological half life can also be used as fusion partners.

Half-life extension via fusion to human serum albumin is disclosed for example in WO93/15199. Albumin binding as a general strategy for improving the pharmacokinetics of proteins is described for example in Dennis et al., The Journal of Biological Chemistry, Vol. 277, No 38, Issue of September 20, pp. 35035-35043. Half-life extension via fusion to human serum albumin binding proteins is disclosed for example in US20100104588. Half-life extension via fusion to human serum albumin or IgG-Fc binding proteins is disclosed for example in WO01/45746. A further example of half-life extension via fusion to human serum albumin binding peptides is disclosed in WO2010/054699.

Half-life extension via fusion to an Fc domain is disclosed for example in WO2001/058957.

The biological activity determines the preferred orientation of the protein of interest to its fusion partner. C-terminal as well as N-terminal orientations of fusion partners are included. In addition, for improvement of the biological half life or other functions, fusion partners may be modified by phosphorylation, sulfation, acrylation, glycosylation, deglycosylation, methylation, farnesylation, acetylation, amidation or others.

Proteinaceous half-life extending moieties are recombinantly fused to the N-terminus and/or C-terminus of the aforementioned fusion polypeptides A-L-B. The fusion can be with or without an additional stretcher polypeptide. Examples of proteinaceous half-life extending moieties are transferrin, transferrin receptor or at least the transferrin-binding portion thereof, serum albumin, serum albumin binding proteins, Immunglobulins, and the Fc domain of an immunoglobulin. Preferred are human proteinaceous half-life extending moieties, e.g human transferrin, human transferrin receptor or at least the transferrin-binding portion thereof, human serum albumin, human immunoglobulin or human Fc domains. Fusion partners are linked either directly or by a stretch of amino acids, also termed stretcher. The fusion junction is defined as the position between the last C-terminal amino acid of the first protein or peptide and the first N-terminal amino acid of the second protein or peptide in a fusion protein. Accordingly, a fusion junction or stretcher includes any amino acid between the last amino acid the N-terminal fusion partner and the first amino acid of the C-terminal fusion partner.

Stretcher Units:

Such stretchers are known in the art and are 1 to about 100 amino acids in length, are 1 to about 50 amino acids in length, are 1 to about 25 amino acids in length, are 1 to about 15 amino acids in length, are 1 to 10 amino acids in length, are 4 to 25 amino acids in length, are 4 to 20 amino acids in length, are 4 to 15 amino acids in length, or are 4 to 10 amino acids in length.

The amino acid composition of stretcher sequences is variable, although a stretcher exhibiting a low immunogenicity score is preferred. In an embodiment of the invention a stretcher polypeptide connecting a fusion polypeptide A-L-B with a proteinaceous half-life extending moiety can be composed of any amino acid. As shown for example the stretcher polypeptide employed in scR-Fc1 is composed of charged and bulky amino acids (e.g. Glu, Arg or Asp) whereas the stretcher polypeptide in scR-Fc2 is composed of uncharged amino acids (e.g. Gly and Ser).

In a preferred embodiment the stretcher polypeptide comprises at least one Gly, Ser, Ile, Glu, Arg, Met, and/or Asp residue. In a more preferred embodiment the stretcher polypeptide comprises Gly and Ser residues. In a further preferred embodiment the stretcher peptide is a glycine-rich linker such as peptides comprising the sequence $[GGGGS]_n$ (SEQ ID NO: 165) as disclosed in U.S. Pat. No. 7,271,149. In other embodiments, a serine-rich strecher polypeptide is used, as described in U.S. Pat. No. 5,525,491. A further preferred embodiment is a stretcher polypeptide which comprises Gly and Ser residues and has a ratio of Gly to Ser of at least 3 to 1. Further preferred are stretcher polypeptides having a Prolin residue at the C- and/or N-terminal end.

Preferred stretcher peptides are [GlyGlySerPro] (SEQ ID NO: 148), [GlyGlySerGlyGlySerPro] (SEQ ID NO: 149), and [GlyGlySerGlyGlySerGlyGlySerPro] (SEQ ID NO: 150).

Such fusion polypeptides with improved half-life can be represented by fusion polypeptide comprising the sequence $(R1)_m$-$(S1)_n$-A-L-B-$(S2)_o$-$(R2)_p$.

A further embodiment of the invention is a fusion polypeptide comprising $(R1)_m$-$(S1)_n$-A-L-B-$(S2)_o$-$(R2)_p$, wherein A, L and B have the definitions as disclosed above,
R1 and R2 are proteinaceous half-life extending moieties,
S1 and S2 are stretcher peptides as defined above,
and wherein m, n, o, and p independently have the integer 0 or 1, provided that at least one of m, n, o, and p are 1. For example, $(S1)_{n=0}$ means that no linker S1 is present in the fusion polypeptide.

In a further embodiment n has the integer 1 if m has the integer 1. In a further embodiment o has the integer 1 if p has the integer 1.

In a preferred embodiment n and m are 0 and o and p are 1. In a further preferred embodiment n and m are 1 and o and p are 0.

A further embodiment of the invention is a fusion polypeptide comprising $(R1)_{m=1}$-$(S1)_{n=0}$-A-L-B-$(S2)_{o=0}$-$(R2)_{p=0}$.

A further embodiment of the invention is a fusion polypeptide comprising $(R1)_{m=0}$-$(S1)_{n=0}$-A-L-B-$(S2)_{o=0}$-$(R2)_{p=1}$.

In a preferred embodiment the proteinaceous half-life extending moiety is selected form the group consisting of serum albumin, transferrin, Fc domain, IgG1 Fc domain, and serum albumin binding protein.

In a further embodiment the aforementioned fusion polypeptides further comprising at least one half-life extending moiety have an extended half-life compared to the corresponding wild type Relaxin, wherein the half-life extension is at least 5, 10, 20, 50, 100 or 500-fold. Preferably, the half-life is determined as serum half-life, meaning detection of the fusion protein in serum or whole blood, for example by using a commercially available quantification ELISA assay (e.g. R&D Systems, Human Relaxin-2 Quantikine ELISA kit, catalogue number DRL200). The half-life is preferably a human blood half-life. Preferably, the half-life is determined as functional in vivo half-life, meaning the activity of fusion polypeptide in serum or blood samples is determined. Assays to determine the activity of a fusion polypeptide A-L-B of the invention are known in the art and are described herein.

A preferred embodiment of the invention is a fusion polypeptide comprising $(R1)_m$-$(S1)_n$-A-L-B-$(S2)_o$-$(R2)_p$, wherein A is a human Relaxin 2 A chain polypeptide (SEQ ID NO: 117) or a functional variant thereof,
B is a human Relaxin 2 B chain polypeptide (SEQ ID NO: 119) or a functional variant thereof,
L is a linker polypeptide, which is 9 amino acids in length,
R1 and R2 are half-life extending moieties, preferably proteinaceous half-life extending moieties,
S1 and S2 are stretcher peptides as defined above,
and wherein m, n, o, and p independently have the integer 0 or 1, provided that at least one of m, n, o, and p are 1, preferably at least m or p is 1, more preferably m and n are 0 and o and p are 1, and most preferably m and n are 1 and o and p are 0.

A preferred embodiment of the invention is a fusion polypeptide comprising (R1)$_m$-(S1)$_n$-A-L-B-(S2)$_o$-(R2)$_p$, wherein A is a human Relaxin 2 A chain polypeptide (SEQ ID NO: 117),
B is a human Relaxin 2 B chain polypeptide (SEQ ID NO: 119),
L is a linker polypeptide, which is 9 amino acids in length,
R1 and R2 are half-life extending moieties, preferably proteinaceous half-life extending moieties,
S1 and S2 are stretcher peptides as defined above,
and wherein m, n, o, and p independently have the integer 0 or 1, provided that at least one of m, n, o, and p are 1, preferably at least m or p is 1, more preferably m and n are 0 and o and p are 1, and most preferably m and n are 1 and o and p are 0.

A preferred embodiment of the invention is a fusion polypeptide comprising (R1)$_m$-(S1)$_n$-A-L-B-(S2)$_o$-(R2)$_p$, wherein A is a human Relaxin 2 A chain polypeptide (SEQ ID NO: 117) or a functional variant thereof,
B is a human Relaxin 2 B chain polypeptide (SEQ ID NO: 119) or a functional variant thereof,
L is a linker polypeptide, which has the sequence GlyGlyGly-SerGlyGlyGlySerGly (SEQ ID NO: 139),
R1 and R2 are half-life extending moieties, preferably proteinaceous half-life extending moieties,
S1 and S2 are stretcher peptides as defined above,
and wherein m, n, o, and p independently have the integer 0 or 1, provided that at least one of m, n, o, and p are 1, preferably at least m or p is 1, more preferably m and n are 0 and o and p are 1, and most preferably m and n are 1 and o and p are 0.

A preferred embodiment of the invention is a fusion polypeptide comprising (R1)$_m$-(S1)$_n$-A-L-B-(S2)$_o$-(R2)$_p$, wherein A is a human Relaxin 2 A chain polypeptide (SEQ ID NO: 117),
B is a human Relaxin 2 B chain polypeptide (SEQ ID NO: 119),
L is a linker polypeptide, which has the sequence GlyGlyGly-SerGlyGlyGlySerGly (SEQ ID NO: 139),
R1 and R2 are half-life extending moieties, preferably proteinaceous half-life extending moieties,
S1 and S2 are stretcher peptides as defined above,
and wherein m, n, o, and p independently have the integer 0 or 1, provided that at least one of m, n, o, and p are 1, preferably at least m or p is 1, more preferably m and n are 0 and o and p are 1, and most preferably m and n are 1 and o and p are 0.

A preferred embodiment of the invention is a fusion polypeptide comprising (R1)-(S1)-A-L-B, wherein A is a human Relaxin 2 A chain polypeptide (SEQ ID NO: 117) or a functional variant thereof,
B is a human Relaxin 2 B chain polypeptide (SEQ ID NO: 119) or a functional variant thereof,
L is a linker polypeptide, which has the sequence GlyGlyGly-SerGlyGlyGlySerGly (SEQ ID NO: 139),
R1 is a half-life extending moiety, preferably a proteinaceous half-life extending moiety, and
S1 is a stretcher peptide as defined above.

A preferred embodiment of the invention is a fusion polypeptide comprising (R1)-(S1)-A-L-B, wherein A is a human Relaxin 2 A chain polypeptide (SEQ ID NO: 117),
B is a human Relaxin 2 B chain polypeptide (SEQ ID NO: 119),
L is a linker polypeptide, which has the sequence GlyGlyGly-SerGlyGlyGlySerGly (SEQ ID NO: 139),
R1 is a half-life extending moiety, preferably a proteinaceous half-life extending moiety, and
S1 is a stretcher peptide as defined above.

A preferred embodiment of the invention is a fusion polypeptide comprising (R1)-(S1)-A-L-B, wherein A is a human Relaxin 2 A chain polypeptide (SEQ ID NO: 117) or a functional variant thereof,
B is a human Relaxin 2 B chain polypeptide (SEQ ID NO: 119) or a functional variant thereof,
L is a linker polypeptide, which has the sequence GlyGlyGly-SerGlyGlyGlySerGly (SEQ ID NO: 139),
R1 is a proteinaceous half-life extending moiety,
S1 is a stretcher peptide being 4-10 amino acids in length, preferably selected from the group consisting of GlyGlySerPro (SEQ ID NO: 148), GlyGlySerGlyGlySerPro (SEQ ID NO: 149), and GlyGlySerGlyGlySerGlyGlySerPro (SEQ ID NO: 150).

A preferred embodiment of the invention is a fusion polypeptide comprising (R1)-(S1)-A-L-B, wherein A is a human Relaxin 2 A chain polypeptide (SEQ ID NO: 117),
B is a human Relaxin 2 B chain polypeptide (SEQ ID NO: 119),
L is a linker polypeptide, which has the sequence GlyGlyGly-SerGlyGlyGlySerGly (SEQ ID NO: 139),
R1 is a proteinaceous half-life extending moiety,
S1 is a stretcher peptide being 4-10 amino acids in length, preferably selected from the group consisting of GlyGlySerPro (SEQ ID NO: 148), GlyGlySerGlyGlySerPro (SEQ ID NO: 149), and GlyGlySerGlyGlySerGlyGlySerPro (SEQ ID NO: 150).

A preferred embodiment of the invention is a fusion polypeptide comprising (R1)-(S1)-A-L-B, wherein A is a human Relaxin 2 A chain polypeptide (SEQ ID NO: 117) or a functional variant thereof,
B is a human Relaxin 2 B chain polypeptide (SEQ ID NO: 119) or a functional variant thereof,
L is a linker polypeptide, which has the sequence GlyGlyGly-SerGlyGlyGlySerGly (SEQ ID NO: 139),
R1 is a proteinaceous half-life extending moiety,
S1 is a stretcher peptide being 10 amino acids in length.

A preferred embodiment of the invention is a fusion polypeptide comprising (R1)-(S1)-A-L-B, wherein A is a human Relaxin 2 A chain polypeptide (SEQ ID NO: 117),
B is a human Relaxin 2 B chain polypeptide (SEQ ID NO: 119),
L is a linker polypeptide, which has the sequence GlyGlyGly-SerGlyGlyGlySerGly (SEQ ID NO: 139),
R1 is a proteinaceous half-life extending moiety,
S1 is a stretcher peptide being 10 amino acids in length.

A preferred embodiment of the invention is a fusion polypeptide comprising (R1)-(S1)-A-L-B, wherein A is a human Relaxin 2 A chain polypeptide (SEQ ID NO: 117) or a functional variant thereof,
B is a human Relaxin 2 B chain polypeptide (SEQ ID NO: 119) or a functional variant thereof,
L is a linker polypeptide, which has the sequence GlyGlyGly-SerGlyGlyGlySerGly (SEQ ID NO: 139),
R1 is a proteinaceous half-life extending moiety,
S1 is a stretcher peptide consisting of GlyGlySerGlyGlySer-GlyGlySerPro (SEQ ID NO: 150).

A preferred embodiment of the invention is a fusion polypeptide comprising (R1)-(S1)-A-L-B, wherein A is a human Relaxin 2 A chain polypeptide (SEQ ID NO: 117),
B is a human Relaxin 2 B chain polypeptide (SEQ ID NO: 119),
L is a linker polypeptide, which has the sequence GlyGlyGly-SerGlyGlyGlySerGly (SEQ ID NO: 139),
R1 is a proteinaceous half-life extending moiety,
S1 is a stretcher peptide consisting of GlyGlySerGlyGlySer-GlyGlySerPro (SEQ ID NO: 150).

A preferred embodiment of the invention is a fusion polypeptide comprising (R1)-(S1)-A-L-B, wherein A is a human Relaxin 2 A chain polypeptide (SEQ ID NO: 117) or a functional variant thereof,
B is a human Relaxin 2 B chain polypeptide (SEQ ID NO: 119) or a functional variant thereof,
L is a linker polypeptide, which has the sequence GlyGlyGly-SerGlyGlyGlySerGly (SEQ ID NO: 139),
R1 is a Fc domain of an antibody, preferably a human IgG1 or IgG2 Fc domain,
S1 is a stretcher peptide consisting of GlyGlySerGlyGlySer-GlyGlySerPro (SEQ ID NO: 150).

A preferred embodiment of the invention is a fusion polypeptide comprising (R1)-(S1)-A-L-B, wherein A is a human Relaxin 2 A chain polypeptide (SEQ ID NO: 117),
B is a human Relaxin 2 B chain polypeptide (SEQ ID NO: 119),
L is a linker polypeptide, which has the sequence GlyGlyGly-SerGlyGlyGlySerGly (SEQ ID NO: 139),
R1 is a Fc domain of an antibody, preferably a human IgG1 or IgG2 Fc domain,
S1 is a stretcher peptide consisting of GlyGlySerGlyGlySer-GlyGlySerPro (SEQ ID NO: 150).

A further preferred embodiment of the invention is a fusion polypeptide comprising a polypeptide as set forth in table 3.

A further preferred embodiment of the invention are fusion polypeptides as set forth in table 3.

TABLE 3

| Construct | SEQ ID NO |
|---|---|
| scR3 | SEQ ID NO: 3 |
| scR4 | SEQ ID NO: 4 |
| scR5 | SEQ ID NO: 5 |
| scR7 | SEQ ID NO: 7 |
| scR8 | SEQ ID NO: 8 |
| scR9 | SEQ ID NO: 9 |
| scR10 | SEQ ID NO: 10 |
| scR11 | SEQ ID NO: 11 |
| scR12 | SEQ ID NO: 12 |
| scR13 | SEQ ID NO: 13 |
| scR14 | SEQ ID NO: 14 |
| scR15 | SEQ ID NO: 15 |
| scR-Fc 1 | SEQ ID NO: 16 |
| scR-Fc 2 | SEQ ID NO: 17 |
| scR-Fc 3 | SEQ ID NO: 18 |
| scR-Fc 4 | SEQ ID NO: 19 |
| scR-Fc 5 | SEQ ID NO: 20 |
| scR-Fc 6 | SEQ ID NO: 21 |
| scR-Fc 7 | SEQ ID NO: 22 |
| scR-Fc 8 | SEQ ID NO: 23 |
| scR-Fc 9 | SEQ ID NO: 24 |
| scR-Fc 10 | SEQ ID NO: 25 |
| scR-Fc 11 | SEQ ID NO: 26 |
| scR-Fc 12 | SEQ ID NO: 27 |
| scR-Fc 13 | SEQ ID NO: 28 |
| scR-Fc 14 | SEQ ID NO: 29 |
| scR-Fc 15 | SEQ ID NO: 30 |
| scR-Fc 16 | SEQ ID NO: 31 |
| scR-Fc 17 | SEQ ID NO: 32 |
| scR-Fc 18 | SEQ ID NO: 33 |
| scR-Var1 | SEQ ID NO: 34 |
| scR-Var2 | SEQ ID NO: 35 |
| scR-Var3 | SEQ ID NO: 36 |
| scR-Var4 | SEQ ID NO: 37 |
| scR-Var5 | SEQ ID NO: 38 |
| scR-Var6 | SEQ ID NO: 39 |
| scR-Var7 | SEQ ID NO: 40 |
| scR-Var8 | SEQ ID NO: 41 |
| scR3 w/o Tag | SEQ ID NO: 44 |
| scR4 w/o Tag | SEQ ID NO: 45 |
| scR5 w/o Tag | SEQ ID NO: 46 |
| scR6 w/o Tag | SEQ ID NO: 47 |
| scR7 w/o Tag | SEQ ID NO: 48 |
| scR8 w/o Tag | SEQ ID NO: 49 |
| scR9 w/o Tag | SEQ ID NO: 50 |
| scR10 w/o Tag | SEQ ID NO: 51 |
| scR-Fc 1 w/o Tag | SEQ ID NO: 52 |
| scR-Fc 8 w/o Tag | SEQ ID NO: 53 |
| scR-Fc 9 w/o Tag | SEQ ID NO: 54 |
| scR-Fc 10 w/o Tag | SEQ ID NO: 55 |
| scR-Fc 11 w/o Tag | SEQ ID NO: 56 |
| scR-Fc 12 w/o Tag | SEQ ID NO: 57 |
| scR-Fc 13 w/o Tag | SEQ ID NO: 58 |
| scR17 | SEQ ID NO: 153 |
| scR19 | SEQ ID NO: 155 |

In a further embodiment the aforementioned fusion polypeptides A-L-B further comprising a half-life extending moiety have Relaxin activity. In a further preferred embodiment the Relaxin activity is activation of the relaxin receptor LGR7. Methods for determining Relaxin activity are known in the art or are provided herein. In an even further preferred embodiment, the activation of the relaxin receptor LGR7 is determined by a method disclosed in experimental methods herein. In an even further preferred embodiment, the determination of the activation of the relaxin receptor LGR7 is determining an $EC_{50}$ value. In an even more preferred embodiment the aforementioned Relaxin activity is less than $10^5$ fold, $10^4$ fold, $10^3$ fold, 100 fold, 75 fold, 50 fold, 25 fold or 10 fold lower compared to the corresponding wild type Relaxin activity. For example, the corresponding wild type Relaxin for a fusion polypeptide A-L-B based on human Relaxin 2 is the human Relaxin 2 protein.

Cloning, Vector Systems, Expression, Hosts, and Purification

The invention also provides for a vector which comprises an isolated nucleic acid molecule encoding a fusion polypeptide of the invention. This vector system is operatively linked to an expression sequence capable of directing its expression in a host cell.

A suitable host cell may be selected from the group consisting of bacterial cells (such as *E. coli*), yeast cells (such as *Saccharomyces cerevisiae*), fungal cells, plant cells, insect cells and animals cells. Animal cells include, but are not limited to, HEK293 cells, CHO cells, COS cells, BHK cells, HeLa cells and various primary mammalian cells. Derivatives of mammalian cells such as HEK293T cells are also applicable.

DNA Molecules of the Invention

The present invention also relates to the DNA molecules that encode a fusion protein of the invention. These sequences include, but are not limited to, those DNA molecules set forth in table 4.

TABLE 4

| Construct | SEQ ID NO |
|---|---|
| scR1 | SEQ ID NO: 59 |
| scR2 | SEQ ID NO: 60 |
| scR3 | SEQ ID NO: 61 |
| scR4 | SEQ ID NO: 62 |
| scR5 | SEQ ID NO: 63 |
| scR6 | SEQ ID NO: 64 |
| scR7 | SEQ ID NO: 65 |
| scR8 | SEQ ID NO: 66 |
| scR9 | SEQ ID NO: 67 |
| scR10 | SEQ ID NO: 68 |
| scR11 | SEQ ID NO: 69 |
| scR12 | SEQ ID NO: 70 |
| scR13 | SEQ ID NO: 71 |
| scR14 | SEQ ID NO: 72 |
| scR15 | SEQ ID NO: 73 |
| scR-Fc 1 | SEQ ID NO: 74 |
| scR-Fc 2 | SEQ ID NO: 75 |
| scR-Fc 3 | SEQ ID NO: 76 |
| scR-Fc 4 | SEQ ID NO: 77 |
| scR-Fc 5 | SEQ ID NO: 78 |
| scR-Fc 6 | SEQ ID NO: 79 |
| scR-Fc 7 | SEQ ID NO: 80 |
| scR-Fc 8 | SEQ ID NO: 81 |
| scR-Fc 9 | SEQ ID NO: 82 |
| scR-Fc 10 | SEQ ID NO: 83 |
| scR-Fc 11 | SEQ ID NO: 84 |
| scR-Fc 12 | SEQ ID NO: 85 |
| scR-Fc 13 | SEQ ID NO: 86 |
| scR-Fc 14 | SEQ ID NO: 87 |
| scR-Fc 15 | SEQ ID NO: 88 |
| scR-Fc 16 | SEQ ID NO: 89 |
| scR-Fc 17 | SEQ ID NO: 90 |
| scR-Fc 18 | SEQ ID NO: 91 |
| scR-Var1 | SEQ ID NO: 92 |
| scR-Var2 | SEQ ID NO: 93 |
| scR-Var3 | SEQ ID NO: 94 |
| scR-Var4 | SEQ ID NO: 95 |
| scR-Var5 | SEQ ID NO: 96 |
| scR-Var6 | SEQ ID NO: 97 |
| scR-Var7 | SEQ ID NO: 98 |
| scR-Var8 | SEQ ID NO: 99 |
| scR3 w/o Tag | SEQ ID NO: 102 |
| scR4 w/o Tag | SEQ ID NO: 103 |
| scR5 w/o Tag | SEQ ID NO: 104 |
| scR6 w/o Tag | SEQ ID NO: 105 |
| scR7 w/o Tag | SEQ ID NO: 106 |
| scR8 w/o Tag | SEQ ID NO: 107 |
| scR9 w/o Tag | SEQ ID NO: 108 |
| scR10 w/o Tag | SEQ ID NO: 109 |

TABLE 4-continued

| Construct | SEQ ID NO |
|---|---|
| scR-Fc 1 w/o Tag | SEQ ID NO: 110 |
| scR-Fc 8 w/o Tag | SEQ ID NO: 111 |
| scR-Fc 9 w/o Tag | SEQ ID NO: 112 |
| scR-Fc 10 w/o Tag | SEQ ID NO: 113 |
| scR-Fc 11 w/o Tag | SEQ ID NO: 114 |
| scR-Fc 12 w/o Tag | SEQ ID NO: 115 |
| scR-Fc 13 w/o Tag | SEQ ID NO: 116 |
| scR17 | SEQ ID NO: 158 |
| scR19 | SEQ ID NO: 160 |

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 supra and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m = 69.3 + 0.41(G+C)\%$
b. The $T_m$ of a duplex DNA decreases by 1° C. with every increase of 1% in the number of mismatched base pairs.
c. $(T_m)_{\mu 2} - (T_m)_{\mu 1} = 18.5 \log_{10} \mu 2/\mu 1$
where $\mu 1$ and $\mu 2$ are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 μg of nonspecific carrier DNA. See Ausubel et al., section 2.9, supplement 27 (1994). Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

An embodiment of the invention is an isolated nucleic acid sequence that encodes a fusion polypeptide of the invention.

Recombinant DNA Constructs and Expression

The present invention further provides recombinant DNA constructs comprising one or more of the nucleotide sequences of the present invention. The recombinant constructs of the present invention are used in connection with a vector, such as a plasmid, phagemid, phage or viral vector, into which a DNA molecule encoding a fusion polypeptide of the invention is inserted.

A fusion polypeptide as provided herein can be prepared by recombinant expression of nucleic acid sequences encoding a fusion polypeptide in a host cell. To express a fusion polypeptide recombinantly, a host cell can be transfected with a recombinant expression vectors carrying DNA fragments encoding a fusion polypeptide such that the fusion polypeptide is expressed in the host cell. Standard recombinant DNA methodologies are used to prepare and/or obtain nucleic acids encoding a fusion polypeptide, incorporate these nucleic acids into recombinant expression vectors and introduce the vectors into host cells, such as those described in Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

To express the fusion polypeptide standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. Suitable host cells are prokaryotic and eukaryotic cells. Examples for prokaryotic host cells are e.g. bacteria, examples for eukaryotic host cells are yeast, insect or mammalian cells. It is understood that the design of the expression vector, including the selection of regulatory sequences is affected by factors such as the choice of the host cell, the level of expression of protein desired and whether expression is constitutive or inducible.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus.*

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced vectors which direct the expression of high levels of fusion polypeptide products that are readily purified may be desirable. Fusion polypeptide of the present invention include purified products, products of chemical synthetic procedures, and products produced by recombinant techniques from a prokaryotic host, including, for example, *E. coli, Bacillus subtilis, Salmonella typhimurium* and various species within the genera *Pseudomonas, Streptomyces,* and *Staphylococcus,* preferably, from *E. coli* cells.

Eukaryotic Expression

Eukaryotic cells can be used to express the polypeptides of the invention. Systems for expression of proteins are known in the art. Such systems include e.g. include the eukaryotic cell, growth media, and corresponding expression vectors. Common eukaryotic cells for expression are e.g. a mammalian cell, a yeast cell, a plant cell, or an insect cell.

Mammalian Expression and Purification

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al. The recombinant expression vectors can also include origins of replication and selectable markers (see e.g., U.S. Pat. Nos. 4,399,216, 4,634,665 and U.S. Pat. No. 5,179,017, by Axel et al.). Suitable selectable markers include genes that confer resistance to drugs such as G418, hygromycin or methotrexate, on a host cell into which the vector has been introduced. For example, the dihydrofolate reductase (DHFR) gene confers resistance to methotrexate and the neo gene confers resistance to G418.

Transfection of the expression vector into a host cell can be carried out using standard techniques such as electroporation, calcium-phosphate precipitation, and DEAE-dextran, lipofection or polycation-mediated transfection.

Suitable mammalian host cells for expressing the fusion polypeptides provided herein include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621, NSO myeloma cells, COS cells and SP2 cells. In some embodiments, the expression vector is designed such that the expressed protein is secreted into the culture medium in which the host cells are grown. Transient transfection/epression of antibodies can for example be achieved following the protocols by Durocher et al (2002) Nucl. Acids Res. Vol 30 e9. Stable transfection/expression of antibodies can for example be achieved following the protocols of the UCOE system (T. Benton et al. (2002) Cytotechnology 38: 43-46).

The fusion polypeptide can be recovered from the culture medium using standard protein purification methods.

A fusion polypeptide of the invention can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Fusion polypeptides of the invention include purified or isolated products, products of chemical synthetic procedures, and products produced by recombinant techniques from a eukaryotic host, including, for example, yeast (for example *Pichia*), higher plant, insect and mammalian cells, preferably from mammalian cells. Depending upon the host employed in a recombinant production procedure, the fusion polypeptide of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20.

Therapeutic Use

An embodiment of the invention is the use of a pharmaceutical composition or a fusion polypeptide of the invention in the treatment of cardiovascular diseases, kidney diseases, pancreatitis, inflammation, cancer, scleroderma, pulmonary, renal, and hepatic fibrosis.

Cardiovascular Diseases

Disorders of the cardiovascular system, or cardiovascular disorders, mean in the context of the present invention for example the following disorders: hypertension (high blood pressure), peripheral and cardiac vascular disorders, coronary heart disease, stable and unstable angina pectoris, myocardial insufficiency, persistent ischemic dysfunction ("hibernating myocardium"), temporary postischemic dysfunction ("stunned myocardium"), heart failure, disturbances of peripheral blood flow, acute coronary syndrome, heart failure and myocardial infarction.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure and acute phases of worsening heart failure.

The compounds according to the invention are further also suitable for reducing the area of myocardium affected by an infarction, and for the prophylaxis of secondary infarctions.

The compounds according to the invention are furthermore suitable for the prophylaxis and/or treatment of thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (CABG), primary percutaneous transluminal coronary angioplasties (PTCAs), PTCAs after thrombolysis, rescue PTCA, heart transplants and open-heart operations, and for organ protection in connection with transplants, bypass operations, catheter examinations and other surgical procedures.

Other areas of indication are, for example, the prevention and/or treatment of respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Kidney Disease

The present invention relates to the use of a fusion polypeptide of the invention as a medicament for the prophylaxis and/or treatment of kidney diseases, especially of acute and chronic kidney diseases and acute and chronic renal insufficiencies, as well as acute and chronic renal failure, including acute and chronic stages of renal failure with and without the requirement of dialysis, as well as the underlying or related kidney diseases such as renal hypoperfusion, dialysis induced hypotension, glomerulopathies, glomerular and tubular proteinuria, renal edema, hematuria, primary, secondary, as well as acute and chronic glomerulonephritis, membranous and membranoproliferative glomerulonephritis, Alport-Syndrome, glomerulosclerosis, interstistial tubular diseases, nephropathic diseases, such as primary and inborn kidney diseases, renal inflammation, immunological renal diseases like renal transplant rejection, immune complex induced renal diseases, as well as intoxication induced nephropathic diseases, diabetic and non-diabetic renal diseases, pyelonephritis, cystic kidneys, nephrosclerosis, hypertensive nephrosclerosis, nephrotic syndrome, that are characterized and diagnostically associated with an abnormal reduction in creatinine clearance and/or water excretion, abnormal increased blood concentrations of urea, nitrogen, potassium and/or creatinine, alteration in the activity of renal enzymes, such as glutamylsynthetase, urine osmolarity and urine volume, increased microalbuminuria, macroalbuminuria, glomerular and arteriolar lesions, tubular dilation, hyperphosphatemia and/or the requirement of dialysis.

In addition, a fusion polypeptide of the invention can be used as a medicament for the prophylaxis and/or treatment of renal carcinomas, after incomplete resection of the kidney, dehydration after overuse of diuretics, uncontrolled blood pressure increase with malignant hypertension, urinary tract obstruction and infection, amyloidosis, as well as systemic diseases associated with glomerular damage, such as Lupus erythematodes, and rheumatic immunological systemic diseases, as well as renal artery stenosis, renal artery thrombosis, renal vein thrombosis, analgetics induced nephropathy and renal tubular acidosis.

In addition, a fusion polypeptide of the invention can be used as a medicament for the prophylaxis and/or treatment of contrast medium induced and drug induced acute and chronic interstitial kidney diseases, metabolic syndrome and dyslipemia.

In addition, the present invention includes the use of a fusion polypeptide of the invention as a medicament for the prophylaxis and/or treatment of aftereffects associated with acute and/or chronic kidney diseases, such as pulmonary edema, heart failure, uremia, anemia, electrolyte disturbances (e.g. hyperkalemia, hyponatremia), as well as bony and carbohydrate metabolism.

Lung Diseases

Furthermore, the fusion polypeptides according to the invention are also suitable for the treatment and/or prophylaxis of lung diseases especially of asthmatic disorders, pulmonary arterial hypertension (PAH) and other forms of pulmonary hypertension (PH) including left-heart disease, HIV, sickle cell anaemia, thromboembolisms (CTEPH), sarkoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

Fibrotic Disorders

The fusion polypeptides according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitreoretinopathy and disorders of the connective tissue (for example sarcoidosis).

Cancer

Cancer is disease in which a group of cells display uncontrolled growth. Cancers are usually classified in carcinomas which is a cancer derived from epithelial cells (This group includes many of the most common cancers, including those of the breast, prostate, lung and colon.); sarcomas, which are derived from connective tissue, or mesenchymal cells; lymphoma and leukemia, derived from hematopoietic cells; germ cell tumor, which is derived from pluripotent; and blastomas, which is a cancer derived from immature "precursor" or embryonic tissue.

The present invention furthermore provides the use of a fusion polypeptide of the invention for preparing a medicament for the treatment and/or prevention of disorders, in particular the disorders mentioned above.

The present invention furthermore provides a method for the treatment and/or prevention of disorders, in particular the disorders mentioned above, using an effective amount of at least one fusion polypeptide of the invention.

The present invention furthermore provides a fusion polypeptide of the invention for use in a method for the treatment and/or prophylaxis of coronary heart disease, acute coronary syndrome, heart failure, and myocardial infarction.

Pharmaceutical Compositions and Administration

The present invention also provides for pharmaceutical compositions comprising a single chain Relaxin fusion protein in a pharmacologically acceptable vehicle. The single chain Relaxin fusion protein may be administrated systemically or locally. Any appropriate mode of administration known in the art may be used including, but not limited to, intravenous, intraperitoneal, intraarterial, intranasal, by inhalation, oral, subcutaneous administration, by local injection or in form of a surgical implant.

The present invention also relates to pharmaceutical compositions which may comprise inventive fusion polypeptides, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished orally or parenterally. Methods of parenteral delivery include topical, intra-arterial, intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

A fusion polypeptide according to the invention can be used alone or, if required, in combination with other active compounds. The present invention furthermore provides medicaments comprising at least one fusion polypeptide according to the invention and one or more further active ingredients, in particular for the treatment and/or prevention of the disorders mentioned above.

Suitable active ingredients for combination are, by way of example and by way of preference: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, LTB$_4$-receptor antagonists), analgesics for example aspirin, antidepressants and other psychopharmaceuticals.

The present invention relates in particular to combinations of at least one of the fusion polypeptides according to the invention with at least one lipid metabolism-altering active ingredient, antidiabetic, blood pressure reducing active ingredient and/or agent having antithrombotic effects.

The fusion polypeptides according to the invention can preferably be combined with one or more lipid metabolism-modulating active ingredients, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulfonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active ingredients, by way of example and by way of preference from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or antithrombotic agents, by way of example and by way of preference from the group of the platelet aggregation inhibitors or the anticoagulants;

diuretics;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphat (cAMP), such as, for example, inhibitors of phosphodiesterases (PDE) 1, 2, 3, 4 and/or 5, in particular PDE 5 inhibitors, such as sildenafil, vardenafil and tadalafil, and also PDE 3 inhibitors, such as milrinone;

natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

agonists of the prostacyclin receptor (IP receptor), such as, by way of example, iloprost, beraprost, cicaprost;

inhibitors of the I$_f$ (funny channel) channel, such as, by way of example, ivabradine;

calcium sensitizers, such as, by way of example and by way of preference, levosimendan;

potassium supplements;

NO-independent, but heme-dependent stimulators of guanylate cyclase, such as, in particular, the compounds described in WO 00/06568, WO 00/06569, WO 02/42301 and WO 03/095451;

NO- and heme-independent activators of guanylate cyclase, such as, in particular, the compounds described in WO 01/19355, WO 01/19776, WO 01/19778, WO 01/19780, WO 02/070462 and WO 02/070510;

inhibitors of human neutrophil elastase (HNE), such as, for example, sivelestat and DX-890 (Reltran);

compounds which inhibit the signal transduction cascade, such as, for example, tyrosine-kinase inhibitors, in particular sorafenib, imatinib, gefitinib and erlotinib; and/or compounds which modulate the energy metabolism of the heart, such as, for example, etomoxir, dichloroacetate, ranolazine and trimetazidine.

Lipid metabolism-modifying active ingredients are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, a fusion polypeptide according to the invention is administered in combination with an HMG-CoA reductase inhibitor from the class of the statins, such as, by way of example and by way of preference, lovastatin, simvastatin, pravastatin, fluvastatin, atorvastatin, rosuvastatin or pitavastatin.

In a preferred embodiment of the invention, the fusion polypeptides according to the invention are administered in combination with a squalene synthesis inhibitor, such as, by way of example and by way of preference, BMS-188494 or TAK-475.

In a preferred embodiment of the invention, the fusion polypeptides according to the invention are administered in combination with an ACAT inhibitor, such as, by way of example and by way of preference, avasimibe, melinamide, pactimibe, eflucimibe or SMP-797.

In a preferred embodiment of the invention, the fusion polypeptides according to the invention are administered in combination with a cholesterol absorption inhibitor, such as, by way of example and by way of preference, ezetimibe, tiqueside or pamaqueside.

In a preferred embodiment of the invention, the fusion polypeptides according to the invention are administered in combination with an MTP inhibitor, such as, by way of example and by way of preference, implitapide, BMS-201038, R-103757 or JTT-130.

In a preferred embodiment of the invention, the fusion polypeptides according to the invention are administered in combination with a lipase inhibitor, such as, by way of example and by way of preference, orlistat.

In a preferred embodiment of the invention, the fusion polypeptides according to the invention are administered in combination with a thyroid hormone and/or thyroid mimetic, such as, by way of example and by way of preference, D-thyroxine or 3,5,3'-triiodothyronine (T3).

In a preferred embodiment of the invention, the fusion polypeptides according to the invention are administered in combination with an agonist of the niacin receptor, such as, by way of example and by way of preference, niacin, acipimox, acifran or radecol.

In a preferred embodiment of the invention, the fusion polypeptides according to the invention are administered in combination with a CETP inhibitor, such as, by way of example and by way of preference, dalcetrapib, BAY 60-5521, anacetrapib or CETP vaccine (CETi-1).

In a preferred embodiment of the invention, the fusion polypeptides according to the invention are administered in combination with a PPAR-γ agonist, for example from the class of the thiazolidinediones, such as, by way of example and by way of preference, pioglitazone or rosiglitazone.

In a preferred embodiment of the invention, the fusion polypeptides according to the invention are administered in combination with a PPAR-δ agonist, such as, by way of example and by way of preference, GW-501516 or BAY 68-5042.

In a preferred embodiment of the invention, the fusion polypeptides according to the invention are administered in combination with a polymeric bile acid adsorber, such as, by way of example and by way of preference, cholestyramine, colestipol, colesolvam, CholestaGel or colestimide.

In a preferred embodiment of the invention, the fusion polypeptides according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the fusion polypeptides according to the invention are administered in combination with an antioxidant/radical scavenger, such as, by way of example and by way of preference, probucol, AGI-1067, BO-653 or AEOL-10150.

In a preferred embodiment of the invention, the fusion polypeptides according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients preferably include sulfonylureas, biguanides, meglitinide derivatives, glucosidase inhibitors and PPAR-gamma agonists.

In a preferred embodiment of the invention, the fusion polypeptides according to the invention are administered in combination with insulin In a preferred embodiment of the invention, the fusion polypeptides according to the invention are administered in combination with a sulfonylurea, such as, by way of example and by way of preference, tolbutamide, glibenclamide, glimepiride, glipizide or gliclazide.

In a preferred embodiment of the invention, the fusion polypeptides according to the invention are administered in combination with a biguanide, such as, by way of example and by way of preference, metformin.

In a preferred embodiment of the invention, the fusion polypeptides according to the invention are administered in combination with a meglitinide derivative, such as, by way of example and by way of preference, repaglinide or nateglinide.

In a preferred embodiment of the invention, the fusion polypeptides according to the invention are administered in combination with a glucosidase inhibitor, such as, by way of example and by way of preference, miglitol or acarbose.

In a preferred embodiment of the invention, the fusion polypeptides according to the invention are administered in combination with a DPP-IV inhibitor, such as, by way of example and by way of preference, sitagliptin and vildagliptin.

In a preferred embodiment of the invention, the fusion polypeptides according to the invention are administered in combination with a PPAR-gamma agonist, for example from the class of the thiazolinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the fusion polypeptides according to the invention are administered in combination with a calcium antagonist, such as, by way of example and by way of preference, nifedipine, amlodipine, verapamil or diltiazem.

In a preferred embodiment of the invention, the fusion polypeptides according to the invention are administered in combination with an angiotensin AII antagonist, such as, by way of example and by way of preference, losartan, valsartan, candesartan, embusartan, olmesartan or telmisartan.

In a preferred embodiment of the invention, the fusion polypeptides according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the fusion polypeptides according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the fusion polypeptides according to the invention are administered in combination with an alpha-receptor blocker, such as, by way of example and by way of preference, prazosin.

In a preferred embodiment of the invention, the fusion polypeptides according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the fusion polypeptides according to the invention are administered in combination with an aldosterone or mineralocorticoid receptor antagonist, such as, by way of example and by way of preference, spironolactone or eplerenone.

In a preferred embodiment of the invention, the fusion polypeptides according to the invention are administered in combination with a vasopressin receptor antagonist, such as, by way of example and by way of preference, conivaptan, tolvaptan, lixivaptan or SR-121463.

In a preferred embodiment of the invention, the fusion polypeptides according to the invention are administered in combination with an organic nitrate or NO donor, such as, by way of example and by way of preference, sodium nitroprusside, nitroglycerol, isosorbide mononitrate, isosorbide dinitrate, molsidomin or SIN-1, or in combination with inhalative NO.

In a preferred embodiment of the invention, the fusion polypeptides according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the fusion polypeptides according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the fusion polypeptides according to the invention are administered in combination with a platelet aggregation inhibitor, such as, by way of example and by way of preference, aspirin, clopidogrel, ticlopidine or dipyridamol.

In a preferred embodiment of the invention, the fusion polypeptides according to the invention are administered in combination with a thrombin inhibitor, such as, by way of example and by way of preference, ximelagatran, melagatran, dabigatran, bivalirudin or clexane.

In a preferred embodiment of the invention, the fusion polypeptides according to the invention are administered in combination with a GPIIb/IIIa antagonist, such as, by way of example and by way of preference, tirofiban or abciximab.

In a preferred embodiment of the invention, the fusion polypeptides according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the fusion polypeptides according to the invention are administered in combination with heparin or a low molecular weight (LMW) heparin derivative.

In a preferred embodiment of the invention, the fusion polypeptides according to the invention are administered in combination with a vitamin K antagonist, such as, by way of example and by way of preference, coumarin.

In the context of the present invention, particular preference is given to combinations comprising at least one of the fusion polypeptides according to the invention and also one or more further active ingredients selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

The present invention furthermore provides medicaments comprising at least one fusion polypeptides according to the invention, usually together with one or more inert nontoxic pharmaceutically suitable auxiliaries, and also their use for the purposes mentioned above.

Therapeutically Effective Dose

Pharmaceutical compositions suitable for use in the present invention include compositions wherein the active ingredients are contained in an effective amount to achieve the intended purpose, e.g. heart failure. The determination of an effective dose is well within the capability of those skilled in the art.

For any compound, the therapeutically effective dose can be estimated initially either in in vitro assays, e.g. LGR7 receptor activation, ex vivo in isolated perfused rat hearts, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of fusion polypeptide that ameliorates the symptoms or condition. Therapeutic efficacy and toxicity of such compounds can be determined by standard pharmaceutical procedures in vitro or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions that exhibit large therapeutic indices are preferred. The data obtained from in vitro assays and animal studies are used in formulating a range of dosage for human use. The dosage of such compounds lies preferably within a range of circulating concentrations what include the ED50 with little or no toxicity. The dosage varies within this range depending upon the dosage form employed, sensitivity of the patient, and the route of administration.

Normal dosage amounts may vary from 0.1 to 100,000 milligrams total dose, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., Molecular Cloning: A Laboratory Manual, 2nd Ed.; Cold Spring Harbor Laboratory Press, Cold Spring Harbor, N.Y., 1989.

Further preferred embodiments are:

1. A fusion polypeptide having Relaxin activity comprising A-L-B,
wherein
B comprises a Relaxin B chain polypeptide or a functional variant thereof,
A comprises a Relaxin A chain poylpeptide or a functional variant thereof, and
L is a linker polypeptide.

2. A fusion polypeptide according to count 1, wherein
B is a Relaxin B chain polypeptide or a functional variant thereof,
A is a Relaxin A chain poylpeptide or a functional variant thereof, and
L is a linker polypeptide.

3. A fusion polypeptide according to count 1 or 2, wherein the Relaxin B chain is a Relaxin 2B or a Relaxin 3B chain.

4. A fusion polypeptide according to anyone of the foregoing counts, wherein the Relaxin A chain is a Relaxin 2A or a Relaxin 3A chain 5. A fusion polypeptide according to anyone of the foregoing counts, wherein the Relaxin A chain is a Relaxin 2A chain.

6. A fusion polypeptide according to anyone of the foregoing counts, wherein the Relaxin A chain is a Relaxin 3A chain 7. A fusion polypeptide according to anyone of the foregoing counts, wherein the Relaxin A chain is a Relaxin 2A chain and the Relaxin B chain is a Relaxin 2B chain 8. A fusion polypeptide according to anyone of the foregoing counts, wherein the Relaxin A and B chains are human Relaxin A and B chains.

9. A fusion polypeptide according to anyone of the foregoing counts, wherein the fusion polypeptide further comprises at least one half-life extending moiety.

10. A fusion polypeptide according to count 9, wherein the half-life extending moiety is a non-proteinaceous or a proteinaceous half-life extending moiety.

11. A fusion polypeptide according to count 9 or 10, wherein the polypeptide has the formula (R1)m-(S1)n-A-L-B-(S2)o-(R2)p, wherein
R1 and R2 are proteinaceous half-life extending moieties,
S1 and S2 are stretcher peptides,
and wherein m, n, o and p are independently the number 0 or 1, provided that at least one of m, n, o, and p are 1.

12. A fusion polypeptide according to count 11, wherein m and n are 0 and o and p are 1.

13. A fusion polypeptide according to count 11, wherein m and n are 1 and o and p are 0.

14. A fusion polypeptide according to count 11, wherein m is 1 and n, o and p are 0.

15. A fusion polypeptide according to count 11, wherein m, n and o are 0 and p is 1.

16. A fusion polypeptide according to any one of counts 11 to 15, wherein R1 and R2 are proteinaceous half-life extending moieties comprised in a group of proteinaceous half-life extending moieties consisting of immunoglobulin Fc domain, serum albumin, transferrin and serum albumin binding protein.

17. A fusion polypeptide according to any one of counts 10 to 16, wherein the proteinaceous half-life extending moiety is an IgG1 Fc domain.

18. A fusion polypeptide according to any one of counts 10 to 17, wherein the proteinaceous half-life extending moiety is human.

19. A fusion polypeptide according to count 10, wherein the non-proteinaceous half-life extending moiety is PEG or HES.

20. A fusion polypeptide according to anyone of counts 11-19, wherein the stretcher polypeptides S1 and S2 are 1-25 amino acids in length.

21. A fusion polypeptide according to anyone of counts 11-20, wherein the stretcher polypeptides S1 and S2 are 4-10 amino acids in length, preferably 10 amino acids in length 22. A fusion polypeptide according to count 21, wherein the stretcher polypeptide S1 and S2 is comprised in the group of stretcher polypeptides consisting of polypeptides as set forth in SEQ ID NO: 148, SEQ ID NO: 149, and SEQ ID NOs: 150.

23. A fusion polypeptide according to anyone of the foregoing counts, wherein the linker polypeptide L is 6-14 amino acids in length.

24. A fusion polypeptide according to anyone of the foregoing counts, wherein the linker polypeptide L is 7-11 amino acids in length.

25. A fusion polypeptide according to anyone of the foregoing counts, wherein the linker polypeptide L is 8, 9, or 10 amino acids in length.

26. A fusion polypeptide according to anyone of the foregoing counts, wherein the linker polypeptide L is 9 amino acids in length.

27. A fusion polypeptide according to anyone of the foregoing counts, wherein the linker polypeptide L is comprised in a group of linkers consisting of linkers having 6, 7, 8, 9, 10, 11, 12, 13 and 14 amino acids in length.

28. A fusion polypeptide according to anyone of the foregoing counts, wherein in the linker polypeptide L all but 4 amino acid residues of the linker L consist of Gly and/or Ser residues and the remaining 4 amino acid residues are selected from the group of natural amino acids.

29. A fusion polypeptide according to anyone of the foregoing counts, wherein the linker polypeptide L comprises at least one Gly, Ser, Arg, Cys, Leu and/or Lys residue.

30. A fusion polypeptide according to anyone of the foregoing counts, wherein the linker polypeptide L comprises Gly and Ser residues.

31. A fusion polypeptide according to anyone of the foregoing counts, wherein the linker polypeptide L consists of Gly and Ser residues.

32. A fusion polypeptide according to anyone of the foregoing counts, wherein the linker polypeptide L comprises Gly and Ser residues and has a Gly to Ser ratio of at least 3 to 1.

33. A fusion polypeptide according to anyone of the foregoing counts, wherein the linker polypeptide L is comprised in the group of linker polypeptides consisting of polypeptides as set forth in SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 145 and SEQ ID NO: 146.

34. A fusion polypeptide according to anyone of the foregoing counts, wherein the Relaxin A chain is human Relaxin 2 A chain (SEQ ID NO: 117) and the Relaxin B chain is human Relaxin 2 B chain (SEQ ID NO: 119).

35. A fusion polypeptide according to anyone of the foregoing counts, wherein A is the human Relaxin 2 A chain (SEQ ID NO: 117) and B is the human Relaxin 2 B chain (SEQ ID NO: 119).

36. A fusion polypeptide according to anyone of the foregoing counts comprising a polypeptide as depicted in table 3.

37. A fusion polypeptide according to anyone of the foregoing counts, wherein A-L-B is selected from the group of A-L-B polypeptides consisting of scR3, scR4, scR5, scR3 w/o Tag, scR4 w/o Tag, scR5 w/o Tag, scR-Fc5, scR-Fc6 and scR-Fc7.

38. A fusion polypeptide as depicted in table 3.

39. A fusion polypeptide selected from the group consisting of scR3, scR4, scR5, scR3 w/o Tag, scR4 w/o Tag, scR5 w/o Tag, scR-Fc5, scR-Fc6 and scR-Fc7.

40. A polynucleotide encoding a fusion polypeptide according to anyone of the foregoing counts.

41. A vector comprising a polynucleotide according to count 40.

42. A host cell comprising a vector according to count 41 or a polynucleotide according to count 40.

43. A host cell according to count 42, wherein the host cell is a eukaryotic or prokaryotic cell.

44. A host cell according to count 42 or 43, wherein the eukaryotic host cell is a mammalian, yeast, insect or plant cell.
45. A host cell according to count 44, wherein the mammalian host cell is a CHO cell.
46. A host cell according to count 43, wherein the prokaryotic host cell is a bacterial cell, preferably an *E. coli* cell.
47. A method of producing a polypeptide according to anyone of counts 1-39 comprising the steps of cultivating a host cell of counts 42-46 and isolating the polypeptide.
48. A pharmaceutical composition comprising a fusion polypeptide according to anyone of counts 1-39.
49. A pharmaceutical composition according to count 48 or a fusion polypeptide according to anyone of counts 1-39 as medicament.
50. A pharmaceutical composition according to count 48 and 49 or a fusion polypeptide according to anyone of counts 1-39 as medicament for the treatment of cardiovascular disease, lung disease, fibrotic disorder or kidney disease.
51. A method of treating a cardiovascular disease, lung disease, fibrotic disorder or kidney disease comprising the administration of a therapeutically effective dose of a pharmaceutical composition according to count 48 and 49 or a fusion polypeptide according to anyone of counts 1-39.
52. A treatment according to counts 50 and 51, wherein the cardiovascular disease is coronary heart disease, acute coronary syndrome, heart failure, and myocardial infarction.

EXAMPLES

Experimental Protocols

Construction of Relaxin Variants:

The cDNA sequences of the Relaxin variants were generated by chemical gene synthesis. The synthesized genes were subcloned into the mammalian expression vector pCEP4 (Invitrogen, catalogue number V044-50). As signal leader sequence for correct secretion of the resulting protein, either the leader sequence of the LDL receptor-related protein (LRP, amino acid composition MLTPPLLLLLPLLSALVAA (SEQ ID NO: 166)) or of CD33 (amino acid composition MPLLLLLPLLWAGALA (SEQ ID NO: 167)) were used. For subcloning of the synthesized constructs the restriction enzymes HindIII and BamHI were used according to manufactures' instruction.

Expression of Relaxin Variants:

For small scale expression (up to 2 milliliter culture volume) HEK293 (ATCC, catalogue number CRL-1573) cells were transiently transfected using Lipofectamine2000 Transfection Reagent (Invitrogen, catalogue number 11668-019) according to manufactures' Instructions. Cells were cultivated in D-Mem F12 (Gibco, #31330), 1% Penicillin-Streptomycin (Gibco, #15140) and 10% fetal calf serum (FCS, Gibco, #11058) in a humified incubator at 5% carbon dioxide at 37° C.

Three to five days following transfection, conditioned medium of the transfected cells were tested for activity using the stably transfected CHO-CRE-GR7 cell line.

For large scale expression (10 milliliter culture volume and more) the constructs were transiently expressed in mammalian cell cells as described in Tom et al., 2007. Briefly, the expression plasmid transfected into HEK293-6E cells and incubated in Fernbach-Flasks or Wave-Bags. Expression was at 37° C. for 5 to 6 days in F17 Medium (Invitrogen). 5 g/l Tryptone TN1 (Organotechnie), 1% Ultra-Low IgG FCS (Invitrogen) and 0.5 mM Valproic acid (Sigma) were supplemented after transfection.

Purification of Relaxin Variants:

Relaxin Fc-Fusion constructs were purified from mammalian cell culture supernatants. First supernatants were clarified from cell debris by centrifugation. Proteins were purified by Protein A (MabSelect Sure, GE Healthcare) affinity chromatography followed by size exclusion chromatography (SEC). Therefore the supernatant was applied to a Protein A column previously equilibrated in PBS pH 7.4 (Sigma/Aldrich), contaminants were removed with 10 column volumes of PBS pH 7.4+500 mM NaCl. Relaxin Fc Fusion constructs were eluted with 50 mM Na-acetate pH 3.5+500 mM NaCl and further purified by SEC on a Superdex 200 column in PBS pH 7.4.

For purification of c-Myc tagged proteins or polypeptides, the c-Myc tagged Protein Mild Purification Gel is used (Biozol Diagnostic, Protein Mild Purification Gel, catalogue number 3306) according to the manufactures instructions.

For purification of His tagged proteins or polypeptides, Ni-NTA spin columns are used (Qiagen, Ni-NTA Spin Kit, catalogue number 31314) according to the manufactures instructions.

Quantification of Expressed Relaxin Variants:

For quantification of secreted and purified recombinant Relaxin variants, the commercially available quantification ELISA (R&D Systems, Human Relaxin-2 Quantikine ELISA Kit, catalogue number DRL200) was used according to the manufactures' instructions.

In addition for some constructs proteins were quantified by using FC-ELISA. For the Fc ELISA, 96 well microtitter plates (Nunc, Maxi Sorp black, catalogue number 460918) were coated with an anti-Fc antibody (SigmaAldrich, catalogue number A2136) over night at 4° C. and a concentration of 5 µg per milliliter. Plates were washed once by using 50 microliter per well of a buffer consisting of PBS and 0.05% Tween 20 (SigmaAldrich, catalogue number 63158) buffer. Thirty microliter of a blocking buffer (Candor Bioscience, catalogue number 113500) was added and the plate incubated for 1 hour at 37° C. Plates were washed 3 times using 50 microliter per well of the PBS/0.05% Tween 20 buffer. Samples were added and the plates incubated were for 1 hour at 37° C. If necessary, samples have to be diluted by using the above mentioned blocking buffer. After incubation, plates were washed 3 times using 50 microliter per well of the PBS/0.05% Tween 20 buffer.

For detection 30 microliter of a Anti-h-Fc-POD (SigmaAldrich, catalogue number A0170) diluted 1:10000 in 10% blocking buffer was added and incubated for 1 hour at 37° C. After incubation, plates were washed 3 times using 50 microliter per well of the PBS/0.05% Tween 20 buffer. Thirty microliter of BM Blue Substrate POD (Roche Diagnostics, catalogue number 11484281001) was added and after five minutes of incubation, the reaction was stopped by the addition of a 1 molar acid sulfur solution. Absorption was measured using the Tecan Infinite 500 reader, absorbance mode, extinction 450 nm, emission 690 nm.

For determination of the concentration of Myc tagged proteins the Human c-Myc ELISA kit (EIAab & USCNLIFE, Wuhan EIAab Science Co., Ltd, catalogue number E1290h) was used according to the manufactures instruction.

For determination of the concentration of His tagged proteins a His-Tag Protein ELISA Kit (BIOCAT GmbH, catalogue number AKR-130) was used according to the manufactures instruction.

For determination of the concentration of HA (hemagglutinin) tagged proteins a Human hemagglutinin, HA ELISA Kit (Hözel Diagnostika, catalogue number CSB-E09360h) was used according to the manufactures instruction.

Activity Testing:

CHO K1 cells (ATCC, catalogue number CCL-61) were stably transfected with the cyclic AMP responsive element (CRE) Luciferase reporter gene construct (Biomyx Technology, pHTS-CRE, catalogue number P2100) resulting in a CHO-CRE-Luciferase cell line.

This cell line was subsequently stably transfected with the human LGR7/RXFP1 receptor (accession numbers NM_021634.2), cloned as 2271 base pair long DNA fragment into the mammalian expression vector pcDNA3.1(−) (Invitrogen, catalogue number V79520), resulting in a CHO-CRE-LGR7 cell line. This cell line was cultivated in D-Mem F12 (Gibco, #31330) 2 mM Glutamax (Gibco, #35050), 100 nM Pyruvat (Gibco, #11360-070), 20 mM Hepes (Gibco, #15630), 1% Penicillin-Streptomycin (Gibco, #15140) and 10% fetal calf serum (FCS, Gibco, #11058).

For stimulation, medium was exchanged by OptiMem (Gibco, #11058)+1% FCS containing different concentrations of the recombinantly expressed Relaxin variant proteins (usually starting at a concentration of 100 nM, followed by 1:2 dilutions). As positive control, commercially available recombinant expressed human Relaxin 2 (Genbank Accession number NP_604390.1) was used (R&D Systems, catalogue number 6586-RN-025). Subsequently, cells were incubated for 6 hours in a humified incubator at 5% carbon dioxide at 37° C. After 6 hours cells were tested for Luciferase activity using a Luciferase Assay System (Promega, #E1500) and using the Tecan Infinite 500 reader, luminescence mode, 1000 milliseconds integration time, measurement time 30 seconds.

Relative luminescence units were used to determine EC50 values of the different molecules by using the computer program Graph Pad Prism Version 5.

For alternative activity testing of Relaxin as well as of fusion polypeptides of the invention, cell lines (e.g. THP1, ATCC catalogue number TIB-202) or primary cells (e.g. Celprogen Inc., Human Cardiomyocyte Cell Culture, catalogue number 36044-15) with endogenous expression of the LGR7 receptor are used. These cells are cultivated according to the manufactures instruction.

Methods for the detection of Relaxin or Relaxin variants induced generation of cAMP are known in the art. For example, such measurement is performed using a cAMP ELISA (e.g. IBL International GmbH, cAMP ELISA, catalogue number CM 581001) according to the manufactures instruction.

Methods for the detection of Relaxin or Relaxin variants induced activation of PI3 kinase are known in the art. For example, such measurement is performed using a PI3-Kinase HTRF Assay according to the manufactures instruction (e.g. Millipore, PI3-Kinase HTRF Assay, catalogue number 33-016).

PEGylation

For PEGylation to cysteine residues the fusion polypeptide is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

It will be understood that the PEGylation is designed so as to produce the optimal molecule with respect to the number of PEG molecules attached, the size and form of such molecules (e.g. whether they are linear or branched, and the attachment site(s) in the fusion polypeptide. The molecular weight of the polymer to be used may e.g. be chosen on the basis of the desired effect to be achieved.

Immunogenicity Testing

Immunogenicity testing is performed by using the computer program NetMHCIIpan (Center for Biological Sequence Analysis; Department of Systems Biology; Technical University of Denmark) which calculates the potential binding affinity of proteins or peptides to MHCII complex. The higher the calculated binding affinity the higher is the risk to induce antibodies directed against the protein or polypeptide of interest.

In vitro determination of mapping T cell epitopes is performed according to the protocol published by Reijonen and Kwok (Reijonen H., Kwok W W. (2003) Use of HLA class II tetramers in tracking antigen-specific T cells and mapping T-cell epitopes. Methods 29:282-288).

Constructs of Single Chain Relaxin Variants

Determination of the Optimal Linker Length of Single Chain Relaxin Variants

Single chain Relaxin variants with different linker length connecting the A and B chain were generated as described above. As depicted in the sequences, for alternative determination of protein expression, in some constructs a Myc Tag (amino acid sequence EQKLISEEDL (SEQ ID NO: 168)) was added to the N terminal end of the A chain either with or without a hemagglutinin tag (amino acid sequence YPYDVPDYA (SEQ ID NO: 169)) as well as a 6 Histidine tag (amino acid sequence HHHHHH (SEQ ID NO: 170)) was added at the C terminal end of the B chain.

Example 1 scR1

In scR1 composition of the linker sequence connecting the A chain and B chain of human Relaxin 2 is three amino in acids length and consist of the polypeptide with the sequence GlyGlyGly (SEQ ID NO: 171). For alternative determination of protein expression, a Myc tag was added at the N terminal end of the A chain and a hemagglutinin tag and a 6 Histidine tag was added at the C terminal end of the B chain.

Example 2 scR2

In scR2 composition of the linker sequence connecting the A chain and B chain of human Relaxin 2 is five amino acids in length and consist of the polypeptide with the sequence GlyGlyGlySerGly (SEQ ID NO: 172). For alternative determination of protein expression, a Myc tag was added at the N terminal end of the A chain and a hemagglutinin tag and a 6 Histidine tag was added at the C terminal end of the B chain.

Example 3 scR3

In scR3 composition of the linker sequence connecting the A chain and B chain of human Relaxin 2 is seven amino acids in length and consist of the polypeptide with the sequence GlyGlyGlySerGlyGlyGly (SEQ ID NO: 138). For alternative determination of protein expression, a Myc tag was added at the N terminal end of the A chain and a hemagglutinin tag and a 6 Histidine tag was added at the C terminal end of the B chain.

Example 4 scR4

In scR4 composition of the linker sequence connecting the A chain and B chain of human Relaxin 2 is nine amino acids in length and consist of the polypeptide with the sequence GlyGlyGlySerGlyGlyGlySerGly (SEQ ID NO: 139). For alternative determination of protein expression, a Myc tag was added at the N terminal end of the A chain and a hemagglutinin tag and a 6 Histidine tag was added at the C terminal end of the B chain.

Example 5 scR5

In scR5 composition of the linker sequence connecting the A chain and B chain of human Relaxin 2 is eleven amino acids in length and consist of the polypeptide with the sequence GlyGlyGlySerGlyGlyGlySerGlyGlyGly (SEQ ID NO: 146). For alternative determination of protein expression, a Myc tag was added at the N terminal end of the A chain and a hemagglutinin tag and a 6 Histidine tag was added at the C terminal end of the B chain.

Example 6 scR6

In scR6 composition of the linker sequence connecting the A chain and B chain of human Relaxin 2 is fifteen amino acids in length and consist of the polypeptide with the sequence GlyGlyGlySerGlyGlyGlySerGlyGlyGlySerGlyGlyGly (SEQ ID NO: 173). For alternative determination of protein expression, a Myc tag was added at the N terminal end of the A chain and a hemagglutinin tag and a 6 Histidine tag was added at the C terminal end of the B chain.

Example 7 scR7

In scR7 composition of the linker sequence connecting the A chain and B chain of human Relaxin 2 is six amino acids in length and consist of the polypeptide with the sequence GlyGlyGlySerGlyGly (SEQ ID NO: 137). For alternative determination of protein expression, a Myc tag is added at the N terminal end of the A chain. Activity is measured according to the protocol as described above.

Example 8 scR8

In scR8 composition of the linker sequence connecting the A chain and B of human Relaxin 2 chain is twelve amino acids in length and consist of the polypeptide with the sequence GlyGlyGlySerGlyGlyGlySerGlyGlyGlySer (SEQ ID NO: 140). For alternative determination of protein expression, a Myc tag is added at the N terminal end of the A chain. Activity is measured according to the protocol described above.

Example 9 scR9

In scR9 composition of the linker sequence connecting the A chain and B chain of human Relaxin 2 is be thirteen amino acids in length and consist of the polypeptide with the sequence GlyGlyGlySerGlyGlyGlySerGlyGlyGlySerGly (SEQ ID NO: 145). For alternative determination of protein expression, a Myc tag is added at the N terminal end of the A chain. Activity is measured according to the protocol described above.

Example 10 scR10

In scR10 composition of the linker sequence connecting the A chain and B chain of human Relaxin 2 is fourteen amino acids in length and consist of the polypeptide with the sequence GlyGlyGlySerGlyGlyGlySerGlyGlyGlySerGlyGly (SEQ ID NO: 143). For alternative determination of protein expression, a Myc tag is added at the N terminal end of the A chain. Activity will be measured according to the protocol described above.

Example 11 scR11

In scR11 composition of the linker sequence connecting the A chain and B of human Relaxin 2 chain is ten amino acids in length and consist of the polypeptide with the sequence GlyGlyGlySerGlyCysGlyGlySerGly (SEQ ID NO: 141). For activity testing of the non-PEGylated fusion polypeptide non-purified protein was used.

To improve the biological half life of this construct, PEGylation of the Cysteine within the linker connecting the A chain and B chain following the protocol as described above is performed. Activity of the PEGylated variant is measured according to the protocol described above.

Example 12 scR12

In scR12 composition of the linker sequence connecting the A chain and B chain of human Relaxin 2 is ten amino acids in length and consist of the polypeptide with the sequence GlyGlyGlySerGlyLysGlyGlySerGly (SEQ ID NO: 142). For activity testing of the non-PEGylated fusion polypeptide non-purified protein was used.

To improve the biological half life of this construct, PEGylation of the Lysine within the linker connecting the A chain and B chain following the protocol as described above could be an option. Activity of the PEGylated variant is measured according to the protocol described above.

Example 13 scR13

In scR13 composition of the linker sequence connecting the C terminal end of the A chain and the N terminal end of the B chain of human Relaxin 2 is nine amino acids long and consists of the polypeptide with the sequence LysArgSerLeuSerArgLysLysArg (SEQ ID NO: 144). For activity testing non-purified fusion polypeptide was used.

Example 14 scR14

In scR14 composition of the linker sequence connecting the C terminal end of the A chain and N terminal end of the B

Example 15 scR15

In scR15 composition of the linker sequence connecting the C terminal end of the A chain and N terminal end of the B chain of human Relaxin 3 (accession number NP_543140.1) is nine amino in acids length and will consist of the polypeptide with the sequence GlyGlyGlySerGlyGlyGlySerGly (SEQ ID NO: 139). Activity is measured according to the protocol described above. For activity testing non-purified fusion polypeptide was used.

Example 16 scR16

In scR16 composition of the linker sequence connecting the C terminal end of the A chain and N terminal end of the B chain of human Relaxin 3 (accession number NP_543140.1) is nine amino in acids length and will consist of the polypeptide with the sequence GlyGlyGlySerGlyGlyGlySerGly (SEQ ID NO: 139). For alternative determination of protein expression, a Myc tag is added at the N terminal end of the A chain. Activity is measured according to the protocol described above.

Example 16 scR16

In scR16 composition of the linker sequence connecting the C-terminus of the B chain and the N-terminus of the A chain of human Relaxin 2 is nine amino in acids length and will consist of the polypeptide with the sequence GlyGlyGlySerGlyGlyGlySerGly (SEQ ID NO: 139). For alternative determination of protein expression, a Myc tag is added at the N terminal end of the A chain. Activity is measured according to the protocol described above.

Example 17 scR17

In scR17 composition of the linker sequence connecting the C-terminus of the A chain of human Relaxin 3 (accession number NP_543140.1) and the N-terminus of the B chain of human Relaxin 2 (accession number NP_604390.1) is nine amino in acids length and will consist of the polypeptide with the sequence GlyGlyGlySerGlyGlyGlySerGly (SEQ ID NO: 139). For alternative determination of protein expression, a Myc tag is added at the N terminal end of the A chain. Activity is measured according to the protocol described above.

Example 18 scR18

In scR18 composition of the linker sequence connecting the C-terminus of the B chain of human Relaxin 2 (accession number NP_604390.1) and the N-terminus of the A chain of human Relaxin 3 (accession number NP_543140.1) is nine amino in acids length and will consist of the polypeptide with the sequence GlyGlyGlySerGlyGlyGlySerGly (SEQ ID NO: 139). For alternative determination of protein expression, a Myc tag is added at the N terminal end of the A chain. Activity is measured according to the protocol described above.

Example 19 scR19

In scR19 composition of the linker sequence connecting the C-terminus of the A chain of human Relaxin 2 (accession number NP_604390.1) and the N-terminus of the B chain of human Relaxin 3 (accession number NP_543140.1) is nine amino in acids length and will consist of the polypeptide with the sequence GlyGlyGlySerGlyGlyGlySerGly (SEQ ID NO: 139). For alternative determination of protein expression, a Myc tag is added at the N terminal end of the A chain. Activity is measured according to the protocol described above.

Example 20 scR20

In scR20 composition of the linker sequence connecting the C-terminus of the B chain of human Relaxin 3 (accession number NP_543140.1) and the N-terminus of the A chain of human Relaxin 2 (accession number NP_604390.1) is nine amino in acids length and will consist of the polypeptide with the sequence GlyGlyGlySerGlyGlyGlySerGly (SEQ ID NO: 139). For alternative determination of protein expression, a Myc tag is added at the N terminal end of the A chain. Activity is measured according to the protocol described above.

A graphical representation of all single chain Relaxin variants is given in FIG. 2.

Table 1 summarizes the results regarding the expression as well as the biological activity of various scR constructs. Whereas single chain Relaxin variants having a linker length of three, five, and fifteen amino acids do not show any detectable biological activity in the assay described above, surprisingly the tested linker lengths of six, seven, nine, ten, eleven, twelve, thirteen, and fourteen amino acids lead to single chain variants exhibiting biological activity comparable to human Relaxin 2.

Although the length of the linker connecting the C-terminus of the A chain with the N-terminus of the B chain is important for the generation of a biological active molecule, the composition of the amino acids of the linker is variable. Examples are scR11 to scR13. Thereby, scR11 and scR12 exhibit an additional amino acid in the linker sequence (C in the linker of scR11 and K in the linker of scR12) or in case of the construct scR13, which exhibits a linker sequence which does not show any homology to the linker sequences mentioned above.

Generation of single chain Relaxin variants is not limited to Relaxin 2. Constructs scR14 and 15 are single chain variants of Relaxin 3. Although the overall sequence homology between Relaxin 2 and Relaxin 3 is low, the genomic organization of these two genes as members of the insulin superfamily is identical. Like Relaxin 2, Relaxin 3 consists of the classical B chain-C chain-A chain structure. Like for Relaxin 2, the C chain is cleaved off from the Relaxin 3 propeptide by Prohormone convertase I and II and the B and A chain are connected via disulfide bridges and by this the active molecule is formed. Constructs scR14 and scR15 are single chain variants of Relaxin 3, exhibiting the same linker molecule connecting the C-terminus of the A chain with the N-terminus of the B chain as for example already shown for Relaxin 2 with the construct scR4. scR14 and scR15 exhibit detectable biological activity.

scR16, scR17, scR18, scR19, and scR20 are chimeras between the A chain of Relaxin 3 and the B chain of Relaxin 2 and vice versa. Thereby, for activation of the LGR7 receptor it is mandatory that the B-chain of the Relaxin 2 and Relaxin 3, respectively, are located in the C-terminal part of a Relaxin 3/Relaxin 2 chimera.

| Clone | Expression | EC$_{50}$ (M)* |
|---|---|---|
| hRelaxin 2 | | 2.60E−11 |
| hRelaxin 3 | | 2.30E−09 |
| scR1 | detectable | not detectable |
| scR2 | detectable | not detectable |
| scR3 | detectable | 7.70E−11 |
| scR4 | detectable | 3.40E−11 |
| scR5 | detectable | 3.70E−11 |
| scR6 | detectable | not detectable |
| scR7 | detectable | 5.30E−08 |
| scR8 | detectable | 2.40E−08 |
| scR9 | detectable | 1.10E−07 |
| scR10 | detectable | 4.40E−08 |
| scR11 | detectable | 2.50E−08 |
| scR12 | detectable | 3.60E−08 |
| scR13 | detectable | active (EC$_{50}$ n.d.) |
| scR14 | detectable | 5.90E−10 |
| scR15 | detectable | 6.20E−10 |
| scR16 | detectable | not detectable |
| scR17 | detectable | 1.30E−08 |
| scR18 | detectable | not detectable |
| scR19 | detectable | active (EC$_{50}$ n.d.) |
| scR20 | detectable | not detectable |

*values are examples of three to five independent experiments.

Figure 4A:
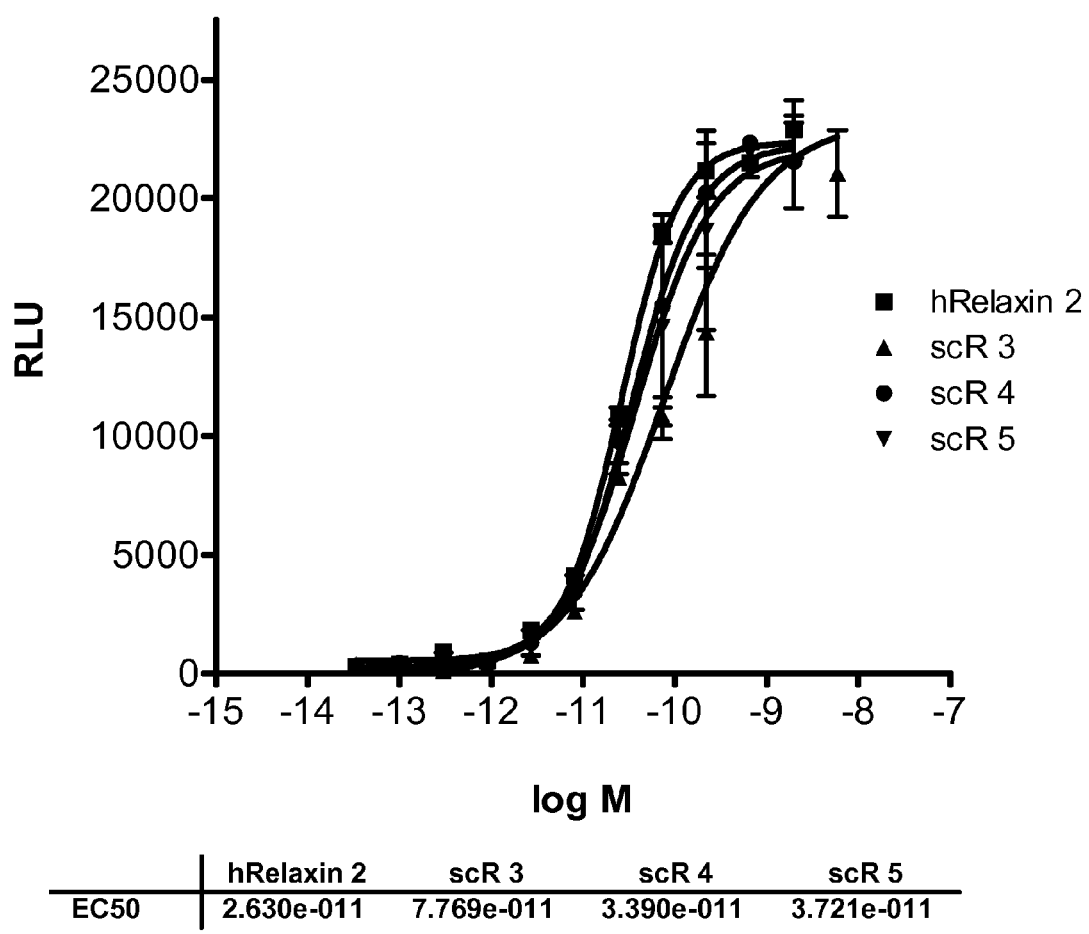
FIG. 4*a-e* Activity in a functional assay of scR 3, scR 4, and scR 5 (FIG. 4*a*), scR 7, scR 8, scR9, and scR10 (FIG. 4*b*), scR11 and scE12 (FIG. 4*c*), human Relaxin 3, scR14, and scR15 (FIG. 4*d*) and scR17 (FIG. 4*e*) using the CHO-CRE-LGR7 cell line. As control, hRelaxin 2 (R&D Systems, catalogue number 6586-RN-025) was used. Data are expressed as Relative Light Units, representing the activity of single chain Relaxin variants and Relaxin 2 induced luciferase expression. Symbols represent means, error bars represent S.E.M.
Figure 4B:
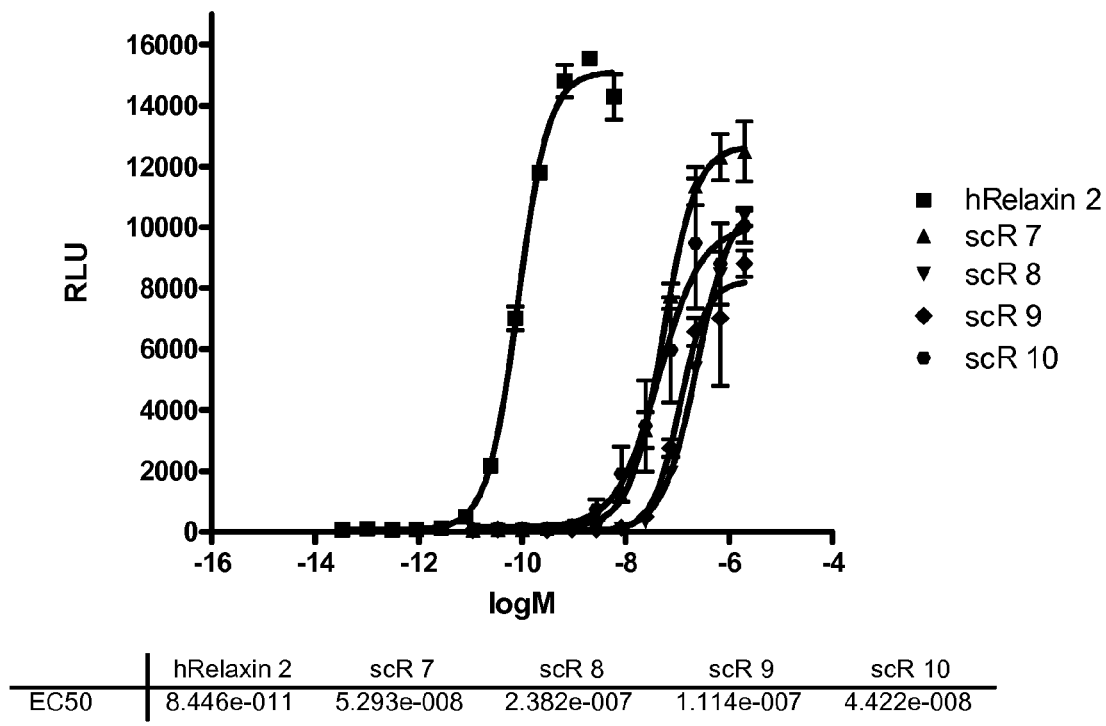
Figure 4C:
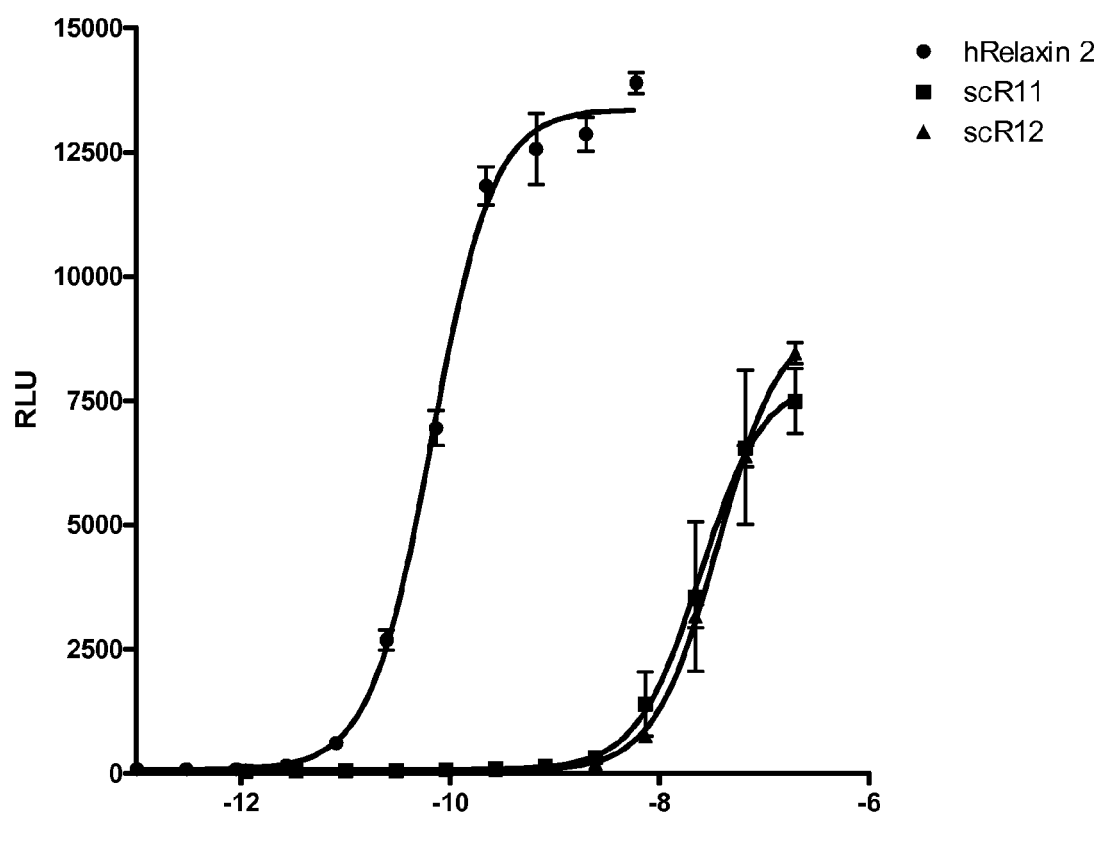
Figure 4D:
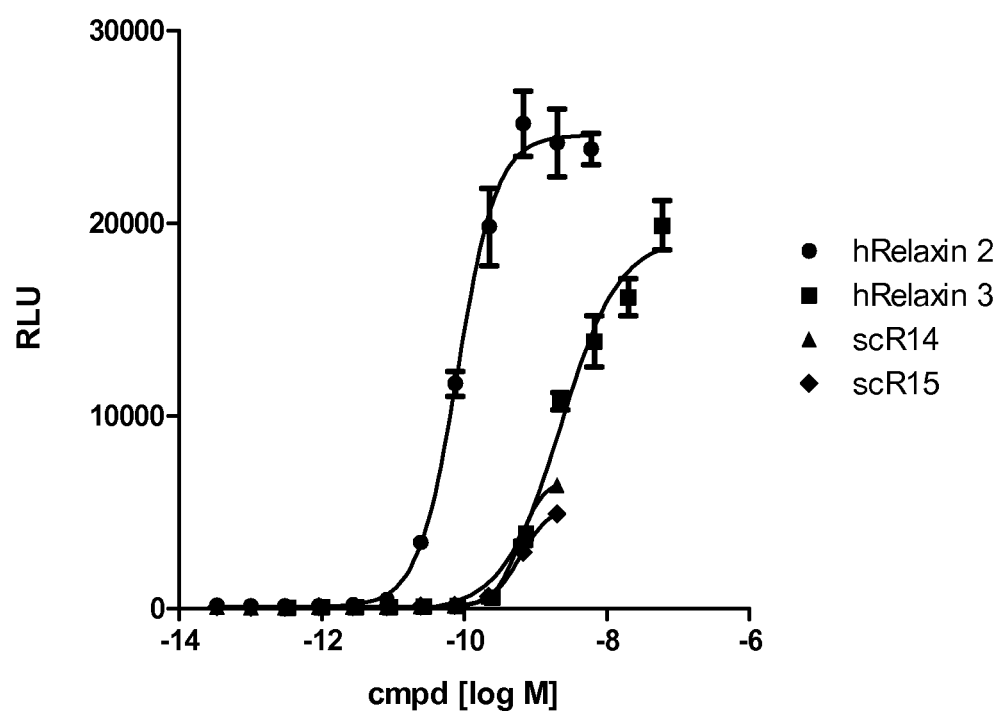
Figure 4E:
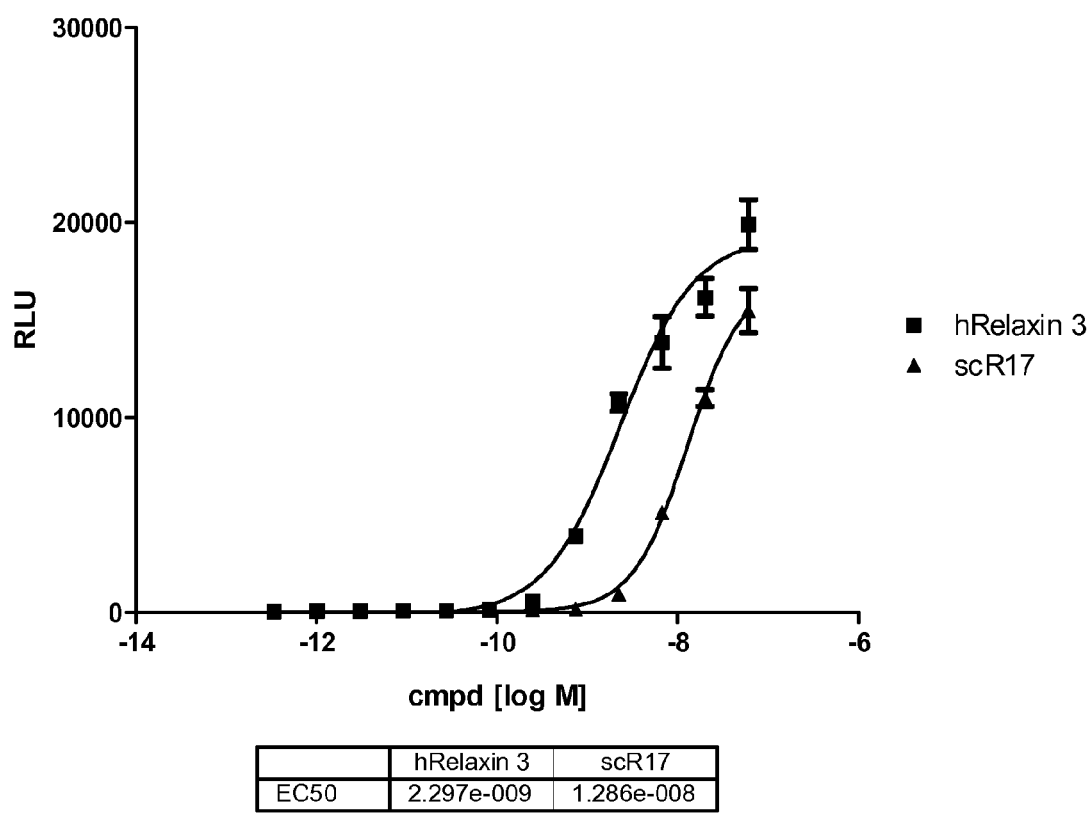
Figure 5:
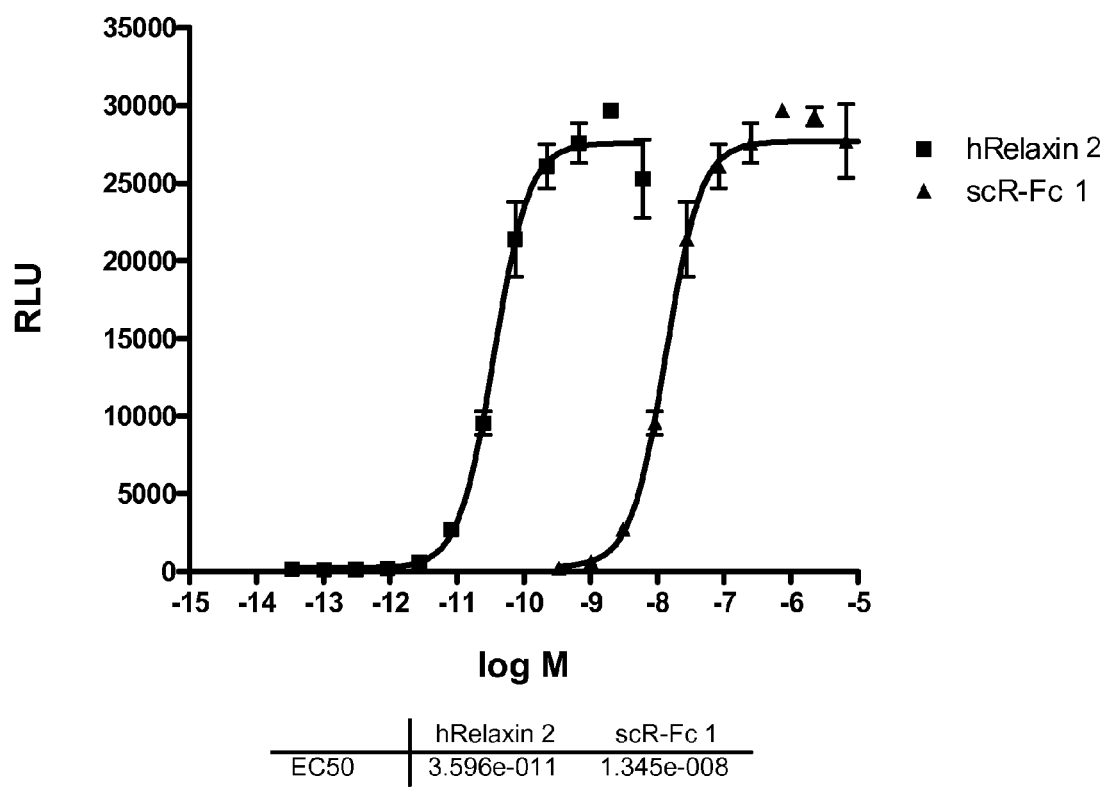
FIG. 5 Activity in a functional assay of scR-Fc 1 by using the CHO-CRE-LGR7 cell line. As control, hRelaxin 2 (R&D Systems, catalogue number 6586-RN-025) was used. Data are expressed as Relative Light Units, representing the activity of scR-Fc 1 and hRelaxin 2 induced luciferase expression. Symbols represent means, error bars represent S.E.M.
Figure 6:
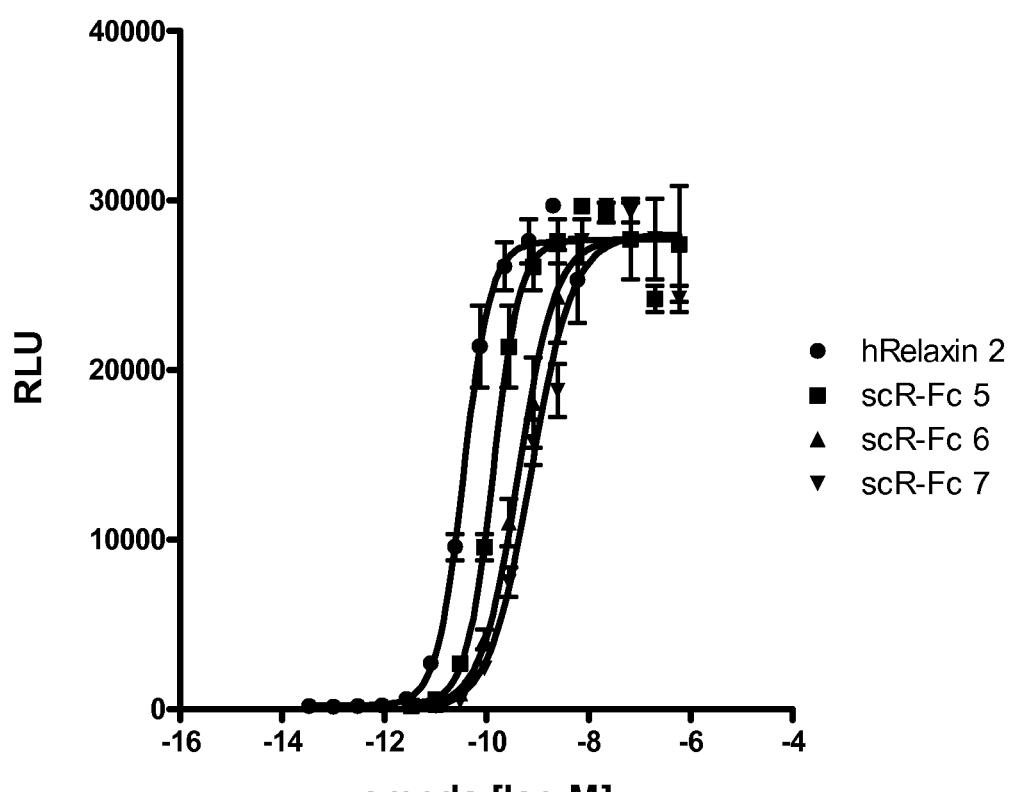
FIG. 6 Activity in a functional assay of scR-Fc 5, scR-Fc 6, and scR-Fc 7 using the CHO-CRE-LGR7 cell line. hRelaxin 2 (R&D Systems, catalogue number 6586-RN-025). was used as control. Data are expressed as Relative Light Units, representing the activity of the scR-Fc variants and hRelaxin 2 induced luciferase expression. Symbols represent means, error bars represent S.E.M.
Figure 7:
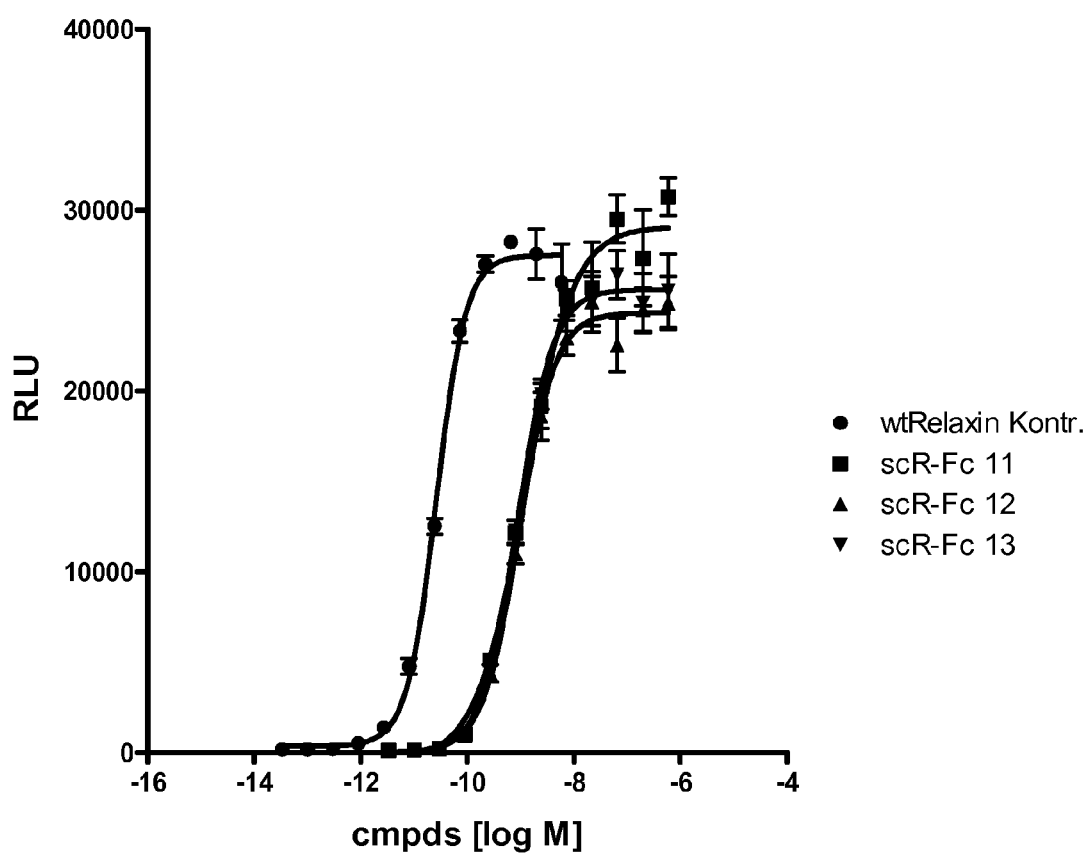
FIG. 7 Activity in a functional assay of scR-Fc 11, scR-Fc 12, and scR-Fc 13 using the CHO-CRE-LGR7 cell line. As control, hRelaxin 2 (R&D Systems, catalogue number 6586-RN-025) was used. Data are expressed as Relative Light Units, representing the activity of scR-Fc variants and hRelaxin 2 induced luciferase expression. Symbols represent means, error bars represent S.E.M.
Figure 8:
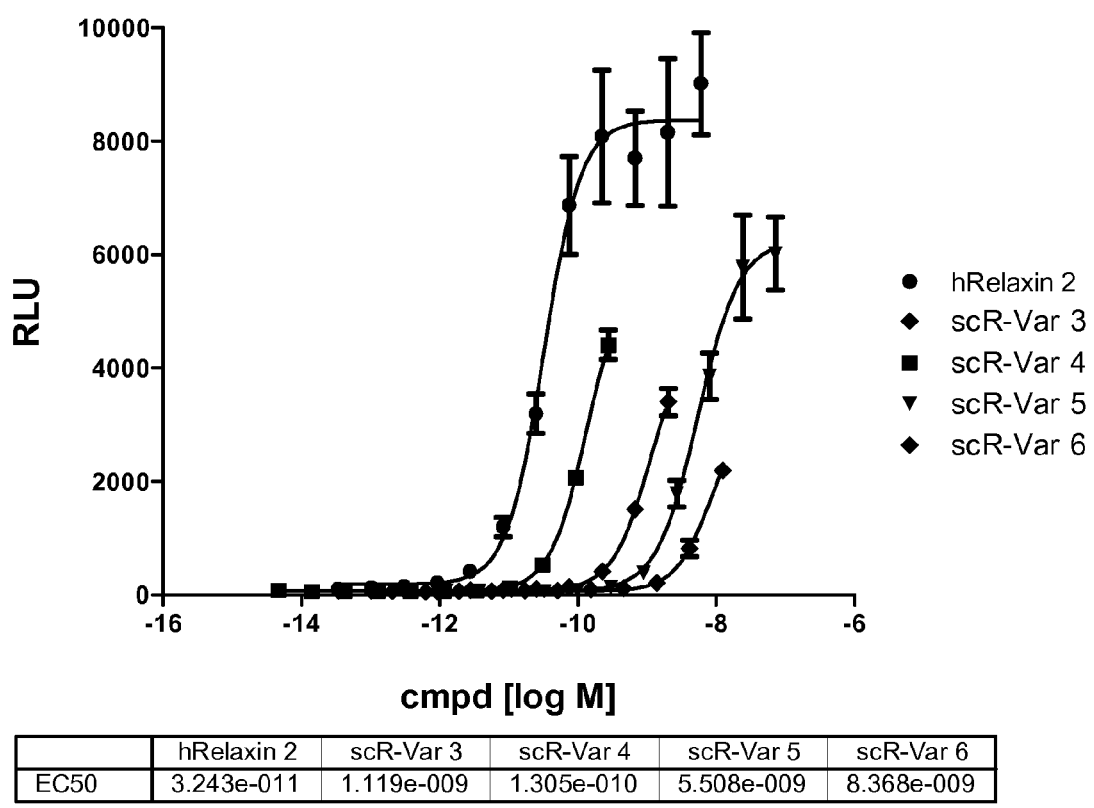
FIG. 8: Activity in a functional assay of scR-Var 3, scR-Var 4, scR-Var 5, and scR-Var 6 using the CHO-CRE-LGR7 cell line. As control, hRelaxin 2 (R&D Systems, catalogue number 6586-RN-025) was used. Data are expressed as Relative Light Units, representing the activity of scR-Fc variants and hRelaxin 2 induced luciferase expression. Symbols represent means, error bars represent S.E.M.

Dose response curves and the corresponding EC$_{50}$ values comparing the activity of hRelaxin 2, scR3, scR4, and scR5 are shown in FIG. 4a, for hRelaxin 2, scR7, scR8, scR9, and scR10 are shown in FIG. 4b, for hRelaxin 2, scR11 and scR12 are shown in FIG. 4c, for hRelaxin 2, hRelaxin 3, scR14 and scR15 are shown in FIG. 4d, and for hRelaxin 3 and scR17 are shown in FIG. 4e.

Conclusion: This shows that a linker length of more than five amino acids and less than fifteen amino acids are required for biological activity of single chain Relaxin variants wherein the C terminus of the A chain is connected via such linkers to the N terminus of the B chain. Furthermore, the generation of single chain Relaxin of the invention is not limited to Relaxin 2.

Binding of Relaxin 2 to its corresponding receptor LGR7 is a two-step process. In a first step, the A chain of human Relaxin 2 binds to the N terminal ectodomain of the receptor. In a second step, this bound ectodomain undergoes a conformational change and secondary interactions between the B chain of Relaxin and the transmembrane domain of LGR7 mediates receptor signaling. This second step is the most relevant in the activation of the ligand-receptor complex. Therefore, due to the fact that the variant scR17 contains the A chain of human Relaxin 3 instead of human Relaxin 2, leads to a construct with reduced activity. A further reduction in the activity is observed with the variant scR19, which contains the B chain of human Relaxin 3 instead of the B chain of human Relaxin 2. Binding to the ectodomain occurs via the A chain of the human Relaxin 2, but the B chain of the human Relaxin 3 is suboptimal for activating LGR7. The corresponding receptor for Relaxin 3 is LGR8. Therefore, it is very likely, that by using the scR19 as ligand and LGR8 as the corresponding receptor, signal intensity were much higher. This is also a mean to modulate the activity of an fusion polypeptide of the invention.

The non-purification of scR13 is an explanation of the lower activity as possible impurities in the sample leads to false determination of the concentration or could have an negative impact on the accuracy the cell based Luciferase assay.

In conclusion this shows that useful linker sequences are not restricted to Glycine/Serine rich sequences as other linker sequences (within the inventive length) also lead to fully active single chain Relaxins.

Construction of Single Chain Relaxin Fusion Proteins with Improved Biological Half Life.

In order to improve the biological half life of single chain Relaxin variants, constructs were designed where the Fc moiety of immunoglobulin molecules were added at the N terminal or C terminal end of the single chain Relaxin variants.

Thereby, single chain Relaxin variants were directly fused to the Fc part of an immunoglobulin or linked by a polypeptide of different length and amino acid compositions.

Another option to improve the biological half life of polypeptides are fusions with polypeptides like Transferrin (accession number P02787) or Albumin (accession number P02768) (SR Schmid (2009)).

PEGylation is a commonly used method to improve the biological half life of polypeptides.

Hereby polyethylene glycol polymer chains are added covalently attached to a polypeptide. Thereby a reactive derivative of PEG is incubated with the target polypeptide. Preferred amino acids reacting with PEG are Cysteins and Lysins.

Pasut and Veronese (2009))

Generation of a Relaxin Fusion Protein—Relaxin-Fc

To improve the biological half life the Fc part of the human IgG1 was combined with human Relaxin 2 by chemically based gene synthesis. The carboxy-terminal part of human Relaxin 2 (according to its genomic organization arranged as follows: B chain-C chain-A chain) was fused to N terminal end of the human IgG1 Fc moiety, whereby these two parts of the fusion protein were connected by a 6 amino acids long linker sequence consisting of a polypeptide with the sequence IleGluGlyArgMetAsp (SEQ ID NO: 147) encoding the coagulation factor Xa cleavage site. However, Relaxin Fc showed no activity determined by a CHO-CRE-LGR7 cell line.

Example 16 scR-Fc 1

In scR-Fc 1 composition of the linker sequence connecting the C terminal end of scR 4 with the N terminal end of the human IgG1 Fc moiety is 6 amino acids long and consists of the polypeptide with the sequence IleGluGlyArgMetAsp (SEQ ID NO: 147) encoding the coagulation factor Xa cleavage site. This polypeptide and Fc moiety replaces the hemagglutinin tag and 6 Histidine tag in scR 4. For alternative determination of protein expression, a Myc tag was added at the N terminal end of the A chain.

Example 17 scR-Fc 2

In scR-Fc 2 composition of the linker sequence connecting the C terminal end of the single chain Relaxin scR4 with the N terminal end of the human IgG1 Fc moiety is 4 amino acids long and consists of the polypeptide with the sequence GlyGlySerPro (SEQ ID NO: 148). In contrast to scR-Fc 1, this construct has no Myc tag at the N terminal end of the A chain.

Example 18 scR-Fc 3

In scR-Fc 3 composition of the linker sequence connecting the C terminal end of the single chain Relaxin scR4 with the N terminal end of the human IgG1 Fc moiety is 7 amino acids long and consists of the polypeptide with the sequence GlyGlySerGlyGlySerPro (SEQ ID NO: 149). In contrast to scR-Fc 1, this construct has no Myc tag at the N terminal end of the A chain.

Example 19 scR-FC 4

In scR-Fc 4 composition of the linker sequence connecting the C terminal end of the single chain Relaxin scR4 with the N terminal end of the human IgG1 Fc moiety is 10 amino acids long and consists of the polypeptide with the sequence GlyGlySerGlyGlySerGlyGlySerPro (SEQ ID NO: 150). In contrast to scR-Fc 1, this construct has no Myc tag at the N terminal end of the A chain.

Example 20 scR-Fc 5

In scR-Fc 5 composition of the linker sequence connecting the N terminal end of the single chain Relaxin scR4 with the C terminal end of the human IgG1 Fc moiety is 4 amino acids long and consists of the polypeptide with the sequence GlyGlySerPro (SEQ ID NO: 148). The Fc moiety replaces the Myc tag at the N terminal end of the A chain. This construct has no hemagglutinin tag and/or 6 Histidine tag at its C terminal end.

Example 21 scR-Fc 6

In scR-Fc 6 composition of the linker sequence connecting the N terminal end of the single chain Relaxin scR4 with the C terminal end of the human IgG1 Fc moiety is 7 amino acids long and consists of the polypeptide with the sequence GlyGlySerGlyGlySerPro (SEQ ID NO: 149). The Fc moiety replaces the Myc tag at the N terminal end of the A chain. This construct has no hemagglutinin tag and/or 6 Histidine tag at its C terminal end.

Example 22 scR-Fc 7

In scR-Fc 7 composition of the linker sequence connecting the N terminal end of the single chain Relaxin scR4 with the C terminal end of the human IgG1 Fc moiety is 10 amino acids long and consists of the polypeptide with the sequence GlyGlySerGlyGlySerGlyGlySerPro (SEQ ID NO: 150). The Fc moiety replaces the Myc tag at the N terminal end of the A chain. This construct has no hemagglutinin tag and/or 6 Histidine tag at its C terminal end.

Example 23 scR-FC 8

In scR-Fc 8 composition of the linker sequence connecting the C terminal end of the single chain Relaxin scR4 with the N terminal end of the rat IgG2b Fc moiety is 4 amino acids long and consists of the polypeptide with the sequence GlyGlySerPro (SEQ ID NO: 148). Additionally a 6 Histidine tag is added at the C terminal end of the Fc part. In contrast to scR4, this construct has no Myc tag the N terminal end of the A chain. The rat IgG2b Fc moiety replaces the hemagglutinin tag and 6 Histidine tag.

Example 24 scR-Fc 9

In scR-Fc 9 composition of the linker sequence connecting the C terminal end of the single chain Relaxin scR4 with the N terminal end of the rat IgG2b Fc moiety is 7 amino acids long and consists of the polypeptide with the sequence GlyGlySerGlyGlySerPro (SEQ ID NO: 149). Additionally a 6 Histidine tag is added at the C terminal end of the Fc part. In contrast to scR4, this construct has no Myc tag the N terminal end of the A chain. The rat IgG2b Fc moiety replaces the hemagglutinin tag and 6 Histidine tag.

Example 25 scR-Fc 10

In scR-Fc 10 composition of the linker sequence connecting the C terminal end of the single chain Relaxin scR4 with the N terminal end of the rat IgG2b Fc moiety is 10 amino acids long and consists of the polypeptide with the sequence GlyGlySerGlyGlySerGlyGlySerPro (SEQ ID NO: 150). Additionally a 6 Histidine tag is added at the C terminal end of the Fc part. In contrast to scR4, this construct has no Myc tag at the N terminal end of the A chain. The rat IgG2b Fc moiety replaces the hemagglutinin tag and 6 Histidine tag.

Example 26 scR-Fc 11

In scR-Fc 11 composition of the linker sequence connecting the N terminal end of the single chain Relaxin scR4 with the C terminal end of the rat IgG2b Fc moiety is 4 amino acids long and consists of the polypeptide with the sequence GlyGlySerPro (SEQ ID NO: 148). Additionally a 6 Histidine tag is added at the N terminal end of the Fc part. The rat IgG2b Fc moiety replaces the Myc tag. Additionally this construct has no hemagglutinin tag and/or 6 Histidine tag at its C terminal end.

Example 27 scR-Fc 12

In scR-Fc 11 composition of the linker sequence connecting the N terminal end of the single chain Relaxin scR1 with the C terminal end of the rat IgG2b Fc moiety is 7 amino acids long and consists of the polypeptide with the sequence GlyGlySerGlyGlySerPro (SEQ ID NO: 149). Additionally a 6 Histidine tag is added at the N terminal end of the Fc part. The rat IgG2b Fc moiety replaces the Myc tag. Additionally this construct has no hemagglutinin tag and/or 6 Histidine tag at its C terminal end.

Example 28 scR-Fc 13

In scR-Fc 11 composition of the linker sequence connecting the N terminal end of the single chain Relaxin scR4 with the C terminal end of the rat IgG2b Fc moiety is 10 amino acids long and consists of the polypeptide with the sequence GlyGlySerGlyGlySerGlyGlySerPro (SEQ ID NO: 150). Additionally a 6 Histidine tag is added at the N terminal end of the Fc part. The rat IgG2b Fc moiety replaces the Myc tag. Additionally this construct has no hemagglutinin tag and/or 6 Histidine tag at its C terminal end.

Example 29 scR-Fc 14

In order to analyze the influence of a linker sequence connecting single chain Relaxin variants and Fc moieties, in scR-Fc 14 the C terminal end of sequence scR4 was directly fused to the Fc part of the human IgG1. This Fc moiety replaces the hemagglutinin tag and 6 Histidine tag in scR4. This construct has no Myc tag at the N terminal end of the A chain.

Example 30 scR-Fc 15

In scR-Fc 15 composition of the linker sequence connecting the C terminal end of the single chain Relaxin scR4 with the N terminal end of the human IgG1 Fc moiety is 6 amino acids long and consists of the polypeptide with the sequence GlySerGlySerGlySer (SEQ ID NO: 151). The human IgG1 Fc moiety replaces the hemagglutinin tag and 6 Histidine tag. This construct has no Myc tag at the N terminal end of the A chain.

Example 31 scR-Fc 16 scR-Fc 16 was designed to analyze the influence of disulfide bridges within the Fc moiety on protein expression and fusion protein activity. For this, the Cysteine residue at position 86 within the Fc part of the human IgG1 in scR-Fc 15 was replaced by Alanin.

Example 32 scR-Fc 17

In scR-Fc 17 composition of the linker sequence connecting the C terminal end of the single chain Relaxin scR4 with the N terminal end of the rat IgG2b Fc moiety is 6 amino acids long and consists of the polypeptide with the sequence GlySerGlySerGlySer (SEQ ID NO: 151). The rat IgG2b Fc moiety replaces the hemagglutinin tag and 6 Histidine tag. This construct has no Myc tag at the N terminal end of the A chain.

Example 33 scR-Fc 18

In scR-Fc 18 composition of the linker sequence connecting the C terminal end of the single chain Relaxin scR4 with the N terminal end of the human IgG1 Fc moiety is 21 amino acids long and consists of the polypeptide with the sequence GlyGlyGlySerGlyGlyGlySerGlyThrLysValThrValSerSerGluSerLysTyrGly (SEQ ID NO: 174). The human IgG1 Fc moiety replaces the hemagglutinin tag and 6 Histidine tag. This construct has no Myc tag at the N terminal end of the A chain.

Example 34 scR-Var 1

In scR-Var1 composition of the linker sequence connecting the A chain and B chain of the human Relaxin 2 is of nine amino acids in length and consist of the polypeptide with the sequence GlyGlyGlySerGlyGlyGlySerGly (SEQ ID NO: 139). Additionally a polypeptide of six amino acids in length and with the sequence GlyGlySerGlyCysGly (SEQ ID NO: 175) was added at the C terminal end of the B chain. For activity testing of the non-PEGylated fusion polypeptide non-purified protein was used.

To improve the biological half life of this construct, PEGylation of the Cysteine within the stretcher polypeptide fused at the C terminal end of the B chain is performed following the protocol as described above. Activity of the PEGylated variant is measured according to the protocol described above.

Example 35 scR-Var 2

In scR-Var2 composition of the linker sequence connecting the A chain and B chain of the human Relaxin 2 is of nine amino acids length and consist of the polypeptide with the sequence GlyGlyGlySerGlyGlyGlySerGly (SEQ ID NO: 139). Additionally a polypeptide of six amino acids in length and with the sequence GlyCysGlySerGlyGly (SEQ ID NO: 176) was added at the N terminal end of the A chain. For activity testing of the non-PEGylated fusion polypeptide non-purified protein was used.

To improve the biological half life of this construct, PEGylation of the Cysteine within the stretcher polypeptide fused at the N terminal end of the A chain is performed following the protocol as described above. Activity of the PEGylated variant is measured according to the protocol described above.

Example 36 scR-Var3

In scR-Var3 composition of the linker sequence connecting the C terminal end of the A chain and the N terminal end of the B chain of of the human Relaxin 2 is of nine amino acids in length and consist of the polypeptide with the sequence GlyGlyGlySerGlyGlyGlySerGly (SEQ ID NO: 139). At the N terminal end of the A chain a polypeptide with the sequence IleGluGlyArgMetAsp encoding the coagulation factor Xa cleavage site connects this variant with the C terminal end of the human Transferrin protein (accession number NP_001054.1). Activity is measured according to the protocol described above.

Example 37 scR-Var4

In scR-Var4 wild type proRelaxin 2 (genomic organization) is fused to Transferrin. For this, at the N terminal end of the B chain is a polypeptide with the sequence IleGluGlyArgMetAsp (SEQ ID NO: 147) encoding the coagulation factor Xa cleavage site connects this variant with the C terminal end of the human Transferrin protein (accession number NP_001054.1). Activity is measured according to the protocol described above.

Example 38 scR-Var5

In scR-Var5 composition of the linker sequence connecting the C terminal end of the A chain and the N terminal end of the B chain of human Relaxin 2 is of nine amino acids length and consist of the polypeptide with the sequence GlyGlyGlySerGlyGlyGlySerGly (SEQ ID NO: 139). At the N terminal end of the A chain a polypeptide with the sequence IleGluGlyArgMetAsp (SEQ ID NO: 147) encoding the coagulation factor Xa cleavage site connects this variant with the C terminal end of the human Albumin protein (accession number NP_000468.1). Activity is measured according to the protocol described above.

Example 39 scR-Var6

In scR-Var6, a polypeptide with the sequence IleGluGlyArgMetAsp (SEQ ID NO: 147) encoding the coagulation factor Xa cleavage site located at the N terminal end of the B chain connects this variant with the C terminal end of the human Albumin protein (accession number NP_000468.1). Activity is measured according to the protocol described above.

Example 40 scR-Var7

In scR-Var7 composition of the linker sequence connecting the C terminal end of the A chain of human Relaxin 2 and the N terminal end of the B chain of human Relaxin 2 is nine amino acids long and consists of the polypeptide with the sequence LysArgSerLeuSerArgLysLysArg (SEQ ID NO: 144), A linker sequence connecting the C terminal end of the B chain with the N terminal end of the human IgG1 Fc moiety is 6 amino acids long and consists of the polypeptide with the sequence IleGluGlyArgMetAsp (SEQ ID NO: 147) encoding the coagulation factor Xa cleavage site.

Example 41 scR-Var8

In scR-Var8 composition of the linker sequence connecting the C terminal end of the A chain and the N terminal end of the B chain is nine amino acids long and consists of the polypeptide with the sequence LysArgSerLeuSerArgLysLysArg (SEQ ID NO: 144).

A linker sequence connecting the N terminal end of the A chain with the C terminal end of the human IgG1 Fc moiety is 6 amino acids long and consists of the polypeptide with the sequence IleGluGlyArgMetAsp (SEQ ID NO: 147) encoding the coagulation factor Xa cleavage site.

A graphical representation of all single chain Relaxin fusion proteins as well as the variants designed for PEGylation is given in FIG. 3.

Table 2 summarizes the results for expression as well as biological activity of various scR fusion protein constructs.

| Clone | Expression | EC$_{50}$ (M)* |
|---|---|---|
| Relaxin |  | 3.50E−11 |
| Relaxin Fc | detectable | not detectable |
| scR-Fc 1 | detectable | 1.30E−08 |
| scR-Fc 2 | detectable | 3.30E−09 |
| scR-Fc 3 | detectable | 2.40E−09 |
| scR-Fc 4 | detectable | 3.10E−09 |
| scR-Fc 5 | detectable | 1.30E−09 |
| scR-Fc 6 | detectable | 4.20E−10 |
| scR-Fc 7 | detectable | 7.40E−10 |
| scR-Fc 8 | detectable | 7.20E−09 |
| scR-Fc 9 | detectable | 9.90E−09 |
| scR-Fc 10 | detectable | 4.80E−09 |
| scR-Fc 11 | detectable | 1.20E−09 |
| scR-Fc 12 | detectable | 9.50E−10 |
| scR-Fc 13 | detectable | 8.90E−10 |
| scR-Fc 14 | detectable | 3.90E−07 |
| scR-Fc 15 | detectable | 3.40E−09 |
| scR-Fc 16 | detectable | 2.50E−09 |
| scR-Fc 17 | detectable | 2.50E−09 |
| scR-Fc 18 | detectable | active (EC$_{50}$ n.d.) |
| scR-Var1 | detectable | 1.10E−07 |
| scR-Var2 | detectable | 4.20E−08 |
| scR-Var3 | detectable | 1.00E−09 |
| scR-Var4 | detectable | 1.30E−10 |
| scR-Var5 | detectable | 5.50E−09 |
| scR-Var6 | detectable | 8.30E−09 |
| scR-Var7 | detectable | active (EC$_{50}$ n.d.) |
| scR-Var8 | detectable | active (EC$_{50}$ n.d.) |

*values are examples of three to five independent experiments.

For all variants listed, expression could be determined by using the Human Relaxin-2 Quantikine ELISA Kit and activity could be measured by using the CHO-CRE-LGR7 cell line. Exemplarily, dose response curves for scR-Fc 1, scR-Fc 5 to scR-Fc 7, scR-Fc 11 to scR-Fc 13, and scR-Var3 to scR-Var6 are shown in FIG. 5, FIG. 6, FIG. 7, and FIG. 8, respectively.

The human wildtype Relaxin 2 molecule with its orientation B chain-C chain-A chain fused to the Fc moiety of the human IgG molecule does not show any detectable activity. Possible explanation for the non-activity of this molecule could be an incomplete processing of the C chain. In contrast, in all fusion constructs containing the single chain human Relaxin 2, a significant activity can be detected. As shown above, the single chain Relaxin exhibits activity comparable to the human wildtype Relaxin 2, although no proteolytic processing takes place.

For the single chain Relaxin 2 fusion constructs, the orientation of the Fc moiety seems to have a significant impact on the activity of these molecules. Constructs carrying the Fc part at the C terminal end of the B chain (e.g. scR-Fc 1 to scR-Fc 4 and scR-Fc 13 to scR-Fc 18) exhibit a slightly lower activity than constructs carrying the Fc moiety at the N terminal end of the A chain (e.g. scR-Fc 5 to scR-Fc 6 and scR-Fc 11 to scR-Fc 12). As mentioned above, after binding of the A chain to the ectodomain of the corresponding receptor LGR7, a conformational change within the receptor molecule brings the B chain in contact with the extracellular loops of the transmembrane domains. The second step than leads to the activation of the receptor. Therefore, the Fc moiety coupled to the B chain could inhibit the optimal binding of the B chain and by this inhibits the full activation of the receptor.

Analysis of the In Vivo Plasma Stability of Fc-Single Chain Relaxin scR-Fc 13 and hRelaxin2 were administrated intravenously in 8 weeks old, male Wistar rats at concentrations of 240 µg/kg. At time points 0 hour, 1 hour, 3 days, 5 days, and 7 days after compound administration, blood samples were taken and the concentrations of the Fc-single chain Relaxin and non-modified hRelaxin2 were determined using the commercially available quantification ELISA (R&D Systems, Human Relaxin-2 Quantikine ELISA Kit, catalogue number DRL200).

Figure 9:
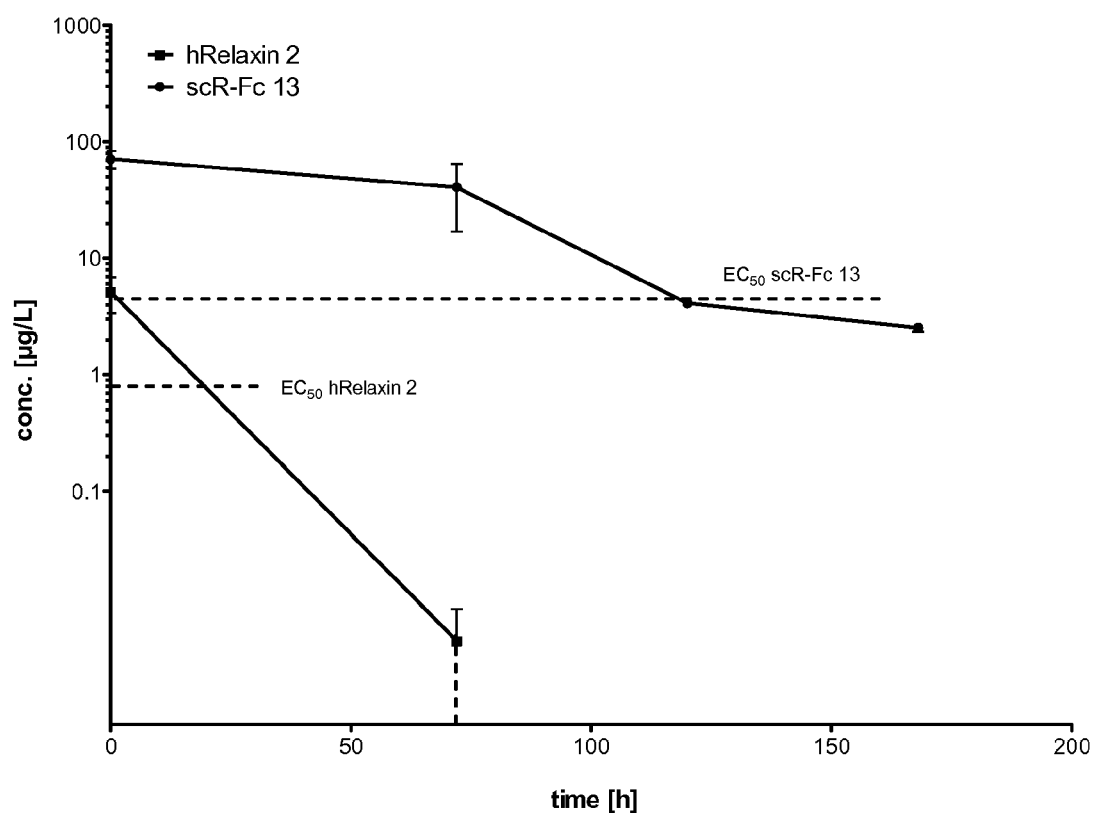
FIG. 9 In vivo half-life analysis of intravenously administrated hRelaxin 2 or scR-Fc 13. Eight weeks old male Wistar rats (three animals per group) were given a single application of human Relaxin 2 and scR-Fc 13, respectively (0.24 mg/kg). Blood samples were collected at the indicated time points after application and serum levels of each protein were measured by using a quantification ELISA.

As shown in FIG. 9, three days after application, non-modified hRelaxin2 was undetectable whereas for scR-Fc13 even 7 days after intravenous administration significant concentrations were detected, that were even above the EC50 value obtained for the CHO-LGR7 based activity test.

Determination of Fc-Single Chain Relaxin Activity Isolated from Plasma.

Figure 10:
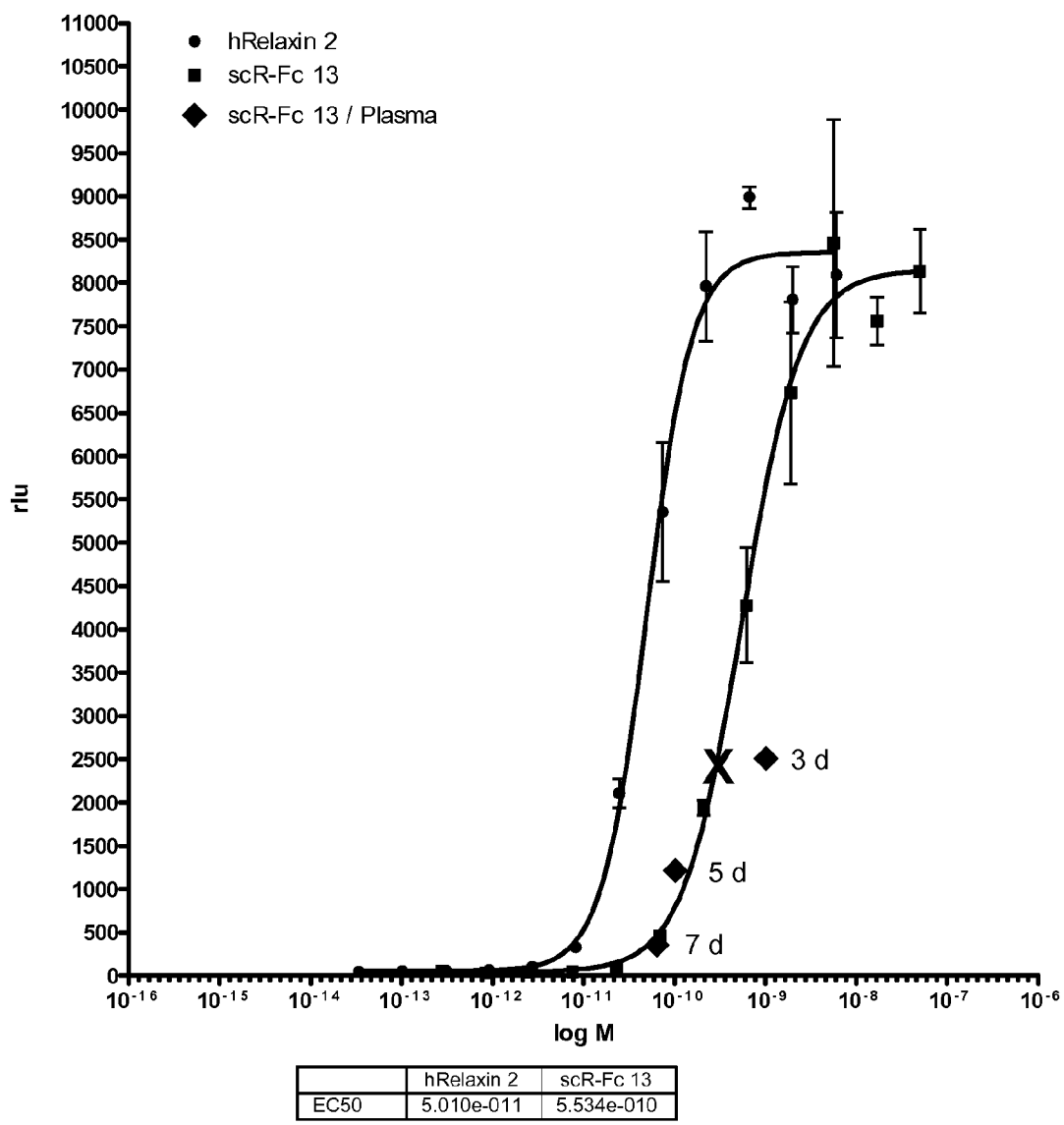
FIG. 10: Activity of Relaxin 2 and Relaxin variants in blood samples

In order to determine whether scR-Fc 13 still exhibits activity after 3, 5, and 7 days after intravenous administration, plasma samples were tested on the CHO-CRE-LGR7 cell line. As shown in FIG. 10, for all three samples activity could be determined and for all three samples, activity values are similar to the $EC_{50}$ value obtained with the purified scR-Fc 13 variant.

Isolated Perfused Rat Heart

Male Wistar rats (200-250 g) were anesthetized using Narcoren (100 mg/kg i.p.). The heart was rapidly excised and connected to a Langendorff perfusion system (FMI GmbH, Seeheim-Ober Beerbach, Germany). The heart was perfused at a constant rate of 10 ml/min with Krebs-Henseleit bicarbonate buffer solution equilibrated with 95% $O_2$-5% $CO_2$. The perfusion solution contained (in mmol/l): NaCl 118; KCl 3; $NaHCO_3$ 22; $KH_2PO_4$ 1,2; $MgSO_4$ 1,2; $CaCl_2$ 1,8; Glucose 10; Na-Pyruvat 2. A pressure transducer registered the perfusion pressure in the perfusion system. The left ventricular pressure (LVP) was measured using a second pressure transducer connected to a water-filled balloon which was inserted into the left ventricle via the left atrium. The end diastolic pressure was initially set to 8 mm Hg by adjusting the volume of the balloon. The hearts were spontaneously beating. The signals from the pressure transducer were amplified, registered and used for the calculation of the heart frequency and +dp/dt by a personal computer.

As shown in FIG. 11, perfusion of human Relaxin 2 (FIG. 11 a-d) as well as scR-Fc 13 (FIG. 11 e-h) are leading to a significant increase in heart rate and coronary flow and to a decrease in the left ventricular diastolic pressure and the left ventricular pressure (+dp/dtmax). Thereby, hRelaxin 2 is ten fold more potent than scR-Fc 13, reflecting the differences in the EC50 values for sc Relaxin fusion protein variants and of Relaxin 2 determined with the CHO-CRE-LGR7 cell line.

TABLE 5

List of constructs and corresponding SEQ ID NOs.

| Construct | type | SEQ ID NO |
|---|---|---|
| scR1 | PRT | SEQ ID NO: 1 |
| scR2 | PRT | SEQ ID NO: 2 |
| scR3 | PRT | SEQ ID NO: 3 |
| scR4 | PRT | SEQ ID NO: 4 |
| scR5 | PRT | SEQ ID NO: 5 |
| scR6 | PRT | SEQ ID NO: 6 |
| scR7 | PRT | SEQ ID NO: 7 |
| scR8 | PRT | SEQ ID NO: 8 |
| scR9 | PRT | SEQ ID NO: 9 |
| scR10 | PRT | SEQ ID NO: 10 |
| scR11 | PRT | SEQ ID NO: 11 |
| scR12 | PRT | SEQ ID NO: 12 |
| scR13 | PRT | SEQ ID NO: 13 |
| scR14 | PRT | SEQ ID NO: 14 |
| scR15 | PRT | SEQ ID NO: 15 |
| scR-Fc 1 | PRT | SEQ ID NO: 16 |
| scR-Fc 2 | PRT | SEQ ID NO: 17 |
| scR-Fc 3 | PRT | SEQ ID NO: 18 |
| scR-Fc 4 | PRT | SEQ ID NO: 19 |
| scR-Fc 5 | PRT | SEQ ID NO: 20 |
| scR-Fc 6 | PRT | SEQ ID NO: 21 |
| scR-Fc 7 | PRT | SEQ ID NO: 22 |
| scR-Fc 8 | PRT | SEQ ID NO: 23 |
| scR-Fc 9 | PRT | SEQ ID NO: 24 |
| scR-Fc 10 | PRT | SEQ ID NO: 25 |
| scR-Fc 11 | PRT | SEQ ID NO: 26 |
| scR-Fc 12 | PRT | SEQ ID NO: 27 |
| scR-Fc 13 | PRT | SEQ ID NO: 28 |
| scR-Fc 14 | PRT | SEQ ID NO: 29 |
| scR-Fc 15 | PRT | SEQ ID NO: 30 |
| scR-Fc 16 | PRT | SEQ ID NO: 31 |
| scR-Fc 17 | PRT | SEQ ID NO: 32 |
| scR-Fc 18 | PRT | SEQ ID NO: 33 |
| scR-Var1 | PRT | SEQ ID NO: 34 |
| scR-Var2 | PRT | SEQ ID NO: 35 |
| scR-Var3 | PRT | SEQ ID NO: 36 |
| scR-Var4 | PRT | SEQ ID NO: 37 |
| scR-Var5 | PRT | SEQ ID NO: 38 |
| scR-Var6 | PRT | SEQ ID NO: 39 |
| scR-Var7 | PRT | SEQ ID NO: 40 |
| scR-Var8 | PRT | SEQ ID NO: 41 |
| scR1 w/o Tag | PRT | SEQ ID NO: 42 |
| scR2 w/o Tag | PRT | SEQ ID NO: 43 |
| scR3 w/o Tag | PRT | SEQ ID NO: 44 |
| scR4 w/o Tag | PRT | SEQ ID NO: 45 |
| scR5 w/o Tag | PRT | SEQ ID NO: 46 |
| scR6 w/o Tag | PRT | SEQ ID NO: 47 |
| scR7 w/o Tag | PRT | SEQ ID NO: 48 |
| scR8 w/o Tag | PRT | SEQ ID NO: 49 |
| scR9 w/o Tag | PRT | SEQ ID NO: 50 |
| scR10 w/o Tag | PRT | SEQ ID NO: 51 |
| scR-Fc 1 w/o Tag | PRT | SEQ ID NO: 52 |
| scR-Fc 8 w/o Tag | PRT | SEQ ID NO: 53 |
| scR-Fc 9 w/o Tag | PRT | SEQ ID NO: 54 |
| scR-Fc 10 w/o Tag | PRT | SEQ ID NO: 55 |
| scR-Fc 11 w/o Tag | PRT | SEQ ID NO: 56 |
| scR-Fc 12 w/o Tag | PRT | SEQ ID NO: 57 |
| scR-Fc 13 w/o Tag | PRT | SEQ ID NO: 58 |
| scR1 | DNA | SEQ ID NO: 59 |
| scR2 | DNA | SEQ ID NO: 60 |
| scR3 | DNA | SEQ ID NO: 61 |
| scR4 | DNA | SEQ ID NO: 62 |
| scR5 | DNA | SEQ ID NO: 63 |
| scR6 | DNA | SEQ ID NO: 64 |
| scR7 | DNA | SEQ ID NO: 65 |
| scR8 | DNA | SEQ ID NO: 66 |
| scR9 | DNA | SEQ ID NO: 67 |
| scR10 | DNA | SEQ ID NO: 68 |
| scR11 | DNA | SEQ ID NO: 69 |
| scR12 | DNA | SEQ ID NO: 70 |
| scR13 | DNA | SEQ ID NO: 71 |
| scR14 | DNA | SEQ ID NO: 72 |
| scR15 | DNA | SEQ ID NO: 73 |
| scR-Fc 1 | DNA | SEQ ID NO: 74 |
| scR-Fc 2 | DNA | SEQ ID NO: 75 |
| scR-Fc 3 | DNA | SEQ ID NO: 76 |
| scR-Fc 4 | DNA | SEQ ID NO: 77 |
| scR-Fc 5 | DNA | SEQ ID NO: 78 |
| scR-Fc 6 | DNA | SEQ ID NO: 79 |
| scR-Fc 7 | DNA | SEQ ID NO: 80 |
| scR-Fc 8 | DNA | SEQ ID NO: 81 |
| scR-Fc 9 | DNA | SEQ ID NO: 82 |
| scR-Fc 10 | DNA | SEQ ID NO: 83 |
| scR-Fc 11 | DNA | SEQ ID NO: 84 |
| scR-Fc 12 | DNA | SEQ ID NO: 85 |
| scR-Fc 13 | DNA | SEQ ID NO: 86 |
| scR-Fc 14 | DNA | SEQ ID NO: 87 |
| scR-Fc 15 | DNA | SEQ ID NO: 88 |
| scR-Fc 16 | DNA | SEQ ID NO: 89 |
| scR-Fc 17 | DNA | SEQ ID NO: 90 |
| scR-Fc 18 | DNA | SEQ ID NO: 91 |
| scR-Var1 | DNA | SEQ ID NO: 92 |
| scR-Var2 | DNA | SEQ ID NO: 93 |
| scR-Var3 | DNA | SEQ ID NO: 94 |

TABLE 5-continued

List of constructs and corresponding SEQ ID NOs.

| Construct | type | SEQ ID NO |
|---|---|---|
| scR-Var4 | DNA | SEQ ID NO: 95 |
| scR-Var5 | DNA | SEQ ID NO: 96 |
| scR-Var6 | DNA | SEQ ID NO: 97 |
| scR-Var7 | DNA | SEQ ID NO: 98 |
| scR-Var8 | DNA | SEQ ID NO: 99 |
| scR1 w/o Tag | DNA | SEQ ID NO: 100 |
| scR2 w/o Tag | DNA | SEQ ID NO: 101 |
| scR3 w/o Tag | DNA | SEQ ID NO: 102 |
| scR4 w/o Tag | DNA | SEQ ID NO: 103 |
| scR5 w/o Tag | DNA | SEQ ID NO: 104 |
| scR6 w/o Tag | DNA | SEQ ID NO: 105 |
| scR7 w/o Tag | DNA | SEQ ID NO: 106 |
| scR8 w/o Tag | DNA | SEQ ID NO: 107 |
| scR9 w/o Tag | DNA | SEQ ID NO: 108 |
| scR10 w/o Tag | DNA | SEQ ID NO: 109 |
| scR-Fc 1 w/o Tag | DNA | SEQ ID NO: 110 |
| scR-Fc 8 w/o Tag | DNA | SEQ ID NO: 111 |
| scR-Fc 9 w/o Tag | DNA | SEQ ID NO: 112 |
| scR-Fc 10 w/o Tag | DNA | SEQ ID NO: 113 |
| scR-Fc 11 w/o Tag | DNA | SEQ ID NO: 114 |
| scR-Fc 12 w/o Tag | DNA | SEQ ID NO: 115 |
| scR-Fc 13 w/o Tag | DNA | SEQ ID NO: 116 |
| RLN2 A chain | PRT | SEQ ID NO: 117 |
| RLN2 minimal A chain | PRT | SEQ ID NO: 118 |
| RLN2 B chain | PRT | SEQ ID NO: 119 |
| Fc IgG1 human | PRT | SEQ ID NO: 120 |
| Fc IgG2b rat | PRT | SEQ ID NO: 121 |
| Transferrin | PRT | SEQ ID NO: 122 |
| Albumin | PRT | SEQ ID NO: 123 |
| RLN3 A chain | PRT | SEQ ID NO: 124 |
| RLN3 B chain | PRT | SEQ ID NO: 125 |
| RLN3 minimal A chain | PRT | SEQ ID NO: 126 |
| RLN2 A chain | DNA | SEQ ID NO: 127 |
| RLN2 minimal A chain | DNA | SEQ ID NO: 128 |
| RLN2 B chain | DNA | SEQ ID NO: 129 |
| Fc IgG1 human | DNA | SEQ ID NO: 130 |
| Fc IgG2b rat | DNA | SEQ ID NO: 131 |
| Transferrin | DNA | SEQ ID NO: 132 |
| Albumin | DNA | SEQ ID NO: 133 |
| RLN3 A chain | DNA | SEQ ID NO: 134 |
| RLN3 B chain | DNA | SEQ ID NO: 135 |
| RLN3 minimal A chain | DNA | SEQ ID NO: 136 |
| linker 1 | PRT | SEQ ID NO: 137 |
| linker 2 | PRT | SEQ ID NO: 138 |
| linker 3 | PRT | SEQ ID NO: 139 |
| linker 4 | PRT | SEQ ID NO: 140 |
| linker 5 | PRT | SEQ ID NO: 141 |
| linker 6 | PRT | SEQ ID NO: 142 |
| linker 7 | PRT | SEQ ID NO: 143 |
| linker 8 | PRT | SEQ ID NO: 144 |
| linker 9 | PRT | SEQ ID NO: 145 |
| linker 10 | PRT | SEQ ID NO: 146 |
| stretcher 1 | PRT | SEQ ID NO: 147 |
| stretcher 2 | PRT | SEQ ID NO: 148 |
| stretcher 3 | PRT | SEQ ID NO: 149 |
| stretcher 4 | PRT | SEQ ID NO: 150 |
| stretcher 5 | PRT | SEQ ID NO: 151 |
| scR16 | PRT | SEQ ID NO: 152 |
| scR17 | PRT | SEQ ID NO: 153 |
| scR18 | PRT | SEQ ID NO: 154 |
| scR19 | PRT | SEQ ID NO: 155 |
| scR20 | PRT | SEQ ID NO: 156 |
| scR16 | DNA | SEQ ID NO: 157 |
| scR17 | DNA | SEQ ID NO: 158 |
| scR18 | DNA | SEQ ID NO: 159 |
| scR19 | DNA | SEQ ID NO: 160 |
| scR20 | DNA | SEQ ID NO: 161 |

FURTHER CITATIONS

Hsu, S. Y. (2003). New insights into the evolution of the relaxin-LGR signaling system. Trends Endocrinol Metab 14:303-309;

Wilkinson, T. N., Speed, T. P., Tregear, G. W., Bathgate, R. A. (2005).Evolution of the relaxin-like peptide family. BMC Evol Biol 5:14).

Hudson P, Haley J, John M, Cronk M, Crawford R, Haralambidis J, Tregear G, Shine J, Niall H. (1983) Structure of a genomic clone encoding biologically active human relaxin. Nature 301: 628-631;

Toth, M., Taskinen, P., & Ruskoaho, H. (1996). Relaxin stimulates atrial natriuretic peptide secretion in perfused rat heart. J Endocrinol 150: 487-495).

Piedras-Renteria, E. S., Sherwood, O. D., and Best, P. M. (1997). Effects of relaxin on rat atrial myocytes: I. Inhibition of I(to) via PKA-dependent phosphorylation. Am J Physiol 272:H1791-H1797).

Bartsch, O., Bartlick, B., and Ivell, R. (2001). Relaxin signaling links tyrosine phosphorylation to phosphodiesterase and adenylyl cyclase activity. Mol Hum Reprod 7:799-809;

Bartsch, O., Bartlick, B., and Ivell, R. (2004). Phosphodiesterase 4 inhibition synergizes with relaxin signaling to promote decidualization of human endometrial stromal cells. J Clin Endocrinol Metab 89:324-334;

Bani-Sacchi, T., Bigazzi, M., Bani, D., Mannaioni, P. F., and Masini, E. (1995) Relaxin-induced increased coronary flow through stimulation of nitric oxide production. Br J Pharmacol 116:1589-1594.), Dschietzig T, Bartsch C, Baumann G, Stangl K. (2006) Relaxin—a pleiotropic hormone and its emerging role for experimental and clinical therapeutics. Pharmacol. Ther. 112:38-56)

McGuane J T, Parry L J. (2005) Relaxin and the extracellularmatrix: Molecular mechanisms of action and implications for cardiovascular disease. Expert. Rev. Mol. Med. 7:1-18;

Nistri, S., Chiappini, L., Sassoli, C. and Bani, D. (2003) Relaxin inhibits lipopolysaccharide-induced adhesion of neutrophils to coronary endothelial cells by a nitric oxide-mediated mechanism. FASEB J. 17:2109-2111;

Perna A M, Masini E, Nistri S, Briganti V, Chiappini L, Stefano P, Bigazzi M, Pieroni C, Bani Sacchi T, Bani D. (2005) Novel drug development opportunity for relaxin in acute myocardial infarction: evidences from a swine model. FASEB J. 19:1525-1527

Bani, D., Masini, E., Bello, M. G., Bigazzi, M. and Sacchi, T. B. (1998) Relaxin protects against myocardial injury caused by ischemia and reperfusion in rat heart. Am. J. Pathol. 152:1367-1376;

Zhang J, Qi Y F, Geng B, Pan C S, Zhao J, Chen L, Yang J, Chang J K, Tang C S. (2005) Effect of relaxin on myocardial ischemia injury induced by isoproterenol. Peptides 26:1632-1639

Teerlink J R, Metra M, Felker G M, Ponikowski P, Voors A A, Weatherley B D, Marmor A, Katz A, Grzybowski J, Unemori E, Teichman S L, Cotter G. (2009) Relaxin for the treatment of patients with acute heart failure (Pre-RELAX-AHF): a multicentre, randomised, placebo-controlled, parallel-group, dose-finding phase IIb study. Lancet. 373:1429-39;

Metra M, Teerlink J R, Felker G M, Greenberg B H, Filippatos G, Ponikowski P, Teichman S L, Unemori E, Voors A A, Weatherley B D, Cotter G. (2010) Dyspnoea and worsening heart failure in patients with acute heart failure: results from the Pre-RELAX-AHF study. Eur J Heart Fail. 12:1130-1139).

Cosen-Binker L I, Binker M G, Cosen R, Negri G, Tiscornia O. (2006) Relaxin prevents the development of severe acute pancreatitis. World J. Gastroenterol. 12:1558-1568;

Santora K, Rasa C, Visco D, Steinetz B G, Bagnell C A. (2007) Antiarthritic effects of relaxin, in combination with estrogen, in rat adjuvant induced arthritis. J. Pharmacol. Exp. Ther. 322:887-893

Bennett R G. (2009) Relaxin and its role in the development and treatment of fibrosis. Transl Res. 154:1-6

Barlos K K, Gatos D, Vasileiou Z, Barlos K. (2010) An optimized chemical synthesis of human relaxin-2. J Pept Sci. 16:200-211.

Park J I, Semyonov J, Yi W, Chang C L, Hsu S Y (2008) Regulation of receptor signaling by relaxin A chain motifs: derivation of pan-specific and LGR7-specific human relaxin analogs. J Biol Chem. 283:32099-32109

Shaw J A, Delday M I, Hart A W, Docherty H M, Maltin C A, Docherty K (2002) Secretion of bioactive human insulin following plasmid-mediated gene transfer to non-neuroendocrine cell lines, primary cultures and rat skeletal muscle in vivo. J Endocrinol 172:653-672

Rajpal G, Liu M, Zhang Y, Aryan P, (2009) Single-Chain Insulins as Receptor Agonists. Mol Endocrinol. 23:679-88

Dschietzig T, Teichmann S, Unemori E, Wood S, Boehmer J, Richter C, Baumann G, Stangl K (2009) Intravenous Recombinant Human Relaxin in Compensated Heart Failure: A Safety, Tolerability, and Pharmacodynamic Trial. J Cardiac Fail 5:182-190

WO2006053299 A2, Site-directed modification of FVIII, Bayer Healthcare LLC;

Harris J M, Martin N E, Modi M. (2001) Pegylation: a novel process for modifying pharmacokinetics. Clin Pharmacokinet. 40:539-551.

Schmid S R, (2009) Fusion-proteins as biopharmaceuticals—applications and challenges. Curr Opin Drug Discov Devel. 12:284-95.

Pasut and Veronese (2009) PEGylation for improving the effectiveness of therapeutic biomolecules. Drugs Today 45:687-695

WO 97/26265
WO 99/03861
WO 00/06568
WO 00/06569
WO 02/42301
WO 03/095451
WO 01/19355
WO 01/19776
WO 01/19778
WO 01/19780
WO 02/070462
WO 02/070510

The invention claimed is:

1. A fusion polypeptide having Relaxin activity comprising A-L-B,
wherein
B comprises a Relaxin 2 B chain polypeptide,
A comprises a Relaxin 2 A chain polypeptide, and
L is a linker polypeptide, wherein the linker polypeptide L is 6-14 amino acids in length.

2. A fusion polypeptide according to claim 1, wherein the fusion polypeptide further comprises at least one half-life extending moiety.

3. A fusion polypeptide according to claim 2, wherein half-life extending moiety is an immunoglobulin Fc domain, PEG or HES.

4. A fusion polypeptide according to claim 3, wherein the immunoglobulin Fc domain is an IgG1 Fc domain.

5. A fusion polypeptide according to claim 1, comprising the sequence of SEQ ID NO: 45.

6. A fusion polypeptide according claim 1, wherein the Relaxin A chain is human Relaxin 2 A chain (SEQ ID NO: 117) and the Relaxin B chain is human Relaxin 2 B chain (SEQ ID NO: 119).

7. A fusion polypeptide according to claim 1, wherein A-L-B is selected from the group of A-L-B polypeptides consisting of scR3, scR4, scR5, scR7, scR8, scR9, scR10, scR11, scR12, scR13, scR14, scR15, scR-Fc 1, scR-Fc 2, scR-Fc 3, scR-Fc 4, scR-Fc 5, scR-Fc 6, scR-Fc 7, scR-Fc 8, scR-Fc 9, scR-Fc 10, scR-Fc 11, scR-Fc 12, scR-Fc 13, scR-Var1, scR-Var2, scR-Var3, scR-Var5, scR-Var7, scR-Var8, scR3 w/o Tag, scR4 w/o Tag, scR5 w/o Tag, scR6 w/o Tag, scR7 w/o Tag, scR8 w/o Tag, scR9 w/o Tag, scR10 w/o Tag, scR-Fc 1 w/o Tag, scR-Fc 8 w/o Tag, scR-Fc 9 w/o Tag, scR-Fc 10 w/o Tag, scR-Fc 11 w/o Tag, scR-Fc 12 w/o Tag and scR-Fc 13 w/o Tag.

8. A fusion polypeptide according to claim 1, wherein A-L-B is selected from the group of A-L-B polypeptides consisting of scR3, scR4, scR5, scR3 w/o Tag, scR4 w/o Tag, scR5 w/o Tag, scR-Fc5, scR-Fc6 and scR-Fc7.

9. A pharmaceutical composition comprising a fusion polypeptide according to claim 1.

10. A method of treating a cardiovascular disease, lung disease, fibrotic disorder or kidney disease comprising the administration of a therapeutically effective dose of a fusion polypeptide according to claim 1.

11. A method according to claim 10, wherein the cardiovascular disease is coronary heart disease, acute coronary syndrome, heart failure, or myocardial infarction.

12. A fusion polypeptide according to claim 1, comprising:

(R1)-(S1)-A-L-B, wherein

A is a human Relaxin 2 A chain polypeptide (SEQ ID NO: 117),

B is a human Relaxin 2 B chain polypeptide (SEQ ID NO: 119),

L is a linker polypeptide having the sequence GlyGlyGly-SerGlyGlyGlySerGly (SEQ ID NO: 139), R1 is a proteinaceous half-life extending moiety, S1 is a stretcher peptide being 4-10 amino acids in length.

13. A fusion polypeptide according to claim 12, wherein S1 is selected from the group consisting of GlyGlySerPro (SEQ ID NO: 148), GlyGlySerGlyGlySerPro (SEQ ID NO: 149), and GlyGlySerGlyGlySerGlyGlySerPro (SEQ ID NO: 150).

14. A polynucleotide encoding a fusion polypeptide having Relaxin activity comprising A-L-B, wherein B comprises a Relaxin 2 B chain polypeptide, A comprises a Relaxin 2 A chain polypeptide, and L is a linker polypeptide, wherein the linker polypeptide L is 6-14 amino acids in length.

15. A vector comprising a polynucleotide according to claim 14.

16. A host cell comprising a polynucleotide according to claim 14.

17. A method of producing a polypeptide comprising the steps of cultivating a host cell according to claim 16 and isolating the polypeptide encoded by said polynucleotide and produced by the host cell.

\* \* \* \* \*